US012180490B2

(12) United States Patent
Kloiber-Maitz et al.

(10) Patent No.: US 12,180,490 B2
(45) Date of Patent: Dec. 31, 2024

(54) PLANTS WITH IMPROVED DIGESTIBILITY AND MARKER HAPLOTYPES

(71) Applicant: KWS SAAT SE & Co. KGaA, Einbeck (DE)

(72) Inventors: Monika Kloiber-Maitz, Einbeck (DE); Therese Bolduan, Einbeck (DE); Milena Ouzunova, Göttingen (DE); Nina Meyer, Einbeck (DE); Carolina Lopez-Duran, Einbeck (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 595 days.

(21) Appl. No.: 17/049,368

(22) PCT Filed: Apr. 24, 2019

(86) PCT No.: PCT/EP2019/060411
§ 371 (c)(1),
(2) Date: Oct. 21, 2020

(87) PCT Pub. No.: WO2019/206927
PCT Pub. Date: Oct. 31, 2019

(65) Prior Publication Data

US 2022/0049265 A1 Feb. 17, 2022

(30) Foreign Application Priority Data

Apr. 24, 2018 (EP) .................................... 18169122

(51) Int. Cl.

*C12N 15/82* (2006.01)
*A01H 1/04* (2006.01)
*C12N 9/02* (2006.01)
*C12Q 1/6895* (2018.01)

(52) U.S. Cl.

CPC ......... *C12N 15/8242* (2013.01); *A01H 1/045* (2021.01); *C12N 9/0071* (2013.01); *C12Q 1/6895* (2013.01); *C12Y 114/13088* (2013.01); *C12Q 2600/13* (2013.01); *C12Q 2600/156* (2013.01)

(58) Field of Classification Search

CPC .......... C12N 15/8242; C12Q 2600/156; C12Q 2600/13; C12Y 114/13088
See application file for complete search history.

(56) References Cited

U.S. PATENT DOCUMENTS 6,479,626 B1 11/2002 Kim et al.
6,534,261 B1 3/2003 Cox, III et al.
6,607,882 B1 8/2003 Cox, III et al.
6,746,838 B1 6/2004 Choo et al.
6,794,136 B1 9/2004 Eisenberg et al.
6,824,978 B1 11/2004 Cox, III et al.
6,866,997 B1 3/2005 Choo et al.
6,903,185 B2 6/2005 Kim et al.
6,933,113 B2 8/2005 Case et al.
6,979,539 B2 12/2005 Cox, III et al.
7,013,219 B2 3/2006 Case et al.
7,030,215 B2 4/2006 Liu et al.
7,220,719 B2 5/2007 Case et al.
7,241,573 B2 7/2007 Choo et al.
7,241,574 B2 7/2007 Choo et al.
7,585,849 B2 9/2009 Lu et al.
7,595,376 B2 9/2009 Kim et al.
8,021,867 B2 9/2011 Smith et al.
8,119,361 B2 2/2012 Smith et al.
8,119,381 B2 2/2012 Smith et al.
8,124,369 B2 2/2012 Smith et al.
8,129,134 B2 3/2012 Smith et al.
8,133,697 B2 3/2012 Smith et al.
8,163,514 B2 4/2012 Smith et al.
8,440,431 B2 5/2013 Voytas et al.
8,440,432 B2 5/2013 Voytas et al.
8,450,471 B2 5/2013 Voytas et al.
8,697,359 B1 4/2014 Zhang
8,771,945 B1 7/2014 Zhang
8,795,965 B2 8/2014 Zhang
8,865,406 B2 10/2014 Zhang et al.
(Continued)

FOREIGN PATENT DOCUMENTS

EP 2 784 162 A1 10/2014
EP 3009511 4/2016
(Continued)

OTHER PUBLICATIONS

Bosch et al., 2011, Identification of genes involved in cell wall biogenesis in grasses by differential gene expression profiling of elongating and non-elongating maize internodes, Journal of Experimental Botany 62: 3545-3561.*
Nakatsuka et al (2006). Mol Gen Genomics, 275:231-241.*
Fornale et al (2015). Plant Science, 236:272-282.*
Nishihara et al (2011). Mol Gen Genomics, 286:371-382.*
Xiong et al 2013 (BMC Genomics 14: p. 697-686) (Year: 2013).*
U.S. Appl. No. 61/758,468, filed Jan. 30, 2013.
U.S. Appl. No. 61/802,174, filed Mar. 15, 2013.
U.S. Appl. No. 61/806,375, filed Mar. 28, 2013.
U.S. Appl. No. 61/814,263, filed Apr. 20, 2013.
U.S. Appl. No. 61/819,803, filed May 6, 2013.
(Continued)

*Primary Examiner* — Matthew R Keogh
(74) *Attorney, Agent, or Firm* — Troutman Pepper Hamilton Sanders LLP

(57) ABSTRACT

The present invention relates to plants, such as maize, sorghum or sugar cane, having improved digestibility, in particular improved stover digestibility. The present invention relates to a QTL allele associated with improved digestibility and specific marker alleles associated with the QTL allele. The present invention further relates to such plants, wherein the F35H gene is mutated or wherein F35H expression is altered. The invention also relates to methods for identifying plants having improved digestibility and methods for obtaining such plants.

10 Claims, 10 Drawing Sheets

Specification includes a Sequence Listing.

(56) References Cited

U.S. PATENT DOCUMENTS

| | | | |
|---|---|---|---|
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 2003/0175732 | A1 | 9/2003 | Puigdomenech et al. |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0227787 | A1 | 8/2014 | Zhang |
| 2014/0234972 | A1 | 8/2014 | Zhang |
| 2014/0242664 | A1 | 8/2014 | Zhang et al. |
| 2014/0242699 | A1 | 8/2014 | Zhang |
| 2014/0242700 | A1 | 8/2014 | Zhang et al. |
| 2014/0248702 | A1 | 9/2014 | Zhang et al. |
| 2014/0256046 | A1 | 9/2014 | Zhang et al. |
| 2014/0273231 | A1 | 9/2014 | Zhang et al. |
| 2014/0273232 | A1 | 9/2014 | Zhang et al. |
| 2014/0273234 | A1 | 9/2014 | Zhang et al. |
| 2014/0287938 | A1 | 9/2014 | Zhang et al. |
| 2014/0310830 | A1 | 10/2014 | Zhang et al. |
| 2015/0184139 | A1 | 7/2015 | Zhang et al. |
| 2015/0232872 | A1 | 8/2015 | Boerjan et al. |
| 2015/0291969 | A1 | 10/2015 | Nair et al. |

FOREIGN PATENT DOCUMENTS

| | | |
|---|---|---|
| WO | 2010/054191 | 5/2010 |
| WO | WO 2010/054191 A1 * | 5/2010 |
| WO | 2014/018423 | 1/2014 |
| WO | 2014/093595 A1 | 6/2014 |
| WO | 2014/093622 | 6/2014 |
| WO | 2014/093635 A1 | 6/2014 |
| WO | 2014/093655 | 6/2014 |
| WO | 2014/093661 | 6/2014 |
| WO | 2014/093694 | 6/2014 |
| WO | 2014/093701 A1 | 6/2014 |
| WO | 2014/093709 A1 | 6/2014 |
| WO | 2014/093712 | 6/2014 |
| WO | 2014/093718 A1 | 6/2014 |
| WO | 2014/204723 | 12/2014 |
| WO | 2014/204724 | 12/2014 |
| WO | 2014/204725 | 12/2014 |
| WO | 2014/204726 | 12/2014 |
| WO | 2014/204727 | 12/2014 |
| WO | 2014/204728 | 12/2014 |
| WO | 2014/204729 | 12/2014 |
| WO | 2015/065964 | 5/2015 |
| WO | 2015/089351 | 6/2015 |
| WO | 2015/089354 | 6/2015 |
| WO | 2015/089364 | 6/2015 |
| WO | 2015/089419 | 6/2015 |
| WO | 2015/089427 | 6/2015 |
| WO | 2015/089462 | 6/2015 |
| WO | 2015/089465 | 6/2015 |
| WO | 2015/089473 | 6/2015 |
| WO | 2015/089486 | 6/2015 |
| WO | 2016/028682 | 2/2016 |
| WO | 2016/049163 | 3/2016 |
| WO | 2016/049258 | 3/2016 |

OTHER PUBLICATIONS

U.S. Appl. No. 61/828,130, filed May 28, 2013.
U.S. Appl. No. 61/836,123, filed Jun. 17, 2013.
U.S. Appl. No. 61/835,931, filed Jun. 17, 2013.
U.S. Appl. No. 61/835,936, filed Jun. 17, 2013.
U.S. Appl. No. 61/835,973, filed Jun. 17, 2013.
U.S. Appl. No. 61/836,080, filed Jun. 17, 2013.
U.S. Appl. No. 61/836,101, filed Jun. 17, 2013.
U.S. Appl. No. 61/836,127, filed Jun. 17, 2013.
U.S. Appl. No. 61/862,468, filed Aug. 5, 2013.
U.S. Appl. No. 61/862,355, filed Aug. 5, 2013.
U.S. Appl. No. 61/871,301, filed Aug. 28, 2013.
U.S. Appl. No. 61/960,777, filed Sep. 25, 2013.
U.S. Appl. No. 61/961,980, filed Oct. 28, 2013.
U.S. Appl. No. 61/915,148, filed Dec. 12, 2013.
U.S. Appl. No. 61/915,150, filed Dec. 12, 2013.
U.S. Appl. No. 61/915,153, filed Dec. 12, 2013.
U.S. Appl. No. 61/915,203, filed Dec. 12, 2013.
U.S. Appl. No. 61/915,251, filed Dec. 12, 2013.
U.S. Appl. No. 61/915,301, filed Dec. 12, 2013.
U.S. Appl. No. 61/915,267, filed Dec. 12, 2013.
U.S. Appl. No. 61/915,397, filed Dec. 12, 2013.
U.S. Appl. No. 61/768,959, filed Feb. 25, 2013.
U.S. Appl. No. 62/010,888, filed Jun. 11, 2014.
U.S. Appl. No. 62/010,879, filed Jun. 11, 2014.
U.S. Appl. No. 62/010,329, filed Jun. 10, 2014.
U.S. Appl. No. 62/010,441, filed Jun. 10, 2014.
U.S. Appl. No. 61/939,228, filed Feb. 12, 2014.
U.S. Appl. No. 61/939,242, filed Feb. 12, 2014.
U.S. Appl. No. 61/980,012, filed Apr. 15, 2014.
U.S. Appl. No. 62/038,358, filed Aug. 17, 2014.
U.S. Appl. No. 62/055,484, filed Sep. 25, 2014.
U.S. Appl. No. 62/055,460, filed Sep. 25, 2014.
U.S. Appl. No. 62/055,487, filed Sep. 25, 2014.
U.S. Appl. No. 62/069,243, filed Oct. 27, 2014.
U.S. Appl. No. 61/930,214, filed Jan. 22, 2014.
U.S. Appl. No. 62/180,709, filed Jun. 17, 2015.
U.S. Appl. No. 62/091,455, filed Dec. 12, 2014.
U.S. Appl. No. 62/096,708, filed Dec. 24, 2014.
U.S. Appl. No. 62/091,462, filed Dec. 12, 2014.
U.S. Appl. No. 62/096,324, filed Dec. 23, 2014.
U.S. Appl. No. 62/180,681, filed Jun. 17, 2015.
U.S. Appl. No. 62/237,496, filed Oct. 5, 2015.
U.S. Appl. No. 62/091,456, filed Dec. 12, 2014.
U.S. Appl. No. 62/180,692, filed Jun. 17, 2015.
U.S. Appl. No. 62/091,461, filed Dec. 12, 2014.
Wu et al, "Genome-wide binding of the CRISPR endonuclease Cas9 in mammalian cells", Nat Biotechnol., 2014, vol. 32, No. 7, pp. 670-676.
Platt et al., "CRISPR-Cas9 Knockin Mice for Genome Editing and Cancer Modeling", Cell, 2014, vol. 159, No. 2, pp. 440-455.
Hsu et al., "Development and Applications of CRISPR-Cas9 for Genome Engineering", Cell, 2014, vol. 157, pp. 1262-1278.
Wang et al., "Genetic screens in human cells using the CRISPR/Cas9 system", Science, 2014, vol. 343, No. 6166, pp. 80-84.
Doench et al., "Rational design of highly active sgRNAs for CRISPR-Cas9-mediated gene inactivation", Nature Biotechnology, 2014, vol. 32, No. 12, pp. 1262-1267.
Swiech et al., "In vivo interrogation of gene function in the mammalian brain using CRISPR-Cas9", Nature Biotechnology, 2015, vol. 33, No. 1, pp. 102-106.
Zetsche et al., "Cpf1 Is a Single RNA-Guided Endonuclease of a Class 2 CRISPR-Cas System", Cell, 2015, vol. 163, pp. 759-771.
Shmakov et al., "Discovery and Functional Characterization of Diverse Class 2 CRISPR-Cas Systems", Molecular Cell, 2015, vol. 60, No. 3, pp. 385-397.
Abudayyeh et al., "C2c2 is a single-component programmable RNA-guided RNA-targeting CRISPR effector", Science, 2016, vol. 353, Issue 6299, 10 pages.
Jore et al., "Structural basis for CRISPR RNA-guided DNA recognition by Cascade", Nature Structural & Molecular Biology, 2011, vol. 18, No. 5, pp. 529-536.
Gaudelli et al., "Programmable base editing of A• T to G• C in genomic DNA without DNA cleavage", Nature, 2017, vol. 551, No. 7681, pp. 464, 24 pages.
Kleinstiver et al., "Engineered CRISPR-Cas9 nucleases with altered PAM specificities", Nature, 2015, vol. 523, No. 7561, pp. 481-485.

(56) References Cited

OTHER PUBLICATIONS

McCallum et al., "Targeted screening for induced mutations", Nat Biotechnol., 2000, vol. 18, No. 4, pp. 455-457.
McCallum et al. "Targeting induced local lesions IN genomes (TILLING) for plant functional genomics", Plant Physiology, 2000, vol. 123, No. 2, pp. 439-442.
Hirsch et al., "Draft Assembly of Elite Inbred Line PH207 Provides Insights into Genomic and Transcriptome Diversity in Maize", The Plant Cell, 2016, vol. 28, No. 11, pp. 2700-2714.
Bosch et al. "Identification of genes involved in cell wall biogenesis in grasses by differential gene expression profiling of elongating and non-elongating maize internodes", Journal of Experimental Botany, 2011, vol. 62, No. 10, pp. 3545-3561.
Riboulet et al., "QTL mapping and candidate gene research from lignin content and cell wall digestibility in a top-cross of a flint maize recombinant inbred line progeny harvested at silage stage", Maydica, 2008, vol. 53, No. 1, pp. 1-9.
Barriere et al., "Genetic variation and breeding strategies for improved cell wall digestibility in annual forage crops. A review", Anim. Res., 2003, vol. 52, No. 3, pp. 193-228.
Guillaumie et al., "Maizewall. Database and developmental gene expression profiling of cell wall biosynthesis and assembly in maize", Plant Physiology, 2007, vol. 143, No. 1, pp. 339-363.
International Search Report and Written Opinion issued in International Application No. PCT/EP2019/060411 dated Jun. 17, 2019.
U.S. Appl. No. 62/094,903, filed Dec. 19, 2014.
U.S. Appl. No. 62/098,059, filed Dec. 30, 2014.
U.S. Appl. No. 62/181,641, filed Jun. 18, 2015.
U.S. Appl. No. 62/181,667, filed Jun. 18, 2015.
U.S. Appl. No. 62/096,656, filed Dec. 24, 2014.
U.S. Appl. No. 62/181,151, filed Jun. 17, 2015.
U.S. Appl. No. 62/054,490, filed Sep. 24, 2014.
U.S. Appl. No. 62/087,537, filed Dec. 4, 2014.
U.S. Appl. No. 62/054,651, filed Sep. 24, 2014.
U.S. Appl. No. 62/067,886, filed Oct. 23, 2014.
U.S. Appl. No. 62/054,675, filed Sep. 24, 2014.
U.S. Appl. No. 62/181,002, filed Jun. 17, 2015.
U.S. Appl. No. 62/087,475, filed Dec. 4, 2014.
U.S. Appl. No. 62/181,690, filed Jun. 18, 2015.
U.S. Appl. No. 62/087,546, filed Dec. 4, 2014.
U.S. Appl. No. 62/181,687, filed Jun. 18, 2015.
U.S. Appl. No. 62/098,285, filed Dec. 30, 2014.
U.S. Appl. No. 62/181,659, filed Jun. 18, 2015.
U.S. Appl. No. 62/207,318, filed Aug. 19, 2015.
U.S. Appl. No. 62/181,663, filed Jun. 18, 2015.
U.S. Appl. No. 62/245,264, filed Oct. 22, 2015.
U.S. Appl. No. 62/181,675, filed Jun. 18, 2015.
U.S. Appl. No. 62/232,067, filed Sep. 24, 2015.
U.S. Appl. No. 62/205,733, filed Aug. 16, 2015.
U.S. Appl. No. 62/201,542, filed Aug. 5, 2015.
U.S. Appl. No. 62/193,507, filed Jul. 16, 2015.
U.S. Appl. No. 62/181,739, filed Jun. 18, 2015.
U.S. Appl. No. 62/245,270, filed Oct. 22, 2015.
U.S. Appl. No. 61/939,256, filed Feb. 12, 2014.
U.S. Appl. No. 62/180,699, filed Jun. 17, 2015.
Cermak et al., "Efficient design and assembly of custom TALEN and other TAL effector-based constructs for DNA targeting", Nucleic Acids Research, 2011, vol. 39, No. 12, e82, 11 pages.
Zhang et al., "Programmable sequence-specific Transcriptional Regulation of Mammalian Genome Using Designer TAL effectors", Nat Biotechnol., 2011, vol. 29, No. 2, pp. 149-153.
Moscou et al., "A Simple Cipher Governs DNA Recognition by TAL Effectors", Science, 2009, vol. 326, p. 1501.
Boch et al., "Breaking the Code of DNA Binding Specificity of TAL-Type III Effectors", Science, 2009, vol. 326, pp. 1509-1512.
Kim et al., "Chimeric restriction endonuclease", Proc. Natl. Acad. Sci. U.S.A., 1994, vol. 91, pp. 883-887.
Kim et al., "Hybrid restriction enzymes: zinc finger fusions to Fok I cleavage domain", Proc. Natl. Acad. Sci. U.S.A., 1996, vol. 93, 1156-1160.
Doyon et al., "Enhancing zinc-finger-nuclease activity with improved obligate heterodimeric architectures", Nature Methods, 2011, vol. 8, pp. 74-79.
Cong et al., "Multiplex Genome Engineering Using CRISPR/Cas Systems", Science, 2013, vol. 339, No. 6121, pp. 819-823.
Jiang et al., "CRISPR-assisted editing of bacterial genomes", Nat Biotechnol., 2013, vol. 31, No. 3, pp. 233-239.
Wang et al., "One-Step Generation of Mice Carrying Mutations in Multiple Genes by CRISPR/Cas-Mediated Genome Engineering", Cell, 2013, vol. 153, No. 4, pp. 910-918.
Konermann et al., "Optical control of mammalian endogenous transcription and epigenetic states", Nature, 2013, vol. 500, No. 7463, pp. 472-476.
Ran et al., "Double Nicking by RNA-Guided CRISPR Cas9 for Enhanced Genome Editing Specificity", Cell, 2013, vol. 154, pp. 1380-1389.
Hsu et al., "DNA targeting specificity of RNA-guided Cas9 nucleases", Nat Biotechnol., 2013, vol. 31, No. 9, pp. 827-832.
Ran et al., "Genome engineering using the CRISPR-Cas9 system", Nature Protocols, 2013, vol. 8, No. 11, pp. 2281-2308.
Shalem et al., "Genome-Scale CRISPR-Cas9 Knockout Screening in Human Cells", Science, 2014, vol. 343, No. 6166, pp. 84-87.
Nishimasu et al., "Crystal structure of Cas9 in complex with guide RNA and target DNA", Cell, 2014, vol. 156, No. 5, pp. 935-949.

* cited by examiner

Figure 3

| ArbNr | Family | Individual | DNDF Mean per group | ma61126d01 | ma60405s01 | PZE-109079170 | ma61222s01 | ma61218s01 | ma61134xxx | ma61225s01 | ma61226s01 | ma61211s01 | ma61125s01 |
|---|---|---|---|---|---|---|---|---|---|---|---|---|---|
| WVP17-51917/002 | 1 | 1 | 62,59 | A | A | A | A | A | A | A | A | A | A |
| WVP17-51917/006 | 1 | 2 | | A | A | A | A | A | A | A | A | A | A |
| WVP17-51918/005 | 1 | 3 | | A | A | A | A | A | A | A | A | A | A |
| WVP17-51918/008 | 1 | 4 | | A | A | A | A | A | A | A | A | A | A |
| WVP17-51918/011 | 1 | 5 | | A | A | A | A | A | A | A | A | A | A |
| WVP17-51918/012 | 1 | 6 | | A | A | A | A | A | A | A | A | A | A |
| WVP17-51918/016 | 1 | 7 | | A | A | A | A | A | A | A | A | A | A |
| WVP17-51919/005 | 1 | 8 | | A | A | A | A | A | A | A | A | A | A |
| WVP17-51916/009 | 1 | 9 | 67,05 | A | A | A | A | A | B | B | B | B | B |
| WVP17-51917/003 | 1 | 10 | | A | A | A | A | A | B | B | B | B | B |
| WVP17-51918/001 | 1 | 11 | | A | A | A | A | A | B | B | B | B | B |
| WVP17-51918/009 | 1 | 12 | | A | A | A | A | A | B | B | B | B | B |
| WVP17-51918/010 | 1 | 13 | | A | A | A | A | A | B | B | B | B | B |
| WVP17-51919/011 | 1 | 14 | | A | A | A | A | A | B | B | B | B | B |
| WVP17-51920/007 | 1 | 15 | | A | A | A | A | A | B | B | B | B | B |
| WVP17-51920/017 | 1 | 16 | | A | A | A | A | A | B | B | B | B | B |
| WVP17-51940/003 | 2 | 1 | 57,12 | A | A | A | A | A | A | A | A | A | A |
| WVP17-51941/009 | 2 | 2 | | A | A | A | A | A | A | A | A | A | A |
| WVP17-51941/010 | 2 | 3 | | A | A | A | A | A | A | A | A | A | A |
| WVP17-51941/015 | 2 | 4 | | A | A | A | A | A | A | A | A | A | A |
| WVP17-51943/014 | 2 | 5 | | A | A | A | A | A | A | A | A | A | A |
| WVP17-51945/013 | 2 | 6 | | A | A | A | A | A | A | A | A | A | A |
| WVP17-51946/003 | 2 | 7 | | A | A | A | A | A | A | A | A | A | A |
| WVP17-51947/008 | 2 | 8 | | A | A | A | A | A | A | A | A | A | A |
| WVP17-51948/001 | 2 | 9 | | A | A | A | A | A | A | A | A | A | A |
| WVP17-51948/005 | 2 | 10 | | A | A | A | A | A | A | A | A | A | A |
| WVP17-51948/007 | 2 | 11 | | A | A | A | A | A | A | A | A | A | A |
| WVP17-51949/002 | 2 | 12 | | A | A | A | A | A | A | A | A | A | A |
| WVP17-51949/011 | 2 | 13 | | A | A | A | A | A | A | A | A | A | A |
| WVP17-51949/016 | 2 | 14 | | A | A | A | A | A | A | A | A | A | A |
| WVP17-51940/001 | 2 | 15 | 60,67 | B | B | B | B | B | B | B | B | A | A |
| WVP17-51941/008 | 2 | 16 | | B | B | B | B | B | B | B | B | A | A |
| WVP17-51941/013 | 2 | 17 | | B | B | B | B | B | B | B | B | A | A |
| WVP17-51941/014 | 2 | 18 | | B | B | B | B | B | B | B | B | A | A |
| WVP17-51942/006 | 2 | 19 | | B | B | B | B | B | B | B | B | A | A |
| WVP17-51942/009 | 2 | 20 | | B | B | B | B | B | B | B | B | A | A |
| WVP17-51944/002 | 2 | 21 | | B | B | B | B | B | B | B | B | A | A |
| WVP17-51944/003 | 2 | 22 | | B | B | B | B | B | B | B | B | A | A |
| WVP17-51944/009 | 2 | 23 | | B | B | B | B | B | B | B | B | A | A |
| WVP17-51945/005 | 2 | 24 | | B | B | B | B | B | B | B | B | A | A |
| WVP17-51945/006 | 2 | 25 | | B | B | B | B | B | B | B | B | A | A |
| WVP17-51946/001 | 2 | 26 | | B | B | B | B | B | B | B | B | A | A |
| WVP17-51946/012 | 2 | 27 | | B | B | B | B | B | B | B | B | A | A |
| WVP17-51948/011 | 2 | 28 | | B | B | B | B | B | B | B | B | A | A |
| WVP17-51949/003 | 2 | 29 | | B | B | B | B | B | B | B | B | A | A |
| WVP17-51949/012 | 2 | 30 | | B | B | B | B | B | B | B | B | A | A |
| WVP17-51949/017 | 2 | 31 | | B | B | B | B | B | B | B | B | A | A |

Fig. 4:

```
SEQ ID NO: 1      1 ATGCAGCTCGCGGCGTTGTGCACCGACCCCGTGGTGCTGTGCAGCGCCTT   50
                    ||||||||||||||||||||||||||||||||||||||||||||||||||
SEQ ID NO: 11     1 ATGCAGCTCGCGGCGTTGTGCACCGACCCCGTGGTGCTGTGCAGCGCCTT   50

SEQ ID NO: 1     51 CCTCTGCCTCCTCCTCCACGTGGCTCTCCGCTCGCTGCTGCACCCTC---   97
                    |||||||||||||||||||||||||||||||||||||||||||||||
SEQ ID NO: 11    51 CCTCTGCCTCCTCCTCCACGTGGCTCTCCGCTCGCTGCTGCACCCTCCTT  100

SEQ ID NO: 1     98 --------------------------------------------------   97

SEQ ID NO: 11   101 CTGCCCAGAAGCGGGCCCAGACATTTGAGATTGGGTATTCAAAAATTCAA  150

SEQ ID NO: 1     98 --------------------------------------------------   97

SEQ ID NO: 11   151 AAGATTAAAGAATTTAGTGTTCTAACGCTATTTTATGCAATACATTATTG  200

SEQ ID NO: 1     98 --------------------------------------------------   97

SEQ ID NO: 11   201 ACAAATTAGTGTTCTAACACTATAGATCACCAAAAACATGGGTATTCAAT  250

SEQ ID NO: 1     98 -----------------------------------CTTCTGCCGCCTCTTC  113
                                                       |||||||||||||||
SEQ ID NO: 11   251 GAATACCCATGAAACCCCCCTGGGCCCGCCCATGCTTCTGCCGCCTCTTC  300

SEQ ID NO: 1    114 CTCCGGGCGCCGCGGGCAGCTCCCGCCGGGGCCACCGGGCCTGCCGATCC  163
                    ||||||||||||||||||||||||||||||||||||||||||||||||||
SEQ ID NO: 11   301 CTCCGGGCGCCGCGGGCAGCTCCCGCCGGGGCCACCGGGCCTGCCGATCC  350

SEQ ID NO: 1    164 TCGGCGCGCTGCCACTCGTGGGCCCAGCCCCGCACGCCGGCCTGGCCGCG  213
                    ||||||||||||||||||||||||||||||||||||||||||||||||||
SEQ ID NO: 11   351 TCGGCGCGCTGCCACTCGTGGGCCCAGCCCCGCACGCCGGCCTGGCCGCG  400

SEQ ID NO: 1    214 CTGGCGCGCAAGTACGGTCCCATCATGTACCTGAAGATGGGCACGGCCGG  263
                    ||||||||||||||||||||||||||||||||||||||||||||||||||
SEQ ID NO: 11   401 CTGGCGCGCAAGTACGGTCCCATCATGTACCTGAAGATGGGCACGGCCGG  450

SEQ ID NO: 1    264 CGTGGTGGTGGCGTCGTCCCCGCGCGCGGCGCGGACGTTCCTCAAGGCGC  313
                    ||||||||||||||||||||||||||||||||||||||||||||||||||
SEQ ID NO: 11   451 CGTGGTGGTGGCGTCGTCCCCGCGCGCGGCGCGGACGTTCCTCAAGGCGC  500

SEQ ID NO: 1    314 TGGACGCGCGGTACGCCAACCGGCCGGCCGTGGCGAGCGCCGCGGACATC  363
                    ||||||||||||||||||||||||||||||||||||||||||||||||||
SEQ ID NO: 11   501 TGGACGCGCGGTACGCCAACCGGCCGGCCGTGGCGAGCGCCGCGGACATC  550

SEQ ID NO: 1    364 ACGTACGGGCGGCAGAACATGGTGTTCGCGGACTACGGGCCCAAGTGGAA  413
                    ||||||||||||||||||||||||||||||||||||||||||||||||||
SEQ ID NO: 11   551 ACGTACGGGCGGCAGAACATGGTGTTCGCGGACTACGGGCCCAAGTGGAA  600

SEQ ID NO: 1    414 GCTGATGCGGAAGCTCGCCAGCGTGCACCTGCTCGGCGCGCGCGCGCTCG  463
                    ||||||||||||||||||||||||||||||||||||||||||||||||||
SEQ ID NO: 11   601 GCTGATGCGGAAGCTCGCCAGCGTGCACCTGCTCGGCGCGCGCGCGCTCG  650

SEQ ID NO: 1    464 CGGACTGGGCGTGCGTGCGGCGCGGCGAGGCCGGCCACGTGCTGCGCGGC  513
                    ||||||||||||||||||||||||||||||||||||||||||||||||||
SEQ ID NO: 11   651 CGGACTGGGCGTGCGTGCGGCGCGGCGAGGCCGGCCACGTGCTGCGCGGC  700

SEQ ID NO: 1    514 GTGGCGGAGGCGGCCGCGGCCGGCAGGCCCGTCGTCGTGCCGGAGCTGCT  563
                    ||||||||||||||||||||||||||||||||||||||||||||||||||
SEQ ID NO: 11   701 GTGGCGGAGGCGGCCGCGGCCGGCAGGCCCGTCGTCGTGCCGGAGCTGCT  750

SEQ ID NO: 1    564 CGTGTGCGCCCTCGCCAACATCGTCGGGCAGATCACAGTGAGCAAGCGGG  613
                    ||||||||||||||||||||||||||||||||||||||||||||||||||
SEQ ID NO: 11   751 CGTGTGCGCCCTCGCCAACATCGTCGGGCAGATCACAGTGAGCAAGCGGG  800

SEQ ID NO: 1    614 TGTTCGACGCGCAGGGGGACGACTCGAACAGGTGAGGATGGGAGGTCCAT  663
                    ||||||||||||||||||||||||||||||||||||||||||||||||||
SEQ ID NO: 11   801 TGTTCGACGCGCAGGGGGACGACTCGAACAGGTGAGGATGGGAGGTCCAT  850
```

Fig. 4 (continued):

```
SEQ ID NO: 1      664  GAAATCCTACCAGCTGTGAGCATGCATAAAAGTTCATTTGGAAAGAAAAG   713
                       ||||||||||||||||||||||||||||||||||||||||||||||||||
SEQ ID NO: 11     851  GAAATCCTACCAGCTGTGAGCATGCATAAAAGTTCATTTGGAAAGAAAAG   900

SEQ ID NO: 1      714  AACATATTTTTCTTACAAATTTATGCTTACTGTTTCTTTAAGTTTCGATA   763
                       ||||||||||||||||||||||||||||||||||||||||||||||||||
SEQ ID NO: 11     901  AACATATTTTTCTTACAAATTTATGCTTACTGTTTCTTTAAGTTTCGATA   950

SEQ ID NO: 1      764  AAGTTTGTAAAAAAAATTTAGGCTAGTTTGAAACTCCATTTAGGATTTCT   813
                       ||||||||||||||||||||||||||||||||||||||||||||||||||
SEQ ID NO: 11     951  AAGTTTGTAAAAAAAATTTAGGCTAGTTTGAAACTCCATTTAGGATTTCT  1000

SEQ ID NO: 1      814  ATTTTCCAAAGAAAAATAAACGAATTTCTCTTGAAAAAATGAAAATTCTT   863
                       ||||||||||||||||||||||||||||||||||||||||||||||||||
SEQ ID NO: 11    1001  ATTTTCCAAAGAAAAATAAACGAATTTCTCTTGAAAAAATGAAAATTCTT  1050

SEQ ID NO: 1      864  TAGAAAAATAGGTTCTCAAACTAGCCCTCAATAAAACTTAATGCGATCGT   913
                       ||||||||||||||||||||||||||||||||||||||||||||||||||
SEQ ID NO: 11    1051  TAGAAAAATAGGTTCTCAAACTAGCCCTCAATAAAACTTAATGCGATCGT  1100

SEQ ID NO: 1      914  TTTCTCTGACTCTCATTCATCTTTCTCTGGTTATCTAATTGGGTCCTTGA   963
                       ||||||||||||||||||||||||||||||||||||||||||||||||||
SEQ ID NO: 11    1101  TTTCTCTGACTCTCATTCATCTTTCTCTGGTTATCTAATTGGGTCCTTGA  1150

SEQ ID NO: 1      964  GAGATGAGTTTACCTGCTTGTCCTTTATTATTGCAAAGACAACATATCTG  1013
                       ||||||||||||||||||||||||||||||||||||||||||||||||||
SEQ ID NO: 11    1151  GAGATGAGTTTACCTGCTTGTCCTTTATTATTGCAAAGACAACATATCTG  1200

SEQ ID NO: 1     1014  ATGCACATGGAACATTGGTGCACATGGTGCACATATGAAATCATCACCAC  1063
                       ||||||||||||||||||||||||||||||||||||||||||||||||||
SEQ ID NO: 11    1201  ATGCACATGGAACATTGGTGCACATGGTGCACATATGAAATCATCACCAC  1250

SEQ ID NO: 1     1064  TCATTTTAAATCTAACGTCTATAGTTGTTTGATATATTTTATTAAGGACA  1113
                       ||||||||||||||||||||||||||||||||||||||||||||||||||
SEQ ID NO: 11    1251  TCATTTTAAATCTAACGTCTATAGTTGTTTGATATATTTTATTAAGGACA  1300

SEQ ID NO: 1     1114  CCCTCCAACGTGGTGGTGTGTAGTGGTGGAAGGTGTTATTTGTAAATTGA  1163
                       ||||||||||||||||||||||||||||||||||||||||||||||||||
SEQ ID NO: 11    1301  CCCTCCAACGTGGTGGTGTGTAGTGGTGGAAGGTGTTATTTGTAAATTGA  1350

SEQ ID NO: 1     1164  ATAATCAACTAGAGACGTTAGATCTAAAATGAGTGGTGATGATTTAATAT  1213
                       ||||||||||||||||||||||||||||||||||||||||||||||||||
SEQ ID NO: 11    1351  ATAATCAACTAGAGACGTTAGATCTAAAATGAGTGGTGATGATTTAATAT  1400

SEQ ID NO: 1     1214  GTGCACCATGTGCACCAGTCTTCTATGTGCACCAGATATGTCCTCTATTG  1263
                       ||||||||||||||||||||||||||||||||||||||||||||||||||
SEQ ID NO: 11    1401  GTGCACCATGTGCACCAGTCTTCTATGTGCACCAGATATGTCCTCTATTG  1450

SEQ ID NO: 1     1264  CAAATGCTAGACGGAACACCAGCTAGCACTAGCAGACTGTTTATGTGGAA  1313
                       ||||||||||||||||||||||||||||||||||||||||||||||||||
SEQ ID NO: 11    1451  CAAATGCTAGACGGAACACCAGCTAGCACTAGCAGACTGTTTATGTGGAA  1500

SEQ ID NO: 1     1314  AGAAAAAACTTAAAAAGATCAGCTAGGAAGCTGCTGTCATCTGTACGTAT  1363
                       ||||||||||||||||||||||||||||||||||||||||||||||||||
SEQ ID NO: 11    1501  AGAAAAAACTTAAAAAGATCAGCTAGGAAGCTGCTGTCATCTGTACGTAT  1550

SEQ ID NO: 1     1364  ATATGGTGAAGACTGAACAATCTGCATGACAAGCAAAACTTAGCTTAAAA  1413
                       ||||||||||||||||||||||||||||||||||||||||||||||||||
SEQ ID NO: 11    1551  ATATGGTGAAGACTGAACAATCTGCATGACAAGCAAAACTTAGCTTAAAA  1600

SEQ ID NO: 1     1414  GCGAAAAGAGCGATGGAAACGGCCGCTCGATAAATAATTAATGAGAGTCT  1463
                       ||||||||||||||||||||||||||||||||||||||||||||||||||
SEQ ID NO: 11    1601  GCGAAAAGAGCGATGGAAACGGCCGCTCGATAAATAATTAATGAGAGTCT  1650

SEQ ID NO: 1     1464  TGGGATTTTTCATGCATGGAAAAAAACAAAGCTGGCATTTTTCATCTAAT  1513
                       ||||||||||||||||||||||||||||||||||||||||||||||||||
SEQ ID NO: 11    1651  TGGGATTTTTCATGCATGGAAAAAAACAAAGCTGGCATTTTTCATCTAAT  1700
```

Fig. 4 (continued):

```
SEQ ID NO: 1    1514 ATAATATATAACGCTGATATCATATTGCGTGCAGATACAAGGACATGATC   1563
                     ||||||||||||||||||||||||||||||||||||||||||||||||||
SEQ ID NO: 11   1701 ATAATATATAACGCTGATATCATATTGCGTGCAGATACAAGGACATGATC   1750

SEQ ID NO: 1    1564 GTGTCGCTGCTGACCGGCACGGGCATGTTCAACATCAGCGACTTCGTGCC   1613
                     ||||||||||||||||||||||||||||||||||||||||||||||||||
SEQ ID NO: 11   1751 GTGTCGCTGCTGACCGGCACGGGCATGTTCAACATCAGCGACTTCGTGCC   1800

SEQ ID NO: 1    1614 GGCGCTGGCGCGTCTGGACCTGCAGGGCGTGCAGGCGAAGCTGCGGCGCG   1663
                     ||||||||||||||||||||||||||||||||||||||||||||||||||
SEQ ID NO: 11   1801 GGCGCTGGCGCGTCTGGACCTGCAGGGCGTGCAGGCGAAGCTGCGGCGCG   1850

SEQ ID NO: 1    1664 TCCACCGCCAGTTCGACGGCCTCATCACCAAGCTGCTGGCCGAGCACGCC   1713
                     ||||||||||||||||||||||||||||||||||||||||||||||||||
SEQ ID NO: 11   1851 TCCACCGCCAGTTCGACGGCCTCATCACCAAGCTGCTGGCCGAGCACGCC   1900

SEQ ID NO: 1    1714 GCGACGGCCGCGGACCGCGCGCGCCAGGGCCGCCCGGACTTCGTCGACCG   1763
                     ||||||||||||||||||||||||||||||||||||||||||||||||||
SEQ ID NO: 11   1901 GCGACGGCCGCGGACCGCGCGCGCCAGGGCCGCCCGGACTTCGTCGACCG   1950

SEQ ID NO: 1    1764 GCTCCGCGCCACGATGGACGCCGGCGCCGCCGCCGACGACGAGAGCGGCG   1813
                     ||||||||||||||||||||||||||||||||||||||||||||||||||
SEQ ID NO: 11   1951 GCTCCGCGCCACGATGGACGCCGGCGCCGCCGCCGACGACGAGAGCGGCG   2000

SEQ ID NO: 1    1814 AGACCATCACCGAGGTCAACATCAAGGGCCTCATCTTCGTAAGCTCCCTG   1863
                     ||||||||||||||||||||||||||||||||||||||||||||||||||
SEQ ID NO: 11   2001 AGACCATCACCGAGGTCAACATCAAGGGCCTCATCTTCGTAAGCTCCCTG   2050

SEQ ID NO: 1    1864 CTTTTTCCTCGCCCCCAACCATGCATCATCATATGCACTTATATTTTACA   1913
                     ||||||||||||||||||||||||||||||||||||||||||||||||||
SEQ ID NO: 11   2051 CTTTTTCCTCGCCCCCAACCATGCATCATCATATGCACTTATATTTTACA   2100

SEQ ID NO: 1    1914 CTTGCTCGGTTTTCCTTTAGTAACTAACTAATCCGTCGCAGCTGCGATAC   1963
                     ||||||||||||||||||||||||||||||||||||||||||||||||||
SEQ ID NO: 11   2101 CTTGCTCGGTTTTCCTTTAGTAACTAACTAATCCGTCGCAGCTGCGATAC   2150

SEQ ID NO: 1    1964 ACGTAGCACTAGTACTACAGCGATGGGTCATCGGTAACTGAATCTAAGGT   2013
                     ||||||||||||||||||||||||||||||||||||||||||||||||||
SEQ ID NO: 11   2151 ACGTAGCACTAGTACTACAGCGATGGGTCATCGGTAACTGAATCTAAGGT   2200

SEQ ID NO: 1    2014 GCAATAGAGTGCACGGCCGCGGGATCATGGCGTGACATGGGAGCTAAGCT   2063
                     ||||||||||||||||||||||||||||||||||||||||||||||||||
SEQ ID NO: 11   2201 GCAATAGAGTGCACGGCCGCGGGATCATGGCGTGACATGGGAGCTAAGCT   2250

SEQ ID NO: 1    2064 AAGCCAGTGGCCACCTAACGAAGGCACTGACCGAAAGCTCAGTGGCGTGT   2113
                     ||||||||||||||||||||||||||||||||||||||||||||||||||
SEQ ID NO: 11   2251 AAGCCAGTGGCCACCTAACGAAGGCACTGACCGAAAGCTCAGTGGCGTGT   2300

SEQ ID NO: 1    2114 TAGGTGGAGATAGTGGATCGAGTTGTTGGAAAGACAATATCAAAACCACT   2163
                     ||||||||||||||||||||||||||||||||||||||||||||||||||
SEQ ID NO: 11   2301 TAGGTGGAGATAGTGGATCGAGTTGTTGGAAAGACAATATCAAAACCACT   2350

SEQ ID NO: 1    2164 CTCCAATTGATGATGTGTAGGGCCTGCAGTGTTTTGAATCCACCTTGTTT   2213
                     ||||||||||||||||||||||||||||||||||||||||||||||||||
SEQ ID NO: 11   2351 CTCCAATTGATGATGTGTAGGGCCTGCAGTGTTTTGAATCCACCTTGTTT   2400

SEQ ID NO: 1    2214 GGTCGAACACATTACTAGAGTGAAATATGGTTCCAATGTTAATTGATAGC   2263
                     ||||||||||||||||||||||||||||||||||||||||||||||||||
SEQ ID NO: 11   2401 GGTCGAACACATTACTAGAGTGAAATATGGTTCCAATGTTAATTGATAGC   2450

SEQ ID NO: 1    2264 GCGAAAGGGTCTCTAGCGTAATGGTTAAACCTTCCGAGTAGCACATCCAG   2313
                     ||||||||||||||||||||||||||||||||||||||||||||||||||
SEQ ID NO: 11   2451 GCGAAAGGGTCTCTAGCGTAATGGTTAAACCTTCCGAGTAGCACATCCAG   2500

SEQ ID NO: 1    2314 GTTGGGTTCGATCCTCTCGAGGGCGAATTTTCAAGCTTTGTTAAAAAAAT   2363
                     ||||||||||||||||||||||||||||||||||||||||||||||||||
SEQ ID NO: 11   2501 GTTGGGTTCGATCCTCTCGAGGGCGAATTTTCAAGCTTTGTTAAAAAAAT   2550
```

Fig. 4 (continued):

```
SEQ ID NO: 1    2364 TATCTCGTTGTGCCCCGTCCGCTCTCAGGAATCGATATTCTACACGACAC   2413
                     ||||||||||||||||||||||||||||||||||||||||||||||||||
SEQ ID NO: 11   2551 TATCTCGTTGTGCCCCGTCCGCTCTCAGGAATCGATATTCTACACGACAC   2600

SEQ ID NO: 1    2414 CCTCCGACTAGTGACAGTTGATTGACTCGTTAGTGATGAGAAGCCATGCT   2463
                     ||||||||||||||||||||||||||||||||||||||||||||||||||
SEQ ID NO: 11   2601 CCTCCGACTAGTGACAGTTGATTGACTCGTTAGTGATGAGAAGCCATGCT   2650

SEQ ID NO: 1    2464 AAAAAAGTGGAGACGTAGATATGATAGAGGTTCCCTTTCCTAAGCAAACG   2513
                     ||||||||||||||||||||||||||||||||||||||||||||||||||
SEQ ID NO: 11   2651 AAAAAAGTGGAGACGTAGATATGATAGAGGTTCCCTTTCCTAAGCAAACG   2700

SEQ ID NO: 1    2514 TGAATGCTATGAAAATTATGCAGTTTAAAAAAAACTTTAAAGATAAACAG   2563
                     ||||||||||||||||||||||||||||||||||||||||||||||||||
SEQ ID NO: 11   2701 TGAATGCTATGAAAATTATGCAGTTTAAAAAAAACTTTAAAGATAAACAG   2750

SEQ ID NO: 1    2564 GAATTCTCTTTTTTGGAACAAACAATACGAATGCACCTCCAAATATCTTA   2613
                     ||||||||||||||||||||||||||||||||||||||||||||||||||
SEQ ID NO: 11   2751 GAATTCTCTTTTTTGGAACAAACAATACGAATGCACCTCCAAATATCTTA   2800

SEQ ID NO: 1    2614 TCGAGTCGACTTTTATGGAATTATTGTTTTTGTTATTTCTAAGATGGGAG   2663
                     ||||||||||||||||||||||||||||||||||||||||||||||||||
SEQ ID NO: 11   2801 TCGAGTCGACTTTTATGGAATTATTGTTTTTGTTATTTCTAAGATGGGAG   2850

SEQ ID NO: 1    2664 CCCAAAATCACATACAAATTATTCAGTGAATGCCTCGGTGTTTTTTTATT   2713
                     ||||||||||||||||||||||||||||||||||||||||||||||||||
SEQ ID NO: 11   2851 CCCAAAATCACATACAAATTATTCAGTGAATGCCTCGGTGTTTTTTTATT   2900

SEQ ID NO: 1    2714 AGTTAAGGGCTCTCATTTTTTTCAAGGGATTTTTATTTTTTTCCAAAAGA   2763
                     ||||||||||||||||||||||||||||||||||||||||||||||||||
SEQ ID NO: 11   2901 AGTTAAGGGCTCTCATTTTTTTCAAGGGATTTTTATTTTTTTCCAAAAGA   2950

SEQ ID NO: 1    2764 AAATAAACTAATCCTCTTTAGAAAAATGGAAATCTATTGGAGAAATGAGG   2813
                     ||||||||||||||||||||||||||||||||||||||||||||||||||
SEQ ID NO: 11   2951 AAATAAACTAATCCTCTTTAGAAAAATGGAAATCTATTGGAGAAATGAGG   3000

SEQ ID NO: 1    2814 TTCCTAAACTAGCTCTAACAGTGAGTCAGTTAATCAGGAGAAGATATTAG   2863
                     ||||||||||||||||||||||||||||||||||||||||||||||||||
SEQ ID NO: 11   3001 TTCCTAAACTAGCTCTAACAGTGAGTCAGTTAATCAGGAGAAGATATTAG   3050

SEQ ID NO: 1    2864 ACTCCTGTATAGTGTGCAGCAACCACATCCGATTCTGACGTTTTAGCTTA   2913
                     ||||||||||||||||||||||||||||||||||||||||||||||||||
SEQ ID NO: 11   3051 ACTCCTGTATAGTGTGCAGCAACCACATCCGATTCTGACGTTTTAGCTTA   3100

SEQ ID NO: 1    2914 ATGTTCGCTATGTAGACGTCGGGCATAGGGAATGCATTGCTACCAGAACA   2963
                     ||||||||||||||||||||||||||||||||||||||||||||||||||
SEQ ID NO: 11   3101 ATGTTCGCTATGTAGACGTCGGGCATAGGGAATGCATTGCTACCAGAACA   3150

SEQ ID NO: 1    2964 CGAATGACAGCTATGCAAGTCTCTAGAACGTTGGAGTAGTTAACAAACGT   3013
                     ||||||||||||||||||||||||||||||||||||||||||||||||||
SEQ ID NO: 11   3151 CGAATGACAGCTATGCAAGTCTCTAGAACGTTGGAGTAGTTAACAAACGT   3200

SEQ ID NO: 1    3014 GATAGATGTAACCTCTGGATCATGGTATGATGTCATTTCCTAGACTAGAA   3063
                     ||||||||||||||||||||||||||||||||||||||||||||||||||
SEQ ID NO: 11   3201 GATAGATGTAACCTCTGGATCATGGTATGATGTCATTTCCTAGACTAGAA   3250

SEQ ID NO: 1    3064 GAATTGGTAGTCAAATCGAGCAAAGTCCCGAAAGCACACTGGGCTTTCGA   3113
                     ||||||||||||||||||||||||||||||||||||||||||||||||||
SEQ ID NO: 11   3251 GAATTGGTAGTCAAATCGAGCAAAGTCCCGAAAGCACACTGGGCTTTCGA   3300

SEQ ID NO: 1    3114 CACAGTGATACCAAAGATGCTGAAAAGAACTGAGGCACGATAAACTGTTC   3163
                     ||||||||||||||||||||||||||||||||||||||||||||||||||
SEQ ID NO: 11   3301 CACAGTGATACCAAAGATGCTGAAAAGAACTGAGGCACGATAAACTGTTC   3350

SEQ ID NO: 1    3164 GGTGTTGGTGTAAACGACCAAAGATGCTGAAAATAACTGATCGTCACCAT   3213
                     ||||||||||||||||||||||||||||||||||||||||||||||||||
SEQ ID NO: 11   3351 GGTGTTGGTGTAAACGACCAAAGATGCTGAAAATAACTGATCGTCACCAT   3400
```

Fig. 4 (continued):

```
SEQ ID NO: 1     3214 CCGTGAATCTAACTTTCGACACACTGTTACCAAATCCTTCGTCAAAATTA   3263
                      ||||||||||||||||||||||||||||||||||||||||||||||||||
SEQ ID NO: 11    3401 CCGTGAATCTAACTTTCGACACACTGTTACCAAATCCTTCGTCAAAATTA   3450

SEQ ID NO: 1     3264 CAGGAATAATTAAGGCGCTTAGACGATGATAAACCATTTTTTGTCACTAA   3313
                      ||||||||||||||||||||||||||||||||||||||||||||||||||
SEQ ID NO: 11    3451 CAGGAATAATTAAGGCGCTTAGACGATGATAAACCATTTTTTGTCACTAA   3500

SEQ ID NO: 1     3314 TTAACCACACTGTTCTTTGCTTGACCGTGACAAAAAAAAACTTTTTTGTG   3363
                      ||||||||||||||||||||||||||||||||||||||||||||||||||
SEQ ID NO: 11    3501 TTAACCACACTGTTCTTTGCTTGACCGTGACAAAAAAAAACTTTTTTGTG   3550

SEQ ID NO: 1     3364 AAGCAGTGTTGCCGTAAACCACAACCATCATGAACTCACTTGCCTTGTCA   3413
                      ||||||||||||||||||||||||||||||||||||||||||||||||||
SEQ ID NO: 11    3551 AAGCAGTGTTGCCGTAAACCACAACCATCATGAACTCACTTGCCTTGTCA   3600

SEQ ID NO: 1     3414 TATGTACTTGTACCATCGAACGCCGCGCGCTAAGACAATGCACCACCCTT   3463
                      ||||||||||||||||||||||||||||||||||||||||||||||||||
SEQ ID NO: 11    3601 TATGTACTTGTACCATCGAACGCCGCGCGCTAAGACAATGCACCACCCTT   3650

SEQ ID NO: 1     3464 CAAGTCTTAGCTCACTGATACCGCTAATTAAGTTAGATAATGTCGATTAC   3513
                      ||||||||||||||||||||||||||||||||||||||||||||||||||
SEQ ID NO: 11    3651 CAAGTCTTAGCTCACTGATACCGCTAATTAAGTTAGATAATGTCGATTAC   3700

SEQ ID NO: 1     3514 TAGTTGTCTTACTTCGAACTATTTCTTTTCGGCAAACTGAAGTAAAGACA   3563
                      ||||||||||||||||||||||||||||||||||||||||||||||||||
SEQ ID NO: 11    3701 TAGTTGTCTTACTTCGAACTATTTCTTTTCGGCAAACTGAAGTAAAGACA   3750

SEQ ID NO: 1     3564 ACGTTTTGTTCCGCAGGACATGTTCACGGCGGGTACGGACACGTCGTCGA   3613
                      ||||||||||||||||||||||||||||||||||||||||||||||||||
SEQ ID NO: 11    3751 ACGTTTTGTTCCGCAGGACATGTTCACGGCGGGTACGGACACGTCGTCGA   3800

SEQ ID NO: 1     3614 TCATCGTGGAGTGGGCGATGGCGGAGATGCTCAAGAACCCGACCGTCATG   3663
                      ||||||||||||||||||||||||||||||||||||||||||||||||||
SEQ ID NO: 11    3801 TCATCGTGGAGTGGGCGATGGCGGAGATGCTCAAGAACCCGACCGTCATG   3850

SEQ ID NO: 1     3664 GCGCGCGCGCAGGAGGAGCTGGACCGCGCGGTGGGCCGGGGCCGGCGCCT   3713
                      ||||||||||||||||||||||||||||||||||||||||||||||||||
SEQ ID NO: 11    3851 GCGCGCGCGCAGGAGGAGCTGGACCGCGCGGTGGGCCGGGGCCGGCGCCT   3900

SEQ ID NO: 1     3714 GGAGGAGTCGGACCTGCCCGGCCTCCCCTACCTGCAGGCGGTGTGCAAGG   3763
                      ||||||||||||||||||||||||||||||||||||||||||||||||||
SEQ ID NO: 11    3901 GGAGGAGTCGGACCTGCCCGGCCTCCCCTACCTGCAGGCGGTGTGCAAGG   3950

SEQ ID NO: 1     3764 AGGCCATGCGGCTGCACCCGTCCACGCCGCTCAGCCTCCCGCACTTCTCC   3813
                      ||||||||||||||||||||||||||||||||||||||||||||||||||
SEQ ID NO: 11    3951 AGGCCATGCGGCTGCACCCGTCCACGCCGCTCAGCCTCCCGCACTTCTCC   4000

SEQ ID NO: 1     3814 TTGGACGCCTGCGACGACGTCGACGGCTACCGCGTCCCGGCCAACACCCG   3863
                      ||||||||||||||||||||||||||||||||||||||||||||||||||
SEQ ID NO: 11    4001 TTGGACGCCTGCGACGACGTCGACGGCTACCGCGTCCCGGCCAACACCCG   4050

SEQ ID NO: 1     3864 CCTGCTCGTCAACGTCTGGGCCATCGGCCGGGACCCGGAGGCCTGGGAGA   3913
                      ||||||||||||||||||||||||||||||||||||||||||||||||||
SEQ ID NO: 11    4051 CCTGCTCGTCAACGTCTGGGCCATCGGCCGGGACCCGGAGGCCTGGGAGA   4100

SEQ ID NO: 1     3914 GGCCCCTCGACTTCCGCCCCGAGCGCTTCCTGCCCGGGGGCGGCGCGGAG   3963
                      ||||||||||||||||||||||||||||||||||||||||||||||||||
SEQ ID NO: 11    4101 GGCCCCTCGACTTCCGCCCCGAGCGCTTCCTGCCCGGGGGCGGCGCGGAG   4150

SEQ ID NO: 1     3964 AAGGTCGACCCCCTGGGGAACTGCTTCGAGCTCATCCCGTTCGGCGCCGG   4013
                      ||||||||||||||||||||||||||||||||||||||||||||||||||
SEQ ID NO: 11    4151 AAGGTCGACCCCCTGGGGAACTGCTTCGAGCTCATCCCGTTCGGCGCCGG   4200

SEQ ID NO: 1     4014 CCGGAGGATCTGCGCGGGGAAGCTGGCGGGCATGGTGTTCGTGCAGTACT   4063
                      ||||||||||||||||||||||||||||||||||||||||||||||||||
SEQ ID NO: 11    4201 CCGGAGGATCTGCGCGGGGAAGCTGGCGGGCATGGTGTTCGTGCAGTACT   4250
```

Fig. 4 (continued):

```
SEQ ID NO: 1    4064 TCCTGGGCACGCTGCTGCACGCGTTCGACTGGCGCCTGCCTGACGGCGAG   4113
                     ||||||||||||||||||||||||||||||||||||||||||||||||||
SEQ ID NO: 11   4251 TCCTGGGCACGCTGCTGCACGCGTTCGACTGGCGCCTGCCTGACGGCGAG   4300

SEQ ID NO: 1    4114 GAGAAGCTGGACATGAGCGAGACGTTCGGCCTCGCGCTGCCCAAGGCAGT   4163
                     ||||||||||||||||||||||||||||||||||||||||||||||||||
SEQ ID NO: 11   4301 GAGAAGCTGGACATGAGCGAGACGTTCGGCCTCGCGCTGCCCAAGGCAGT   4350

SEQ ID NO: 1    4164 GCCGCTCCGCGCCGTCGCCACGCCACGGCTCGTGCCGGAAGCCTATGCCT   4213
                     ||||||||||||||||||||||||||||||||||||||||||||||||||
SEQ ID NO: 11   4351 GCCGCTCCGCGCCGTCGCCACGCCACGGCTCGTGCCGGAAGCCTATGCCT   4400

SEQ ID NO: 1    4214 GA   4215
                     ||
SEQ ID NO: 11   4401 GA   4402
```

PLANTS WITH IMPROVED DIGESTIBILITY AND MARKER HAPLOTYPES

CROSS-REFERENCE TO RELATED APPLICATIONS

This application is a U.S. National Phase of International Patent Application No. PCT/EP2019/060411, filed on Apr. 24, 2019, which claims priority to EP application Ser. No. 18/169,122.1, filed Apr. 24, 2018. The entire contents of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created in Apr. 24, 2019, is named SL KWS0277PCT ST25 and is 156,509 bytes in size.

FIELD OF THE INVENTION

The invention relates to quantitative trait loci (QTL) and associated markers involved in and/or associated with improved digestibility of plants and plant parts, such as maize. The invention further relates to uses of such QTL or markers for identification and/or selection purposes, as well as transgenic or non-transgenic plants.

BACKGROUND OF THE INVENTION

Maize (*Zea mays* L.) is the most important annual forage crop in the world. More than 3 million hectares of maize are ensiled each year, mainly in Northern Europe. Due to high energy content and feed conversion efficiency, the forage maize is an important food crop for dairy and beef cattle, and is affecting significantly the milk and meat production. There is a wide genetic variation in forage characteristics for both the entire maize plant and stover (Geiger et al. 1992; Barrière et al. 2003).

Therefore, improving digestibility is a major goal for forage maize breeding programs. The energy supplied by forage to a ruminant or herbivore animal diet is related to forage ingestibility and digestibility. The digestibility of any forage constituent (dry matter, organic matter, or cell wall) is measured as percentage of silage absorbed in the animal digestive tract (Barrière et al. 2003). The overall digestibility of forage maize is affected by the highly digestible grain and stover fraction. Stover composition and digestibility limits forage maize quality. Major stover fractions are hemicelluloses, cellulose, and lignins. Modern forage maize cultivars combine high dry matter yield with high stover digestibility.

It is too costly to perform digestibility measurements with animals, especially when conducting large scale evaluation of germplasm in plant breeding programs. Biological and chemical methods have been developed to assay the digestibility of maize and other forage crops (Van Soest et al. 1963). Neutral detergent fiber (NDF), the residual after removing cell soluble content, is an important plant cell wall and cellulose indicator. In vitro NDF digestibility (IVNDFD) of forages is an estimate of cell wall digestibility assuming that the non-NDF part of plant material was completely digestible (Méchin et al. 2000). Additionally, the use of NIRS has been reported to measure digestibility traits accurately in many forage crops including maize (Lübberstedt et al. 1997a, b; Zimmer et al. 1990).

Lübberstedt et al. (1997a, b) first published QTL related to forage maize agronomic and quality traits, and QTL for whole plant digestibility. Exploiting available genetic variation for stover digestibility by marker-assisted selection (MAS) seems to be a promising way to improve forage digestibility. Besides genetic variance, environmental variation might be the reason for those inconsistent traits. QTL analyses of forage traits in four different maize populations revealed only few QTL showing epistatic interactions or interactions with the environment (Lübberstedt et al. 1998). Seven QTL for DNDF were detected by using 242 RILs derived from the cross F838×F286 which were evaluated in per se value experiments in six environments, and found two major QTL (Barrière et al. 2010). Additional QTL analyses were conducted by using RIL progeny derived from a cross between an old dent and modern Iodent lines, and new QTL in bins 2.06 and 5.04 for ADL/NDF and DNDF were first reported (Barrière et al. 2012).

It is therefore an objective of the present invention to address one or more of the shortcomings of the prior art. There is a persistent need for improving digestibility of fodder crops, as well as the identification of plants, including particular plant parts or derivatives having increased digestibility. In particular, it is an aim of the present invention to provide new major QTL for digestibility and the causative gene(s) and the provision of markers which allow the economical use of these QTL in maize development and breeding.

SUMMARY OF THE INVENTION

The present invention is based on the identification of a major QTL for plant digestibility as well as the identification of a F35H gene linked to and responsible for the QTL for plant digestibility and description of a unique marker haplotype for improved digestibility.

Molecular markers have been identified which are associated with plant digestibility, and marker alleles associated with improved digestibility are described. One of the described marker alleles is a mutated F35H gene.

The invention in particular relates to methods for detecting the identified QTL allele associated with improved digestibility, as well as detection of any of the described marker alleles. The invention further relates to the described marker alleles and polynucleic acids useful for detection of the marker alleles, such as primers and probes, and kits comprising such. The invention further relates to methods for improving plant digestibility, in particular by naturally or artificially introducing in plants and/or selecting plants comprising, the marker alleles described herein, such as in particular inducing F35H mutations, preferably mutations altering F35H expression or F35H enzymatic activity, e.g. reducing or eliminating F35H expression or F35H activity or otherwise reducing F35H expression or F35H activity, or increasing F35H activity. The invention further relates to plants having improved digestibility, as well as plant parts, in particular stover, having improved digestibility.

The present invention is in particular captured by any one or any combination of one or more of the below numbered items [01] to [25], with any other item and/or embodiments.

[01] A method for identifying a plant or plant part having improved digestibility or for selecting a plant or plant part having improved digestibility comprising (i) optionally, isolating genetic material, preferably genetic material, from at least one cell of the plant or plant part;

(ii) a) screening for the presence of a QTL allele, such as a QTL allele associated with improved digestibility, said QTL allele comprising a nucleotide sequence of a gene encoding a cytochrome P450 flavonoid 3',5'-hydroxylase (F35H), having a mutation, preferably a mutation leading to altered expression of the mRNA of the gene and/or the F35H protein, or a mutation leading to an F35H protein having altered enzymatic activity upon translation, more preferably a mutation leading to reduced or absent expression of the mRNA of the gene and/or the F35H protein (such as a knock-down or knock-out mutation), or a mutation leading to a non-functional F35H protein (e.g., truncated F35H protein) or an F35H protein having reduced enzymatic activity upon translation, or an F35H protein having increased enzymatic activity upon translation, or (ii) b) screening for altered expression of the mRNA of a gene encoding a cytochrome P450 flavonoid 3',5'-hydroxylase (F35H) and/or the F35H protein or for an F35H protein having altered enzymatic activity, preferably for reduced or absent expression of the mRNA of a gene encoding a cytochrome P450 flavonoid 3',5'-hydroxylase (F35H) and/or the F35H protein or for a non-functional F35H protein (e.g., truncated F35H protein) or an F35H protein having reduced enzymatic activity, or for an F35H protein having increased enzymatic activity or (ii) c) screening for the presence of a mutation leading to altered expression of the mRNA of a gene encoding a cytochrome P450 flavonoid 3',5'-hydroxylase (F35H) and/or the F35H protein, or a mutation, preferably a mutation leading to an F35H protein having altered enzymatic activity upon translation, preferably leading to reduced or absent expression of the mRNA of a gene encoding a cytochrome P450 flavonoid 3',5'-hydroxylase (F35H) and/or the F35H protein (such as a knock-down or knock-out mutation), or a mutation, preferably a mutation leading to a non-functional F35H protein (e.g., truncated F35H protein) or an F35H protein having reduced enzymatic activity upon translation or an F35H protein having increased enzymatic activity upon translation;

(iii) optionally selecting the plant or plant part in which the QTL or the mutation is present or in which the F35H mRNA and/or protein expression is altered or the enzymatic F35H activity is altered, preferably the F35H mRNA and/or protein expression is reduced or eliminated or the enzymatic F35H activity is reduced or increased.

[02] The method according to item [01], preferably wherein said plant is a maize plant, the method comprising screening for the presence of the molecular marker allele of ma61134xxx and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

[03] A plant or plant part comprising a QTL allele, such as a QTL allele associated with improved digestibility, said QTL allele comprising a nucleotide sequence of a gene encoding a cytochrome P450 flavonoid 3',5'-hydroxylase (F35H), having a mutation preferably a mutation leading to altered expression of the mRNA of the gene and/or the F35H protein, or a mutation leading to an F35H protein having altered enzymatic activity upon translation, more preferably a mutation leading to reduced or absent expression of the mRNA of the gene and/or the F35H protein, or a mutation leading to a non-functional F35H protein (e.g., truncated F35H protein) or an F35H protein having reduced enzymatic activity upon translation, or an F35H protein having increased enzymatic activity upon translation; or a plant or plant part comprising a nucleotide sequence of a gene encoding a cytochrome P450 flavonoid 3',5'-hydroxylase (F35H), having a mutation, preferably a mutation leading to altered expression of the mRNA of the gene and/or the F35H protein, or a mutation leading to an F35H protein having altered enzymatic activity upon translation, more preferably a mutation leading to reduced or absent expression of the mRNA of the gene and/or the F35H protein, or a mutation leading to a non-functional F35H protein (e.g., truncated F35H protein) or an F35H protein having reduced enzymatic activity upon translation, or an F35H protein having increased enzymatic activity upon translation; or a plant or plant part comprising a nucleotide sequence of a gene encoding a cytochrome P450 flavonoid 3',5'-hydroxylase (F35H) having reduced or absent expression of the mRNA of the gene and/or the F35H protein or having reduced enzymatic activity, preferably having reduced enzymatic activity or having increased enzymatic activity; or a plant or plant part comprising an RNAi molecule, such as dsRNA, siRNA, shRNA, or miRNA, directed against, targeting, or hybridizing with a nucleotide sequence encoding an F35H protein, or comprising a polynucleotide sequence encoding (and expressing or being capable of expressing) an RNAi molecule directed against, targeting, or hybridizing with a nucleotide sequence encoding an F35H protein; or a plant or plant part comprising an RNA-specific CRISPR/Cas system, such as a CRISPR/Cas13a system, directed against or targeting a nucleotide sequence encoding a cytochrome P450 flavonoid 3',5'-hydroxylase (F35H) or one or more polynucleotide sequence(s) encoding (and expressing or being capable of expressing) said RNA-specific CRISPR/Cas system.

[04] The plant or plant part according to item [03], preferably wherein said plant is a maize plant, comprising the marker allele of ma61134xxx.

[05] The plant or plant part according to item [03] or [04], wherein said plant comprising said QTL allele, said marker allele, and/or said nucleotide sequence of the gene encoding the cytochrome P450 flavonoid 3',5'-hydroxylase (F35H) having the mutation as introgression.

[06] The plant or plant part according to item [03] or [04], wherein said plant comprising said QTL allele, said marker allele, said nucleotide sequence of the gene encoding the cytochrome P450 flavonoid 3',5'-hydroxylase (F35H) having the mutation, said RNAi molecule or said polynucleotide sequence encoding (and expressing or being capable of expressing) the RNAi molecule, said RNA-specific CRISPR/Cas system and/or said one or more polynucleotide sequence(s) encoding (and expressing or being capable of expressing) the RNA-specific CRISPR/Cas system as transgene or as (gene-) edited endogene.

[07] A method for improving digestibility of a plant or plant part, comprising introducing or introgressing into the genome of a plant or plant part (a) a nucleotide sequence of a gene encoding a cytochrome P450 flavonoid 3',5'-hydroxylase (F35H), having a mutation, preferably a mutation leading to altered expression of the mRNA of the gene and/or the F35H protein, or a mutation leading to an F35H protein having altered enzymatic activity upon translation, more preferably a mutation leading to reduced or absent expression of the mRNA of the gene and/or the F35H protein (such as a knock-down or knock-out mutation), or a mutation leading to a non-functional F35H protein (e.g., truncated F35H protein) or an F35H protein having reduced enzymatic activity upon translation, or an F35H protein having increased enzymatic activity upon translation, or (b) a QTL allele, such as a QTL allele associated with improved digestibility, and comprising a nucleotide sequence of a gene encoding a cytochrome P450 flavonoid 3',5'-hydroxylase (F35H), having a mutation, preferably a mutation leading to altered expression of the mRNA of the gene and/or the F35H protein, or a mutation leading to an F35H protein having altered enzymatic activity upon translation, more preferably a mutation leading to reduced or absent expression of the mRNA of the gene and/or the F35H protein (such as a knock-down or knock-out mutation), or a mutation leading to a non-functional F35H protein (e.g., truncated F35H protein) or an F35H protein having reduced enzymatic activity upon translation, or an F35H protein having increased enzymatic activity upon translation.

[08] A method for improving digestibility of a plant or plant part, comprising altering the expression of the mRNA of a gene encoding a cytochrome P450 flavonoid 3',5'-hydroxylase (F35H) and/or the F35H protein, altering the enzymatic activity of a cytochrome P450 flavonoid 3',5'-hydroxylase (F35H), preferably reducing, eliminating or inhibiting expression of the mRNA of a gene encoding a cytochrome P450 flavonoid 3',5'-hydroxylase (F35H) and/or the F35H protein, reducing the enzymatic activity of a cytochrome P450 flavonoid 3',5'-hydroxylase (F35H), inhibiting the F35H protein, or increasing the enzymatic activity of a cytochrome P450 flavonoid 3',5'-hydroxylase (F35H).

[09] The method according to item [08], comprising (a) introducing into a nucleotide sequence of an endogenous gene encoding the cytochrome P450 flavonoid 3',5'-hydroxylase (F35H) (in the genome of the plant or the plant part) a mutation, preferably a mutation leading to altered expression of the mRNA of the gene and/or the F35H protein, or a mutation leading to an F35H protein having altered enzymatic activity upon translation, more preferably a mutation leading to reduced or absent expression of the mRNA of the gene and/or the F35H protein (such as a knock-down or knock-out mutation), or a mutation leading to a non-functional F35H protein (e.g., truncated F35H protein) or an F35H protein having reduced enzymatic activity upon translation, or an F35H protein having increased enzymatic activity upon translation, or (b) introducing into the plant or the plant part an RNAi molecule, such as dsRNA, siRNA, shRNA, or miRNA, directed against, targeting, or hybridizing with a nucleotide sequence encoding the F35H protein, or a polynucleotide sequence encoding (and expressing or being capable of expressing) an RNAi molecule directed against, targeting, or hybridizing with a nucleotide sequence encoding the F35H protein, or (c) introducing into the plant or the plant part an RNA-specific CRISPR/Cas system, such as a CRISPR/Cas13a system, directed against or targeting a nucleotide sequence encoding the F35H protein, or one or more polynucleotide sequence(s) encoding (and expressing or being capable of expressing) said RNA-specific CRISPR/Cas system, or (d) introducing into the plant or the plant part a chemical compound or an antibody altering (or being capable to alter) the enzymatic activity of the F35H protein upon interaction with said F35H, preferably reducing (or being capable to reduce) the enzymatic activity of the F35H protein or inhibiting (or being capable to inhibit) the enzymatic activity of the F35H protein or increasing (or being capable to increase) the enzymatic activity of the F35H protein upon interaction with said F35H.

[10] A method for producing a plant or plant part having improved digestibility, comprising (a) introducing or introgressing into the genome of a plant or plant part a nucleotide sequence of a gene encoding a cytochrome P450 flavonoid 3',5'-hydroxylase (F35H), having a mutation, preferably a mutation leading to altered expression of the mRNA of the gene and/or the F35H protein, or a mutation leading to an F35H protein having altered enzymatic activity upon translation, more preferably a mutation leading to reduced or absent expression of the mRNA of the gene and/or the F35H protein (such as a knock-down or knock-out mutation), or a mutation leading to a non-functional F35H protein (e.g., truncated F35H protein) or an F35H protein having reduced enzymatic activity upon translation, or an F35H protein having increased enzymatic activity upon translation, or (b) introducing or introgressing into the genome of a plant or plant part a QTL allele, such as a QTL allele associated with improved digestibility, and comprising a nucleotide sequence of a gene encoding a cytochrome P450 flavonoid 3',5'-hydroxylase (F35H), having a mutation, preferably a mutation leading to altered expression of the mRNA of the gene and/or the F35H protein, or a mutation leading to an F35H protein having altered enzymatic activity upon translation, more preferably a mutation leading to reduced or absent expression of the mRNA of the gene and/or the F35H protein (such as a knock-down or knock-out mutation), or a mutation leading to a non-functional F35H protein (e.g., truncated F35H protein) or an F35H protein having reduced enzymatic activity upon translation, or an F35H protein having increased enzymatic activity upon translation.

(c) introducing into a nucleotide sequence of an endogenous gene encoding the cytochrome P450 flavonoid 3',5'-hydroxylase (F35H) (in the genome of the plant or a plant part) a mutation, preferably a mutation leading to altered expression of the mRNA of the gene and/or the F35H protein, or a mutation leading to an F35H protein having altered enzymatic activity upon translation, more preferably a mutation leading to reduced or absent expression of the mRNA of the gene and/or the F35H protein (such as a knock-down or knock-out mutation), or a mutation leading to a non-functional F35H protein or an F35H protein having reduced enzymatic activity upon translation, or an F35H protein having increased enzymatic activity upon translation, or (d) introducing into the plant or the plant part an RNAi molecule, such as dsRNA, siRNA, shRNA, or miRNA, directed against, targeting, or hybridizing with a nucleotide sequence encoding the F35H protein, or a polynucleotide sequence encoding (and expressing or being capable of expressing) an RNAi molecule directed against, targeting, or hybridizing with a nucleotide sequence encoding the F35H protein, or (e) introducing into the plant or the plant part an RNA-specific CRISPR/Cas system, such as a CRISPR/Cas13a system, directed against or targeting a nucleotide sequence encoding the F35H protein, or one or more polynucleotide sequence(s) encoding (and expressing or being capable of expressing) said RNA-specific CRISPR/Cas system, or (f) introducing into the plant or the plant part a chemical compound or an antibody altering (or being capable to alter) the enzymatic activity of the F35H protein upon interaction with said F35H, preferably reducing (or being capable to reduce) the enzymatic activity of the F35H protein or inhibiting (or being capable to inhibit) the F35H protein or increasing (or being capable to increase) the enzymatic activity of the F35H protein upon interaction with said F35H; and (g) optionally, regenerating a plant from the plant part of any of (a) to (e).

[11] A plant or plant part produced by the method according to item [10].

[12] A progeny of the plant according to any one of item [03] to [06] or [11].

[13] The method, plant, or plant part according to any of the preceding items, wherein said plant is a maize plant, the QTL is located on chromosome 9 and comprises and/or is flanked by marker alleles ma61070s01 and ma30168s02, preferably by marker alleles ma50827s01 and ma16983s02, more preferably by marker alleles ma17117s01 and ma61125s01.

[14] The method, plant, or plant part according to any of the preceding items, wherein ma61134xxx is an insertion of one or more nucleotides between position 134254381 and 134254382 of chromosome 9 referenced to line PH207, preferably an insertion as set forth in SEQ ID NO: 12; and/or ma61070s01 is a single nucleotide polymorphism (SNP) at position 121588825 of chromosome 9 referenced to line PH207, wherein said nucleotide is A or T, preferably a single nucleotide polymorphism (SNP) as set forth in SEQ ID NO: 13; and/or ma30168s02 is a single nucleotide polymorphism (SNP) at position 139452428 of chromosome 9 referenced to line PH207, wherein said nucleotide is A or G, preferably a single nucleotide polymorphism (SNP) as set forth in SEQ ID NO: 14; and/or ma50827s01 is a single nucleotide polymorphism (SNP) at position 127454426 of chromosome 9 referenced to line PH207, wherein said nucleotide is A or G, preferably a single nucleotide polymorphism (SNP) as set forth in SEQ ID NO: 15; and/or ma16983s02 is a single nucleotide polymorphism (SNP) at position 137363784 of chromosome 9 referenced to line PH207, wherein said nucleotide is A or G, preferably a single nucleotide polymorphism (SNP) as set forth in SEQ ID NO: 16; and/or ma17117s01 is a single nucleotide polymorphism (SNP) at position 132038900 of chromosome 9 referenced to line PH207, wherein said nucleotide is A or G, preferably a single nucleotide polymorphism (SNP) as set forth in SEQ ID NO: 17; and/or ma61125s01 is a single nucleotide polymorphism (SNP) at position 135947973 of chromosome 9 referenced to line PH207, wherein said nucleotide is A or G, preferably a single nucleotide polymorphism (SNP) as set forth in SEQ ID NO: 18.

[15] The method, plant, or plant part according to any of the preceding items, wherein the nucleotide sequence of the unmutated F35H gene comprises a sequence selected from the group consisting of:

(i) a nucleotide sequence of SEQ ID NO: 1, 4, or 7;

(ii) a nucleotide sequence having the cDNA of SEQ ID NO: 2, 5, or 8;

(iii) a nucleotide sequence encoding for an amino acid sequence of SEQ ID NO: 3, 6, or 9;

(iv) a nucleotide sequence having at least 60% identity to the sequence of SEQ ID NO: 1, 2, 4, 5, 7, or 8;

(v) a nucleotide sequence encoding for a polypeptide having at least 60% identity to the sequence of SEQ ID NO: 3, 6, or 9;

(vi) a nucleotide sequence hybridizing with the reverse complement of a nucleotide sequence as defined in (i), (ii) or (iii) under stringent hybridization conditions; and (vii) a nucleotide sequence encoding a protein derived from the amino acid sequence encoded by the nucleotide sequence of (i) to (vi) by way of substitution, deletion and/or addition of one or more amino acid(s) of the amino acid sequence encoded by the nucleotide sequence of (i) to (vi).

[16] The method, plant, or plant part according to any of the preceding items, wherein the mutation is a frameshift mutation or a non-sense-mutation, results in an altered expression of the nucleotide sequence or an altered enzymatic activity of the encoded protein, preferably in a reduced or absent expression of the nucleotide sequence or a reduced enzymatic activity of the encoded protein or an increased enzymatic activity of the encoded protein, results in an altered protein sequence encoded by the nucleotide sequence, or is an insertion, deletion or substitution of at least one nucleotide in a coding region, in a splicing signal or in a regulatory element of said nucleotide sequence.

[17] The method, plant, or plant part according to any of the preceding items, wherein the mutation is an insertion, preferably in an exon, preferably an insertion in the first exon, of one or more nucleotides, preferably a frame shift insertion, more preferably the insertion is 187 nucleotides or about 187 nucleotides and/or the insertion is between position 97 and 98 of the F35H gene represented by the nucleotide sequence of SEQ ID NO: 1. In a particular preferred embodiment the mutated F35H comprises the nucleotide sequence of SEQ ID NO: 11. Alternatively, the mutation is a substitution, preferably a substitution of at least one nucleic acid resulting in an exchange of at least one amino acid or resulting in the change of an amino acid coding codon into a stop codon. In preferred embodiments, the mutated F35H comprises the nucleotide sequence encoding one of the amino acid sequences selected from the group consisting of SEQ ID NO: 20, 22, 24, 26, 28, 30, 32, 34, 36, 38 or 40. Such nucleotide sequence may be selected from the group consisting of SEQ ID NO: 19, 21, 23, 25, 27, 29, 31, 33, 35, 37 or 39.

[18] The method, plant or plant part according to any of the preceding items, wherein said plant part is not propagation material.

[19] The method, plant, or plant part according to any of the preceding items, wherein said plant part is stover.

[20] The method, plant, or plant part according to any of the preceding items, wherein the plant is or the plant part is from maize, *Sorghum* or sugar cane.

[21] A polynucleic acid, such as an allele specific polynucleic acid (molecular marker), specifically hybridising with any of the sequences of SEQ ID NO: 10, 12, 13, 14, 15, 16, 17 or 18, or the complement or the reverse complement thereof.

[22] Use of the polynucleic acid according to item [21] or polynucleic acid, such as an allele specific polynucleic acid (molecular marker), for identification of a plant or plant part having improved digestibility or for selection of a plant or plant part having improved digestibility according to any one of item [03] to [06], preferably in the method according to item [01] or [02], wherein preferably the polynucleic acid is suitable for hybridization as forward primer and reverse primer to a locus in a chromosomal interval which co-segregates with the improved digestibility, wherein the chromosomal interval is on chromosome 9 and flanked by marker alleles ma61070s01 and ma30168s02, preferably by marker alleles ma50827s01 and ma16983s02, more preferably by marker alleles ma17117s01 and ma61125s01.

[23] A method for producing an ensilaged plant material or animal feed having improved digestibility, comprising (a) growing the plant according to any one of item [03] to [06] or [11], (b) harvesting the plant or a part thereof, (c) optionally, chopping and/or crushing the plant or a part thereof, and (d) ensiling the plant or a part thereof of (b) or (c), optionally by adding a stimulant like a bacterial inoculant, a sugar, and an enzyme.

[24] An ensilaged plant material or animal feed produced by the method of item [23].

[25] A method for producing biogas or bioethanol, comprising the following steps:

(a) providing the plant according to any one of item [03] to [06] or [11] or the ensilaged plant material according to item [24], and (b) producing biogas or bioethanol from the plant or the ensilaged plant material.

BRIEF DESCRIPTION OF THE FIGURES

FIG. 3: Fine-mapped genetic region of silage QTL by molecular markers in different recombinant genotypes.

FIG. 4: Nucleotide sequence alignment of an F35H reference gene and a mutated F35H gene according to an embodiment of the invention.

DETAILED DESCRIPTION OF THE INVENTION

Figure 1:
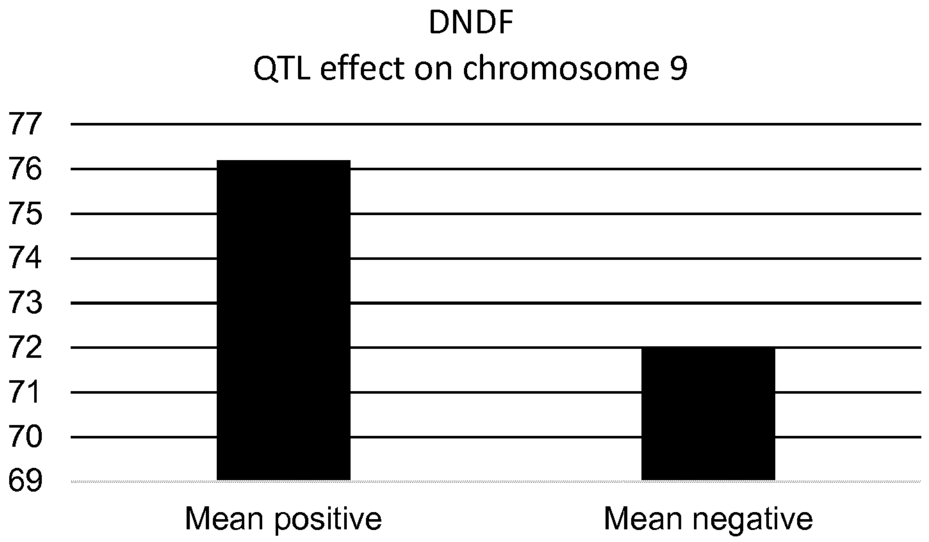
FIG. 1: DNDF (Digestible Neutral Detergent Fiber) effects of QTL on chromosome 9 of maize (*Zea mays*). Identification of a strong QTL for digestibility on chromosome 9. Percentage of DNDF of maize stover is indicated.

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms “a”, “an”, and “the” include both singular and plural referents unless the context clearly dictates otherwise.

The terms “comprising”, “comprises” and “comprised of” as used herein are synonymous with “including”, “includes” or “containing”, “contains”, and are inclusive or open-ended and do not exclude additional, non-recited members, elements or method steps. It will be appreciated that the terms “comprising”, “comprises” and “comprised of” as used herein comprise the terms “consisting of”, “consists” and “consists of”, as well as the terms “consisting essentially of”, “consists essentially” and “consists essentially of”.

The recitation of numerical ranges by endpoints includes all numbers and fractions subsumed within the respective ranges, as well as the recited endpoints.

The term “about” or “approximately” as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier “about” or “approximately” refers is itself also specifically, and preferably, disclosed.

Whereas the terms “one or more” or “at least one”, such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) (“Ausubel et al. 1992”); the series Methods in Enzymology (Academic Press, Inc.); Innis et al., PCR Protocols: A Guide to Methods and Applications, Academic Press: San Diego, 1990; PCR 2: A Practical Approach (M. J. MacPherson, B. D. Hames and G. R. Taylor eds. (1995); Harlow and Lane, eds. (1988) Antibodies, a Laboratory Manual; and Animal Cell Culture (R. I. Freshney, ed. (1987). General principles of microbiology are set forth, for example, in Davis, B. D. et al., Microbiology, 3rd edition, Harper & Row, publishers, Philadelphia, Pa. (1980).

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the following detailed description of the invention, reference is made to the accompanying drawings that form a part hereof, and in which are shown by way of illustration only of specific embodiments in which the invention may be practiced. It is to be understood that other embodiments may be utilised and structural or logical changes may be made without departing from the scope of the present invention. The following detailed description, therefore, is not to be taken in a limiting sense, and the scope of the present invention is defined by the appended claims.

Preferred items (features) and embodiments of this invention are set herein below. Each items and embodiments of the invention so defined may be combined with any other item and/or embodiments unless clearly indicated to the contrary. In particular, any feature indicated as being preferred or advantageous may be combined with any other feature or features or items indicated as being preferred or advantageous.

As used herein, "maize" refers to a plant of the species *Zea mays*, preferably *Zea mays* ssp *mays*.

As used herein, "*Sorghum*" refers to a plant of the genus *Sorghum*, and includes without limitation *Sorghum bicolor, Sorghum sudanense, Sorghum bicolor* x *Sorghum sudanense, Sorghum* x *almum* (*Sorghum bicolor* x *Sorghum halepense*), *Sorghum arundinaceum, Sorghum* x *drummondii, Sorghum halepense* and/or *Sorghum propinquum.*

As used herein, "sugar cane" refers to a plant of the species *Saccharum officinarum.*

The term "plant" includes whole plants, including descendants or progeny thereof. The term "plant part" includes any part or derivative of the plant, including particular plant tissues or structures, plant cells, plant protoplast, plant cell or tissue culture from which plants can be regenerated, plant calli, plant clumps and plant cells that are intact in plants or parts of plants, such as seeds, kernels, cobs, flowers, cotyledons, leaves, stems, buds, roots, root tips, stover, and the like. Plant parts may include processed plant parts or derivatives, including flower, oils, extracts etc. In certain embodiments, the plant part or derivative as referred to herein is stover.

Stover as used herein has its ordinary meaning known in the art. By means of further guidance, and without limitation, stover may comprise, consist of, or consist essentially of the leaves and stalks of field crops, such as maize or *Sorghum* that are commonly left in a field after harvesting the grain, or as sugar cane. Stover may also include cobs (e.g. the central core of an ear of maize, without the kernels). Stover may also exclude cobs. Stover may also include husks or hulls (e.g. the leafy outer covering of an ear of maize). Stover may also exclude husks or hulls. Stover is similar to straw, the residue left after any cereal grain or grass has been harvested at maturity for its seed. It can be directly grazed by cattle or dried for use as fodder. (Maize) stover can be used as feed, whether grazed as forage, chopped as silage to be used later for fodder, or collected for direct (non-ensilaged) fodder use. Maize forage is usually ensiled in cooler regions, but it can be harvested year-round in the tropics and fed as green forage to the animals. In the silage use case, it is usual for the entire plant (grain and stover together) to be chopped into pieces which are then crushed between rollers while harvesting. In addition to the stalks, leaves, husks, and cobs remaining in the field, kernels of grain may also be left over from harvest. These left over kernels, along with the corn stover, serve as an additional feed source for grazing cattle.

In certain embodiments, the plant part or derivative comprises, consists of, or consists essentially of one or more, preferably all of stalks, leaves, and cobs. In certain embodiments, the plant part or derivative is leaves. In certain embodiments, the plant part or derivative is stalks. In certain embodiments, the plant part or derivative is cobs. In certain embodiments, the plant part or derivative comprises, consists of, or consists essentially of one or more, preferably all of stalks and leaves. In certain embodiments, the plant part or derivative comprises, consists of, or consists essentially of one or more, preferably all of stalks, and cobs. In certain embodiments, the plant part or derivative comprises, consists of, or consists essentially of one or more, preferably all of leaves and cobs. In certain embodiments, the plant part or derivative is not (functional) propagation material, such as germplasm, a seed, or plant embryo or other material from which a plant can be regenerated. In certain embodiments, the plant part or derivative does not comprise (functional) male and female reproductive organs. In certain embodiments, the plant part or derivative is or comprises propagation material, but propagation material which does not or cannot be used (anymore) to produce or generate new plants, such as propagation material which have been chemically, mechanically or otherwise rendered non-functional, for instance by heat treatment, acid treatment, compaction, crushing, chopping, ensilaging etc.

As used herein, "digestibility" refers to and is measured as percentage of product (such as a maize, *Sorghum* or sugar cane plant or plant part or derivative, including for instance dry matter, organic matter, or cell wall of the product) absorbed in the animal digestive tract (Barrière et al. 2003). Biological and chemical methods have been developed to assay the digestibility of maize and other forage crops (Van Soest et al. 1963). Neutral detergent fiber (NDF), the residual after removing cell soluble content, is an important plant cell wall and cellulose indicator. In vitro NDF digestibility (IVNDFD) of forages is an estimate of cell wall digestibility assuming that the non-NDF part of plant material was completely digestible (Méchin et al. 2000). Additionally, the use of NIRS has been reported to measure digestibility traits accurately in many forage crops including maize (Lübberstedt et al. 1997a, b; Zimmer et al. 1990). In certain embodiments, the animal is a mammal. In certain embodiments, the animal is a ruminant. In certain embodiments, the animal is a herbivore. In certain embodiments, the animal is a herbivorous mammal.

Improved digestibility as referred to herein, relates to increased digestibility of a plant or plant part or derivative having a characteristic according to the invention, such as a mutation, marker, SNP, or QTL as described herein elsewhere, compared to a plant or plant part or derivative not having such characteristic. In certain embodiments, an improved or increased digestibility refers to an increase in mean DNDF by at least 1%, such as at least 2%, at least 3%, at least 4%, at least 5%, at least 6%, at least 7%, at least 8%, at least 9%, or at least 10%, preferably at least 2%, more preferably at least 3%, such as at least 4%.

The term "locus" (loci plural) means a specific place or places or a site on a chromosome where for example a QTL, a gene or genetic marker is found. As used herein, the term "quantitative trait locus" or "QTL" has its ordinary meaning known in the art. By means of further guidance, and without limitation, a QTL may refer to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" can comprise multiple genes or other genetic factors within a contiguous genomic region or linkage group, such as a haplotype. An allele of a QTL can denote a haplotype within a specified window wherein said window is a contiguous genomic region that can be defined, and tracked, with a set of one or more monomorphic and/or polymorphic markers. A haplotype can be defined by the unique fingerprint of alleles at each marker within the specified window. A QTL may encode for one or more alleles that affect the expressivity of a continuously distributed (quantitative) phenotype. In certain embodiments, the QTL as described herein may be homozygous. In certain embodiments, the QTL as described herein may be heterozygous.

As used herein, the term "allele" or "alleles" refers to one or more alternative forms, i.e. different nucleotide sequences, of a locus.

As used herein, the term "mutant alleles" or "mutation" of alleles include alleles having one or more mutations, such as insertions, deletions, stop codons, base changes (e.g., transitions or transversions), or alterations in splice junctions/splicing signal sites, which may or may not give rise to altered gene products. Modifications in alleles may arise in coding or non-coding regions (e.g. promoter regions, exons, introns or splice junctions).

As used herein, the terms "introgression", "introgressed" and "introgressing" refer to both a natural and artificial process whereby chromosomal fragments or genes of one species, variety or cultivar are moved into the genome of another species, variety or cultivar, by crossing those species. The process may optionally be completed by backcrossing to the recurrent parent. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. In any case, offspring comprising the desired allele can be repeatedly backcrossed to a line having a desired genetic background and selected for the desired allele, to result in the allele becoming fixed in a selected genetic background. "Introgression fragment" or "introgression segment" or "introgression region" refers to a chromosome fragment (or chromosome part or region) which has been introduced into another plant of the same or related species either artificially or naturally such as by crossing or traditional breeding techniques, such as backcrossing, i.e. the introgressed fragment is the result of breeding methods referred to by the verb "to introgress" (such as backcrossing). It is understood that the term "introgression fragment" never includes a whole chromosome, but only a part of a chromosome. The introgression fragment can be large, e.g. even three quarter or half of a chromosome, but is preferably smaller, such as about 50 Mb or less, such as about 30 Mb or less, about 20 Mb or less, about 25 Mb or less, about 10 Mb or less, about 9 Mb or less, about 8 Mb or less, about 7 Mb or less, about 6 Mb or less, about 5 Mb or less, about 4 Mb or less, about 3 Mb or less, about 2.5 Mb or 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

A genetic element, a locus, an introgression fragment, an QTL, or a gene or allele conferring a trait (such as improved digestibility) is said to be "obtainable from" or can be "obtained from" or "derivable from" or can be "derived from" or "as present in" or "as found in" a plant or plant part as described herein elsewhere if it can be transferred from the plant in which it is present into another plant in which it is not present (such as a line or variety) using traditional breeding techniques without resulting in a phenotypic change of the recipient plant apart from the addition of the trait conferred by the genetic element, locus, introgression fragment, QTL, gene or allele. The terms are used interchangeably and the genetic element, locus, introgression fragment, QTL, gene or allele can thus be transferred into any other genetic background lacking the trait. Not only pants comprising the genetic element, locus, introgression fragment, QTL, gene or allele can be used, but also progeny/descendants from such plants which have been selected to retain the genetic element, locus, introgression fragment, QTL, gene or allele, can be used and are encompassed herein. Whether a plant (or genomic DNA, cell or tissue of a plant) comprises the same genetic element, locus, introgression fragment, QTL, gene or allele as obtainable from such plant can be determined by the skilled person using one or more techniques known in the art, such as phenotypic assays, whole genome sequencing, molecular marker analysis, trait mapping, chromosome painting, allelism tests and the like, or combinations of techniques. It will be understood that transgenic or gene-edited plants may also be encompassed.

As used herein the terms "transformation" and "transgenic modification" are all used herein as synonyms for the transfer of isolated and cloned nucleic acid molecule into the DNA, usually the chromosomal DNA or genome, of another organism/species or of the same organism/species but at a location which differs from the location at which the nucleic acid molecule naturally is located in the chromosomal DNA or genome.

"Introducing" in the meaning of the present invention includes stable or transient integration by means of transformation including *Agrobacterium*-mediated transformation, transfection, microinjection, biolistic bombardment, insertion using gene editing technology like CRISPR systems (e.g. CRISPR/Cas, in particular CRISPR/Cas9 or CRISPR/Cpf1), CRISPR/CasX, or CRISPR/CasY), TALENs, zinc finger nucleases or meganucleases, homologous recombination optionally by means of one of the below mentioned gene editing technology including preferably a repair template, modification of endogenous gene using random or targeted mutagenesis like TILLING or above mentioned gene editing technology, etc.

"Transgenic" or "genetically modified organisms" (GMOs) as used herein are organisms whose genetic material has been altered using techniques generally known as "recombinant DNA technology". Recombinant DNA technology encompasses the ability to combine DNA molecules from different sources into one molecule ex vivo (e.g. in a test tube). This terminology generally does not cover organisms whose genetic composition has been altered by conventional cross-breeding or by "mutagenesis" breeding, as these methods predate the discovery of recombinant DNA techniques. "Non-transgenic" as used herein refers to plants and food products derived from plants that are not "transgenic" or "genetically modified organisms" as defined above.

"Transgene" or "exogene" refers to a nucleic acid molecule or a genetic locus comprising a DNA sequence, such as a recombinant gene, which has been introduced into the genome of a plant by transformation, such as *Agrobacterium* mediated transformation. A plant comprising a transgene stably integrated into its genome is referred to as "transgenic plant". "Endogene" refers to a nucleic acid molecule or a genetic locus that naturally occurs in the genome of a plant. "Gene editing" or "genome editing" refers to genetic engineering in which DNA or RNA is inserted, deleted, modified or replaced in the genome of an organism. Gene editing may comprise targeted or non-targeted (random) mutagenesis. Targeted mutagenesis may be accomplished for instance with designer nucleases, such as for instance with meganucleases, zinc finger nucleases (ZFNs), transcription activator-like effector-based nucleases (TALEN), and the clustered regularly interspaced short palindromic repeats (CRISPR/Cas) system. These nucleases create site-specific double-strand breaks (DSBs) at desired locations in the genome. The induced double-strand breaks are repaired through nonhomologous end-joining (NHEJ) or homologous recombination (HR) or homology directed repair (HDR), resulting in targeted mutations or nucleic acid modifications. The use of designer nucleases, optionally together with a repair template/recombination template, is particularly suitable for generating gene knockouts or knockdowns. In certain embodiments, designer nucleases are developed which specifically induce a mutation in the F35H gene, as described herein elsewhere, such as to generate a mutated F35H or a knockout of the F35H gene. In certain embodiments, designer nucleases, in particular RNA-specific CRISPR/Cas systems are developed which specifically target the F35H mRNA, such as to cleave the F35H mRNA and generate a knockdown of the F35H gene/mRNA/protein. Delivery and expression systems of designer nuclease systems are well known in the art.

In certain embodiments, the nuclease or targeted/site-specific/homing nuclease is, comprises, consists essentially of, or consists of a (modified) CRISPR/Cas system or complex, a (modified) Cas protein, a (modified) zinc finger, a (modified) zinc finger nuclease (ZFN), a (modified) transcription factor-like effector (TALE), a (modified) transcription factor-like effector nuclease (TALEN), or a (modified) meganuclease. In certain embodiments, said (modified) nuclease or targeted/site-specific/homing nuclease is, comprises, consists essentially of, or consists of a (modified) RNA-guided nuclease. It will be understood that in certain embodiments, the nucleases may be codon optimized for expression in plants. As used herein, the term "targeting" of a selected nucleic acid sequence means that a nuclease or nuclease complex is acting in a nucleotide sequence specific manner. For instance, in the context of the CRISPR/Cas system, the guide RNA is capable of hybridizing with a selected nucleic acid sequence. As uses herein, "hybridization" or "hybridizing" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PGR, or the cleavage of a polynucleotide by an enzyme. A sequence capable of hybridizing with a given sequence is referred to as the "complement" of the given sequence.

Gene editing may involve transient, inducible, or constitutive expression of the gene editing components or systems. Gene editing may involve genomic integration or episomal presence of the gene editing components or systems. Gene editing components or systems may be provided on vectors, such as plasmids, which may be delivered by appropriate delivery vehicles, as is known in the art. Preferred vectors are expression vectors.

Gene editing may comprise the provision of recombination templates, to effect homology directed repair (HDR). For instance, a genetic element may be replaced by gene editing in which a recombination template is provided. The DNA may be cut upstream and/or downstream of a sequence which needs to be replaced. As such, the sequence to be replaced is excised from the DNA. Through HDR, the excised sequence is then replaced by the template. In certain embodiments, the QTL allele of the invention as described herein may be provided on/as a template. By designing the system such that double strand breaks are introduced upstream and/or downstream of the corresponding region in the genome of a plant not comprising the QTL allele, this region is excised and can be replaced with the template comprising the QTL allele of the invention. In this way, introduction of the QTL allele of the invention in a plant need not involve multiple backcrossing, in particular in a plant of specific genetic background. Similarly, the mutated F35H of the invention may be provided on/as a template. More advantageously however, the mutated F35H of the invention may be generated without the use of a recombination template, but solely through the endonuclease action leading to a double strand DNA break which is repaired by NHEJ, resulting in the generation of indels.

In certain embodiments, the nucleic acid modification or mutation is effected by a (modified) transcription activator-like effector nuclease (TALEN) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference. By means of further guidance, and without limitation, naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26. The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

In certain embodiments, the nucleic acid modification or mutation is effected by a (modified) zinc-finger nuclease (ZFN) system. The ZFN system uses artificial restriction enzymes generated by fusing a zinc finger DNA-binding domain to a DNA-cleavage domain that can be engineered to target desired DNA sequences. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference. By means of further guidance, and without limitation, artificial zinc-finger (ZF) technology involves arrays of ZF modules to target new DNA-binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In certain embodiments, the nucleic acid modification is effected by a (modified) meganuclease, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

In certain embodiments, the nucleic acid modification is effected by a (modified) CRISPR/Cas complex or system. With respect to general information on CRISPR/Cas Systems, components thereof, and delivery of such components, including methods, materials, delivery vehicles, vectors, particles, and making and using thereof, including as to amounts and formulations, as well as Cas9CRISPR/Cas-expressing eukaryotic cells, Cas-9 CRISPR/Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622

(PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), PCT/US2015/051691, PCT/US2015/051830. Reference is also made to US provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/835,973, 61/836,080, 61/836,101, and 61/836,127, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT/US2014/62558 filed Oct. 28, 2014, and U.S. Provisional Patent Applications Ser. Nos. 61/915,148, 61/915,150, 61/915,153, 61/915,203, 61/915,251, 61/915,301, 61/915,267, 61/915,260, and 61/915,397, each filed Dec. 12, 2013; 61/757,972 and 61/768,959, filed on Jan. 29, 2013 and Feb. 25, 2013; 62/010,888 and 62/010,879, both filed Jun. 11, 2014; 62/010,329, 62/010,439 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/055,484, 62/055,460 and 62/055,487, each filed Sep. 25, 2014; and 62/069,243, filed Oct. 27, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to PCT application designating, inter alia, the United States, application No. PCT/US14/41806, filed Jun. 10, 2014. Mention is also made of U.S. application 62/180,709, 17-Jun.-15, PROTECTED GUIDE RNAS (PGRNAS); U.S. application 62/091,455, filed, 12-Dec.-14, PROTECTED GUIDE RNAS (PGRNAS); U.S. application 62/096,708, 24-Dec.-14, PROTECTED GUIDE RNAS (PGRNAS); U.S. applications 62/091,462, 12-Dec.-14, 62/096,324, 23-Dec.-14, 62/180,681, 17 Jun. 2015, and 62/237,496, 5 Oct. 2015, DEAD GUIDES FOR CRISPR TRANSCRIPTION FACTORS; U.S. application 62/091,456, 12-Dec.-14 and 62/180,692, 17 Jun. 2015, ESCORTED AND FUNCTIONALIZED GUIDES FOR CRISPR-CAS SYSTEMS; U.S. application 62/091,461, 12-Dec.-14, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19-Dec.-14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24-Dec.-14, ENGINEERING OF SYSTEMS, METHODS AND OPTIMIZED ENZYME AND GUIDE SCAFFOLDS FOR SEQUENCE MANIPULATION; U.S. application 62/098,059, 30-Dec.-14, 62/181,641, 18-Jun.-2015, and 62/181,667, 18 Jun. 2015, RNA-TARGETING SYSTEM; U.S. application 62/096,656, 24-Dec.-14 and 62/181,151, 17 Jun. 2015, CRISPR HAVING OR ASSOCIATED WITH DESTABILIZATION DOMAINS; U.S. application 62/096,697, 24-Dec.-14, CRISPR HAVING OR ASSOCIATED WITH AAV; U.S. application 62/098,158, 30-Dec.-14, ENGINEERED CRISPR COMPLEX INSERTIONAL TARGETING SYSTEMS; U.S. application 62/151,052, 22-Apr.-15, CELLULAR TARGETING FOR EXTRACELLULAR EXOSOMAL REPORTING; U.S. application 62/054,490, 24-Sep.-14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12-Feb.-14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25-Sep.-14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4-Dec.-14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24-Sep.-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23-Oct.-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24-Sep.-14 and 62/181,002, 17-Jun.-2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24-Sep.-14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25-Sep.-14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25-Sep.-14, MULTIFUNCTIONAL-CRISPR COMPLEXES AND/OR OPTIMIZED ENZYME LINKED FUNCTIONAL-CRISPR COMPLEXES; U.S. application 62/087,475, 4-Dec.-14 and 62/181,690, 18 Jun. 2015, FUNCTIONAL SCREENING WITH OPTIMIZED FUNCTIONAL CRISPR-CAS SYSTEMS; U.S. application 62/055,487, 25-Sep.-14, FUNCTIONAL SCREENING WITH OPTIMIZED FUNCTIONAL CRISPR-CAS SYSTEMS; U.S. application 62/087,546, 4-Dec.-14 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30-Dec.-14, CRISPR MEDIATED IN VIVO MODELING AND GENETIC SCREENING OF TUMOR GROWTH AND METASTASIS. Mention is made of U.S. applications 62/181,659, 18-Jun.-2015 and 62/207,318, 19 Aug. 2015, ENGINEERING AND OPTIMIZA- TION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, filed 22 Oct. 2015, NOVEL CRISPR ENZYMES AND SYSTEMS, U.S. application 62/232,067, 24 Sep. 2015, U.S. application 62/205,733, 16-Aug.-2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES. European patent application EP3009511. Reference is further made to Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013); RNA-guided editing of bacterial genomes using CRISPR-Cas systems. Jiang W., Bikard D., Cox D., Zhang F, Marraffini L A. Nat Biotechnol March; 31(3):233-9 (2013); One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013); Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature12466. Epub 2013 Aug. 23; Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5. (2013); DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013); Genome engineering using the CRISPR-Cas9 system. Ran, F A., Hsu, P D., Wright, J., Agarwala, V., Scott, D A., Zhang, F. Nature Protocols November; 8(11):2281-308. (2013); Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print]; Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27. (2014). 156(5):935-49; Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. (2014) Apr. 20. doi: 10.1038/nbt.2889; CRISPR-Cas9 Knockin Mice for Genome Editing and Cancer Modeling, Platt et al., Cell 159(2): 440-455 (2014) DOI: 10.1016/j.cell.2014.09.014; Development and Applications of CRISPR-Cas9 for Genome Engineering, Hsu et al, Cell 157, 1262-1278 (Jun. 5, 2014) (Hsu 2014); Genetic screens in human cells using the CRISPR/Cas9 system, Wang et al., Science. 2014 Jan. 3; 343(6166): 80-84. doi:10.1126/science.1246981; Rational design of highly active sgRNAs for CRISPR-Cas9-mediated gene inactivation, Doench et al., Nature Biotechnology 32(12):1262-7 (2014) published online 3 Sep. 2014; doi: 10.1038/nbt.3026, and In vivo interrogation of gene function in the mammalian brain using CRISPR-Cas9, Swiech et al, Nature Biotechnology 33, 102-106 (2015) published online 19 Oct. 2014; doi:10.1038/nbt.3055, Cpf1 Is a Single RNA-Guided Endonuclease of a Class 2 CRISPR-Cas System, Zetsche et al., Cell 163, 1-13 (2015); Discovery and Functional Characterization of Diverse Class 2 CRISPR-Cas Systems, Shmakov et al., Mol Cell 60(3): 385-397 (2015); C2c2 is a single-component programmable RNA-guided RNA-targeting CRISPR effector, Abudayyeh et al, Science (2016) published online Jun. 2, 2016 doi: 10.1126/science.aaf5573. Each of these publications, patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In certain embodiments, the CRISPR/Cas system or complex is a class 2 CRISPR/Cas system. In certain embodiments, said CRISPR/Cas system or complex is a type II, type V, or type VI CRISPR/Cas system or complex. The CRISPR/Cas system does not require the generation of customized proteins to target specific sequences but rather a single Cas protein can be programmed by an RNA guide (gRNA) to recognize a specific nucleic acid target, in other words the Cas enzyme protein can be recruited to a specific nucleic acid target locus (which may comprise or consist of RNA and/or DNA) of interest using said short RNA guide.

In general, the CRISPR/Cas or CRISPR system is as used herein foregoing documents refers collectively to transcripts and other elements involved in the expression of or directing the activity of CRISPR-associated ("Cas") genes, including sequences encoding a Cas gene and one or more of, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and, where applicable, transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides.

In certain embodiments, the gRNA is a chimeric guide RNA or single guide RNA (sgRNA). In certain embodiments, the gRNA comprises a guide sequence and a tracr mate sequence (or direct repeat). In certain embodiments, the gRNA comprises a guide sequence, a tracr mate sequence (or direct repeat), and a tracr sequence. In certain embodiments, the CRISPR/Cas system or complex as described herein does not comprise and/or does not rely on the presence of a tracr sequence (e.g. if the Cas protein is Cpf1).

As used herein, the term "crRNA" or "guide RNA" or "single guide RNA" or "sgRNA" or "one or more nucleic acid components" of a CRISPR/Cas locus effector protein, as applicable, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay.

A guide sequence, and hence a nucleic acid-targeting guide RNA may be selected to target any target nucleic acid sequence. The target sequence may be DNA. The target sequence may be genomic DNA. The target sequence may be mitochondrial DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In certain embodiments, the gRNA comprises a stem loop, preferably a single stem loop. In certain embodiments, the direct repeat sequence forms a stem loop, preferably a single stem loop. In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In particular embodiments, the CRISPR/Cas system requires a tracrRNA. The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and gRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop may correspond to the tracr mate sequence, and the portion of the sequence 3' of the loop then corresponds to the tracr sequence. In a hairpin structure the portion of the sequence 5' of the final "N" and upstream of the loop may alternatively correspond to the tracr sequence, and the portion of the sequence 3' of the loop corresponds to the tracr mate sequence. In alternative embodiments, the CRISPR/Cas system does not require a tracrRNA, as is known by the skilled person.

In certain embodiments, the guide RNA (capable of guiding Cas to a target locus) may comprise (1) a guide sequence capable of hybridizing to a target locus and (2) a tracr mate or direct repeat sequence (in 5' to 3' orientation, or alternatively in 3' to 5' orientation, depending on the type of Cas protein, as is known by the skilled person). In particular embodiments, the CRISPR/Cas protein is characterized in that it makes use of a guide RNA comprising a guide sequence capable of hybridizing to a target locus and a direct repeat sequence, and does not require a tracrRNA. In particular embodiments, where the CRISPR/Cas protein is characterized in that it makes use of a tracrRNA, the guide sequence, tracr mate, and tracr sequence may reside in a single RNA, i.e. an sgRNA (arranged in a 5' to 3' orientation or alternatively arranged in a 3' to 5' orientation), or the tracr RNA may be a different RNA than the RNA containing the guide and tracr mate sequence. In these embodiments, the tracr hybridizes to the tracr mate sequence and directs the CRISPR/Cas complex to the target sequence.

Typically, in the context of an endogenous nucleic acid-targeting system, formation of a nucleic acid-targeting complex (comprising a guide RNA hybridized to a target sequence and complexed with one or more nucleic acid-targeting effector proteins) results in modification (such as cleavage) of one or both DNA or RNA strands in or near (e.g., within 1, 2, 3, 4, 5, 6, 7, 8, 9, 10, 20, 50, or more base pairs from) the target sequence. As used herein the term "sequence(s) associated with a target locus of interest" refers to sequences near the vicinity of the target sequence (e.g. within 1, 2, 3, 4, 5, 6, 7, 8, 9, 10, 20, 50, or more base pairs from the target sequence, wherein the target sequence is comprised within a target locus of interest). The skilled person will be aware of specific cut sites for selected CRISPR/Cas systems, relative to the target sequence, which as is known in the art may be within the target sequence or alternatively 3' or 5' of the target sequence.

In some embodiments, the unmodified nucleic acid-targeting effector protein may have nucleic acid cleavage activity. In some embodiments, the nuclease as described herein may direct cleavage of one or both nucleic acid (DNA, RNA, or hybrids, which may be single or double stranded) strands at the location of or near a target sequence, such as within the target sequence and/or within the complement of the target sequence or at sequences associated with the target sequence. In some embodiments, the nucleic acid-targeting effector protein may direct cleavage of one or both DNA or RNA strands within about 1, 2, 3, 4, 5, 6, 7, 8, 9, 10, 15, 20, 25, 50, 100, 200, 500, or more base pairs from the first or last nucleotide of a target sequence. In some embodiments, the cleavage may be blunt (e.g. for Cas9, such as SaCas9 or SpCas9). In some embodiments, the cleavage may be staggered (e.g. for Cpf1), i.e. generating sticky ends. In some embodiments, the cleavage is a staggered cut with a 5' overhang. In some embodiments, the cleavage is a staggered cut with a 5' overhang of 1 to 5 nucleotides, preferably of 4 or 5 nucleotides. In some embodiments, the cleavage site is upstream of the PAM. In some embodiments, the cleavage site is downstream of the PAM. In some embodiments, the nucleic acid-targeting effector protein that may be mutated with respect to a corresponding wild-type enzyme such that the mutated nucleic acid-targeting effector protein lacks the ability to cleave one or both DNA or RNA strands of a target polynucleotide containing a target sequence. As a further example, two or more catalytic domains of a Cas protein (e.g. RuvC I, RuvC II, and RuvC III or the HNH domain of a Cas9 protein) may be mutated to produce a mutated Cas protein substantially lacking all DNA cleavage activity. In some embodiments, a nucleic acid-targeting effector protein may be considered to substantially lack all DNA and/or RNA cleavage activity when the cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form. As used herein, the term "modified" Cas generally refers to a Cas protein having one or more modifications or mutations (including point mutations, truncations, insertions, deletions, chimeras, fusion proteins, etc.) compared to the wild type Cas protein from which it is derived. By derived is meant that the derived enzyme is largely based, in the sense of having a high degree of sequence homology with, a wildtype enzyme, but that it has been mutated (modified) in some way as known in the art or as described herein.

In a particular embodiment, a mutated nucleic acid-targeting effector protein based on CRISPR system as described above which lacks the ability to cleave one or both DNA or RNA strands of a target polynucleotide containing a target sequence can be fused to other tools like other nucleases, nickases, recombinases, transposases, base editors or molecular complexes including these tools. A "base editor" as used herein refers to a protein or a fragment thereof having the same catalytical activity as the protein it is derived from, which protein or fragment thereof, alone or when provided as molecular complex, referred to as base editing complex herein, has the capacity to mediate a targeted base modification, i.e., the conversion of a base of interest resulting in a point mutation of interest. Preferably, the at least one base editor in the context of the present invention is temporarily or permanently linked to at least one site-specific effector, or optionally to a component of at least one site-specific effector complex (e.g., DNA recognition domain of CRISPR system, zinc finger or TAL effectors). The linkage can be covalent and/or non-covalent.

Multiple publications have shown targeted base conversion, primarily cytidine (C) to thymine (T), using a CRISPR/Cas9 nickase or non-functional nuclease linked to a cytidine deaminase domain, Apolipoprotein B mRNA-editing catalytic polypeptide (APOBEC1), e.g., APOBEC derived from rat. The deamination of cytosine (C) is catalysed by cytidine deaminases and results in uracil (U), which has the base-pairing properties of thymine (T). Most known cytidine deaminases operate on RNA, and the few examples that are known to accept DNA require single-stranded (ss) DNA. Studies on the dCas9-target DNA complex reveal that at least nine nucleotides (nt) of the displaced DNA strand are unpaired upon formation of the Cas9-guide RNA-DNA 'R-loop' complex (Jore et al., Nat. Struct. Mol. Biol., 18, 529-536 (2011)). Indeed, in the structure of the Cas9 R-loop complex, the first 11 nt of the protospacer on the displaced DNA strand are disordered, suggesting that their movement is not highly restricted. It has also been speculated that Cas9 nickase-induced mutations at cytosines in the non-template strand might arise from their accessibility by cellular cytosine deaminase enzymes. It was reasoned that a subset of this stretch of ssDNA in the R-loop might serve as an efficient substrate for a dCas9-tethered cytidine deaminase to effect direct, programmable conversion of C to U in DNA (Komor et al., supra). Recently, Goudelli et al ((2017). Programmable base editing of A.T to G.C in genomic DNA without DNA cleavage. *Nature,* 551(7681), 464.) described adenine base editors (ABEs) that mediate the conversion of A.T to G.C in genomic DNA.

Any base editing complex according to the present invention can thus comprise at least one cytidine deaminase, or a catalytically active fragment thereof. The at least one base editing complex can comprise the cytidine deaminase, or a domain thereof in the form of a catalytically active fragment, as base editor.

In another embodiment, the at least one first targeted base modification is a conversion of any nucleotide C, A, T, or G, to any other nucleotide. Any one of a C, A, T or G nucleotide can be exchanged in a site-directed way as mediated by a base editor, or a catalytically active fragment thereof, to another nucleotide. The at least one base editing complex can thus comprise any base editor, or a base editor domain or catalytically active fragment thereof, which can convert a nucleotide of interest into any other nucleotide of interest in a targeted way.

In certain embodiments, the target sequence for CRISPR/Cas should be associated with a PAM (protospacer adjacent motif) or PFS (protospacer flanking sequence or site); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. Further, engineering of the PAM Interacting (PI) domain may allow programing of PAM specificity, improve target site recognition fidelity, and increase the versatility of the Cas, e.g. Cas9, genome engineering platform. Cas proteins, such as Cas9 proteins may be engineered to alter their PAM specificity, for example as described in Kleinstiver B P et al. Engineered CRISPR-Cas9 nucleases with altered PAM specificities. Nature. 2015 Jul. 23; 523(7561):481-5. doi: 10.1038/nature14592. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. The skilled person will understand that other Cas proteins may be modified analogously.

The Cas protein as referred to herein, such as without limitation Cas9, Cpf1 (Cas12a), C2c1 (Cas12b), C2c2 (Cas13a), C2c3, Cas13b protein, may originate from any suitable source, and hence may include different orthologues, originating from a variety of (prokaryotic) organisms, as is well documented in the art. In certain embodiments, the Cas protein is (modified) Cas9, preferably (modified) *Staphylococcus aureus* Cas9 (SaCas9) or (modified) *Streptococcus pyogenes* Cas9 (SpCas9). In certain embodiments, the Cas protein is (modified) Cpf1, preferably Acidaminococcus sp., such as Acidaminococcus sp. BV3L6 Cpf1 (AsCpf1) or Lachnospiraceae bacterium Cpf1, such as Lachnospiraceae bacterium MA2020 or Lachnospiraceae bacterium MD2006 (LbCpf1). In certain embodiments, the Cas protein is (modified) C2c2, preferably *Leptotrichia wadei* C2c2 (LwC2c2) or *Listeria newyorkensis* FSL M6-0635 C2c2 (LbFSLC2c2). In certain embodiments, the (modified) Cas protein is C2c1. In certain embodiments, the (modified) Cas protein is C2c3. In certain embodiments, the (modified) Cas protein is Cas13b.

In certain embodiments, the nucleic acid modification is effected by random mutagenesis. Cells or organisms may be exposed to mutagens such as UV radiation or mutagenic chemicals (such as for instance such as ethyl methanesulfonate (EMS)), and mutants with desired characteristics are then selected. Mutants can for instance be identified by TILLING (Targeting Induced Local Lesions in Genomes). The method combines mutagenesis, such as mutagenesis using a chemical mutagen such as ethyl methanesulfonate (EMS) with a sensitive DNA screening-technique that identifies single base mutations/point mutations in a target gene. The TILLING method relies on the formation of DNA heteroduplexes that are formed when multiple alleles are amplified by PCR and are then heated and slowly cooled. A “bubble” forms at the mismatch of the two DNA strands, which is then cleaved by a single stranded nucleases. The products are then separated by size, such as by HPLC. See also McCallum et al. “Targeted screening for induced mutations”; Nat Biotechnol. 2000 April; 18(4):455-7 and McCallum et al. “Targeting induced local lesions IN genomes (TILLING) for plant functional genomics”; Plant Physiol. 2000 June; 123(2):439-42.

RNA interference (RNAi) is a biological process in which RNA molecules inhibit gene expression or translation, by neutralizing targeted mRNA molecules. Two types of small ribonucleic acid (RNA) molecules—microRNA (miRNA) and small interfering RNA (siRNA)—are central to RNA interference. RNAs are the direct products of genes, and these small RNAs can bind to other specific messenger RNA (mRNA) molecules and either increase or decrease their activity, for example by preventing an mRNA from being translated into a protein. The RNAi pathway is found in many eukaryotes, including animals, and is initiated by the enzyme Dicer, which cleaves long double-stranded RNA (dsRNA) molecules into short double-stranded fragments of about 21 nucleotide siRNAs (small interfering RNAs). Each siRNA is unwound into two single-stranded RNAs (ssRNAs), the passenger strand and the guide strand. The passenger strand is degraded and the guide strand is incorporated into the RNA-induced silencing complex (RISC). Mature miRNAs are structurally similar to siRNAs produced from exogenous dsRNA, but before reaching maturity, miRNAs must first undergo extensive post-transcriptional modification. A miRNA is expressed from a much longer RNA-coding gene as a primary transcript known as a pri-miRNA which is processed, in the cell nucleus, to a 70-nucleotide stem-loop structure called a pre-miRNA by the microprocessor complex. This complex consists of an RNase III enzyme called Drosha and a dsRNA-binding protein DGCR8. The dsRNA portion of this pre-miRNA is bound and cleaved by Dicer to produce the mature miRNA molecule that can be integrated into the RISC complex; thus, miRNA and siRNA share the same downstream cellular machinery. A short hairpin RNA or small hairpin RNA (shRNA/Hairpin Vector) is an artificial RNA molecule with a tight hairpin turn that can be used to silence target gene expression via RNA interference. The most well-studied outcome is post-transcriptional gene silencing, which occurs when the guide strand pairs with a complementary sequence in a messenger RNA molecule and induces cleavage by Argonaute 2 (Ago2), the catalytic component of the RISC. As used herein, an RNAi molecule may be an siRNA, shRNA, or a miRNA. In will be understood that the RNAi molecules can be applied as such to/in the plant, or can be encoded by appropriate vectors, from which the RNAi molecule is expressed. Delivery and expression systems of RNAi molecules, such as siRNAs, shRNAs or miRNAs are well known in the art.

As used herein, the term “homozygote” refers to an individual cell or plant having the same alleles at one or more or all loci. When the term is used with reference to a specific locus or gene, it means at least that locus or gene has the same alleles. As used herein, the term “homozygous” means a genetic condition existing when identical alleles reside at corresponding loci on homologous chromosomes. As used herein, the term “heterozygote” refers to an individual cell or plant having different alleles at one or more or all loci. When the term is used with reference to a specific locus or gene, it means at least that locus or gene has different alleles. As used herein, the term “heterozygous” means a genetic condition existing when different alleles reside at corresponding loci on homologous chromosomes. In certain embodiments, the QTL and/or one or more marker(s) as described herein is/are homozygous. In certain embodiments, the QTL and/or one or more marker(s) as described herein are heterozygous. In certain embodiments, the QTL allele and/or one or more marker(s) allele(s) as described herein is/are homozygous. In certain embodiments, the QTL allele and/or one or more marker(s) allele(s) as described herein are heterozygous.

A “marker” is a (means of finding a position on a) genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker may consist of complementary primers flanking the locus and/or complementary probes that hybridize to polymorphic alleles at the locus. The term marker locus is the locus (gene, sequence or nucleotide) that the marker detects. "Marker" or "molecular marker" or "marker locus" may also be used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population. With regard to a SNP marker, allele refers to the specific nucleotide base present at that SNP locus in that individual plant.

"Fine-mapping" refers to methods by which the position of a QTL can be determined more accurately (narrowed down) and by which the size of the introgression fragment comprising the QTL is reduced. For example Near Isogenic Lines for the QTL (QTL-NILs) can be made, which contain different, overlapping fragments of the introgression fragment within an otherwise uniform genetic background of the recurrent parent. Such lines can then be used to map on which fragment the QTL is located and to identify a line having a shorter introgression fragment comprising the QTL.

"Marker assisted selection" (of MAS) is a process by which individual plants are selected based on marker genotypes. "Marker assisted counter-selection" is a process by which marker genotypes are used to identify plants that will not be selected, allowing them to be removed from a breeding program or planting. Marker assisted selection uses the presence of molecular markers, which are genetically linked to a particular locus or to a particular chromosome region (e.g. introgression fragment, transgene, polymorphism, mutation, etc), to select plants for the presence of the specific locus or region (introgression fragment, transgene, polymorphism, mutation, etc). For example, a molecular marker genetically linked to a digestibility QTL as defined herein, can be used to detect and/or select plants comprising the QTL on chromosome 9. The closer the genetic linkage of the molecular marker to the locus (e.g. about 7 cM, 6 cM, 5 cM, 4 cM, 3 cM, 2 cM, 1 cM, 0.5 cM or less), the less likely it is that the marker is dissociated from the locus through meiotic recombination. Likewise, the closer two markers are linked to each other (e.g. within 7 cM or 5 cM, 4 cM, 3 cM, 2 cM, 1 cM or less) the less likely it is that the two markers will be separated from one another (and the more likely they will co-segregate as a unit). "LOD-score" (logarithm (base 10) of odds) refers to a statistical test often used for linkage analysis in animal and plant populations. The LOD score compares the likelihood of obtaining the test data if the two loci (molecular marker loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

"Genetic markers" are nucleic acids that are polymorphic in a population and where the alleles of which can be detected and distinguished by one or more analytic methods, e.g., RFLP, AFLP, isozyme, SNP, SSR, and the like. The terms "molecular marker" and "genetic marker" are used interchangeably herein. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel". The term "indel" refers to an insertion or deletion, wherein one line may be referred to as having an inserted nucleotide or piece of DNA relative to a second line, or the second line may be referred to as having a deleted nucleotide or piece of DNA relative to the first line.

"Physical distance" between loci (e.g. between molecular markers and/or between phenotypic markers) on the same chromosome is the actually physical distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

An allele "negatively" correlates with a trait when it is linked to it and when presence of the allele is an indicator that a desired trait or trait form will not occur in a plant comprising the allele. An allele "positively" correlates with a trait when it is linked to it and when presence of the allele is an indicator that the desired trait or trait form will occur in a plant comprising the allele.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

The term "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful with respect to the subject matter of the current disclosure when they demonstrate a significant probability of co-segregation (linkage) with a desired trait (e.g., resistance to gray leaf spot). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

"Linkage" refers to the tendency for alleles to segregate together more often than expected by chance if their transmission was independent. Typically, linkage refers to alleles on the same chromosome. Genetic recombination occurs with an assumed random frequency over the entire genome. Genetic maps are constructed by measuring the frequency of recombination between pairs of traits or markers. The closer the traits or markers are to each other on the chromosome, the lower the frequency of recombination, and the greater the degree of linkage. Traits or markers are considered herein to be linked if they generally co-segregate. A 1/100 probability of recombination per generation is defined as a genetic map distance of 1.0 centiMorgan (1.0 cM). The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

As used herein, the term "sequence identity" refers to the degree of identity between any given nucleic acid sequence and a target nucleic acid sequence. Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN and BLASTP. This stand-alone version of BLASTZ can be obtained from Fish & Richardson's web site (World Wide Web at fr.com/blast) or the U.S. government's National Center for Biotechnology Information web site (World Wide Web at ncbi.nlm.nih.gov). Instructions explaining how to use the Bl2seq program can be found in the readme file accompanying BLASTZ. Bl2seq performs a comparison between two sequences using either the BLASTN or BLASTP algorithm.

BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq I .txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. The following command will generate an output file containing a comparison between two sequences: C:\B12seq -i c:\seql.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences. Once aligned, a length is determined by counting the number of consecutive nucleotides from the target sequence presented in alignment with the sequence from the identified sequence starting with any matched position and ending with any other matched position. A matched position is any position where an identical nucleotide is presented in both the target and identified sequences. Gaps presented in the target sequence are not counted since gaps are not nucleotides. Likewise, gaps presented in the identified sequence are not counted since target sequence nucleotides are counted, not nucleotides from the identified sequence. The percent identity over a particular length is determined by counting the number of matched positions over that length and dividing that number by the length followed by multiplying the resulting value by 100. For example, if (i) a 500-base nucleic acid target sequence is compared to a subject nucleic acid sequence, (ii) the Bl2seq program presents 200 bases from the target sequence aligned with a region of the subject sequence where the first and last bases of that 200-base region are matches, and (iii) the number of matches over those 200 aligned bases is 180, then the 500-base nucleic acid target sequence contains a length of 200 and a sequence identity over that length of 90% (i.e., 180/200×100=90). It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome. When referring to a "sequence" herein, it is understood that the molecule having such a sequence is referred to, e.g. the nucleic acid molecule. A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

When reference is made to a nucleic acid sequence (e.g. DNA or genomic DNA) having "substantial sequence identity to" a reference sequence or having a sequence identity of at least 60%, e.g. at least 70%, 75%, 80%, 85%, 90%, 95%, 98% or 99% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions. "Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically, stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001). Examples of high stringent hybridization conditions are conditions under which primarily only those nucleic acid molecules that have at least 90% or at least 95% sequence identity undergo hybridization. Such high stringent hybridization conditions are, for example: 4×SSC at 65° C. and subsequent multiple washes in 0.1×SSC at 65° C. for approximately 1 hour. The term "high stringent hybridization conditions" as used herein may also mean: hybridization at 68° C. in 0.25 M sodium phosphate, pH 7.2, 7% SDS, 1 mM EDTA and 1% BSA for 16 hours and subsequently washing twice with 2×SSC and 0.1% SDS at 68° C. Preferably, hybridization takes place under stringent conditions. Less stringent hybridization conditions are, for example: hybridizing in 4×SSC at 37° C. and subsequent multiple washing in 1×SSC at room temperature.

As used herein, F35H (ExPASy enzyme entry EC 1.14.13.88) refers to the flavonoid 3',5'-hydroxylase gene or protein. F35H is also known as F3'S'H, F3',5'H, cytochrome P450 flavonoid 3',5'-hydroxylase, or flavanone, NADPH: oxygen oxidoreductase. F35H catalyzes the following reaction: flavanone+2NADPH+2O(2)<=>3',5'-dihydroxyflavanone+2NADP(+)+2H(2)O.

In an aspect, the invention relates to a method for identifying a plant or plant part having improved digestibility, preferably improved stover digestibility, or for selecting a plant or plant part having improved digestibility, preferably improved stover digestibility, comprising screening for the presence of a QTL allele (such as in isolated genetic material from the plant or plant part) associated with improved digestibility, preferably improved stover digestibility, said QTL allele comprising a nucleotide sequence of a gene encoding a cytochrome P450 flavonoid 3',5'-hydroxylase (F35H), having a mutation.

In an embodiment, the invention relates to a method for identifying a plant or plant part having improved digestibility, preferably improved stover digestibility, or for selecting a plant or plant part having improved digestibility, preferably improved stover digestibility, comprising isolating genetic material from at least one cell of the plant or plant part, and screening in said genetic material for the presence of a QTL allele associated with improved digestibility, preferably improved stover digestibility, said QTL allele comprising a nucleotide sequence of a gene encoding a cytochrome P450 flavonoid 3',5'-hydroxylase (F35H), having a mutation.

In an embodiment, the invention relates to a method for identifying a plant or plant part having improved digestibility, preferably improved stover digestibility, or for selecting a plant or plant part having improved digestibility, preferably improved stover digestibility, comprising screening for the presence of a QTL allele (such as in isolated genetic material from the plant or plant part) associated with improved digestibility, preferably improved stover digestibility, said QTL allele comprising a nucleotide sequence of a gene encoding a cytochrome P450 flavonoid 3',5'-hydroxylase (F35H) having a mutation, and selecting a plant or plant part in which the QTL allele is present.

In an embodiment, the invention relates to a method for identifying a plant or plant part having improved digestibility, preferably improved stover digestibility, or for selecting a plant or plant part having improved digestibility, preferably improved stover digestibility, comprising isolating genetic material from at least one cell of the plant or plant part, screening in said genetic material for the presence of a QTL allele associated with improved digestibility, preferably improved stover digestibility, said QTL allele comprising a nucleotide sequence of a gene encoding a cytochrome P450 flavonoid 3',5'-hydroxylase (F35H), having a mutation, and selecting a plant or plant part in which the QTL allele is present.

In an aspect, the invention relates to a method for identifying a plant or plant part having improved digestibility, preferably improved stover digestibility, or for selecting a plant or plant part having improved digestibility, preferably improved stover digestibility, comprising screening for the presence of a QTL allele (such as in isolated genetic material from the plant or plant part) comprising a nucleotide sequence of a gene encoding a cytochrome P450 flavonoid 3',5'-hydroxylase (F35H), having a mutation.

In an embodiment, the invention relates to a method for identifying a plant or plant part having improved digestibility, preferably improved stover digestibility, or for selecting a plant or plant part having improved digestibility, preferably improved stover digestibility, comprising isolating genetic material from at least one cell of the plant or plant part, and screening in said genetic material for the presence of a QTL allele comprising a nucleotide sequence of a gene encoding a cytochrome P450 flavonoid 3',5'-hydroxylase (F35H), having a mutation.

In an embodiment, the invention relates to a method for identifying a plant or plant part having improved digestibility, preferably improved stover digestibility, or for selecting a plant or plant part having improved digestibility, preferably improved stover digestibility, comprising screening for the presence of a QTL allele (such as in isolated genetic material from the plant or plant part) comprising a nucleotide sequence of a gene encoding a cytochrome P450 flavonoid 3',5'-hydroxylase (F35H) having a mutation, and selecting a plant or plant part in which the QTL allele is present.

In an embodiment, the invention relates to a method for identifying a plant or plant part having improved digestibility, preferably improved stover digestibility, or for selecting a plant or plant part having improved digestibility, preferably improved stover digestibility, comprising isolating genetic material from at least one cell of the plant or plant part, screening in said genetic material for the presence of a QTL allele comprising a nucleotide sequence of a gene encoding a cytochrome P450 flavonoid 3',5'-hydroxylase (F35H) having a mutation, and selecting a plant or plant part in which the QTL allele is present.

In certain embodiments, the plant is maize and the QTL allele is located on chromosome 9 and comprises and/or is flanked by (molecular) marker alleles ma61070s01 and ma30168s02, preferably by marker alleles ma50827s01 and ma16983s02, more preferably by marker alleles ma17117s01 and ma61125s01.

In certain embodiments, the plant is maize and the QTL allele is located on chromosome 9 and comprises the (molecular) marker allele of ma61134xxx.

In certain embodiments, the plant is maize and the QTL allele is located on a chromosomal interval comprising and/or flanked by (molecular) marker alleles ma61070s01 and ma30168s02, preferably by marker alleles ma50827s01 and ma16983s02, more preferably by marker alleles ma17117s01 and ma61125s01.

In certain embodiments, the plant is maize and the QTL allele is located on a chromosomal interval comprising the marker allele of ma61134xxx and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

In an aspect, the invention relates to a method for identifying a plant or plant part having improved digestibility, preferably improved stover digestibility, or for selecting a plant or plant part having improved digestibility, preferably improved stover digestibility, comprising screening (such as in isolated genetic material from the plant or plant part) for the presence of a mutation in a nucleotide sequence of a gene encoding a cytochrome P450 flavonoid 3',5'-hydroxylase (F35H) or for the presence of a mutation leading to altered expression of the mRNA of a gene encoding a cytochrome P450 flavonoid 3',5'-hydroxylase (F35H) and/or the F35H protein, or a mutation, preferably a mutation leading to an F35H protein having altered enzymatic activity upon translation, preferably leading to reduced or absent expression of the mRNA of a gene encoding a cytochrome P450 flavonoid 3',5'-hydroxylase (F35H) and/or the F35H protein (such as a knock-down or knock-out mutation), or a mutation, preferably a mutation leading to a non-functional F35H protein or an F35H protein having reduced enzymatic activity upon translation or an F35H protein having increased enzymatic activity upon translation.

In an embodiment, the invention relates to a method for identifying a plant or plant part having improved digestibility, preferably improved stover digestibility, or for selecting a plant or plant part having improved digestibility, preferably improved stover digestibility, comprising isolating genetic material from at least one cell of the plant or plant part, and screening in said genetic material for the presence of a mutation in a nucleotide sequence of a gene encoding a cytochrome P450 flavonoid 3',5'-hydroxylase (F35H) or for the presence of a mutation leading to altered expression of the mRNA of a gene encoding a cytochrome P450 flavonoid 3',5'-hydroxylase (F35H) and/or the F35H protein, or a mutation, preferably a mutation leading to an F35H protein having altered enzymatic activity upon translation, preferably leading to reduced or absent expression of the mRNA of a gene encoding a cytochrome P450 flavonoid 3',5'-hydroxylase (F35H) and/or the F35H protein (such as a knock-down or knock-out mutation), or a mutation, preferably a mutation leading to a non-functional F35H protein or an F35H protein having reduced enzymatic activity upon translation or an F35H protein having increased enzymatic activity upon translation.

In an embodiment, the invention relates to a method for identifying a plant or plant part having improved digestibility, preferably improved stover digestibility, or for selecting a plant or plant part having improved digestibility, preferably improved stover digestibility, comprising screening (such as in isolated genetic material from the plant or plant part) for the presence of a mutation in a nucleotide sequence of a gene encoding a cytochrome P450 flavonoid 3',5'-hydroxylase (F35H), or for the presence of a mutation leading to altered expression of the mRNA of a gene encoding a cytochrome P450 flavonoid 3',5'-hydroxylase (F35H) and/or the F35H protein, or a mutation, preferably a mutation leading to an F35H protein having altered enzymatic activity upon translation, preferably leading to reduced or absent expression of the mRNA of a gene encoding a cytochrome P450 flavonoid 3',5'-hydroxylase (F35H) and/or the F35H protein (such as a knock-down or knock-out mutation), or a mutation, preferably a mutation leading to a non-functional F35H protein or an F35H protein having reduced enzymatic activity upon translation or an F35H protein having increased enzymatic activity upon translation, and selecting a plant or plant part in which the mutation in said F35H is present.

In an embodiment, the invention relates to a method for identifying a plant or plant part having improved digestibility, preferably improved stover digestibility, or for selecting a plant or plant part having improved digestibility, preferably improved stover digestibility, comprising isolating genetic material from at least one cell of the plant or plant part, screening in said genetic material for the presence of a mutation in a nucleotide sequence of a gene encoding a cytochrome P450 flavonoid 3',5'-hydroxylase (F35H), or for the presence of a mutation leading to altered expression of the mRNA of a gene encoding a cytochrome P450 flavonoid 3',5'-hydroxylase (F35H) and/or the F35H protein, or a mutation, preferably a mutation leading to an F35H protein having altered enzymatic activity upon translation, preferably leading to reduced or absent expression of the mRNA of a gene encoding a cytochrome P450 flavonoid 3',5'-hydroxylase (F35H) and/or the F35H protein (such as a knock-down or knock-out mutation), or a mutation, preferably a mutation leading to a non-functional F35H protein or an F35H protein having reduced enzymatic activity upon translation or an F35H protein having increased enzymatic activity upon translation, and selecting a plant or plant part in which a mutation in said F35H is present.

In an aspect, the invention relates to a method for identifying a plant or plant part having improved digestibility, preferably improved stover digestibility, or for selecting a plant or plant part having improved digestibility, preferably improved stover digestibility, comprising (such as in isolated material from the plant or plant part) analysing the (protein and/or mRNA) expression level of a gene encoding a cytochrome P450 flavonoid 3',5'-hydroxylase (F35H) and/or screening for altered expression of the mRNA of a gene encoding a cytochrome P450 flavonoid 3',5'-hydroxylase (F35H) and/or the F35H protein or an F35H protein having altered enzymatic activity, preferably for reduced or absent expression of the mRNA of a gene encoding a cytochrome P450 flavonoid 3',5'-hydroxylase (F35H) and/or the F35H protein or for a non-functional F35H protein or an F35H protein having reduced enzymatic activity or an F35H protein having reduced enzymatic activity.

In an embodiment, the invention relates to a method for identifying a plant or plant part having improved digestibility, preferably improved stover digestibility, or for selecting a plant or plant part having improved digestibility, preferably improved stover digestibility, comprising isolating material from at least one cell of the plant or plant part, and analysing the (protein and/or mRNA) expression level of a gene encoding a cytochrome P450 flavonoid 3',5'-hydroxylase (F35H) in said material and/or screening for altered expression of the mRNA of a gene encoding a cytochrome P450 flavonoid 3',5'-hydroxylase (F35H) and/or the F35H protein or an F35H protein having altered enzymatic activity, preferably for reduced or absent expression of the mRNA of a gene encoding a cytochrome P450 flavonoid 3',5'-hydroxylase (F35H) and/or the F35H protein or for a non-functional F35H protein or an F35H protein having reduced enzymatic activity or an F35H protein having reduced enzymatic activity in said material.

In an embodiment, the invention relates to a method for identifying a plant or plant part having improved digestibility, preferably improved stover digestibility, or for selecting a plant or plant part having improved digestibility, preferably improved stover digestibility, comprising analysing (such as in isolated material from the plant or plant part) the (protein and/or mRNA) expression level of a gene encoding a cytochrome P450 flavonoid 3',5'-hydroxylase (F35H), and selecting a plant or plant part in which the F35H mRNA and/or protein expression or the enzymatic F35H activity is altered, preferably is reduced or eliminated or the enzymatic F35H activity is reduced or increased.

In an embodiment, the invention relates to a method for identifying a plant or plant part having improved digestibility, preferably improved stover digestibility, or for selecting a plant or plant part having improved digestibility, preferably improved stover digestibility, comprising isolating material from at least one cell of the plant or plant part, analysing the (protein and/or mRNA) expression level of a gene encoding a cytochrome P450 flavonoid 3',5'-hydroxylase (F35H) in said material and/or screening for altered expression of the mRNA of a gene encoding a cytochrome P450 flavonoid 3',5'-hydroxylase (F35H) and/or the F35H protein or an F35H protein having altered enzymatic activity, preferably for reduced or absent expression of the mRNA of a gene encoding a cytochrome P450 flavonoid 3',5'-hydroxylase (F35H) and/or the F35H protein or for a non-functional F35H protein or an F35H protein having reduced enzymatic activity or an F35H protein having reduced enzymatic activity in said material, and selecting a plant or plant part in which the F35H mRNA and/or protein expression or the enzymatic F35H activity is altered, preferably reduced or eliminated or the enzymatic F35H activity is reduced or increased.

In certain embodiments, if the (protein and/or mRNA) expression level of the F35H, in particular the wild type or native F35H, is altered, then the plant or plant part has improved digestibility. In certain embodiments, if the (protein and/or mRNA) expression level of the F35H, in particular the wild type or native F35H, is altered compared to a reference expression level, then the plant or plant part has improved digestibility. In certain embodiments, if the (protein and/or mRNA) expression level of the F35H, in particular the wild type or native F35H, is altered compared to the reference expression level in a reference plant or plant part, then the plant or plant part has improved digestibility. In certain embodiments, the reference plant (or plant part) is the maize inbred line PH207, as described in "Draft Assembly of Elite Inbred Line PH207 Provides Insights into Genomic and Transcriptome Diversity in Maize", Hirsch et al., Plant Cell. 2016 November; 28(11): 2700-2714. Published online 2016 Nov. 1. doi: 10.1105/tpc.16.00353, or a maize plant comprising the QTL allele comprising the wild type or native (unmutated) nucleotide sequence of a gene encoding a cytochrome P450 flavonoid 3',5'-hydroxylase (F35H) (e.g., derived from PH207), preferably the reference plant (or plant part) is derived from a near isogenic line.

As used herein, altered (protein and/or mRNA) expression levels refers to increased or decreased expression levels of about at least 10%, preferably at least 30%, more preferably at least 50%, such as at least 20%, 40%, 60%, 80% or more, such as at least 85%, at least 90%, at least 95%, or more.

In a particular embodiments, if the (protein and/or mRNA) expression level of the F35H, in particular the wild type or native F35H, is reduced or expression is (substantially) absent or eliminated, then the plant or plant part has improved digestibility. In certain embodiments, if the (protein and/or mRNA) expression level of the F35H, in particular the wild type or native F35H, is reduced or expression is (substantially) absent or eliminated compared to a reference expression level, then the plant or plant part has improved digestibility. In certain embodiments, if the (protein and/or mRNA) expression level of the F35H, in particular the wild type or native F35H, is reduced or expression is (substantially) absent or eliminated compared to the reference expression level in a reference plant or plant part, then the plant or plant part has improved digestibility. In certain embodiments, the reference plant (or plant part) is the maize inbred line PH207, as described in "Draft Assembly of Elite Inbred Line PH207 Provides Insights into Genomic and Transcriptome Diversity in Maize", Hirsch et al., Plant Cell. 2016 November; 28(11): 2700-2714. Published online 2016 Nov. 1. doi: 10.1105/tpc.16.00353, or a maize plant comprising the QTL allele comprising the wild type or native (unmutated) nucleotide sequence of a gene encoding a cytochrome P450 flavonoid 3',5'-hydroxylase (F35H) (e.g., derived from PH207), preferably the reference plant (or plant part) is derived from a near isogenic line.

As used herein, reduced (protein and/or mRNA) expression levels refers to decreased expression levels of about at least 10%, preferably at least 30%, more preferably at least 50%, such as at least 20%, 40%, 60%, 80% or more, such as at least 85%, at least 90%, at least 95%, or more. Expression is (substantially) absent or eliminated if expression levels are reduced at least 80%, preferably at least 90%, more preferably at least 95%. In certain embodiments, expression is (substantially) absent, if no protein and/or mRNA, in particular the wild type or native protein and/or mRNA, can be detected, such as by standard detection methods, including for instance (quantitative) PCR, northern blot, western blot, ELISA, etc.

In an aspect, the invention relates to a method for identifying a plant or plant part having improved digestibility, preferably improved stover digestibility, or for selecting a plant or plant part having improved digestibility, preferably improved stover digestibility, comprising screening (such as in isolated genetic material from the plant or plant part) for the presence of one or more (molecular) marker allele associated with improved digestibility, said (molecular) marker allele being the molecular marker allele of ma61134xxx, and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

In an embodiment, the invention relates to a method for identifying a plant or plant part having improved digestibility, preferably improved stover digestibility, or for selecting a plant or plant part having improved digestibility, preferably improved stover digestibility, comprising isolating genetic material from at least one cell of the plant or plant part, and screening in said genetic material for the presence of one or more (molecular) marker allele associated with improved digestibility, said (molecular) marker allele being the molecular marker allele of ma61134xxx, and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

In an embodiment, the invention relates to a method for identifying a plant or plant part having improved digestibility, preferably improved stover digestibility, or for selecting a plant or plant part having improved digestibility, preferably improved stover digestibility, comprising screening (such as in isolated genetic material from the plant or plant part) for the presence of one or more (molecular) marker allele associated with improved digestibility, said (molecular) marker allele being the molecular marker allele of ma61134xxx, and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility, and selecting a plant or plant part in which the one or more (molecular) marker allele is present.

In an embodiment, the invention relates to a method for identifying a plant or plant part having improved digestibility, preferably improved stover digestibility, or for selecting a plant or plant part having improved digestibility, preferably improved stover digestibility, comprising isolating genetic material from at least one cell of the plant or plant part, screening in said genetic material for the presence of one or more (molecular) marker allele associated with improved digestibility, said (molecular) marker allele being the molecular marker allele of ma61134xxx, and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility, and selecting a plant or plant part in which the one or more (molecular) marker allele is present.

In an aspect, the invention relates to a method for identifying a plant or plant part having improved digestibility, preferably improved stover digestibility, or for selecting a plant or plant part having improved digestibility, preferably improved stover digestibility, comprising screening (such as in isolated genetic material from the plant or plant part) for the presence of the molecular marker allele of ma61134xxx, and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

In an embodiment, the invention relates to a method for identifying a plant or plant part having improved digestibility, preferably improved stover digestibility, or for selecting a plant or plant part having improved digestibility, preferably improved stover digestibility, comprising isolating genetic material from at least one cell of the plant or plant part, and screening in said genetic material for the presence of the molecular marker allele of ma61134xxx, and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

In an embodiment, the invention relates to a method for identifying a plant or plant part having improved digestibility, preferably improved stover digestibility, or for selecting a plant or plant part having improved digestibility, preferably improved stover digestibility, comprising screening (such as in isolated genetic material from the plant or plant part) for the presence of the molecular marker allele of ma61134xxx, and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility, and selecting a plant or plant part in which the one or more (molecular) marker allele is present.

In an embodiment, the invention relates to a method for identifying a plant or plant part having improved digestibility, preferably improved stover digestibility, or for selecting a plant or plant part having improved digestibility, preferably improved stover digestibility, comprising isolating genetic material from at least one cell of the plant or plant part, screening in said genetic material for the presence of the molecular marker allele of ma61134xxx, and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility, and selecting a plant or plant part in which the one or more (molecular) marker allele is present.

It will be understood that in the methods as described above, when the QTL allele or (molecular) marker allele is present, then the plant or plant part is identified as having improved digestibility.

Methods for screening for the presence of a QTL allele or (molecular) marker allele as described herein are known in the art. Without limitation, screening may encompass or comprise sequencing, hybridization based methods (such as (dynamic) allele-specific hybridization, molecular beacons, SNP microarrays), enzyme based methods (such as PCR, KASP (Kompetitive Allele Specific PCR), RFLP, ALFP, RAPD, Flap endonuclease, primer extension, 5'-nuclease, oligonucleotide ligation assay), post-amplification methods based on physical properties of DNA (such as single strand conformation polymorphism, temperature gradient gel electrophoresis, denaturing high performance liquid chromatography, high-resolution melting of the entire amplicon, use of DNA mismatch-binding proteins, SNPlex, surveyor nuclease assay), etc.

In an aspect, the invention relates to a method, such as a method for generating/producing a plant or plant part having improved digestibility, preferably improved stover digestibility, and/or improving digestibility of a plant or plant part, preferably stover digestibility, comprising introducing or introgressing into the genome of a plant or plant part a QTL allele associated with improved digestibility and comprising a nucleotide sequence of a gene encoding a cytochrome P450 flavonoid 3',5'-hydroxylase having a mutation.

In an aspect, the invention relates to a method, such as a method for generating/producing a plant or plant part having improved digestibility, preferably improved stover digestibility, and/or for improving digestibility of a plant or plant part, preferably stover digestibility, comprising introducing or introgressing into the genome of a plant or plant part a QTL allele comprising a nucleotide sequence of a gene encoding a cytochrome P450 flavonoid 3',5'-hydroxylase having a mutation.

In certain embodiments, the mutation leads to altered expression of the mRNA of the gene and/or the F35H protein, or the mutation leads to an F35H protein having altered enzymatic activity upon translation, more preferably the mutation leads to reduced or absent expression of the mRNA of said gene and/or the F35H protein, to a knock-out or knock-down of said gene or a mutation leading to a non-functional F35H protein (e.g., truncated F35H protein) (e.g., truncated F35H protein) or an F35H protein having reduced enzymatic activity upon translation or an F35H protein having increased enzymatic activity upon translation.

In certain embodiments of both aforementioned aspects related to the method for generating/producing a plant or plant part and/or for improving digestibility of a plant or plant part, preferably stover digestibility, the QTL allele is located on chromosome 9 and comprises and/or is flanked by marker alleles ma61070s01 and ma30168s02, preferably by marker alleles ma50827s01 and ma16983s02, more preferably by marker alleles ma17117s01 and ma61125s01.

In certain embodiments, the QTL allele is located on chromosome 9 and comprises the (molecular) marker allele of ma61134xxx.

In certain embodiments, the QTL allele is located on a chromosomal interval comprising and/or flanked by (molecular) marker alleles ma61070s01 and ma30168s02, preferably by marker alleles ma50827s01 and ma16983s02, more preferably by marker alleles ma17117s01 and ma61125s01.

In certain embodiments, the QTL allele is located on a chromosomal interval comprising the marker allele of ma61134xxx and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

In an aspect, the invention relates to a method, such as a method for generating/producing a plant or plant part having improved digestibility, preferably improved stover digestibility, and/or for improving digestibility of a plant or plant part, preferably stover digestibility, comprising introducing into the genome of a plant or plant part a QTL allele associated with improved digestibility and comprising the marker allele of ma61134xxx and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

In an aspect, the invention relates to a method, such as a method for generating/producing a plant or plant part having improved digestibility, preferably improved stover digestibility, and/or for improving digestibility of a plant or plant part, preferably stover digestibility, comprising introducing into the genome of a plant or plant part a QTL allele comprising the marker allele of ma61134xxx and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

In an aspect, the invention relates to a method, such as a method for generating/producing a plant or plant part having improved digestibility, preferably improved stover digestibility, and/or for improving digestibility of a plant or plant part, preferably stover digestibility, comprising introducing or introgressing into the genome of a plant or plant part a nucleotide sequence of a gene encoding a cytochrome P450 flavonoid 3',5'-hydroxylase (F35H) having a mutation.

In an aspect, the invention relates to a method, such as a method for generating/producing a plant or plant part having improved digestibility, preferably improved stover digestibility, and/or for improving digestibility of a plant or plant part, preferably stover digestibility, comprising introducing into the genome of a plant or plant, in particular into a nucleotide sequence of an endogenous gene encoding a cytochrome P450 flavonoid 3',5'-hydroxylase a mutation.

In an aspect, the invention relates to a method, such as a method for generating/producing a plant or plant part having improved digestibility, preferably improved stover digestibility, and/or for improving digestibility of a plant or plant part, preferably stover digestibility, comprising altering an endogenous gene encoding a cytochrome P450 flavonoid 3',5'-hydroxylase gene, preferably knocking out an endogenous gene encoding a cytochrome P450 flavonoid 3',5'-hydroxylase gene.

In an aspect, the invention relates to a method, such as a method for generating/producing a plant or plant part having improved digestibility, preferably improved stover digestibility, and/or for improving digestibility of a plant or plant part, preferably stover digestibility, comprising altering mRNA expression of gene encoding a cytochrome P450 flavonoid 3',5'-hydroxylase gene (F35H) and/or the encoded F35H protein, preferably knocking down mRNA expression of gene encoding a cytochrome P450 flavonoid 3',5'-hydroxylase gene (F35H) and/or the encoded F35H protein.

In an aspect, the invention relates to a method, such as a method for generating/producing a plant or plant part having improved digestibility, preferably improved stover digestibility, and/or for improving digestibility of a plant or plant part, preferably stover digestibility, comprising altering the expression of mRNA of a gene encoding a cytochrome P450 flavonoid 3',5'-hydroxylase and/or the F35H protein or altering the enzymatic activity of a cytochrome P450 flavonoid 3',5'-hydroxylase (F35H), preferably eliminating or reducing or inhibiting expression of mRNA of a gene encoding a cytochrome P450 flavonoid 3',5'-hydroxylase and/or the F35H protein, reducing the enzymatic activity of a cytochrome P450 flavonoid 3',5'-hydroxylase (F35H) or inhibiting the F35H protein, or increasing the enzymatic activity of a cytochrome P450 flavonoid 3',5'-hydroxylase (F35H).

In certain embodiments, the invention relates to a method, such as a method generating/producing a plant or plant part having improved digestibility, preferably improved stover digestibility, and/or for improving digestibility, preferably stover digestibility, of a plant or plant part, comprising A. introducing into a nucleotide sequence of an endogenous gene of the plant or plant part encoding a cytochrome P450 flavonoid 3',5'-hydroxylase a mutation or other genetic event leading to altered expression of the mRNA of the gene and/or the F35H protein, or a mutation leading to an F35H protein having altered enzymatic activity upon translation, more preferably a mutation leading reduced or absent expression of the mRNA of said gene and/or the F35H protein, to a knock-out or knock-down of said gene or a mutation leading to a non-functional F35H protein (e.g., truncated F35H protein) or an F35H protein having reduced enzymatic activity upon translation, or an F35H protein having increased enzymatic activity upon translation; or B. introducing into the genome of the plant or plant part a first double-stranded DNA and a second double-stranded DNA, wherein the nucleotide sequences of the coding strands of the first and second DNA are reverse complements of each other, so that a transcript of the first DNA and a transcript of the second DNA are capable of hybridizing to form a double-stranded RNA, wherein the coding strand of the first or the second DNA comprises:

a. at least 19 successive nucleotides of the nucleotide sequence of SEQ ID NO: 2, 5, or 8 or of a nucleotide sequence having at least 60% identity, preferably at least 70% or at least 80%, more preferably at least 90%, at least 92%, at least 94%, at least 95%, at least 96%, at least 97%, at least 98% or at least 99% to the sequence of SEQ ID NO: 2, 5, or 8; or b. a nucleotide sequence which is complementary to at least 19 successive nucleotides of the nucleotide sequence of SEQ ID NO: 2, 5, or 8 or of a nucleotide sequence having at least 60% identity, preferably at least 70% or at least 80%, more preferably at least 90%, at least 92%, at least 94%, at least 95%, at least 96%, at least 97%, at least 98% or at least 99% to the sequence of SEQ ID NO: 2, 5, or 8; or C. a double-stranded RNA, wherein one strand corresponds to:

a. at least 19 successive nucleotides of the nucleotide sequence of SEQ ID NO: 2, 5, or 8 or of a nucleotide sequence having at least 60% identity, preferably at least 70% or at least 80%, more preferably at least 90%, at least 92%, at least 94%, at least 95%, at least 96%, at least 97%, at least 98% or at least 99% to the sequence of SEQ ID NO: 2, 5, or 8, wherein T is replaced by U; or b. a nucleotide sequence which is complementary to at least 19 successive nucleotides of the nucleotide sequence of SEQ ID NO: 2, 5, or 8 or of a nucleotide sequence having at least 60% identity, preferably at least 70% or at least 80%, more preferably at least 90%, at least 92%, at least 94%, at least 95%, at least 96%, at least 97%, at least 98% or at least 99% to the sequence of SEQ ID NO: 2, 5, or 8, wherein T is replaced by U; or D. introducing into the plant or the plant part an RNA-specific CRISPR/Cas system, such as a CRISPR/Cas13a system, directed against or targeting a nucleotide sequence encoding the F35H protein, or into the genome of the plant or plant part one or more polynucleotide sequence(s) encoding (and expressing or being capable of expressing) said RNA-specific CRISPR/Cas system; or E. introducing into the plant or the plant part a chemical compound or an antibody altering (or being capable to alter) the enzymatic activity of the F35H protein upon interaction with said F35H, preferably reducing (or being capable to reduce) the enzymatic activity of the F35H protein or inhibiting (or being capable to inhibit) the enzymatic activity of F35H protein or increasing (or being capable to increase) the enzymatic activity of the F35H protein upon interaction with said F35H.

In certain embodiments, the invention relates to a method, such as a method generating/producing a plant or plant part having improved digestibility, preferably improved stover digestibility, and/or for improving digestibility, preferably stover digestibility, of a plant or plant part, comprising regenerating a plant from the plant part of aforementioned modified plants or plant parts.

In an aspect, the invention relates to a plant or plant part comprising a QTL allele associated with improved digestibility, preferably improved stover digestibility, said QTL allele comprising a nucleotide sequence of a gene encoding a cytochrome P450 flavonoid 3',5'-hydroxylase (F35H) having a mutation.

In an aspect, the invention relates to a plant or plant part comprising a QTL allele comprising a nucleotide sequence of a gene encoding a cytochrome P450 flavonoid 3',5'-hydroxylase (F35H) having a mutation.

In certain embodiments, the mutation leads to altered expression of the mRNA of said gene and/or the F35H protein, or the mutation leads to an F35H protein having altered enzymatic activity upon translation. Altered expression of F35H may be effected for instance by any of the mutagenesis methods described herein.

In certain embodiments, the mutation leads to reduced or absent expression of the mRNA of said gene and/or the F35H protein, to a knock-out or knock-down of said gene or a mutation leading to a non-functional F35H protein (e.g., truncated F35H protein) or an F35H protein having reduced or increased enzymatic activity upon translation. Knock-down or knockout of F35H may be effected for instance by any of the mutagenesis methods described herein.

In certain embodiments, the QTL allele is located on chromosome 9 and comprises and/or is flanked by (molecular) marker alleles ma61070s01 and ma30168s02, preferably by marker alleles ma50827s01 and ma16983s02, more preferably by marker alleles ma17117s01 and ma61125s01.

In certain embodiments, the QTL allele is located on chromosome 9 and comprises the marker allele of ma61134xxx and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

In certain embodiments, the QTL allele is located on a chromosomal interval comprising and/or flanked by (molecular) marker alleles ma61070s01 and ma30168s02, preferably by marker alleles ma50827s01 and ma16983s02, more preferably by marker alleles ma17117s01 and ma61125s01.

In certain embodiments, the QTL allele is located on a chromosomal interval comprising the marker allele of ma61134xxx and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

In an aspect, the invention relates to a plant or plant part comprising a nucleotide sequence of a gene encoding a cytochrome P450 flavonoid 3',5'-hydroxylase (F35H) having a mutation.

In an aspect, the invention relates to a plant or plant part comprising the marker allele of ma61134xxx and/or one or more molecular marker alleles located in a chromosomal interval on chromosome 9 flanked by marker alleles ma61070s01 and ma30168s02, preferably by marker alleles ma50827s01 and ma16983s02, more preferably by marker alleles ma17117s01 and ma61125s01, preferably wherein the one or more molecular marker alleles are detectable by a polynucleic acid, such as an allele specific polynucleic acid (molecular marker), suitable for hybridization as forward primer and reverse primer to a locus in the chromosomal interval which co-segregates with the improved digestibility.

In an aspect, the invention relates to a plant or plant part comprising

A. a gene encoding a cytochrome P450 flavonoid 3',5'-hydroxylase (F35H) having a mutation or other genetic event, preferably a mutation or other genetic event leading to altered expression of the mRNA of the gene and/or the F35H protein, or a mutation leading to an F35H protein having altered enzymatic activity upon translation, more preferably a mutation leading to a knock-out or knock-down of said gene, or having reduced or eliminated mRNA and/or protein expression of an F35H gene, or a mutation or other genetic event leading to a non-functional F35H protein (e.g., truncated F35H protein) or an F35H protein having reduced enzymatic activity upon translation or an F35H protein having increased enzymatic activity upon translation; or B. a (stably integrated) first double-stranded DNA and a (stably integrated) second double-stranded DNA, wherein the nucleotide sequences of the coding strands of the first and second DNA are reverse complements of each other, so that a transcript of the first DNA and a transcript of the second DNA are capable of hybridizing to form a double-stranded RNA, wherein the coding strand of the first or the second DNA comprises:

a. at least 19 successive nucleotides of the nucleotide sequence of SEQ ID NO: 2, 5, or 8 or of a nucleotide sequence having at least 60% identity, preferably at least 70% or at least 80%, more preferably at least 90%, at least 92%, at least 94%, at least 95%, at least 96%, at least 97%, at least 98% or at least 99% to the sequence of SEQ ID NO: 2, 5, or 8, or b. a nucleotide sequence which is complementary to at least 19 successive nucleotides of the nucleotide sequence of SEQ ID NO: 2, 5, or 8 or of a nucleotide sequence having at least 60% identity, preferably at least 70% or at least 80%, more preferably at least 90%, at least 92%, at least 94%, at least 95%, at least 96%, at least 97%, at least 98% or at least 99% to the sequence of SEQ ID NO: 2, 5, or 8; or C. a double-stranded RNA, wherein one strand corresponds to:

a. at least 19 successive nucleotides of the nucleotide sequence of SEQ ID NO: 2, 5, or 8 or of a nucleotide sequence having at least 60% identity, preferably at least 70% or at least 80%, more preferably at least 90%, at least 92%, at least 94%, at least 95%, at least 96%, at least 97%, at least 98% or at least 99% to the sequence of SEQ ID NO: 2, 5, or 8, wherein T is replaced by U; or b. a nucleotide sequence which is complementary to at least 19 successive nucleotides of the nucleotide sequence of SEQ ID NO: 2, 5, or 8 or of a nucleotide sequence having at least 60% identity, preferably at least 70% or at least 80%, more preferably at least 90%, at least 92%, at least 94%, at least 95%, at least 96%, at least 97%, at least 98% or at least 99% to the sequence of SEQ ID NO: 2, 5, or 8, wherein T is replaced by U; or D. an RNA-specific CRISPR/Cas system, such as a CRISPR/Cas13a system, directed against or targeting a nucleotide sequence encoding the F35H protein, or one or more polynucleotide sequence(s) encoding (and expressing or being capable of expressing) said RNA-specific CRISPR/Cas system; or E. a chemical compound or an antibody altering (or being capable to alter) the enzymatic activity of the F35H protein upon interaction with said F35H, preferably reducing (or being capable to reduce) the enzymatic activity of the F35H protein or inhibiting (or being capable to inhibit) the F35H protein upon interaction with said F35H or increasing (or being capable to increase) the F35H protein upon interaction with said F35H.

In certain embodiments, the plant is not a plant variety.

In an aspect, the invention relates to a method for obtaining or generating or producing a plant or plant part, such as a maize or *Sorghum* plant or sugar cane or plant part, preferably a maize plant or plant part, comprising (a) providing a first plant having a QTL allele, such as a QTL allele associated with improved digestibility as described herein elsewhere, optionally wherein said QTL allele is located on a chromosomal interval, preferably on chromosome 9, comprising and flanked by (molecular) marker alleles ma61070s01 and ma30168s02, preferably by marker alleles ma50827s01 and ma16983s02, more preferably by marker alleles ma17117s01 and ma61125s01, (b) crossing said first plant with a second plant, such as a second plant not having said QTL allele, (c) selecting progeny plants having said QTL allele, and optionally (d) harvesting said plant part from said progeny.

In certain embodiments, the QTL allele comprises one or more of the marker alleles of the invention as described herein elsewhere.

In certain embodiments, the QTL allele comprises a mutated F35H gene as described herein elsewhere.

In an aspect, the invention relates to a method for obtaining or generating or producing a plant or plant part, such as a maize or *Sorghum* or sugar cane plant or plant part, preferably a maize plant or plant part, comprising (a) providing a first plant having a (molecular) marker allele, such as a (molecular) marker allele associated with improved digestibility as described herein elsewhere, optionally wherein said (molecular) marker allele is located on a chromosomal interval, preferably on chromosome 9, comprising and flanked by (molecular) marker alleles ma61070s01 and ma30168s02, preferably by marker alleles ma50827s01 and ma16983s02, more preferably by marker alleles ma17117s01 and ma61125s01; (b) crossing said first plant with a second plant, such as a second plant not having said (molecular) marker allele, (c) selecting progeny plants having said (molecular) marker allele, and optionally (d) harvesting said plant part from said progeny.

In an aspect, the invention relates to a method for obtaining or generating or producing a plant or plant part, such as a maize or *Sorghum* or sugar cane plant or plant part, comprising (a) providing a first plant having a mutated F35H gene or a first plant in which mRNA and/or protein expression of a F35H gene is altered, such as described herein elsewhere, preferably reduced or (substantially) eliminated or absent, such as described herein elsewhere, optionally wherein said mutated F35H gene is located on a chromosomal interval, preferably on chromosome 9, comprising and flanked by (molecular) marker alleles ma61070s01 and ma30168s02, preferably by marker alleles ma50827s01 and ma16983s02, more preferably by marker alleles ma17117s01 and ma61125s01, (b) crossing said first plant with a second plant, such as a second plant not having said mutated F35H gene, (c) selecting progeny plants having said mutated F35H gene, and optionally (d) harvesting said plant part from said progeny.

In certain embodiments, the QTL allele, marker allele, and/or F35H mutation in the first plant is present in a homozygous state. In certain embodiments the QTL allele, marker allele, and/or F35H mutation in the first plant is present in a heterozygous state. In certain embodiments, the QTL allele, marker allele, and/or F35H mutation in the second plant is present in a heterozygous state. In certain embodiments the QTL allele, marker allele, and/or F35H mutation in the second plant is not present.

In certain embodiments, the progeny is selected in which the QTL allele, marker allele, and/or mutated F35H is present in a homozygous state. In certain embodiments, the progeny is selected in which the QTL allele, marker allele, and/or mutated F35H is present in a heterozygous state.

In certain embodiments, the plant is or plant part is from maize.

In certain embodiments, the plant is or the plant part is from *Sorghum*.

In certain embodiments, the plant is or the plant part is from sugar cane.

In certain embodiments, the methods for obtaining plants or plant parts as described herein according to the invention, such as the methods for obtaining plants or plant parts having improved digestibility, involve or comprise transgenesis and/or gene editing and/or base editing, such as including CRISPR/Cas, TALEN, ZFN, meganucleases; (induced) mutagenesis, which may or may not be random mutagenesis, such as TILLING. In certain embodiments, the methods for obtaining plants or plant parts as described herein according to the invention, such as the methods for obtaining plants or plant parts having improved digestibility, involve or comprise RNAi applications, which may or may not be, comprise, or involve transgenic applications. By means of example, non-transgenic applications may for instance involve applying RNAi components such as double stranded siRNAs to plants or plant surfaces, such as for instance as a spray. Stable integration into the plant genome is not required.

In certain embodiments, the methods for obtaining plants or plant parts as described herein according to the invention, such as the methods for obtaining plants or plant parts having improved digestibility, do not involve or comprise transgenesis, gene editing, base editing and/or mutagenesis.

In certain embodiments, the methods for obtaining plants or plant parts as described herein according to the invention, such as the methods for obtaining plants or plant parts having improved digestibility, involve, comprise or consist of breeding and selection.

In certain embodiments, the methods for obtaining plants or plant parts as described herein according to the invention, such as the methods for obtaining plants or plant parts having improved digestibility, do not involve, comprise or consist of breeding and selection.

In an aspect, the invention relates to a plant or plant part obtained or obtainable by the methods of the invention as described herein, such as the methods for obtaining plants or plant parts having improved digestibility.

In certain embodiments, the wild type or unmutated F35H gene comprises (i) a nucleotide sequence comprising the sequence of SEQ ID NO: 1, 4, or 7;

(ii) a nucleotide sequence having the cDNA or coding sequence of SEQ ID NO: 2, 5, or 8;

(iii) a nucleotide sequence encoding for a polypeptide having the amino acid sequence of SEQ ID NO: 3, 6, or 9;

(iv) a nucleotide sequence having at least 60% identity to the sequence of SEQ ID NO: 1, 2, 4, 5, 7, or 8; such as at least 65%, 70%, 75%, 80%, 85%, 90%, 92%, 94%, 95%, 96%, 97%, 98%, 99% or more sequence identity, preferably at least 85% sequence identity, more preferably at least 90% sequence identity or at least 95% sequence identity;

(v) a nucleotide sequence encoding for a polypeptide having at least 60% identity to the sequence of SEQ ID NO: 3, 6, or 9; such as at least 65%, 70%, 75%, 80%, 85%, 90%, 92%, 94%, 95%, 96%, 97%, 98%, 99% or more sequence identity, preferably at least 85% sequence identity, more preferably at least 90% sequence identity or at least 95% sequence identity;

(vi) a nucleotide sequence hybridizing with the reverse complement of a nucleotide sequence as defined in (i), (ii) or (iii) under stringent hybridization conditions; and (vii) a nucleotide sequence encoding a protein derived from the polypeptide encoded by the nucleotide sequence of any of (i) to (vi) by way of substitution, deletion and/or addition of one or more amino acid(s).

In certain embodiments, the wild type or unmutated F35H gene comprises (i) a nucleotide sequence comprising the sequence of SEQ ID NO: 1, 4, or 7;

(ii) a nucleotide sequence having the cDNA or coding sequence of SEQ ID NO: 2, 5, or 8;

(iii) a nucleotide sequence encoding for a polypeptide having the amino acid sequence of SEQ ID NO: 3, 6, or 9;

In certain embodiments, the wild type or unmutated F35H gene comprises (i) a nucleotide sequence having at least 60% identity to the sequence of SEQ ID NO: 1, 2, 4, 5, 7, or 8; such as at least 65%, 70%, 75%, 80%, 85%, 90%, 92%, 94%, 95%, 96%, 97%, 98%, 99% or more sequence identity, preferably at least 85% sequence identity, more preferably at least 90% sequence identity or at least 95% sequence identity; or (ii) a nucleotide sequence encoding for a polypeptide having at least 60% identity to the sequence of SEQ ID NO: 3, 6, or 9; such as at least 65%, 70%, 75%, 80%, 85%, 90%, 92%, 94%, 95%, 96%, 97%, 98%, 99% or more sequence identity, preferably at least 85% sequence identity, more preferably at least 90% sequence identity or at least 95% sequence identity.

In certain embodiments, the wild type or unmutated F35H gene comprises (i) a nucleotide sequence having at least 60% identity to the sequence of SEQ ID NO: 2, 5, or 8; such as at least 65%, 70%, 75%, 80%, 85%, 90%, 92%, 94%, 95%, 96%, 97%, 98%, 99% or more sequence identity, preferably at least 85% sequence identity, more preferably at least 90% sequence identity or at least 95% sequence identity; or (ii) a nucleotide sequence encoding for a polypeptide having at least 60% identity to the sequence of SEQ ID NO: 3, 6, or 9; such as at least 65%, 70%, 75%, 80%, 85%, 90%, 92%, 94%, 95%, 96%, 97%, 98%, 99% or more sequence identity, preferably at least 85% sequence identity, more preferably at least 90% sequence identity or at least 95% sequence identity.

In certain embodiments, the wild type or unmutated F35H gene comprises (i) a nucleotide sequence comprising the sequence of SEQ ID NO: 1, 4, or 7;

(ii) a nucleotide sequence having the cDNA or coding sequence of SEQ ID NO: 2, 5, or 8;

(iii) a nucleotide sequence encoding for a polypeptide having the amino acid sequence of SEQ ID NO: 3, 6, or 9;

(iv) a nucleotide sequence having at least 60% identity to the sequence of SEQ ID NO: 1, 2, 4, 5, 7, or 8 or SEQ ID NO: 2, 5, or 8; such as at least 65%, 70%, 75%, 80%, 85%, 90%, 92%, 94%, 95%, 96%, 97%, 98%, 99% or more sequence identity, preferably at least 85% sequence identity, more preferably at least 90% sequence identity or at least 95% sequence identity;

(v) a nucleotide sequence encoding for a polypeptide having at least 60% identity to the sequence of SEQ ID NO: 3, 6, or 9; such as at least 65%, 70%, 75%, 80%, 85%, 90%, 92%, 94%, 95%, 96%, 97%, 98%, 99% or more sequence identity, preferably at least 85% sequence identity, more preferably at least 90% sequence identity or at least 95% sequence identity;

In certain embodiments, the wild type or unmutated F35H gene comprises (i) a nucleotide sequence hybridizing with the reverse complement of a nucleotide sequence of SEQ ID NO: 1, 4, or 7 or SEQ ID NO: 2, 5, or 8, under stringent hybridization conditions.

In certain embodiments, the wild type or unmutated F35H gene comprises (i) a nucleotide sequence encoding a protein derived from the polypeptide encoded by the nucleotide sequence of SEQ ID NO: 1, 4, or 7 or SEQ ID NO: 2, 5, or 8 by way of substitution, deletion and/or addition of one or more amino acid(s).

The skilled person will understand that the wild type or unmutated F35H gene product is a functional gene product having enzymatic activity, as defined herein elsewhere. The skilled person will further understand that sequence variations described above for the wild type F35H do not include frame shift or nonsense mutations.

As used herein, the mutated F35H or the mutation in the F35H may comprise or may refer to any type of F35H mutation. In certain embodiments the mutation alters expression of the wild type or native F35H protein and/or mRNA. In certain embodiments the mutation reduces or eliminates expression of the (wild type or native) F35H protein and/or mRNA, as described herein elsewhere. Mutations may affect transcription and/or translation. Mutations may occur in exons or introns. Mutations may occur in regulatory elements, such as promotors, enhancers, terminators, insulators, etc. Mutations may occur in coding sequences. Mutations may occur in splicing signal sites, such as splice donor or splice acceptor sites. Mutations may be frame shift mutations. Mutations may be nonsense mutations. Mutations may be insertion or deletion of one or more nucleotides. Mutations may be non-conservative mutations (in which one or more wild type amino acids are replaced with one or more non-wild type amino acids). Mutations may affect or alter the function of the F35H protein, such as enzymatic activity. Mutations may reduce or (substantially) eliminate the function of the F35H protein, such as enzymatic activity. Reduced function, such as reduced enzymatic activity, may refer to a reduction of about at least 10%, preferably at least 30%, more preferably at least 50%, such as at least 20%, 40%, 60%, 80% or more, such as at least 85%, at least 90%, at least 95%, or more. (Substantially) eliminated function, such as (substantially) eliminated enzymatic activity, may refer to a reduction of at least 80%, preferably at least 90%, more preferably at least 95%. Mutations may be dominant negative mutations. In certain embodiments, mutations are evaluated with reference to maize inbred line PH207, as defined herein elsewhere.

In certain embodiments, the F35H mutation is an insertion of one or more nucleotides in the coding sequence. In certain embodiments, the F35H mutation is a nonsense mutation. In certain embodiments, the F35H mutation results in altered expression of the F35H gene. In certain embodiments, the F35H mutation results in knockout of the F35H gene or knockdown of the F35H mRNA and/or protein. In certain embodiments, the mutation results in a frame shift of the coding sequence of F35H. In certain embodiments, the mutation results in an altered protein sequence encoded by the F35H gene.

In certain embodiments, the F35H mutation is an insertion, preferably in an exon, preferably an insertion in the first exon, of one or more nucleotides, preferably a frame shift insertion. In certain embodiments, the insertion is 187 nucleotides or about 187 nucleotides. In certain embodiments, the insertion is between position 97 and 98 of the F35H gene represented by the nucleotide sequence of SEQ ID NO: 1. The skilled person is capable of determining the corresponding position in F35H homologues or orthologues. In certain embodiments, the insertion comprises or consists of the nucleotide sequence of SEQ ID NO: 10. In certain embodiments, the mutated F35H comprises the nucleotide sequence of SEQ ID NO: 11. Alternatively, the mutation is a substitution, preferably a substitution of at least one nucleic acid resulting in an exchange of at least one amino acid or resulting in the change of an amino acid coding codon into a stop codon. In preferred embodiments, the mutated F35H comprises the nucleotide sequence encoding one of the amino acid sequences selected from the group consisting of SEQ ID NO: 20, 22, 24, 26, 28, 30, 32, 34, 36, 38 or 40. Such nucleotide sequence may be selected from the group consisting of SEQ ID NO: 19, 21, 23, 25, 27, 29, 31, 33, 35, 37 or 39. More specific sequence information can be found in Table 3.

F35H mRNA and/or protein expression may be reduced or eliminated by mutating the F35H gene itself (including coding, non-coding, and regulatory element). Methods for introducing mutations are described herein elsewhere. Alternatively, F35H mRNA and/or protein expression may be reduced or eliminated by (specifically) interfering with transcription and/or translation, such as to decrease or eliminate mRNA and/or protein transcription or translation. Alternatively, F35H mRNA and/or protein expression may be reduced or eliminated by (specifically) interfering with mRNA and/or protein stability, such as to reduce mRNA and/or protein stability. By means of example, mRNA (stability) may be reduced by means of RNAi, as described herein elsewhere. Also miRNA can be used to affect mRNA (stability). In certain embodiments, a reduced F35H expression which is achieved by reducing mRNA or protein stability is also encompassed by the term "mutated" F35H. In certain embodiments, a reduced F35H expression which is achieved by reducing mRNA or protein stability is not encompassed by the term "mutated" F35H.

In certain embodiments, the (molecular) marker alleles which are associated with improved digestibility as described herein are defined as follows:

- ma61134xxx is an insertion of one or more nucleotides between position 134254381 and 134254382 of chromosome 9 referenced to line PH207, preferably an insertion as set forth in SEQ ID NO: 12; and/or
- ma61070s01 is a single nucleotide polymorphism (SNP) at position 121588825 of chromosome 9 referenced to line PH207, wherein said nucleotide is A or T, preferably a single nucleotide polymorphism (SNP) as set forth in SEQ ID NO: 13; and/or
- ma30168s02 is a single nucleotide polymorphism (SNP) at position 139452428 of chromosome 9 referenced to line PH207, wherein said nucleotide is A or G, preferably a single nucleotide polymorphism (SNP) as set forth in SEQ ID NO: 14; and/or
- ma50827s01 is a single nucleotide polymorphism (SNP) at position 127454426 of chromosome 9 referenced to line PH207, wherein said nucleotide is A or G, preferably a single nucleotide polymorphism (SNP) as set forth in SEQ ID NO: 15; and/or
- ma16983s02 is a single nucleotide polymorphism (SNP) at position 137363784 of chromosome 9 referenced to line PH207, wherein said nucleotide is A or G, preferably a single nucleotide polymorphism (SNP) as set forth in SEQ ID NO: 16; and/or
- ma17117s01 is a single nucleotide polymorphism (SNP) at position 132038900 of chromosome 9 referenced to line PH207, wherein said nucleotide is A or G, preferably a single nucleotide polymorphism (SNP) as set forth in SEQ ID NO: 17; and/or
- ma61125s01 is a single nucleotide polymorphism (SNP) at position 135947973 of chromosome 9 referenced to line PH207, wherein said nucleotide is A or G, preferably a single nucleotide polymorphism (SNP) as set forth in SEQ ID NO: 18;
- preferably wherein PH207 refers to *Zea mays* inbred line as described in "Draft Assembly of Elite Inbred Line PH207 Provides Insights into Genomic and Transcriptome Diversity in Maize", Hirsch et al., Plant Cell. 2016 November; 28(11): 2700-2714. Published online 2016 Nov. 1. doi: 10.1105/tpc.16.00353.

In certain embodiments, the insertion associated with marker allele ma61134xxx is a frame shift insertion. In certain embodiments, the insertion associated with marker allele ma61134xxx is an insertion of the nucleotide sequence of SEQ ID NO: 10. In certain embodiments, marker allele ma61134xxx comprises or consists of the (contiguous) nucleotide sequence of SEQ ID NO: 12.

In certain embodiments, marker allele ma61070s01 comprises or consists of the (contiguous) nucleotide sequence of SEQ ID NO: 13.

In certain embodiments, marker allele ma30168s02 comprises or consists of the (contiguous) nucleotide sequence of SEQ ID NO: 14.

In certain embodiments, marker allele ma50827s01 comprises or consists of the (contiguous) nucleotide sequence of SEQ ID NO: 15.

In certain embodiments, marker allele ma16983s02 comprises or consists of the (contiguous) nucleotide sequence of SEQ ID NO: 16.

In certain embodiments, marker allele ma17117s01 comprises or consists of the (contiguous) nucleotide sequence of SEQ ID NO: 17.

In certain embodiments, marker allele 61125s01 comprises or consists of the (contiguous) nucleotide sequence of SEQ ID NO: 18.

In an aspect, the invention relates to the use of one or more of the (molecular) markers described herein for identifying a plant or plant part having improved digestibility. In an aspect, the invention relates to the use of one or more of the (molecular) markers described herein which are able to detect at least one diagnostic marker allele for identifying a plant or plant part having improved digestibility. In an aspect, the invention relates to the detection of one or more of the (molecular) marker alleles described herein for identifying a plant or plant part having improved digestibility.

The marker alleles of the invention as described herein may be diagnostic marker alleles which are useable for identifying or selecting plants or plant parts having improved digestibility, preferably improved stover digestibility.

In an aspect, the invention relates to a (isolated) polynucleic acid comprising a (molecular) marker allele of the invention, or the complement or the reverse complement of a (molecular) marker allele of the invention. In certain embodiments, the invention relates to a polynucleic acid comprising at least 10 contiguous nucleotides, preferably at least 15 contiguous nucleotides or at least 20 contiguous nucleotides of a (molecular) marker allele of the invention, or the complement or the reverse complement of a (molecular) marker allele of the invention. In certain embodiments, the invention relates to a polynucleic acid comprising at least 10 contiguous nucleotides, preferably at least 15 contiguous nucleotides or at least 20 contiguous nucleotides of any of SEQ ID NOs: 10, 12, 13, 14, 15, 16, 17, or 18, or the complement or the reverse complement of any of SEQ ID NOs: 10, 12, 13, 14, 15, 16, 17, or 18. In certain embodiments, the polynucleic acid is capable of discriminating between a (molecular) marker allele of the invention and a non-molecular marker allele, such as to specifically hybridise with a (molecular) marker allele of the invention. In certain embodiments, the polynucleic acid is capable of hybridising with a unique nucleotide fragment or section of any of SEQ ID NOs: 10, 12, 13, 14, 15, 16, 17, or 18, or the complement or the reverse complement of any of SEQ ID NOs: 10, 12, 13, 14, 15, 16, 17, or 18. It will be understood that a unique section or fragment preferably refers to a section or fragment comprising the SNP or the respective marker alleles of the invention (such as marker alleles ma61070s01, ma30168s02, ma50827s01, ma16983s02, ma17117s01 or ma61125s01), or a section or fragment comprising the 5' or 3' junction of the insert of a marker allele of the invention or a section or fraction comprised within the insert of a marker allele of the invention (such as marker allele ma61134xxx). In certain embodiments, the polynucleic acid or the complement or reverse complement thereof does not (substantially) hybridise with or bind to (genomic) DNA originating from maize inbred line PH207. In certain embodiments, the sequence of the polynucleic acid or the complement or reverse complement thereof does not occur or is not present in maize inbred line PH207.

In an aspect, the invention relates to a polynucleic acid capable of specifically hybridizing with a (molecular) marker allele of the invention, or the complement thereof, or the reverse complement thereof.

In certain embodiments, the invention relates to a polynucleic acid specifically hybridising with any of the sequences of SEQ ID NOs: 10, 12, 13, 14, 15, 16, 17, or 18, or the complement or the reverse complement thereof.

In certain embodiments, the polynucleic acid is a primer. In certain embodiments, the polynucleic acid is a probe.

In certain embodiments, the polynucleic acid is an allele specific polynucleic acid, such as an allele specific primer or probe.

In certain embodiments, the polynucleic acid comprises at least 15 nucleotides, such as 16, 17, 18, 19, 20, 21, 22, 23, 24, or 25 nucleotides, such as at least 30, 35, 40, 45, or 50 nucleotides, such as at least 100, 200, 300, or 500 nucleotides.

It will be understood that "specifically hybridizing" means that the polynucleic acid hybridises with the (molecular) marker allele (such as under stringent hybridisation conditions, as defined herein elsewhere), but does not (substantially) hybridise with a polynucleic acid not comprising the marker allele or is (substantially) incapable of being used as a PCR primer. By means of example, in a suitable readout, the hybridization signal with the marker allele or PCR amplification of the marker allele is at least 5 times, preferably at least 10 times stronger or more than the hybridisation signal with a non-marker allele, or any other sequence.

In an aspect, the invention relates to a kit comprising such polynucleic acids, such as primers (comprising forward and/or reverse primers) and/or probes. The kit may further comprise instructions for use.

In will be understood that in embodiments relating to a set of forward and reverse primers, only one of both primers (forward or reverse) may need to be capable of discriminating between a (molecular) marker allele of the invention and a non-marker allele, and hence may be unique. The other primer may or may not be capable of discriminating between a (molecular) marker allele of the invention and a non-marker allele, and hence may be unique.

In a further aspect, the invention relates to a method for producing an ensilaged plant material or animal feed having improved digestibility, comprising (a) growing the plant according to the present invention, (b) harvesting the plant or plant parts, (c) optionally, chopping and/or crushing the plant, and (c) ensiling the plant, optionally by adding a stimulant like a bacterial inoculant, a sugar, and an enzyme. Furthermore, the invention relates to an ensilaged plant material or animal feed produced by said method.

In an aspect, the invention relates to a method for producing biogas or bioethanol, comprising the following steps: (a) providing the plant or plant parts according to the present invention or the ensilaged plant material according to the present invention, and (b) producing biogas or bioethanol from the plant or the ensilaged plant material.

The aspects and embodiments of the invention are further supported by the following non-limiting examples.

EXAMPLES

Example 1

A QTL experiment on stover digestibility was carried out in two DH (double haploid) populations. In both populations, a QTL with strong effect was identified on the same chromosomal position on chromosome 9 (FIG. 1). The QTL region seems to not contain any of known characterized genes of the lignin metabolism.

Marker analysis using high density SNP genotyping with a SNP array showed no polymorphisms between the line harbouring the positive allele of the QTL and other commercially available lines. Taking advantage of this effect, a sequence capture experiment was carried out using a QTL carrying line and a control line. As at that time, the only genomic reference sequence was AGPv02, probes for sequence capture were developed on this reference. Data analysis turned out to be very difficult due to high repetitiveness of the region and partly low similarity between the region in B73 (AGPv02) and the QTL allele. Out of this experiment one marker, ma60405s01, was developed showing a polymorphism between the two lines in the QTL region.

Figure 2:
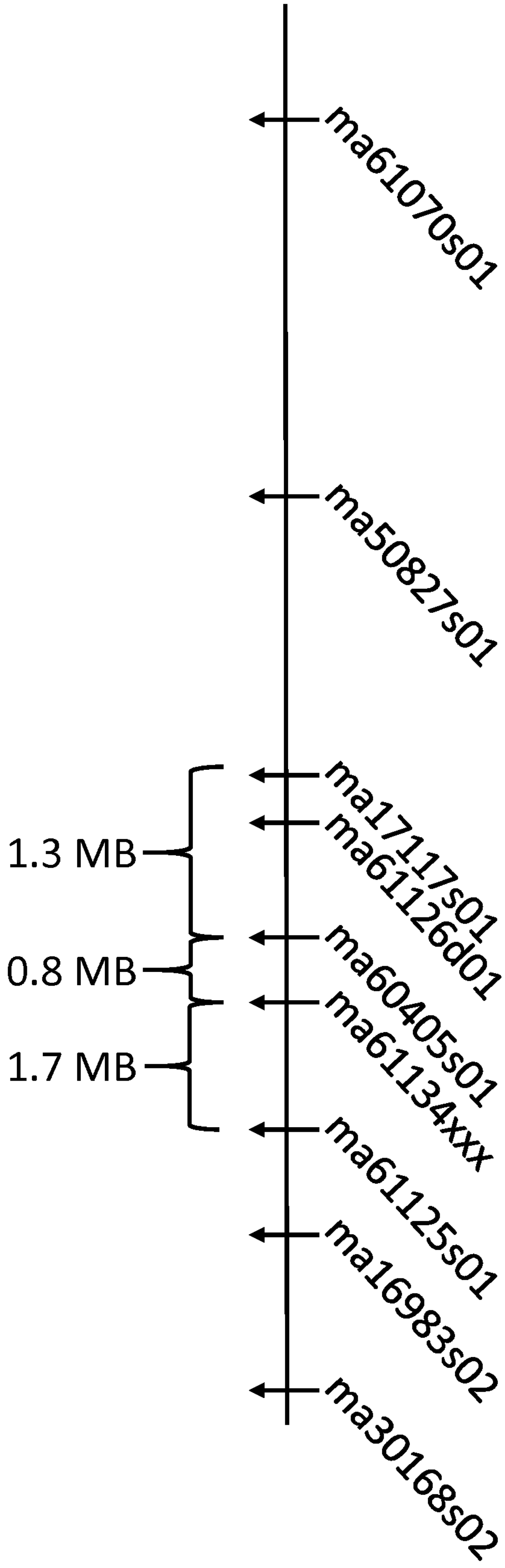
FIG. 2: Positions of marker loci for silage QTL. Markers have been found by SeqCapture on the basis of AGPv02 and WGS (whole genome sequencing) of QTL line and comparison to PH207 reference.

In order to identify further preferably polymorphic markers, a WGS (Whole Genome Sequencing) of one QTL carrying line was performed. Scaffolds covering the target were selected and compared to the reference genome of PH207 ("Draft Assembly of Elite Inbred Line PH207 Provides Insights into Genomic and Transcriptome Diversity in Maize", Hirsch et al., Plant Cell. 2016 November; 28(11): 2700-2714. Published online 2016 Nov. 1. doi: 10.1105/tpc.16.00353). Three more polymorphic markers could be identified (ma61126d01, ma61134xxx and ma61125s01, see FIG. 2). Their QTL specific alleles are unique and cannot be detected in any KWS line used for silage maize breeding.

Fine-mapping of the QTL has narrow down the region first to 16.7 MB and in the last step to approx. 719 kb on the PH207 reference (see FIG. 3 and Table 1). FIG. 3 shows two families of recombinants derived of the QTL line (B) crosses with a line not carrying the QTL (A). The indicated DNDF is the mean of all family members with or without QTL respectively. The marker, which is best associated with the phenotype in the latest recombinants, is ma61134xxx. It represents an insertion of 187 bp in a gene coding for a cytochrome P450 flavonoid 3',5'-hydroxylase (called F35H, see FIG. 4). This insertion causes an elongation of the N-terminus of the protein and an early stop codon leading likely to a knockout of the gene. The corresponding gene of AGPv02 is expressed in leaves and stem. It stands at the beginning of the flavonoid metabolism taking resources from the lignin metabolic pathway.

TABLE 1

List of markers for silage QTL or the gene as such.

| marker | Chrom | genetic map [position in cM] | PH207-public [position in bp] |
|---|---|---|---|
| ma61070s01 | 9 | | 121588825 |
| ma50827s01 | 9 | | 127454426 |
| ma17117s01 | 9 | | 132038900 |
| ma60405s01 | 9 | 55,054 | 133444836 |
| ma61134xxx | 9 | 55,98 | 134254381 |
| ma61125s01 | 9 | 56,224 | 135947973 |
| ma16983s02 | 9 | | 137363784 |
| ma30168s02 | 9 | | 139452428 |

Within the region of 133.4-135.9 MB of chromosome 9 in PH207 all other hypothetical genes derived of internal maker annotation of PH207 were checked for polymorphism between the QTL line and PH207. Out of more than 100 genes, only the described one showed a polymorphism. 79 genes were identical. The rest was mostly repetitive or only partly represented in the assembly of the QTL-line.

The capillary marker ma61134xxx could be converted to a pair of dominant KASP markers and to a codominant KASP marker, all three are available for routine use.

Most important diagnostic marker ma61134xxx is directed to the insertion in the causative gene. The insertion is present in the genotype carrying the silage QTL and absent in reference line PH207. In PH207 the following sequence is not present in the gene (SEQ ID NO: 10):

```
CTTCTGCCCAGAAGCGGGCCCAGACATTTGAGATTGGGTATTCAAAAT
TCAAAAGATTAAAGAATTTAGTGTTCTAACGCTATTTTATGCAATACAT
TATTGACAAATTAGTGTTCTAACACTATAGATCACCAAAAACATGGGTA
TTCAATGAATACCCATGAAACCCCCCTGGGCCCGCCCATG
```

The person skilled in the art is able to design markers for known marker systems which allows the detection of the presence or absence of the insertion.

Furthermore, one skilled in the art is also able to find markers for known marker systems which are suitable for further analysing of the silage QTL region as well as markers with diagnostic value basing for instances on single nucleotide polymorphisms (SNPs) or InDels (see exemplary Table 2)

TABLE 2

Marker alleles in QTL line

| Marker | Allele of QTL line |
|---|---|
| ma61070s01 | T (comprised in SEQ ID NO: 13) |
| ma50827s01 | A (comprised in SEQ ID NO: 15) |
| ma17117s01 | A (comprised in SEQ ID NO: 17) |
| ma61134xxx | cttctgcccagaagcgggcccagacatttgagattgggtattcaaa aattcaaaagattaaagaatttagtgttctaacgctattttatgca atacattattgacaaattagtgttctaacactatagatcaccaaaa acatgggtattcaatgaatacccatgaaacccccctgggcccgccc atg (SEQ ID NO: 10, comprised in SEQ ID NO: 12) |
| ma61125s01 | G (comprised in SEQ ID NO: 18) |
| ma16983s02 | G (comprised in SEQ ID NO: 16) |
| ma30168s02 | G (comprised in SEQ ID NO: 14) |

In conclusion, the present invention describes the identification of a marker haplotype spanning 3.8 MB of PH207 (see FIG. 2) and describing the genotype of the QTL line in the target region: The set of markers identified during the mapping (see Table 1 and 2) can be used to integrate the positive QTL in any relevant genetic background. Most important is the marker diagnostic for the insertion which is the functional mutation. However, the use of markers outside of the gene in flanking region closely linked to the gene can also be used in order to identify the genotype of QTL line. The unique haplotype of markers (see FIG. 2) can be used for marker assisted applications, i.e. for trait introgression through backcrossing or forward breeding and for monitoring of the presence of the unique silage haplotype. In addition, the developed markers can be used to increase the genetic variation in this chromosomal region and keeping the advantageous silage allele. Further described is the identification of a gene for the target: The knowledge of the gene and the found insertion (functional mutation) can be used for increasing genetic variability in this locus either by tilling or by genome editing or genetic modification to further improve the effect.

Example 2

Figure 5:
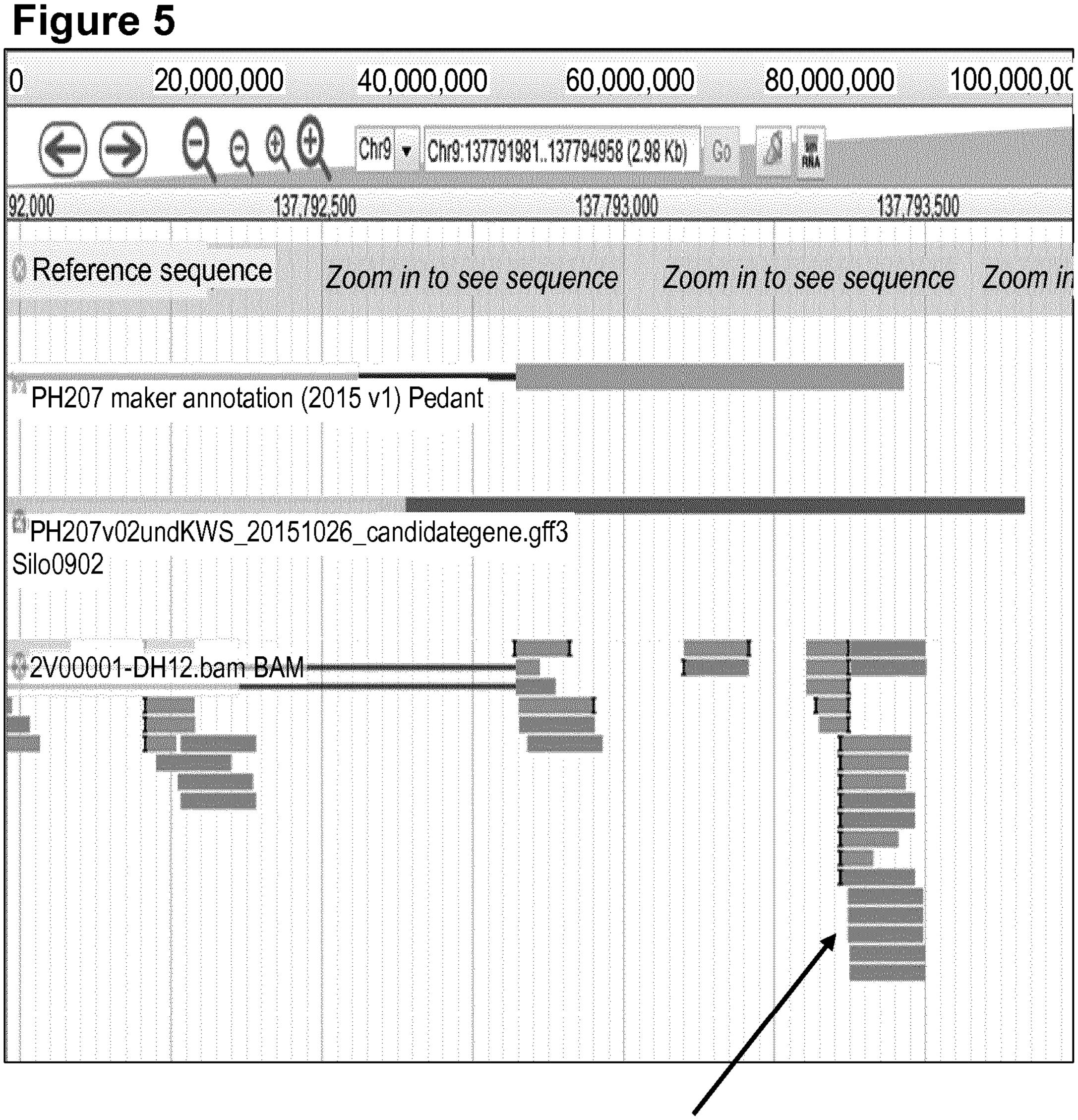
FIG. 5: Functional validation by RNAseq experiment. Arrow shows that the insertion is expressed and causes a frameshift.

For functional validation RNAseq analyses on leaf material of two QTL lines carrying the mutated F35H in a dent and a flint background are conducted. Line 5F279 without mutated F35H serves as control. The results show that the insertion is expressed and causes a frameshift (FIG. 5).

Additionally, several TILLING mutants for the native F35H gene have been identified in an EMS Tilling population of PH207 and predicted (Table 3). Two TILLING mutants (P434L (called PH207m023a) and W426stop (called PH207m023b)) has been used for validation.

TABLE 3

Identified and predicted (*) TILLING mutations

| gene | mutant ID | mutation | gDNA | protein |
|---|---|---|---|---|
| F35H-MUT | PH207m023a | P434L | SEQ ID NO: 19 | SEQ ID NO: 20 |
| F35H-MUT | PH207m023b | W426stop | SEQ ID NO: 21 | SEQ ID NO: 22 |
| F35H-MUT | PH207m023c | R252W | SEQ ID NO: 23 | SEQ ID NO: 24 |
| F35H-MUT | PH207m023d | R405H | SEQ ID NO: 25 | SEQ ID NO: 26 |

TABLE 3-continued

Identified and predicted (*) TILLING mutations

| gene | mutant ID | mutation | gDNA | protein |
|---|---|---|---|---|
| F35H-MUT | PH207m023e | P407L | SEQ ID NO: 27 | SEQ ID NO: 28 |
| F35H-MUT | PH207m023f | E427K | SEQ ID NO: 29 | SEQ ID NO: 30 |
| F35H-MUT | PH207m023g | G450R | SEQ ID NO: 31 | SEQ ID NO: 32 |
| F35H-MUT | PH207m023h* | P429S | SEQ ID NO: 33 | SEQ ID NO: 34 |
| F35H-MUT | PH207m023i* | P429L | SEQ ID NO: 35 | SEQ ID NO: 36 |
| F35H-MUT | PH207m023j* | R436C | SEQ ID NO: 37 | SEQ ID NO: 38 |
| F35H-MUT | PH207m023k* | Q44stop | SEQ ID NO: 39 | SEQ ID NO: 40 |

In pre-trial it has been showed already that the identified QTL effect can be rapidly screened under greenhouse conditions. In a first generation, seeds from the new identified F35H mutants has been grown to plants, selfed and homozygous wildtype and homozygous mutant plants have been selected. Every homozygous class represents one class. The classes are distinguished by different fixation of background mutations. From these selected homozygous seeds plants have been grown for phenotyping in a second generation. Thereby, different mutant classes could be tested and phenotyped. All classes were tested for DNDF (Digestible Neutral Detergent Fiber; Table 4) and the average for wildtype and mutant classes was calculated. For the wildtype group, the average was 56.7 and for the mutant group, it was 63.7, which is significantly higher.

TABLE 4

Greenhouse trial for fast validation of Mutants for the F35H gene

| gene | mutant ID | repetitions | versions | PDNDF |
|---|---|---|---|---|
| F35H-MUT | PH207m023a | 1 | 20 | 63.7 |
| F35H-WT | PH207m023a | 1 | 20 | 56.4 |
| F35H-MUT | PH207m023b | 4 | 2 | 64.1 |
| F35H-WT | PH207m023b | 2 | 1 | 62.9 |

Figure 6:
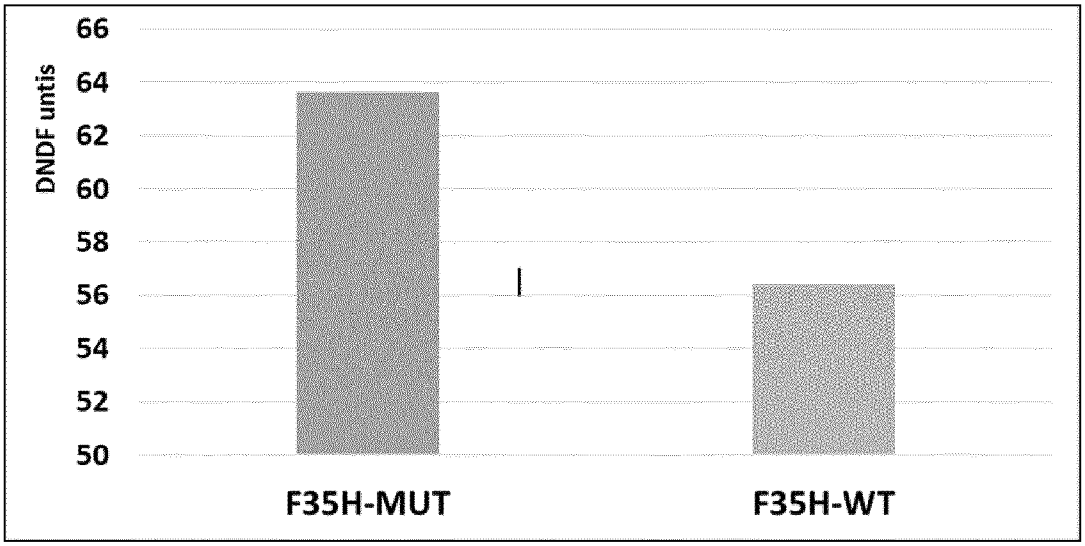
FIG. 6: Greenhouse trial for fast validation of Mutants for the F35H gene: Digestibility results of mutant and wildtype plants for identified QTL. On average PH207m023a mutant and wildtype showed a difference of 7.3 DNDF units.

Mutant lines showed the same or even improved effects with respect to digestibility. Thus, the newly identified mutations in F35H represents allelic variants which improves digestibility significantly. In particular mutant PH207m023a showed a strong effect (FIG. 6).

The invention claimed is:

1. A method for improving digestibility of a maize plant or plant part, comprising introgressing into the genome of the maize plant or plant part (a) a nucleotide sequence of a gene encoding a cytochrome P450 flavonoid 3',5'-hydroxylase (F35H) located on chromosome 9, having a mutation leading to reduced or absent expression of the mRNA of the gene and/or the F35H protein, or a mutation leading to an F35H protein having reduced enzymatic activity upon translation or a nonfunctional F35H protein, or (b) a QTL allele associated with improved digestibility, and comprising a nucleotide sequence of a gene encoding F35H located on chromosome 9, having a mutation leading to reduced or absent expression of the mRNA of the gene and/or the F35H protein or a mutation leading to an F35H protein having reduced enzymatic activity upon translation or a nonfunctional F35H protein, wherein the maize plant or plant part comprising the nucleotide sequence of (a), or the QTL allele of step (b) has improved digestibility relative to a maize plant or plant part that does not comprise the nucleotide sequence of (a), or the QTL allele of step (b), and wherein the unmutated F35H is selected from the group consisting of:

(i) a nucleotide sequence comprising the sequence of SEQ ID NO: 1;

(ii) a nucleotide sequence having the cDNA of SEQ ID NO: 2;

(iii) a nucleotide sequence encoding for an amino acid sequence having the amino acid sequence of SEQ ID NO: 3;

(iv) a nucleotide sequence having at least 90% identity to the sequence of SEQ ID NO: 1 or 2; and (v) a nucleotide sequence encoding for a polypeptide having at least 90% identity to the sequence of SEQ ID NO: 3.

2. A method for producing a maize plant or plant part having improved digestibility, comprising (a) introgressing into the genome of the maize plant or plant part a nucleotide sequence of a gene encoding a cytochrome P450 flavonoid 3',5'-hydroxylase (F35H) located on chromosome 9, having a mutation leading to reduced or absent expression of the mRNA of the gene and/or the F35H protein, or a mutation leading to an F35H protein having reduced enzymatic activity upon translation or a nonfunctional F35H protein, or (b) introgressing into the genome of the maize plant or plant part a QTL allele associated with improved digestibility, and comprising a nucleotide sequence of a gene encoding F35H located on chromosome 9, having a mutation leading to reduced or absent expression of the mRNA of the gene and/or the F35H protein, or a mutation leading to an F35H protein having reduced enzymatic activity upon translation or a non-functional F35H protein, wherein the maize plant or plant part comprising the nucleotide sequence of (a) or the QTL allele of step (b) has improved digestibility relative to a maize plant or plant part that does not comprise the nucleotide sequence of (a) or the QTL allele of step (b), and wherein the unmutated F35H is selected from the group consisting of:

(i) a nucleotide sequence comprising the sequence of SEQ ID NO: 1;

(ii) a nucleotide sequence having the cDNA of SEQ ID NO: 2;

(iii) a nucleotide sequence encoding for an amino acid sequence having the amino acid sequence of SEQ ID NO: 3;

(iv) a nucleotide sequence having at least 90% identity to the sequence of SEQ ID NO: 1 or 2; and (v) a nucleotide sequence encoding for a polypeptide having at least 90% identity to the sequence of SEQ ID NO: 3.

3. The method according to claim 1, wherein the QTL is flanked by marker alleles ma61070s01 (SEQ ID NO: 13) and ma30168s02 (SEQ ID NO: 14), or by marker alleles ma50827s01 (SEQ ID NO: 15) and ma16983s02 (SEQ ID NO: 16), or comprises and is flanked by marker alleles ma17117s01 (SEQ ID NO: 17) and ma61125s01 (SEQ ID NO: 18).

4. The method according to claim 2, wherein the QTL is flanked by marker alleles ma61070s01 (SEQ ID NO: 13) and ma30168s02 (SEQ ID NO: 14), or by marker alleles ma50827s01 (SEQ ID NO: 15) and ma16983s02 (SEQ ID NO: 16), or comprises and is flanked by marker alleles ma17117s01 (SEQ ID NO: 17) and ma61125s01 (SEQ ID NO: 18).

5. A plant or plant part having improved digestibility produced by the method according to claim 2.

6. A method for improving digestibility of a maize plant or plant part, comprising (a) reducing or suppressing activity of a gene encoding a cytochrome P450 flavonoid 3',5'-hydroxylase (F35H) located on maize chromosome 9 having the nucleotide sequence of SEQ ID NO: 1 or 2, or having a nucleotide sequence having at least 90% identity to the sequence of SEQ ID NO: 1 or 2; and/or (b) reducing or eliminating activity of a cytochrome P450 flavonoid 3',5'-hydroxylase (F35H) enzyme encoded by a gene located on maize chromosome 9 having the amino acid sequence of SEQ ID NO: 3, or having an amino acid sequence having at least 90% identity to the sequence of SEQ ID NO: 3.

7. The method of claim 6, wherein the reducing or suppressing activity of the gene encoding a F35H is achieved by:

(i) introducing into the maize plant or the plant part an RNAi molecule directed against an mRNA produced by the gene encoding a F35H;

(ii) introducing into the maize plant or the plant part an RNA-specific CRISPR/Cas system directed against the gene encoding a F35H; or (iii) introducing a mutation into the gene encoding the F35H.

8. The method of claim 6, wherein the unmutated F35H is selected from the group consisting of:

(i) a nucleotide sequence comprising the sequence of SEQ ID NO: 1;

(ii) a nucleotide sequence having the cDNA of SEQ ID NO: 2;

(iii) a nucleotide sequence encoding for an amino acid sequence having the amino acid sequence of SEQ ID NO: 3.

9. The method of claim 6, further comprising regenerating a maize plant with improved digestibility from the maize plant part having reduced F35H gene or protein activity.

10. A plant produced by the method according to claim 9.

* * * * *

SEQUENCE LISTING

```
<160> NUMBER OF SEQ ID NOS: 40

<210> SEQ ID NO 1
<211> LENGTH: 4215
<212> TYPE: DNA
<213> ORGANISM: Zea mays

<400> SEQUENCE: 1

atgcagctcg cggcgttgtg caccgacccc gtggtgctgt gcagcgcctt cctctgcctc      60

ctcctccacg tggctctccg ctcgctgctg caccctcctt ctgccgcctc ttcctccggg     120

cgccgcgggc agctcccgcc ggggccaccg ggcctgccga tcctcggcgc gctgccactc     180

gtgggcccag ccccgcacgc cggcctggcc gcgctggcgc gcaagtacgg tcccatcatg     240
```

-continued

```
tacctgaaga tgggcacggc cggcgtggtg gtggcgtcgt ccccgcgcgc ggcgcggacg    300
ttcctcaagg cgctggacgc gcggtacgcc aaccggccgg ccgtggcgag cgccgcggac    360
atcacgtacg ggcggcagaa catggtgttc gcggactacg ggcccaagtg gaagctgatg    420
cggaagctcg ccagcgtgca cctgctcggc gcgcgcgcgc tcgcggactg ggcgtgcgtg    480
cggcgcggcg aggccggcca cgtgctgcgc ggcgtggcgg aggcggccgc ggccggcagg    540
cccgtcgtcg tgccggagct gctcgtgtgc gccctcgcca acatcgtcgg gcagatcaca    600
gtgagcaagc gggtgttcga cgcgcagggg gacgactcga acaggtgagg atgggaggtc    660
catgaaatcc taccagctgt gagcatgcat aaaagttcat ttggaaagaa aagaacatat    720
ttttcttaca aatttatgct tactgtttct ttaagtttcg ataaagtttg taaaaaaaat    780
ttaggctagt ttgaaactcc atttaggatt tctattttcc aaagaaaaat aaacgaattt    840
ctcttgaaaa aatgaaaatt ctttagaaaa ataggttctc aaactagccc tcaataaaac    900
ttaatgcgat cgttttctct gactctcatt catctttctc tggttatcta attgggtcct    960
tgagagatga gtttacctgc ttgtccttta ttattgcaaa gacaacatat ctgatgcaca   1020
tggaacattg gtgcacatgg tgcacatatg aaatcatcac cactcatttt aaatctaacg   1080
tctatagttg tttgatatat tttattaagg acaccctcca acgtggtggt gtgtagtggt   1140
ggaaggtgtt atttgtaaat tgaataatca actagagacg ttagatctaa aatgagtggt   1200
gatgatttaa tatgtgcacc atgtgcacca gtcttctatg tgcaccagat atgtcctcta   1260
ttgcaaatgc tagacggaac accagctagc actagcagac tgtttatgtg gaaagaaaaa   1320
acttaaaaag atcagctagg aagctgctgt catctgtacg tatatatggt gaagactgaa   1380
caatctgcat gacaagcaaa acttagctta aaagcgaaaa gagcgatgga aacggccgct   1440
cgataaataa ttaatgagag tcttgggatt tttcatgcat ggaaaaaaac aaagctggca   1500
tttttcatct aatataatat ataacgctga tatcatattg cgtgcagata caaggacatg   1560
atcgtgtcgc tgctgaccgg cacgggcatg ttcaacatca gcgacttcgt gccggcgctg   1620
gcgcgtctgg acctgcaggg cgtgcaggcg aagctgcggc gcgtccaccg ccagttcgac   1680
ggcctcatca ccaagctgct ggccgagcac gccgcgacgg ccgcggaccg cgcgcgccag   1740
ggccgcccgg acttcgtcga ccggctccgc gccacgatgg acgccggcgc cgccgccgac   1800
gacgagagcg gcgagaccat caccgaggtc aacatcaagg gcctcatctt cgtaagctcc   1860
ctgctttttc ctcgcccccca accatgcatc atcatatgca cttatatttt acacttgctc   1920
ggttttcctt tagtaactaa ctaatccgtc gcagctgcga tacacgtagc actagtacta   1980
cagcgatggg tcatcggtaa ctgaatctaa ggtgcaatag agtgcacggc cgcgggatca   2040
tggcgtgaca tgggagctaa gctaagccag tggccaccta acgaaggcac tgaccgaaag   2100
ctcagtggcg tgttaggtgg agatagtgga tcgagttgtt ggaaagacaa tatcaaaacc   2160
actctccaat tgatgatgtg tagggcctgc agtgttttga atccaccttg tttggtcgaa   2220
cacattacta gagtgaaata tggttccaat gttaattgat agcgcgaaag ggtctctagc   2280
gtaatggtta aaccttccga gtagcacatc caggttgggt tcgatcctct cgagggcgaa   2340
ttttcaagct ttgttaaaaa aattatctcg ttgtgccccg tccgctctca ggaatcgata   2400
ttctacacga caccctccga ctagtgacag ttgattgact cgttagtgat gagaagccat   2460
gctaaaaaag tggagacgta gatatgatag aggttccctt tcctaagcaa acgtgaatgc   2520
tatgaaaatt atgcagttta aaaaaaactt taaagataaa caggaattct ctttttgga    2580
```

```
acaaacaata cgaatgcacc tccaaatatc ttatcgagtc gacttttatg gaattattgt   2640

ttttgttatt tctaagatgg gagcccaaaa tcacatacaa attattcagt gaatgcctcg   2700

gtgttttttt attagttaag ggctctcatt tttttcaagg gatttttatt tttttccaaa   2760

agaaaataaa ctaatcctct ttagaaaaat ggaaatctat tggagaaatg aggttcctaa   2820

actagctcta acagtgagtc agttaatcag gagaagatat tagactcctg tatagtgtgc   2880

agcaaccaca tccgattctg acgttttagc ttaatgttcg ctatgtagac gtcgggcata   2940

gggaatgcat tgctaccaga acacgaatga cagctatgca agtctctaga acgttggagt   3000

agttaacaaa cgtgatagat gtaacctctg gatcatggta tgatgtcatt tcctagacta   3060

gaagaattgg tagtcaaatc gagcaaagtc ccgaaagcac actgggcttt cgacacagtg   3120

ataccaaaga tgctgaaaag aactgaggca cgataaactg ttcggtgttg gtgtaaacga   3180

ccaaagatgc tgaaaataac tgatcgtcac catccgtgaa tctaactttc gacacactgt   3240

taccaaatcc ttcgtcaaaa ttacaggaat aattaaggcg cttagacgat gataaaccat   3300

tttttgtcac taattaacca cactgttctt tgcttgaccg tgacaaaaaa aaactttttt   3360

gtgaagcagt gttgccgtaa accacaacca tcatgaactc acttgccttg tcatatgtac   3420

ttgtaccatc gaacgccgcg cgctaagaca atgcaccacc cttcaagtct tagctcactg   3480

ataccgctaa ttaagttaga taatgtcgat tactagttgt cttacttcga actatttctt   3540

ttcggcaaac tgaagtaaag acaacgtttt gttccgcagg acatgttcac ggcgggtacg   3600

gacacgtcgt cgatcatcgt ggagtgggcg atggcggaga tgctcaagaa cccgaccgtc   3660

atggcgcgcg cgcaggagga gctggaccgc gcggtgggcc ggggccggcg cctggaggag   3720

tcggacctgc ccggcctccc ctacctgcag gcggtgtgca aggaggccat gcggctgcac   3780

ccgtccacgc cgctcagcct cccgcacttc tccttggacg cctgcgacga cgtcgacggc   3840

taccgcgtcc cggccaacac ccgcctgctc gtcaacgtct gggccatcgg ccgggacccg   3900

gaggcctggg agaggcccct cgacttccgc cccgagcgct tcctgcccgg gggcggcgcg   3960

gagaaggtcg acccccctggg gaactgcttc gagctcatcc cgttcggcgc cggccggagg   4020

atctgcgcgg ggaagctggc gggcatggtg ttcgtgcagt acttcctggg cacgctgctg   4080

cacgcgttcg actggcgcct gcctgacggc gaggagaagc tggacatgag cgagacgttc   4140

ggcctcgcgc tgcccaaggc agtgccgctc cgcgccgtcg ccacgccacg gctcgtgccg   4200

gaagcctatg cctga                                                    4215
```

<210> SEQ ID NO 2
<211> LENGTH: 1584
<212> TYPE: DNA
<213> ORGANISM: Artificial Sequence
<220> FEATURE:
<223> OTHER INFORMATION: cDNA of SEQ ID NO: 1

<400> SEQUENCE: 2

```
atgcagctcg cggcgttgtg caccgacccc gtggtgctgt gcagcgcctt cctctgcctc     60

ctcctccacg tggctctccg ctcgctgctg caccctcctt ctgccgcctc ttcctccggg    120

cgccgcgggc agctcccgcc ggggccaccg ggcctgccga tcctcggcgc gctgccactc    180

gtgggcccag ccccgcacgc cggcctggcc gcgctggcgc gcaagtacgg tcccatcatg    240

tacctgaaga tgggcacggc cggcgtggtg gtggcgtcgt ccccgcgcgc ggcgcggacg    300

ttcctcaagg cgctggacgc gcggtacgcc aaccggccgg ccgtggcgag cgccgcggac    360

atcacgtacg ggcggcagaa catggtgttc gcggactacg ggcccaagtg gaagctgatg    420
```

-continued

```
cggaagctcg ccagcgtgca cctgctcggc gcgcgcgcgc tcgcggactg ggcgtgcgtg     480

cggcgcggcg aggccggcca cgtgctgcgc ggcgtggcgg aggcggccgc ggccggcagg     540

cccgtcgtcg tgccggagct gctcgtgtgc gccctcgcca acatcgtcgg gcagatcaca     600

gtgagcaagc gggtgttcga cgcgcagggg gacgactcga acagatacaa ggacatgatc     660

gtgtcgctgc tgaccggcac gggcatgttc aacatcagcg acttcgtgcc ggcgctggcg     720

cgtctggacc tgcagggcgt gcaggcgaag ctgcggcgcg tccaccgcca gttcgacggc     780

ctcatcacca agctgctggc cgagcacgcc gcgacggccg cggaccgcgc gcgccagggc     840

cgcccggact tcgtcgaccg gctccgcgcc acgatggacg ccggcgccgc cgccgacgac     900

gagagcggcg agaccatcac cgaggtcaac atcaagggcc tcatcttcga catgttcacg     960

gcgggtacgg acacgtcgtc gatcatcgtg gagtgggcga tggcggagat gctcaagaac    1020

ccgaccgtca tggcgcgcgc gcaggaggag ctggaccgcg cggtgggccg gggccggcgc    1080

ctggaggagt cggacctgcc cggcctcccc tacctgcagg cggtgtgcaa ggaggccatg    1140

cggctgcacc cgtccacgcc gctcagcctc ccgcacttct ccttggacgc ctgcgacgac    1200

gtcgacggct accgcgtccc ggccaacacc cgcctgctcg tcaacgtctg ggccatcggc    1260

cgggacccgg aggcctggga gaggcccctc gacttccgcc ccgagcgctt cctgcccggg    1320

ggcggcgcgg agaaggtcga ccccctgggg aactgcttcg agctcatccc gttcggcgcc    1380

ggccggagga tctgcgcggg gaagctggcg ggcatggtgt tcgtgcagta cttcctgggc    1440

acgctgctgc acgcgttcga ctggcgcctg cctgacggcg aggagaagct ggacatgagc    1500

gagacgttcg gcctcgcgct gcccaaggca gtgccgctcc gcgccgtcgc cacgccacgg    1560

ctcgtgccgg aagcctatgc ctga                                           1584
```

<210> SEQ ID NO 3
<211> LENGTH: 527
<212> TYPE: PRT
<213> ORGANISM: Zea mays

<400> SEQUENCE: 3

```
Met Gln Leu Ala Ala Leu Cys Thr Asp Pro Val Val Leu Cys Ser Ala
1               5                   10                  15

Phe Leu Cys Leu Leu Leu His Val Ala Leu Arg Ser Leu Leu His Pro
            20                  25                  30

Pro Ser Ala Ala Ser Ser Ser Gly Arg Arg Gly Gln Leu Pro Pro Gly
        35                  40                  45

Pro Pro Gly Leu Pro Ile Leu Gly Ala Leu Pro Leu Val Gly Pro Ala
    50                  55                  60

Pro His Ala Gly Leu Ala Ala Leu Ala Arg Lys Tyr Gly Pro Ile Met
65                  70                  75                  80

Tyr Leu Lys Met Gly Thr Ala Gly Val Val Val Ala Ser Ser Pro Arg
                85                  90                  95

Ala Ala Arg Thr Phe Leu Lys Ala Leu Asp Ala Arg Tyr Ala Asn Arg
            100                 105                 110

Pro Ala Val Ala Ser Ala Ala Asp Ile Thr Tyr Gly Arg Gln Asn Met
        115                 120                 125

Val Phe Ala Asp Tyr Gly Pro Lys Trp Lys Leu Met Arg Lys Leu Ala
    130                 135                 140

Ser Val His Leu Leu Gly Ala Arg Ala Leu Ala Asp Trp Ala Cys Val
145                 150                 155                 160
```

-continued

```
Arg Arg Gly Glu Ala Gly His Val Leu Arg Gly Val Ala Glu Ala Ala
            165                 170                 175

Ala Ala Gly Arg Pro Val Val Val Pro Glu Leu Leu Val Cys Ala Leu
            180                 185                 190

Ala Asn Ile Val Gly Gln Ile Thr Val Ser Lys Arg Val Phe Asp Ala
        195                 200                 205

Gln Gly Asp Asp Ser Asn Arg Tyr Lys Asp Met Ile Val Ser Leu Leu
    210                 215                 220

Thr Gly Thr Gly Met Phe Asn Ile Ser Asp Phe Val Pro Ala Leu Ala
225                 230                 235                 240

Arg Leu Asp Leu Gln Gly Val Gln Ala Lys Leu Arg Arg Val His Arg
                245                 250                 255

Gln Phe Asp Gly Leu Ile Thr Lys Leu Leu Ala Glu His Ala Ala Thr
            260                 265                 270

Ala Ala Asp Arg Ala Arg Gln Gly Arg Pro Asp Phe Val Asp Arg Leu
        275                 280                 285

Arg Ala Thr Met Asp Ala Gly Ala Ala Ala Asp Asp Glu Ser Gly Glu
    290                 295                 300

Thr Ile Thr Glu Val Asn Ile Lys Gly Leu Ile Phe Asp Met Phe Thr
305                 310                 315                 320

Ala Gly Thr Asp Thr Ser Ser Ile Ile Val Glu Trp Ala Met Ala Glu
                325                 330                 335

Met Leu Lys Asn Pro Thr Val Met Ala Arg Ala Gln Glu Glu Leu Asp
            340                 345                 350

Arg Ala Val Gly Arg Gly Arg Arg Leu Glu Glu Ser Asp Leu Pro Gly
        355                 360                 365

Leu Pro Tyr Leu Gln Ala Val Cys Lys Glu Ala Met Arg Leu His Pro
    370                 375                 380

Ser Thr Pro Leu Ser Leu Pro His Phe Ser Leu Asp Ala Cys Asp Asp
385                 390                 395                 400

Val Asp Gly Tyr Arg Val Pro Ala Asn Thr Arg Leu Leu Val Asn Val
                405                 410                 415

Trp Ala Ile Gly Arg Asp Pro Glu Ala Trp Glu Arg Pro Leu Asp Phe
            420                 425                 430

Arg Pro Glu Arg Phe Leu Pro Gly Gly Gly Ala Glu Lys Val Asp Pro
        435                 440                 445

Leu Gly Asn Cys Phe Glu Leu Ile Pro Phe Gly Ala Gly Arg Arg Ile
    450                 455                 460

Cys Ala Gly Lys Leu Ala Gly Met Val Phe Val Gln Tyr Phe Leu Gly
465                 470                 475                 480

Thr Leu Leu His Ala Phe Asp Trp Arg Leu Pro Asp Gly Glu Glu Lys
                485                 490                 495

Leu Asp Met Ser Glu Thr Phe Gly Leu Ala Leu Pro Lys Ala Val Pro
            500                 505                 510

Leu Arg Ala Val Ala Thr Pro Arg Leu Val Pro Glu Ala Tyr Ala
        515                 520                 525
```

<210> SEQ ID NO 4
<211> LENGTH: 5903
<212> TYPE: DNA
<213> ORGANISM: Sorghum bicolor

<400> SEQUENCE: 4

```
cccctacgat gtatatgtag ctcgtctgaa aacggttaaa taaaaaaaaa agataacaac     60
```

-continued

```
ggtcccgaga tttcgagtac acagcgcctc atcaccaata taaaaaccgt cgtgctcgcg    120
gaggcatcct tagcttgggc aggtcctcct ccctagctag ctagcacagt aacgccacca    180
tgaagctcgc cgcgttgtgc accgaccccg tcgtgctctc ctgcgccttc ctctgcctcc    240
tcctccacct cgctctccgg tccctgctgc acccttcttc tgccgcctct tcctctggcc    300
gccgcgccgg cgccggcggc cacctcccgc cggggccacc gggcctgccg atcctcggcg    360
cgctgccact cgtcggccct gccccgcatg ccggcctggc cgcgctggcg cgcaagtacg    420
gtcccatcat gtacctgaag atgggcacga cgggcgtcgt ggtggcgtcg tccccgtgcg    480
cggcgaagac gttcctcaag gcgctggacg cgaagtacgc caaccggccg gcggtggcga    540
gcgccgccga catcacgtac cggcgccaga acatggtgtt cgcggactac gggcccaagt    600
ggaagctgat gcggaagctc gccagcgtgc acctgctcgg ggcgcgcgcg ctcgccgact    660
gggcgtgcgt gcggcgcgac gaggccggcc acctgctccg cggcgtggcg gaggcggccg    720
cggcccggcg gcccgtcgtc gtgccggagc tgctcgtgtg cgcgctcgcc aacatcgtcg    780
ggcagatcac cgtcagcaag cgggtgttcg acgcgcaggg ggatgactca aacaggtgag    840
gatcgatcaa agctgcatga aatcctatca acaagacaat gaccatatat atataaggca    900
taaaatccaa gttcatttcg aaaggaaagc acatgttttt cttccaaaat ttcatgatta    960
tcgggtgcct taagttggga tgaggtttac aatatctttg aatgggacta gtgagatcag   1020
ttgaactagt tatccttaat taatgcaatg cttgacggaa tgaacatcag cagaccgtta   1080
atgcggaaag ccggggataa aaaaattaaa aagttcagct aggaagctgc tgtcatcggg   1140
tacgtatgag aagactgaag aatcggcatg acgagcactt agtactggca tttagccgga   1200
atgtccttgt tagtgcagag agtcgctcac caaaacctga aagcgaaaag agagcgatcg   1260
aaacggcccc tccatcgaca aataataagg agaatcttgt catttttcat gcatgcattc   1320
atggaaaaaa cacaaactga tcaagtattt ttcgtctaaa catataataa ttctgatacc   1380
atatatgcgt gctgcgtgct gcgtgctgcg tgcaggtaca aggacatgat cgtgtcgctg   1440
ctgacgggca cgggcatgtt caacatcagc gacttcgtgc cggcgctggc gcgtctggac   1500
ctgcagggcg tgcaggccaa gctgcggcgg atccaccacc agttcgacgg cctcatcacc   1560
aagctgctgg ccgagcacgc cgcgacggcg gcggaccgcg cgcgccaggg ccgccaggac   1620
ttcgtcgaca ggctccgcgc cacgatggac gccggcgccg acgacgagag cggcgagacc   1680
atcaccgagg tcaacatcaa gggcctcatc ttcgtaagct ctcgctctct ttatattttc   1740
ctcaccccca acctctcttc atgcatttat attttaattg cttgcttccc ttggttgcta   1800
actaaccaac tactaatctg tcgtagctgc aaaaatatgt aatactactg caacaatcga   1860
tcatggccat gggtaactga atcatatact ccctccatcc caaattgtaa gtcattccaa   1920
gaattttgaa gagtcaaact tttcaaagtt tgaccaaatt tatatgataa aataataatt   1980
attatgatac caactaaata tcattagatt cttccttaat tatattttca tagtatactc   2040
atcttacgtt acaaatctta gtatttcact ctataatttt ggtcaaacgt gaaaatgctt   2100
tgactctcca agattcttgg aatgacttac aatttgagat ggagggagta tatcttcgct   2160
gaaaatgaag tgcacggcat tttggtgtga cataggagct aagctaagct aagctagtag   2220
ccaccggacc taacggagca ctgacactga ccgaaagctc agcgtgttag gtgaagctgc   2280
tagtggagtt gttggaaaga caatatcaaa atcacaatct cgaactcatg agatgatgtg   2340
gggcctgcag ggccggtttt gagtcctcca tgatggtgat agctcaaggc ttgtttggtt   2400
caaacattac tagagcaaaa tatggttcaa acattaattg ctaaccgttg aagagtagaa   2460
```

-continued

```
tgcatatata tgcctgtcat gccatggttt tatgagaaga tgcttactat atatttttat   2520
tagataacaa tagggatcac tagatttaat tatctgccga gagaacatac agatttaatc   2580
caacctaaat tcacccccgt ctccttgttc tcacggtgga aatatatagt gggtaaactg   2640
acaaaaaagg catttggttc ctatactttg ttggaacata tttttaattt gttaggctat   2700
atagcataca gatccaacaa attccaccca taaaatatct atcaatacgc ataaaagtag   2760
tttaaggaaa tctagaaata ttggaaccac tactagctag aatctgtatg ttttcctagg   2820
attttaattc ctacgaatag aactaaaata tgtaaggaaa acatttccct atcatatttt   2880
gcaccaaaaa aaattctatc gatgcataaa tagtaaaaca cgaaaaatgt tgggacaata   2940
gggacttatt taccccaagg gaaccaaagc acctaaaaat tatacatttc ctgaaggaaa   3000
tttagatagt agttccaaga aaaactagaa aagtggtggc atagatatgc tagggaattc   3060
attccctaag ggaatgagaa tgtatgaaaa ttatacaatt tcaaataagc tctaaagata   3120
aagaggtatt ctcttttctg gaacaaacaa aatatgaaag tgcctccaaa gatcttattg   3180
agtcaacttt tatagaatta tatattgttt ttattatttt taagatggcg tgcaaaatca   3240
agtctaaatt attcagtgaa agcctcgaga ttctttaagg attaaaaata agtgaagcgg   3300
ttaagattta atcaggaaaa cgatattgga ctcctgtcct ccaaccaaac ttgattatga   3360
cgttttagct taatgttcac tttgtagacg tcggatatat agggatgcga accgaaagga   3420
aaaggctgac gttttaacaa actgcacata tatgttacca gaactcgaat agcagctttg   3480
taagtctcta gaatgttgga gtagttaaca acgtgataga cgatgtaaca cctggaccat   3540
gttattatgt catttcctag aagaattgta atcaaatcta ttaattaatc aagcaaagaa   3600
ttgaaagcta taaatggctt aaggcaacat ctggttgtga gttgtgtgat taattattgg   3660
tgaatgtcgt gtcagcacta acattattaa ggtcagtctc aatgcatagt ttcatgacac   3720
agttaccaag actataaact aggtaaccga gccacaagag tttcatgggg atgaaactcc   3780
tctctcatct gatgaaactc cttcatttaa tgactctgcc aactcagcaa ttttgcttat   3840
gtggcaccat atttaatgtg catgacactc tcataaaaca tgcattgaga ctggcctaag   3900
ggggtgttta gtgttggact ctttagatcg tctactaggt cgtagatcgg tggggaattt   3960
acttctattt gggataaacc acatagaatt tcatggatct agagaggaat ggaggacgag   4020
aggatgtgtt atatactgaa ccatacettt ggggttggcg gagaagcgcg tggtcgaggc   4080
agtggcggtg gcggactttc cgtcgctggc agtgcctccc tctcgatcgg tctagggtta   4140
gatggggact cgcggcattg tagcggtgaa ccttgtaact tgtgctctag cctccaccct   4200
ctcttttata cactgcgcga caggggcctg gcagccaagt tattgggcta gacgcccccg   4260
atcagggcgt ggtcaagggt ccggccaagt ctttggactt gggccagtgg agatcaatct   4320
aacatttagt tccccataaa atacaaaatg tcaactactt tggaatgatg aaatgcaaaa   4380
tatcaaaaat ttcaggttag atccatccaa aatgcagaat ttattgctct cattatagcc   4440
tcttgagact tttttggact tttttggcct cttgaggcca aaatacaaaa tagagaataa   4500
ccacattttt gttaaaattt ttgcatagta tttattttta ttatgtaaaa taatacacca   4560
aaactcagaa ttttttggga tggaagggga actaaacacc ccgtgaatct agtcggcaca   4620
atgactcaag caatgaaacc actactgttt cagtataagg ttggaaaaca ctgttctcaa   4680
cataacatcg cattgactct ctctttgtgg gctgtgtggc tttgtgggtc agcttgattg   4740
gagctcctta acatatataa catacactgt gcctgctgat gctgaggttg tactgtcatc   4800
```

-continued

```
aaacacacta aaacagtgca ccacaccctt caataatgtc aggtcaaact atataaccag   4860
cttatattat atacagtgtt aaacttaaac ccaacccaac gatatataat tcacttgcac   4920
atacttcaaa accatgtata tatatctcgt tgaaaaaaat tataggagta ataatgtttg   4980
cgtgcgacgc atcgctgctt tgcatgcacg caggacatgt tcacggcggg cacggacacg   5040
tcgtccatca tcgtggagtg ggcgatggcg gagatgctca agaacccgtc cgtgatggcg   5100
cgcgcgcagg aggagctgga ccgcgtggtg ggccgcggcc gccgcctgga ggagtcggac   5160
ctgcccagcc tcccctacct gcaggccgtc tgcaaggagg ccatgcggct gcacccgtcg   5220
acgccgctca gcctcccgca cttctccttc gacgcctgcg acgacgacgt cgccgccggc   5280
ggctaccgcg tcccggccaa cacccggctg ctcatcaaca tctgggccat cggccgggac   5340
ccggcggcgt ggaagaagcc cctggagttc cggcccgagc ggttcctgcc gggcggcggc   5400
gccgagaagg tcgacccgat ggggaactgc ttcgagctca tcccgttcgg cgccggcagg   5460
aggatctgcg ccgggaagct ggccggcatg gtgttcgtgc agtacttcct gggcacgctg   5520
ctgcacgcgt tcgactggag cttgcctgac ggcgaggaga agctggacat gagcgagacg   5580
ttcggcctcg cgctgcctaa ggctgtgccg ctccgcgccg tcgtcacgcc acggctcgtg   5640
ccggaagcct acgcctgagc tagctgtcag tggttcgcgt gtgttgttgt tgccttcctg   5700
catacgtaca taacttgtta tgaatcctac acttgcattg gttgcctagt accagtattt   5760
gaaattatat acggaccttg catggtttca gttttttgac acaaccgatg atggttgatc   5820
agaagacgga tctgtagagt tgttctttaa caatgcgcta acctatatat caagggactg   5880
tttggttttc catgactaaa att                                            5903
```

<210> SEQ ID NO 5
<211> LENGTH: 1599
<212> TYPE: DNA
<213> ORGANISM: Artificial Sequence
<220> FEATURE:
<223> OTHER INFORMATION: cDNA of SEQ ID NO: 4

<400> SEQUENCE: 5

```
atgaagctcg ccgcgttgtg caccgacccc gtcgtgctct cctgcgcctt cctctgcctc     60
ctcctccacc tcgctctccg gtccctgctg cacccttctt ctgccgcctc ttcctctggc    120
cgccgcgccg gcgccggcgg ccacctcccg ccggggccac cgggcctgcc gatcctcggc    180
gcgctgccac tcgtcggccc tgccccgcat gccggcctgg ccgcgctggc gcgcaagtac    240
ggtcccatca tgtacctgaa gatgggcacg acgggcgtcg tggtggcgtc gtccccgtgc    300
gcggcgaaga cgttcctcaa ggcgctggac gcgaagtacg ccaaccggcc ggcggtggcg    360
agcgccgccg acatcacgta ccggcgccag aacatggtgt tcgcggacta cgggcccaag    420
tggaagctga tgcggaagct cgccagcgtg cacctgctcg ggcgcgcgc gctcgccgac     480
tgggcgtgcg tgcggcgcga cgaggccggc cacctgctcc gcggcgtggc ggaggcggcc    540
gcggcccggc ggcccgtcgt cgtgccggag ctgctcgtgt gcgcgctcgc caacatcgtc    600
gggcagatca ccgtcagcaa gcgggtgttc gacgcgcagg gggatgactc aaacaggtac    660
aaggacatga tcgtgtcgct gctgacgggc acgggcatgt tcaacatcag cgacttcgtg    720
ccggcgctgg cgcgtctgga cctgcagggc gtgcaggcca agctgcggcg gatccaccac    780
cagttcgacg gcctcatcac caagctgctg gccgagcacg ccgcgacggc ggcggaccgc    840
gcgcgccagg gccgccagga cttcgtcgac aggctccgcg ccacgatgga cgccggcgcc    900
gacgacgaga gcggcgagac catcaccgag gtcaacatca agggcctcat cttcgacatg    960
```

```
ttcacggcgg gcacggacac gtcgtccatc atcgtggagt gggcgatggc ggagatgctc   1020

aagaacccgt ccgtgatggc gcgcgcgcag gaggagctgg accgcgtggt gggccgcggc   1080

cgccgcctgg aggagtcgga cctgcccagc ctcccctacc tgcaggccgt ctgcaaggag   1140

gccatgcggc tgcacccgtc gacgccgctc agcctcccgc acttctcctt cgacgcctgc   1200

gacgacgacg tcgccgccgg cggctaccgc gtcccggcca acacccggct gctcatcaac   1260

atctgggcca tcggccggga cccggcggcg tggaagaagc ccctggagtt ccggcccgag   1320

cggttcctgc cgggcggcgg cgccgagaag gtcgacccga tggggaactg cttcgagctc   1380

atcccgttcg gcgccggcag gaggatctgc gccgggaagc tggccggcat ggtgttcgtg   1440

cagtacttcc tgggcacgct gctgcacgcg ttcgactgga gcttgcctga cggcgaggag   1500

aagctggaca tgagcgagac gttcggcctc gcgctgccta aggctgtgcc gctccgcgcc   1560

gtcgtcacgc cacggctcgt gccggaagcc tacgcctag                          1599
```

<210> SEQ ID NO 6
<211> LENGTH: 532
<212> TYPE: PRT
<213> ORGANISM: Sorghum bicolor

<400> SEQUENCE: 6

```
Met Lys Leu Ala Ala Leu Cys Thr Asp Pro Val Val Leu Ser Cys Ala
1               5                   10                  15

Phe Leu Cys Leu Leu Leu His Leu Ala Leu Arg Ser Leu Leu His Pro
            20                  25                  30

Ser Ser Ala Ala Ser Ser Ser Gly Arg Arg Ala Gly Ala Gly Gly His
        35                  40                  45

Leu Pro Pro Gly Pro Pro Gly Leu Pro Ile Leu Gly Ala Leu Pro Leu
    50                  55                  60

Val Gly Pro Ala Pro His Ala Gly Leu Ala Ala Leu Ala Arg Lys Tyr
65                  70                  75                  80

Gly Pro Ile Met Tyr Leu Lys Met Gly Thr Thr Gly Val Val Val Ala
                85                  90                  95

Ser Ser Pro Cys Ala Ala Lys Thr Phe Leu Lys Ala Leu Asp Ala Lys
            100                 105                 110

Tyr Ala Asn Arg Pro Ala Val Ala Ser Ala Ala Asp Ile Thr Tyr Arg
        115                 120                 125

Arg Gln Asn Met Val Phe Ala Asp Tyr Gly Pro Lys Trp Lys Leu Met
    130                 135                 140

Arg Lys Leu Ala Ser Val His Leu Leu Gly Ala Arg Ala Leu Ala Asp
145                 150                 155                 160

Trp Ala Cys Val Arg Arg Asp Glu Ala Gly His Leu Leu Arg Gly Val
                165                 170                 175

Ala Glu Ala Ala Ala Ala Arg Arg Pro Val Val Val Pro Glu Leu Leu
            180                 185                 190

Val Cys Ala Leu Ala Asn Ile Val Gly Gln Ile Thr Val Ser Lys Arg
        195                 200                 205

Val Phe Asp Ala Gln Gly Asp Asp Ser Asn Arg Tyr Lys Asp Met Ile
    210                 215                 220

Val Ser Leu Leu Thr Gly Thr Gly Met Phe Asn Ile Ser Asp Phe Val
225                 230                 235                 240

Pro Ala Leu Ala Arg Leu Asp Leu Gln Gly Val Gln Ala Lys Leu Arg
                245                 250                 255
```

-continued

```
Arg Ile His His Gln Phe Asp Gly Leu Ile Thr Lys Leu Leu Ala Glu
            260                 265                 270

His Ala Ala Thr Ala Ala Asp Arg Ala Arg Gln Gly Arg Gln Asp Phe
        275                 280                 285

Val Asp Arg Leu Arg Ala Thr Met Asp Ala Gly Ala Asp Asp Glu Ser
    290                 295                 300

Gly Glu Thr Ile Thr Glu Val Asn Ile Lys Gly Leu Ile Phe Asp Met
305                 310                 315                 320

Phe Thr Ala Gly Thr Asp Thr Ser Ser Ile Ile Val Glu Trp Ala Met
                325                 330                 335

Ala Glu Met Leu Lys Asn Pro Ser Val Met Ala Arg Ala Gln Glu Glu
            340                 345                 350

Leu Asp Arg Val Val Gly Arg Gly Arg Arg Leu Glu Glu Ser Asp Leu
        355                 360                 365

Pro Ser Leu Pro Tyr Leu Gln Ala Val Cys Lys Glu Ala Met Arg Leu
    370                 375                 380

His Pro Ser Thr Pro Leu Ser Leu Pro His Phe Ser Phe Asp Ala Cys
385                 390                 395                 400

Asp Asp Asp Val Ala Ala Gly Gly Tyr Arg Val Pro Ala Asn Thr Arg
                405                 410                 415

Leu Leu Ile Asn Ile Trp Ala Ile Gly Arg Asp Pro Ala Ala Trp Lys
            420                 425                 430

Lys Pro Leu Glu Phe Arg Pro Glu Arg Phe Leu Pro Gly Gly Gly Ala
        435                 440                 445

Glu Lys Val Asp Pro Met Gly Asn Cys Phe Glu Leu Ile Pro Phe Gly
    450                 455                 460

Ala Gly Arg Arg Ile Cys Ala Gly Lys Leu Ala Gly Met Val Phe Val
465                 470                 475                 480

Gln Tyr Phe Leu Gly Thr Leu Leu His Ala Phe Asp Trp Ser Leu Pro
                485                 490                 495

Asp Gly Glu Glu Lys Leu Asp Met Ser Glu Thr Phe Gly Leu Ala Leu
            500                 505                 510

Pro Lys Ala Val Pro Leu Arg Ala Val Val Thr Pro Arg Leu Val Pro
        515                 520                 525

Glu Ala Tyr Ala
    530
```

<210> SEQ ID NO 7
<211> LENGTH: 3752
<212> TYPE: DNA
<213> ORGANISM: Sorghum bicolor

<400> SEQUENCE: 7

```
atatagcttg tctgagttcc gagtacgcag ccgcaggagc gcagcgtgct gcagggtgca      60

acgcctcatc aggaatataa agccgtcgtc caggagacac ccttagcttg ggaaggtcct     120

cctccctggc acagcacagt agcacgccac catgcagctc gccgcgttgt gcatcgaccc     180

cctcgtgctc tcctgcgcct tcctctgcct cctcctccac gtcgcgctcc gctccctgct     240

gcacccttct tctgcctcgt cctccggccg ccgcggcggc caccaccagc tcccgccggg     300

gccaccggga ctaccgatcc tcggcgcgct gccactcgtc ggcccagccc cgcacgccgg     360

cctggccgcg ctggcgcgca agtacggtcc catcatgtac ctgaagatgg gcacgacggg     420

cgtcgtggtg gcgtcgtccc cgggcgcggc gaggacgttc ctcaaggcgc tggacgcgaa     480

gtacgccaac cggccggcgg tggcgagcgc cgccgacatc acgtacgggt gccagaacat     540
```

-continued

```
ggtgttcgcc aactacgggc ccaagtggaa gctgatgcgg aagctcgcca gcgtgcacct    600
gctcggggcg cgcgcgctcg cggactgggc gcacgtgcgg cgcgacgagg ccggccacct    660
gctccgcggc gtggcggagg cggccgcggc ccggcggccc gtcgtcgtgc cggaggtgct    720
ggtgtgcgcc ctcgccaata tcgtcgggca gatcaccgtg agtaagcggg tgttcgacgc    780
acagggggac gagtccaaca ggtcagaact gaaccgaaag gccttttcag tgaatagaat    840
cgctcaccaa aatacgaatg tgaaatatgt gtgtgcaggt acaaggacat gatcgtgtca    900
ctgctgactg gcgcgggact gttcaacatc agcgacttcg tgccggcgct ggcgcgtctg    960
gacctgcagg gcgtgcaggc caagctgcgg cgtgtgcacc accagttcga cggcctcatc   1020
accaagctgc tggccgagca cgccgcgacg gccgcggacc gcgcgcgcga cggccgccag   1080
gacttcgtcg acaggctccg cgccgccatt gacgccggcg ctgacgacga gagcggcgag   1140
accatcaccg aggtcaacat caagggcctc atcttcgtaa gctcgctttc ctcacctcag   1200
ctacatacat atatactctt tccttccttc cattgctttc gttgttttat caagtaaagt   1260
aatgcattcc gtcgcggtaa gaatgtaaga tatgcagcag ctagtaccga tcatgaaaga   1320
aagtaactga gaatcttgtg ctcaaaataa ggcattgttt agttccgaaa aaaatttacc   1380
aaaaatttta gccgttaaat taaatcttgc ggcatatata tggagtatta aagatataaa   1440
aataaaaatt aattacatag tttgcctgta atttatgaga cgaaccttta aacctagtta   1500
gtttataatt ggacaatatt tgtcaaataa aaataaaaat gctacagtat ctgaaattcc   1560
aaaattttgt caactgaaca aggccttaga tgcatttagg ccatgtttgg tttcaaatgt   1620
taaagtttat cgctcgacac atcgaatgtt tagtacacat gcatagagta ctaaatatag   1680
actatttatg aaactaaaaa cacagctaga gagtaatttg cgagatgaat cttttaaacc   1740
taattaatct atgattagac attaattgtt aaataagatg aaaatgttac aacccaacca   1800
agcaccccct tacgtcgtcg cgttggtgcg gccgagcagg agagttaggt ggactagtgg   1860
gttgttggaa agtgacgatc gaagcgaaag cacacattag ctcgagctga tatgtttggt   1920
ttatggtcta attcataccg tgagggcctg caggttctga gtctttcatg attagtcaag   1980
gtgatatcgg tagctgatgg ctttgtttgg taccaaagtg cagactagag caaaatatgg   2040
ttcaaatgtt gataacattt ggtaccgtga agtgaataga atacctaccg gttgtgccat   2100
ggttgtcctc aaaattcatg ttttttaat accccatcta ttttaaatta caagacattt   2160
tgacttttct agataaattg atttttctat gtatctagat atagtgtcta tctaaatgta   2220
tagtaaagat tacatatatt taaaaaagct aaacatttta taattagaat agggggagta   2280
tataattaaa agagagtatc tgtttatagt gatatttctc aagtacagtc cacatacaga   2340
atgcaccgag accattctaa aacctcaaac atgttgcaaa gatctaatgt tctggaacca   2400
aaatatatga actgaatatc gacgattgaa tcattgggta caacaaatat tgtagatttc   2460
aggatctatg accattgatc catcaagttg gacgcttgac ttctccgcag ctaccaatgg   2520
tgacgtcaat gacctggagt taatatctct acggagtatt actcgtcctt gcacaaggat   2580
gaccttatcg tggccatgaa aatagacata tagacaatgt agggtttatc tagaataatc   2640
actaataaga ataagatgag attgaataac atccaaacag tgtcggatct actcatttgg   2700
ttaattggta actttaccca caaaacactg aagtaattcg tgtccattta attttttccg   2760
tcctatacaa tgtttgcatg caacgcatcc aggacatgtt cacggcgggc acggacacat   2820
cgtcgatcat cgtggagtgg gcgatgtctg aaatgctcaa gaacccgccc gtcatggcac   2880
```

-continued

```
gagcgcagga ggagctggac cgcacggtcg gccgcggccg ccgcctggaa gagtcggacc   2940

tgcccagcct cccctacctg caggccgtct gcaaggaggc catgcggctg cacccgtcga   3000

cgccgctcag cctcccgcac ttctccttcg acgcctgcga cgacgtcggc ggcggctacc   3060

gcgtcccggc caacacccgg ctgctcatca acgtctgggc catcggccgg gacccggcga   3120

cgtgggaggc gcccctcgag ttccggccag agcggttcct gccgggggcc gcggcggaga   3180

aggtcgaccc gatggggaac tacttcgagc tcatcccctt cggcgccggc cggaggatct   3240

gcgccgggaa gctggccggc atggtgttcg tgcagtactt cctgggcacg ctgctgcacg   3300

cgttcaactg gcgcctcgcc gacggcgagg agctggacat gcgcgagacg ttcgggctca   3360

cgctgcctaa ggccgtaccg ctccgcgcca ttgtcacgcc gcggctcctg ccggaagcct   3420

atgcttgagt tagttgtcac ttgtcagtct cagtccgcgc tgtggaagga tgatcggaag   3480

gtttgtgctt gccaacctgc atacatattc tgtttatatg tttttttata gaaactacat   3540

ggtattcatc atatacacaa acgcacatct ctctatgctt aattgcaagg catttgatat   3600

ggaaaatcca ccttggattc aatagtttga caactactga tcttactgaa caaatgatta   3660

ttccggtcca ttaaaatgaa cttttacagg cagttttgta agaccgttca tgtgcttcaa   3720

cttcaagcag taaggcctca tttggttgca tc                                  3752
```

<210> SEQ ID NO 8
<211> LENGTH: 1584
<212> TYPE: DNA
<213> ORGANISM: Artificial Sequence
<220> FEATURE:
<223> OTHER INFORMATION: cDNA of SEQ ID NO: 7

<400> SEQUENCE: 8

```
atgcagctcg ccgcgttgtg catcgacccc ctcgtgctct cctgcgcctt cctctgcctc     60

ctcctccacg tcgcgctccg ctccctgctg cacccttctt ctgcctcgtc ctccggccgc    120

cgcggcggcc accaccagct cccgccgggg ccaccgggac taccgatcct cggcgcgctg    180

ccactcgtcg gcccagcccc gcacgccggc ctggccgcgc tggcgcgcaa gtacggtccc    240

atcatgtacc tgaagatggg cacgacgggc gtcgtggtgg cgtcgtcccc gggcgcggcg    300

aggacgttcc tcaaggcgct ggacgcgaag tacgccaacc ggccggcggt ggcgagcgcc    360

gccgacatca cgtacgggtg ccagaacatg gtgttcgcca actacgggcc caagtggaag    420

ctgatgcgga agctcgccag cgtgcacctg ctcggggcgc gcgcgctcgc ggactgggcg    480

cacgtgcggc gcgacgaggc cggccacctg ctccgcggcg tggcggaggc ggccgcggcc    540

cggcggcccg tcgtcgtgcc ggaggtgctg gtgtgcgccc tcgccaatat cgtcgggcag    600

atcaccgtga gtaagcgggt gttcgacgca caggggggacg agtccaacag gtacaaggac    660

atgatcgtgt cactgctgac tggcgcggga ctgttcaaca tcagcgactt cgtgccggcg    720

ctggcgcgtc tggacctgca gggcgtgcag gccaagctgc ggcgtgtgca ccaccagttc    780

gacggcctca tcaccaagct gctggccgag cacgccgcga cggccgcgga ccgcgcgcgc    840

gacggccgcc aggacttcgt cgacaggctc cgcgccgcca ttgacgccgg cgctgacgac    900

gagagcggcg agaccatcac cgaggtcaac atcaagggcc tcatcttcga catgttcacg    960

gcgggcacgg acacatcgtc gatcatcgtg gagtgggcga tgtctgaaat gctcaagaac   1020

ccgcccgtca tggcacgagc gcaggaggag ctggaccgca cggtcggccg cggccgccgc   1080

ctggaagagt cggacctgcc cagcctcccc tacctgcagg ccgtctgcaa ggaggccatg   1140

cggctgcacc cgtcgacgcc gctcagcctc ccgcacttct ccttcgacgc ctgcgacgac   1200
```

```
gtcggcggcg gctaccgcgt cccggccaac acccggctgc tcatcaacgt ctgggccatc   1260

ggccgggacc cggcgacgtg ggaggcgccc ctcgagttcc ggccagagcg gttcctgccg   1320

ggggccgcgg cggagaaggt cgacccgatg ggaactact tcgagctcat cccccttcggc   1380

gccggccgga ggatctgcgc cgggaagctg gccggcatgg tgttcgtgca gtacttcctg   1440

ggcacgctgc tgcacgcgtt caactggcgc ctcgccgacg gcgaggagct ggacatgcgc   1500

gagacgttcg ggctcacgct gcctaaggcc gtaccgctcc gcgccattgt cacgccgcgg   1560

ctcctgccgg aagcctatgc ttga                                          1584
```

<210> SEQ ID NO 9
<211> LENGTH: 527
<212> TYPE: PRT
<213> ORGANISM: Sorghum bicolor

<400> SEQUENCE: 9

```
Met Gln Leu Ala Ala Leu Cys Ile Asp Pro Leu Val Leu Ser Cys Ala
1               5                   10                  15

Phe Leu Cys Leu Leu Leu His Val Ala Leu Arg Ser Leu Leu His Pro
            20                  25                  30

Ser Ser Ala Ser Ser Ser Gly Arg Arg Gly Gly His His Gln Leu Pro
        35                  40                  45

Pro Gly Pro Pro Gly Leu Pro Ile Leu Gly Ala Leu Pro Leu Val Gly
    50                  55                  60

Pro Ala Pro His Ala Gly Leu Ala Ala Leu Ala Arg Lys Tyr Gly Pro
65                  70                  75                  80

Ile Met Tyr Leu Lys Met Gly Thr Thr Gly Val Val Val Ala Ser Ser
                85                  90                  95

Pro Gly Ala Ala Arg Thr Phe Leu Lys Ala Leu Asp Ala Lys Tyr Ala
            100                 105                 110

Asn Arg Pro Ala Val Ala Ser Ala Ala Asp Ile Thr Tyr Gly Cys Gln
        115                 120                 125

Asn Met Val Phe Ala Asn Tyr Gly Pro Lys Trp Lys Leu Met Arg Lys
    130                 135                 140

Leu Ala Ser Val His Leu Leu Gly Ala Arg Ala Leu Ala Asp Trp Ala
145                 150                 155                 160

His Val Arg Arg Asp Glu Ala Gly His Leu Leu Arg Gly Val Ala Glu
                165                 170                 175

Ala Ala Ala Ala Arg Arg Pro Val Val Val Pro Glu Val Leu Val Cys
            180                 185                 190

Ala Leu Ala Asn Ile Val Gly Gln Ile Thr Val Ser Lys Arg Val Phe
        195                 200                 205

Asp Ala Gln Gly Asp Glu Ser Asn Arg Tyr Lys Asp Met Ile Val Ser
    210                 215                 220

Leu Leu Thr Gly Ala Gly Leu Phe Asn Ile Ser Asp Phe Val Pro Ala
225                 230                 235                 240

Leu Ala Arg Leu Asp Leu Gln Gly Val Gln Ala Lys Leu Arg Arg Val
                245                 250                 255

His His Gln Phe Asp Gly Leu Ile Thr Lys Leu Leu Ala Glu His Ala
            260                 265                 270

Ala Thr Ala Ala Asp Arg Ala Arg Asp Gly Arg Gln Asp Phe Val Asp
        275                 280                 285

Arg Leu Arg Ala Ala Ile Asp Ala Gly Ala Asp Asp Glu Ser Gly Glu
    290                 295                 300
```

-continued

Thr Ile Thr Glu Val Asn Ile Lys Gly Leu Ile Phe Asp Met Phe Thr
305 310 315 320

Ala Gly Thr Asp Thr Ser Ser Ile Ile Val Glu Trp Ala Met Ser Glu
325 330 335

Met Leu Lys Asn Pro Pro Val Met Ala Arg Ala Gln Glu Glu Leu Asp
340 345 350

Arg Thr Val Gly Arg Gly Arg Arg Leu Glu Glu Ser Asp Leu Pro Ser
355 360 365

Leu Pro Tyr Leu Gln Ala Val Cys Lys Glu Ala Met Arg Leu His Pro
370 375 380

Ser Thr Pro Leu Ser Leu Pro His Phe Ser Phe Asp Ala Cys Asp Asp
385 390 395 400

Val Gly Gly Gly Tyr Arg Val Pro Ala Asn Thr Arg Leu Leu Ile Asn
405 410 415

Val Trp Ala Ile Gly Arg Asp Pro Ala Thr Trp Glu Ala Pro Leu Glu
420 425 430

Phe Arg Pro Glu Arg Phe Leu Pro Gly Ala Ala Ala Glu Lys Val Asp
435 440 445

Pro Met Gly Asn Tyr Phe Glu Leu Ile Pro Phe Gly Ala Gly Arg Arg
450 455 460

Ile Cys Ala Gly Lys Leu Ala Gly Met Val Phe Val Gln Tyr Phe Leu
465 470 475 480

Gly Thr Leu Leu His Ala Phe Asn Trp Arg Leu Ala Asp Gly Glu Glu
485 490 495

Leu Asp Met Arg Glu Thr Phe Gly Leu Thr Leu Pro Lys Ala Val Pro
500 505 510

Leu Arg Ala Ile Val Thr Pro Arg Leu Leu Pro Glu Ala Tyr Ala
515 520 525

<210> SEQ ID NO 10
<211> LENGTH: 187
<212> TYPE: DNA
<213> ORGANISM: Zea mays

<400> SEQUENCE: 10
cttctgccca gaagcgggcc cagacatttg agattgggta ttcaaaaatt caaaagatta 60
aagaatttag tgttctaacg ctattttatg caatacatta ttgacaaatt agtgttctaa 120
cactatagat caccaaaaac atgggtattc aatgaatacc catgaaaccc ccctgggccc 180
gcccatg 187

<210> SEQ ID NO 11
<211> LENGTH: 4402
<212> TYPE: DNA
<213> ORGANISM: Zea mays

<400> SEQUENCE: 11
atgcagctcg cggcgttgtg caccgacccc gtggtgctgt gcagcgcctt cctctgcctc 60
ctcctccacg tggctctccg ctcgctgctg caccctcctt ctgcccagaa gcgggcccag 120
acatttgaga ttgggtattc aaaaattcaa aagattaaag aatttagtgt tctaacgcta 180
ttttatgcaa tacattattg acaaattagt gttctaacac tatagatcac caaaaacatg 240
ggtattcaat gaatacccat gaaacccccc tgggcccgcc catgcttctg ccgcctcttc 300
ctccgggcgc cgcgggcagc tcccgccggg gccaccgggc ctgccgatcc tcggcgcgct 360

-continued

```
gccactcgtg ggcccagccc cgcacgccgg cctggccgcg ctggcgcgca agtacggtcc    420
catcatgtac ctgaagatgg gcacggccgg cgtggtggtg gcgtcgtccc cgcgcgcggc    480
gcggacgttc ctcaaggcgc tggacgcgcg gtacgccaac cggccggccg tggcgagcgc    540
cgcggacatc acgtacgggc ggcagaacat ggtgttcgcg gactacgggc ccaagtggaa    600
gctgatgcgg aagctcgcca gcgtgcacct gctcggcgcg cgcgcgctcg cggactgggc    660
gtgcgtgcgg cgcggcgagg ccggccacgt gctgcgcggc gtggcggagg cggccgcggc    720
cggcaggccc gtcgtcgtgc cggagctgct cgtgtgcgcc ctcgccaaca tcgtcgggca    780
gatcacagtg agcaagcggg tgttcgacgc gcagggggac gactcgaaca ggtgaggatg    840
ggaggtccat gaaatcctac cagctgtgag catgcataaa agttcatttg gaaagaaaag    900
aacatatttt tcttacaaat ttatgcttac tgtttcttta agtttcgata aagtttgtaa    960
aaaaaattta ggctagtttg aaactccatt taggatttct attttccaaa gaaaaataaa   1020
cgaatttctc ttgaaaaaat gaaaattctt tagaaaaata ggttctcaaa ctagccctca   1080
ataaaactta atgcgatcgt tttctctgac tctcattcat ctttctctgg ttatctaatt   1140
gggtccttga gagatgagtt tacctgcttg tcctttatta ttgcaaagac aacatatctg   1200
atgcacatgg aacattggtg cacatggtgc acatatgaaa tcatcaccac tcattttaaa   1260
tctaacgtct atagttgttt gatatatttt attaaggaca ccctccaacg tggtggtgtg   1320
tagtggtgga aggtgttatt tgtaaattga ataatcaact agagacgtta gatctaaaat   1380
gagtggtgat gatttaatat gtgcaccatg tgcaccagtc ttctatgtgc accagatatg   1440
tcctctattg caaatgctag acggaacacc agctagcact agcagactgt ttatgtggaa   1500
agaaaaaact taaaaagatc agctaggaag ctgctgtcat ctgtacgtat atatggtgaa   1560
gactgaacaa tctgcatgac aagcaaaact tagcttaaaa gcgaaaagag cgatggaaac   1620
ggccgctcga taaataatta atgagagtct tgggattttt catgcatgga aaaaaacaaa   1680
gctggcattt ttcatctaat ataatatata acgctgatat catattgcgt gcagatacaa   1740
ggacatgatc gtgtcgctgc tgaccggcac gggcatgttc aacatcagcg acttcgtgcc   1800
ggcgctggcg cgtctggacc tgcagggcgt gcaggcgaag ctgcggcgcg tccaccgcca   1860
gttcgacggc ctcatcacca agctgctggc cgagcacgcc gcgacggccg cggaccgcgc   1920
gcgccagggc cgcccggact tcgtcgaccg gctccgcgcc acgatggacg ccggcgccgc   1980
cgccgacgac gagagcggcg agaccatcac cgaggtcaac atcaagggcc tcatcttcgt   2040
aagctccctg ctttttcctc gcccccaacc atgcatcatc atatgcactt atattttaca   2100
cttgctcggt tttcctttag taactaacta atccgtcgca gctgcgatac acgtagcact   2160
agtactacag cgatgggtca tcggtaactg aatctaaggt gcaatagagt gcacggccgc   2220
gggatcatgg cgtgacatgg gagctaagct aagccagtgg ccacctaacg aaggcactga   2280
ccgaaagctc agtggcgtgt taggtggaga tagtggatcg agttgttgga aagacaatat   2340
caaaaccact ctccaattga tgatgtgtag ggcctgcagt gttttgaatc caccttgttt   2400
ggtcgaacac attactagag tgaaatatgg ttccaatgtt aattgatagc gcgaaagggt   2460
ctctagcgta atggttaaac cttccgagta gcacatccag gttgggttcg atcctctcga   2520
gggcgaattt tcaagctttg ttaaaaaaat tatctcgttg tgccccgtcc gctctcagga   2580
atcgatattc tacacgacac cctccgacta gtgacagttg attgactcgt tagtgatgag   2640
aagccatgct aaaaaagtgg agacgtagat atgatagagg ttccctttcc taagcaaacg   2700
tgaatgctat gaaaattatg cagtttaaaa aaaactttaa agataaacag gaattctctt   2760
```

-continued ttttggaaca aacaatacga atgcacctcc aaatatctta tcgagtcgac ttttatggaa 2820
ttattgtttt tgttatttct aagatgggag cccaaaatca catacaaatt attcagtgaa 2880
tgcctcggtg ttttttattt agttaagggc tctcattttt ttcaagggat ttttattttt 2940
ttccaaaaga aaataaacta atcctcttta gaaaaatgga aatctattgg agaaatgagg 3000
ttcctaaact agctctaaca gtgagtcagt taatcaggag aagatattag actcctgtat 3060
agtgtgcagc aaccacatcc gattctgacg ttttagctta atgttcgcta tgtagacgtc 3120
gggcataggg aatgcattgc taccagaaca cgaatgacag ctatgcaagt ctctagaacg 3180
ttggagtagt taacaaacgt gatagatgta acctctggat catggtatga tgtcatttcc 3240
tagactagaa gaattggtag tcaaatcgag caaagtcccg aaagcacact gggctttcga 3300
cacagtgata ccaaagatgc tgaaaagaac tgaggcacga taaactgttc ggtgttggtg 3360
taaacgacca aagatgctga aaataactga tcgtcaccat ccgtgaatct aactttcgac 3420
acactgttac caaatccttc gtcaaaatta caggaataat taaggcgctt agacgatgat 3480
aaaccatttt ttgtcactaa ttaaccacac tgttctttgc ttgaccgtga caaaaaaaaa 3540 ctttttttgtg aagcagtgtt gccgtaaacc acaaccatca tgaactcact tgccttgtca 3600
tatgtacttg taccatcgaa cgccgcgcgc taagacaatg caccaccctt caagtcttag 3660
ctcactgata ccgctaatta agttagataa tgtcgattac tagttgtctt acttcgaact 3720
atttcttttc ggcaaactga agtaaagaca acgttttgtt ccgcaggaca tgttcacggc 3780
gggtacggac acgtcgtcga tcatcgtgga gtgggcgatg gcggagatgc tcaagaaccc 3840
gaccgtcatg gcgcgcgcgc aggaggagct ggaccgcgcg gtgggccggg gccggcgcct 3900
ggaggagtcg gacctgcccg gcctccccta cctgcaggcg gtgtgcaagg aggccatgcg 3960
gctgcacccg tccacgccgc tcagcctccc gcacttctcc ttggacgcct gcgacgacgt 4020
cgacggctac cgcgtcccgg ccaacacccg cctgctcgtc aacgtctggg ccatcggccg 4080
ggacccggag gcctgggaga ggcccctcga cttccgcccc gagcgcttcc tgcccggggg 4140
cggcgcggag aaggtcgacc ccctggggaa ctgcttcgag ctcatcccgt tcggcgccgg 4200
ccggaggatc tgcgcgggga agctggcggg catggtgttc gtgcagtact tcctgggcac 4260
gctgctgcac gcgttcgact ggcgcctgcc tgacggcgag gagaagctgg acatgagcga 4320
gacgttcggc ctcgcgctgc ccaaggcagt gccgctccgc gccgtcgcca cgccacggct 4380
cgtgccggaa gcctatgcct ga 4402

<210> SEQ ID NO 12
<211> LENGTH: 387
<212> TYPE: DNA
<213> ORGANISM: Zea mays
<220> FEATURE:
<221> NAME/KEY: misc_feature
<222> LOCATION: (101)..(287)
<223> OTHER INFORMATION: insertion of 187 nucleotides as present in QTL
line

<400> SEQUENCE: 12
accatgcagc tcgcggcgtt gtgcaccgac cccgtggtgc tgtgcagcgc cttcctctgc 60
ctcctcctcc acgtggctct ccgctcgctg ctgcaccctc cttctgccca gaagcgggcc 120
cagacatttg agattgggta ttcaaaaatt caaaagatta aagaatttag tgttctaacg 180
ctattttatg caatacatta ttgacaaatt agtgttctaa cactatagat caccaaaaac 240
atgggtattc aatgaatacc catgaaaccc ccctgggccc gcccatgctt ctgccgcctc 300

```
ttcctccggg cgccgcgggc agctcccgcc ggggccaccg ggcctgccga tcctcggcgc    360

gctgccactc gtgggcccag ccccgca                                        387


<210> SEQ ID NO 13
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: single nucleotide polymorphism

<400> SEQUENCE: 13

tgatgaaagc cgtgcaggag taaatagraa amtggagttg tggcgtgara ctctagaatc     60

caaacgtttt agactcttta gaactaaaac cgaatatata wgttgtgact ttggcactac    120

tacatatgac gaaggagata ttagtttgga aggtcaagta gtgccctgra aggatacctt    180

ttggtattta gtatcaatgc t                                              201


<210> SEQ ID NO 14
<211> LENGTH: 121
<212> TYPE: DNA
<213> ORGANISM: Zea mays
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (61)..(61)
<223> OTHER INFORMATION: single nucleotide polymorphism

<400> SEQUENCE: 14

caaggaacct aggatggggg cggattcatt aacaaggagg ggggccctaa tcccctgncg     60

rtctgcacgg gcaataatct agtcagaccc cgaggtcagt agaggcggag gacgcgtcac    120

g                                                                    121


<210> SEQ ID NO 15
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: single nucleotide polymorphism

<400> SEQUENCE: 15

cagcacatat tgtgttgaaa tgaatgagca cactgcatcc atatcaccac tggtacacaa     60

rggcatagtt taagtcatgt tatgatgtag cgcaccgagc aaggtatttt gacacacata    120

a                                                                    121


<210> SEQ ID NO 16
<211> LENGTH: 101
<212> TYPE: DNA
<213> ORGANISM: Zea mays
<220> FEATURE:
<221> NAME/KEY: misc_feature
<222> LOCATION: (51)..(51)
<223> OTHER INFORMATION: single nucleotide polymorphism

<400> SEQUENCE: 16

aatgtgggaa gagctggagc agcaaatcta gacgtcattc aagaagtcga rtatgtaaag     60
```

-continued gaagatgcta gaattatata cctccttgaa tgcctccaaa a 101

<210> SEQ ID NO 17
<211> LENGTH: 101
<212> TYPE: DNA
<213> ORGANISM: Zea mays
<220> FEATURE:
<221> NAME/KEY: misc_feature
<222> LOCATION: (51)..(51)
<223> OTHER INFORMATION: single nucleotide polymorphism

<400> SEQUENCE: 17
ctctttctgc agctcgtgat cgagttgtgt gtgctccatt cccaaattat rtatgatcga 60
ttagtagcgt taggggttaa ccagtagccg ctgtgtactt g 101

<210> SEQ ID NO 18
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: single nucleotide polymorphism

<400> SEQUENCE: 18
ttatggggga ggcagattgt cgtggggcgc gggggagggc gagcttgggg gcgccgcaga 60
gcgagggaca ttgccgagat tgccatggag tgagggcacg rcgagattgc cgcgagggag 120
agggcgcttg ccgaggcaga ttgccgcggg ggaggggcgc ttgccgaggc ggagacgtgg 180
tgaagccgtg gtggacgccc a 201

<210> SEQ ID NO 19
<211> LENGTH: 4215
<212> TYPE: DNA
<213> ORGANISM: Artificial Sequence
<220> FEATURE:
<223> OTHER INFORMATION: genomic DNA of F35H mutant P434L

<400> SEQUENCE: 19
atgcagctcg cggcgttgtg caccgacccc gtggtgctgt gcagcgcctt cctctgcctc 60
ctcctccacg tggctctccg ctcgctgctg caccctcctt ctgccgcctc ttcctccggg 120
cgccgcgggc agctcccgcc ggggccaccg ggcctgccga tcctcggcgc gctgccactc 180
gtgggcccag ccccgcacgc cggcctggcc gcgctggcgc gcaagtacgg tcccatcatg 240
tacctgaaga tgggcacggc cggcgtggtg gtggcgtcgt ccccgcgcgc ggcgcggacg 300
ttcctcaagg cgctggacgc gcggtacgcc aaccggccgg ccgtggcgag cgccgcggac 360
atcacgtacg ggcggcagaa catggtgttc gcggactacg ggcccaagtg gaagctgatg 420
cggaagctcg ccagcgtgca cctgctcggc gcgcgcgcgc tcgcggactg ggcgtgcgtg 480
cggcgcggcg aggccggcca cgtgctgcgc ggcgtggcgg aggcggccgc ggccggcagg 540
cccgtcgtcg tgccggagct gctcgtgtgc gccctcgcca acatcgtcgg gcagatcaca 600
gtgagcaagc gggtgttcga cgcgcagggg gacgactcga acaggtgagg atgggaggtc 660
catgaaatcc taccagctgt gagcatgcat aaaagttcat ttggaaagaa aagaacatat 720
ttttcttaca aatttatgct tactgtttct ttaagtttcg ataaagtttg taaaaaaaat 780
ttaggctagt ttgaaactcc atttaggatt tctattttcc aaagaaaaat aaacgaattt 840
ctcttgaaaa aatgaaaatt ctttagaaaa ataggttctc aaactagccc tcaataaaac 900
ttaatgcgat cgttttctct gactctcatt catctttctc tggttatcta attgggtcct 960

-continued tgagagatga gtttacctgc ttgtccttta ttattgcaaa gacaacatat ctgatgcaca 1020
tggaacattg gtgcacatgg tgcacatatg aaatcatcac cactcatttt aaatctaacg 1080
tctatagttg tttgatatat tttattaagg acaccctcca acgtggtggt gtgtagtggt 1140
ggaaggtgtt atttgtaaat tgaataatca actagagacg ttagatctaa aatgagtggt 1200
gatgatttaa tatgtgcacc atgtgcacca gtcttctatg tgcaccagat atgtcctcta 1260
ttgcaaatgc tagacggaac accagctagc actagcagac tgtttatgtg gaaagaaaaa 1320
acttaaaaag atcagctagg aagctgctgt catctgtacg tatatatggt gaagactgaa 1380
caatctgcat gacaagcaaa acttagctta aaagcgaaaa gagcgatgga aacggccgct 1440
cgataaataa ttaatgagag tcttgggatt tttcatgcat ggaaaaaaac aaagctggca 1500
tttttcatct aatataatat ataacgctga tatcatattg cgtgcagata caaggacatg 1560
atcgtgtcgc tgctgaccgg cacgggcatg ttcaacatca gcgacttcgt gccggcgctg 1620
gcgcgtctgg acctgcaggg cgtgcaggcg aagctgcggc gcgtccaccg ccagttcgac 1680
ggcctcatca ccaagctgct ggccgagcac gccgcgacgg ccgcggaccg cgcgcgccag 1740
ggccgcccgg acttcgtcga ccggctccgc gccacgatgg acgccggcgc cgccgccgac 1800
gacgagagcg gcgagaccat caccgaggtc aacatcaagg gcctcatctt cgtaagctcc 1860
ctgctttttc ctcgccccca accatgcatc atcatatgca cttatatttt acacttgctc 1920
ggttttcctt tagtaactaa ctaatccgtc gcagctgcga tacacgtagc actagtacta 1980
cagcgatggg tcatcggtaa ctgaatctaa ggtgcaatag agtgcacggc cgcgggatca 2040
tggcgtgaca tgggagctaa gctaagccag tggccaccta acgaaggcac tgaccgaaag 2100
ctcagtggcg tgttaggtgg agatagtgga tcgagttgtt ggaaagacaa tatcaaaacc 2160
actctccaat tgatgatgtg tagggcctgc agtgttttga atccaccttg tttggtcgaa 2220
cacattacta gagtgaaata tggttccaat gttaattgat agcgcgaaag ggtctctagc 2280
gtaatggtta aaccttccga gtagcacatc caggttgggt tcgatcctct cgagggcgaa 2340
ttttcaagct ttgttaaaaa aattatctcg ttgtgccccg tccgctctca ggaatcgata 2400
ttctacacga caccctccga ctagtgacag ttgattgact cgttagtgat gagaagccat 2460
gctaaaaaag tggagacgta gatatgatag aggttccctt tcctaagcaa acgtgaatgc 2520
tatgaaaatt atgcagttta aaaaaaactt taaagataaa caggaattct cttttttgga 2580
acaaacaata cgaatgcacc tccaaatatc ttatcgagtc gacttttatg gaattattgt 2640
ttttgttatt tctaagatgg gagcccaaaa tcacatacaa attattcagt gaatgcctcg 2700
gtgttttttt attagttaag ggctctcatt tttttcaagg gatttttatt tttttccaaa 2760
agaaaataaa ctaatcctct ttagaaaaat ggaaatctat tggagaaatg aggttcctaa 2820
actagctcta acagtgagtc agttaatcag gagaagatat tagactcctg tatagtgtgc 2880
agcaaccaca tccgattctg acgttttagc ttaatgttcg ctatgtagac gtcgggcata 2940
gggaatgcat tgctaccaga acacgaatga cagctatgca agtctctaga acgttggagt 3000
agttaacaaa cgtgatagat gtaacctctg gatcatggta tgatgtcatt tcctagacta 3060
gaagaattgg tagtcaaatc gagcaaagtc ccgaaagcac actgggcttt cgacacagtg 3120
ataccaaaga tgctgaaaag aactgaggca cgataaactg ttcggtgttg gtgtaaacga 3180
ccaaagatgc tgaaaataac tgatcgtcac catccgtgaa tctaactttc gacacactgt 3240
taccaaatcc ttcgtcaaaa ttacaggaat aattaaggcg cttagacgat gataaaccat 3300

-continued

```
tttttgtcac taattaacca cactgttctt tgcttgaccg tgacaaaaaa aaactttttt   3360

gtgaagcagt gttgccgtaa accacaacca tcatgaactc acttgccttg tcatatgtac   3420

ttgtaccatc gaacgccgcg cgctaagaca atgcaccacc cttcaagtct tagctcactg   3480

ataccgctaa ttaagttaga taatgtcgat tactagttgt cttacttcga actatttctt   3540

ttcggcaaac tgaagtaaag acaacgtttt gttccgcagg acatgttcac ggcgggtacg   3600

gacacgtcgt cgatcatcgt ggagtgggcg atggcggaga tgctcaagaa cccgaccgtc   3660

atggcgcgcg cgcaggagga gctggaccgc gcggtgggcc ggggccggcg cctggaggag   3720

tcggacctgc ccggcctccc ctacctgcag gcggtgtgca aggaggccat gcggctgcac   3780

ccgtccacgc cgctcagcct cccgcacttc tccttggacg cctgcgacga cgtcgacggc   3840

taccgcgtcc cggccaacac ccgcctgctc gtcaacgtct gggccatcgg ccgggacccg   3900

gaggcctggg agaggcccct cgacttccgc ctcgagcgct tcctgcccgg gggcggcgcg   3960

gagaaggtcg acccccctggg gaactgcttc gagctcatcc cgttcggcgc cggccggagg   4020

atctgcgcgg ggaagctggc gggcatggtg ttcgtgcagt acttcctggg cacgctgctg   4080

cacgcgttcg actggcgcct gcctgacggc gaggagaagc tggacatgag cgagacgttc   4140

ggcctcgcgc tgcccaaggc agtgccgctc cgcgccgtcg ccacgccacg gctcgtgccg   4200

gaagcctatg cctga                                                     4215


<210> SEQ ID NO 20
<211> LENGTH: 527
<212> TYPE: PRT
<213> ORGANISM: Artificial Sequence
<220> FEATURE:
<223> OTHER INFORMATION: amino acid sequence of F35H mutant P434L

<400> SEQUENCE: 20

Met Gln Leu Ala Ala Leu Cys Thr Asp Pro Val Val Leu Cys Ser Ala
1               5                   10                  15

Phe Leu Cys Leu Leu Leu His Val Ala Leu Arg Ser Leu Leu His Pro
            20                  25                  30

Pro Ser Ala Ala Ser Ser Ser Gly Arg Arg Gly Gln Leu Pro Pro Gly
        35                  40                  45

Pro Pro Gly Leu Pro Ile Leu Gly Ala Leu Pro Leu Val Gly Pro Ala
    50                  55                  60

Pro His Ala Gly Leu Ala Ala Leu Ala Arg Lys Tyr Gly Pro Ile Met
65                  70                  75                  80

Tyr Leu Lys Met Gly Thr Ala Gly Val Val Val Ala Ser Ser Pro Arg
                85                  90                  95

Ala Ala Arg Thr Phe Leu Lys Ala Leu Asp Ala Arg Tyr Ala Asn Arg
            100                 105                 110

Pro Ala Val Ala Ser Ala Ala Asp Ile Thr Tyr Gly Arg Gln Asn Met
        115                 120                 125

Val Phe Ala Asp Tyr Gly Pro Lys Trp Lys Leu Met Arg Lys Leu Ala
    130                 135                 140

Ser Val His Leu Leu Gly Ala Arg Ala Leu Ala Asp Trp Ala Cys Val
145                 150                 155                 160

Arg Arg Gly Glu Ala Gly His Val Leu Arg Gly Val Ala Glu Ala Ala
                165                 170                 175

Ala Ala Gly Arg Pro Val Val Val Pro Glu Leu Leu Val Cys Ala Leu
            180                 185                 190

Ala Asn Ile Val Gly Gln Ile Thr Val Ser Lys Arg Val Phe Asp Ala
```

-continued

```
        195                 200                 205

Gln Gly Asp Asp Ser Asn Arg Tyr Lys Asp Met Ile Val Ser Leu Leu
    210                 215                 220

Thr Gly Thr Gly Met Phe Asn Ile Ser Asp Phe Val Pro Ala Leu Ala
225                 230                 235                 240

Arg Leu Asp Leu Gln Gly Val Gln Ala Lys Leu Arg Arg Val His Arg
                245                 250                 255

Gln Phe Asp Gly Leu Ile Thr Lys Leu Leu Ala Glu His Ala Ala Thr
            260                 265                 270

Ala Ala Asp Arg Ala Arg Gln Gly Arg Pro Asp Phe Val Asp Arg Leu
        275                 280                 285

Arg Ala Thr Met Asp Ala Gly Ala Ala Ala Asp Asp Glu Ser Gly Glu
    290                 295                 300

Thr Ile Thr Glu Val Asn Ile Lys Gly Leu Ile Phe Asp Met Phe Thr
305                 310                 315                 320

Ala Gly Thr Asp Thr Ser Ser Ile Ile Val Glu Trp Ala Met Ala Glu
                325                 330                 335

Met Leu Lys Asn Pro Thr Val Met Ala Arg Ala Gln Glu Glu Leu Asp
            340                 345                 350

Arg Ala Val Gly Arg Gly Arg Arg Leu Glu Glu Ser Asp Leu Pro Gly
        355                 360                 365

Leu Pro Tyr Leu Gln Ala Val Cys Lys Glu Ala Met Arg Leu His Pro
    370                 375                 380

Ser Thr Pro Leu Ser Leu Pro His Phe Ser Leu Asp Ala Cys Asp Asp
385                 390                 395                 400

Val Asp Gly Tyr Arg Val Pro Ala Asn Thr Arg Leu Leu Val Asn Val
                405                 410                 415

Trp Ala Ile Gly Arg Asp Pro Glu Ala Trp Glu Arg Pro Leu Asp Phe
            420                 425                 430

Arg Leu Glu Arg Phe Leu Pro Gly Gly Gly Ala Glu Lys Val Asp Pro
        435                 440                 445

Leu Gly Asn Cys Phe Glu Leu Ile Pro Phe Gly Ala Gly Arg Arg Ile
    450                 455                 460

Cys Ala Gly Lys Leu Ala Gly Met Val Phe Val Gln Tyr Phe Leu Gly
465                 470                 475                 480

Thr Leu Leu His Ala Phe Asp Trp Arg Leu Pro Asp Gly Glu Glu Lys
                485                 490                 495

Leu Asp Met Ser Glu Thr Phe Gly Leu Ala Leu Pro Lys Ala Val Pro
            500                 505                 510

Leu Arg Ala Val Ala Thr Pro Arg Leu Val Pro Glu Ala Tyr Ala
        515                 520                 525
```

<210> SEQ ID NO 21
<211> LENGTH: 4215
<212> TYPE: DNA
<213> ORGANISM: Artificial Sequence
<220> FEATURE:
<223> OTHER INFORMATION: genomic DNA of F35H mutant W426stop

<400> SEQUENCE: 21

```
atgcagctcg cggcgttgtg caccgacccc gtggtgctgt gcagcgcctt cctctgcctc     60

ctcctccacg tggctctccg ctcgctgctg caccctcctt ctgccgcctc ttcctccggg    120

cgccgcgggc agctcccgcc ggggccaccg ggcctgccga tcctcggcgc gctgccactc    180

gtgggcccag ccccgcacgc cggcctggcc gcgctggcgc gcaagtacgg tcccatcatg    240
```

-continued

```
tacctgaaga tgggcacggc cggcgtggtg gtggcgtcgt ccccgcgcgc ggcgcggacg    300
ttcctcaagg cgctggacgc gcggtacgcc aaccggccgg ccgtggcgag cgccgcggac    360
atcacgtacg ggcggcagaa catggtgttc gcggactacg ggcccaagtg gaagctgatg    420
cggaagctcg ccagcgtgca cctgctcggc gcgcgcgcgc tcgcggactg ggcgtgcgtg    480
cggcgcggcg aggccggcca cgtgctgcgc ggcgtggcgg aggcggccgc ggccggcagg    540
cccgtcgtcg tgccggagct gctcgtgtgc gccctcgcca acatcgtcgg gcagatcaca    600
gtgagcaagc gggtgttcga cgcgcagggg gacgactcga acaggtgagg atgggaggtc    660
catgaaatcc taccagctgt gagcatgcat aaaagttcat ttggaaagaa aagaacatat    720
ttttcttaca aatttatgct tactgtttct ttaagtttcg ataaagtttg taaaaaaaat    780
ttaggctagt ttgaaactcc atttaggatt tctattttcc aaagaaaaat aaacgaattt    840
ctcttgaaaa aatgaaaatt ctttagaaaa ataggttctc aaactagccc tcaataaaac    900
ttaatgcgat cgttttctct gactctcatt catctttctc tggttatcta attgggtcct    960
tgagagatga gtttacctgc ttgtccttta ttattgcaaa gacaacatat ctgatgcaca   1020
tggaacattg gtgcacatgg tgcacatatg aaatcatcac cactcatttt aaatctaacg   1080
tctatagttg tttgatatat tttattaagg acaccctcca acgtggtggt gtgtagtggt   1140
ggaaggtgtt atttgtaaat tgaataatca actagagacg ttagatctaa aatgagtggt   1200
gatgatttaa tatgtgcacc atgtgcacca gtcttctatg tgcaccagat atgtcctcta   1260
ttgcaaatgc tagacggaac accagctagc actagcagac tgtttatgtg gaaagaaaaa   1320
acttaaaaag atcagctagg aagctgctgt catctgtacg tatatatggt gaagactgaa   1380
caatctgcat gacaagcaaa acttagctta aaagcgaaaa gagcgatgga aacggccgct   1440
cgataaataa ttaatgagag tcttgggatt tttcatgcat ggaaaaaaac aaagctggca   1500
tttttcatct aatataatat ataacgctga tatcatattg cgtgcagata caaggacatg   1560
atcgtgtcgc tgctgaccgg cacgggcatg ttcaacatca gcgacttcgt gccggcgctg   1620
gcgcgtctgg acctgcaggg cgtgcaggcg aagctgcggc gcgtccaccg ccagttcgac   1680
ggcctcatca ccaagctgct ggccgagcac gccgcgacgg ccgcggaccg cgcgcgccag   1740
ggccgcccgg acttcgtcga ccggctccgc gccacgatgg acgccggcgc cgccgccgac   1800
gacgagagcg gcgagaccat caccgaggtc aacatcaagg gcctcatctt cgtaagctcc   1860
ctgctttttc ctcgccccca accatgcatc atcatatgca cttatatttt acacttgctc   1920
ggttttcctt tagtaactaa ctaatccgtc gcagctgcga tacacgtagc actagtacta   1980
cagcgatggg tcatcggtaa ctgaatctaa ggtgcaatag agtgcacggc cgcgggatca   2040
tggcgtgaca tgggagctaa gctaagccag tggccaccta acgaaggcac tgaccgaaag   2100
ctcagtggcg tgttaggtgg agatagtgga tcgagttgtt ggaaagacaa tatcaaaacc   2160
actctccaat tgatgatgtg tagggcctgc agtgttttga atccaccttg tttggtcgaa   2220
cacattacta gagtgaaata tggttccaat gttaattgat agcgcgaaag ggtctctagc   2280
gtaatggtta aaccttccga gtagcacatc caggttgggt tcgatcctct cgagggcgaa   2340
ttttcaagct ttgttaaaaa aattatctcg ttgtgccccg tccgctctca ggaatcgata   2400
ttctacacga caccctccga ctagtgacag ttgattgact cgttagtgat gagaagccat   2460
gctaaaaaag tggagacgta gatatgatag aggttccctt tcctaagcaa acgtgaatgc   2520
tatgaaaatt atgcagttta aaaaaaactt taaagataaa caggaattct ctttttttgga   2580
```

-continued

```
acaaacaata cgaatgcacc tccaaatatc ttatcgagtc gacttttatg gaattattgt   2640

ttttgttatt tctaagatgg gagcccaaaa tcacatacaa attattcagt gaatgcctcg   2700

gtgttttttt attagttaag ggctctcatt tttttcaagg gatttttatt tttttccaaa   2760

agaaaataaa ctaatcctct ttagaaaaat ggaaatctat tggagaaatg aggttcctaa   2820

actagctcta acagtgagtc agttaatcag gagaagatat tagactcctg tatagtgtgc   2880

agcaaccaca tccgattctg acgttttagc ttaatgttcg ctatgtagac gtcgggcata   2940

gggaatgcat tgctaccaga acacgaatga cagctatgca agtctctaga acgttggagt   3000

agttaacaaa cgtgatagat gtaacctctg gatcatggta tgatgtcatt tcctagacta   3060

gaagaattgg tagtcaaatc gagcaaagtc ccgaaagcac actgggcttt cgacacagtg   3120

ataccaaaga tgctgaaaag aactgaggca cgataaactg ttcggtgttg gtgtaaacga   3180

ccaaagatgc tgaaaataac tgatcgtcac catccgtgaa tctaactttc gacacactgt   3240

taccaaatcc ttcgtcaaaa ttacaggaat aattaaggcg cttagacgat gataaaccat   3300

tttttgtcac taattaacca cactgttctt tgcttgaccg tgacaaaaaa aaactttttt   3360

gtgaagcagt gttgccgtaa accacaacca tcatgaactc acttgccttg tcatatgtac   3420

ttgtaccatc gaacgccgcg cgctaagaca atgcaccacc cttcaagtct tagctcactg   3480

ataccgctaa ttaagttaga taatgtcgat tactagttgt cttacttcga actatttctt   3540

ttcggcaaac tgaagtaaag acaacgtttt gttccgcagg acatgttcac ggcgggtacg   3600

gacacgtcgt cgatcatcgt ggagtgggcg atggcggaga tgctcaagaa cccgaccgtc   3660

atggcgcgcg cgcaggagga gctggaccgc gcggtgggcc ggggccggcg cctggaggag   3720

tcggacctgc ccggcctccc ctacctgcag gcggtgtgca aggaggccat gcggctgcac   3780

ccgtccacgc cgctcagcct cccgcacttc tccttggacg cctgcgacga cgtcgacggc   3840

taccgcgtcc cggccaacac ccgcctgctc gtcaacgtct gggccatcgg ccgggacccg   3900

gaggcctagg agaggcccct cgacttccgc cccgagcgct tcctgcccgg gggcggcgcg   3960

gagaaggtcg accccctggg gaactgcttc gagctcatcc cgttcggcgc cggccggagg   4020

atctgcgcgg ggaagctggc gggcatggtg ttcgtgcagt acttcctggg cacgctgctg   4080

cacgcgttcg actggcgcct gcctgacggc gaggagaagc tggacatgag cgagacgttc   4140

ggcctcgcgc tgcccaaggc agtgccgctc cgcgccgtcg ccacgccacg gctcgtgccg   4200

gaagcctatg cctga                                                    4215
```

<210> SEQ ID NO 22
<211> LENGTH: 425
<212> TYPE: PRT
<213> ORGANISM: Artificial Sequence
<220> FEATURE:
<223> OTHER INFORMATION: amino acid sequence of F35H mutant W426stop

<400> SEQUENCE: 22

```
Met Gln Leu Ala Ala Leu Cys Thr Asp Pro Val Val Leu Cys Ser Ala
1               5                   10                  15

Phe Leu Cys Leu Leu Leu His Val Ala Leu Arg Ser Leu Leu His Pro
            20                  25                  30

Pro Ser Ala Ala Ser Ser Ser Gly Arg Arg Gly Gln Leu Pro Pro Gly
        35                  40                  45

Pro Pro Gly Leu Pro Ile Leu Gly Ala Leu Pro Leu Val Gly Pro Ala
    50                  55                  60

Pro His Ala Gly Leu Ala Ala Leu Ala Arg Lys Tyr Gly Pro Ile Met
```

```
65                  70                  75                  80

Tyr Leu Lys Met Gly Thr Ala Gly Val Val Val Ala Ser Ser Pro Arg
                85                  90                  95

Ala Ala Arg Thr Phe Leu Lys Ala Leu Asp Ala Arg Tyr Ala Asn Arg
            100                 105                 110

Pro Ala Val Ala Ser Ala Ala Asp Ile Thr Tyr Gly Arg Gln Asn Met
        115                 120                 125

Val Phe Ala Asp Tyr Gly Pro Lys Trp Lys Leu Met Arg Lys Leu Ala
    130                 135                 140

Ser Val His Leu Leu Gly Ala Arg Ala Leu Ala Asp Trp Ala Cys Val
145                 150                 155                 160

Arg Arg Gly Glu Ala Gly His Val Leu Arg Gly Val Ala Glu Ala Ala
                165                 170                 175

Ala Ala Gly Arg Pro Val Val Val Pro Glu Leu Leu Val Cys Ala Leu
            180                 185                 190

Ala Asn Ile Val Gly Gln Ile Thr Val Ser Lys Arg Val Phe Asp Ala
        195                 200                 205

Gln Gly Asp Asp Ser Asn Arg Tyr Lys Asp Met Ile Val Ser Leu Leu
    210                 215                 220

Thr Gly Thr Gly Met Phe Asn Ile Ser Asp Phe Val Pro Ala Leu Ala
225                 230                 235                 240

Arg Leu Asp Leu Gln Gly Val Gln Ala Lys Leu Arg Arg Val His Arg
                245                 250                 255

Gln Phe Asp Gly Leu Ile Thr Lys Leu Leu Ala Glu His Ala Ala Thr
            260                 265                 270

Ala Ala Asp Arg Ala Arg Gln Gly Arg Pro Asp Phe Val Asp Arg Leu
        275                 280                 285

Arg Ala Thr Met Asp Ala Gly Ala Ala Ala Asp Asp Glu Ser Gly Glu
    290                 295                 300

Thr Ile Thr Glu Val Asn Ile Lys Gly Leu Ile Phe Asp Met Phe Thr
305                 310                 315                 320

Ala Gly Thr Asp Thr Ser Ser Ile Ile Val Glu Trp Ala Met Ala Glu
                325                 330                 335

Met Leu Lys Asn Pro Thr Val Met Ala Arg Ala Gln Glu Glu Leu Asp
            340                 345                 350

Arg Ala Val Gly Arg Gly Arg Arg Leu Glu Glu Ser Asp Leu Pro Gly
        355                 360                 365

Leu Pro Tyr Leu Gln Ala Val Cys Lys Glu Ala Met Arg Leu His Pro
    370                 375                 380

Ser Thr Pro Leu Ser Leu Pro His Phe Ser Leu Asp Ala Cys Asp Asp
385                 390                 395                 400

Val Asp Gly Tyr Arg Val Pro Ala Asn Thr Arg Leu Leu Val Asn Val
                405                 410                 415

Trp Ala Ile Gly Arg Asp Pro Glu Ala
            420                 425


<210> SEQ ID NO 23
<211> LENGTH: 4215
<212> TYPE: DNA
<213> ORGANISM: Artificial Sequence
<220> FEATURE:
<223> OTHER INFORMATION: genomic DNA of F35H mutant R252W

<400> SEQUENCE: 23

atgcagctcg cggcgttgtg caccgacccc gtggtgctgt gcagcgcctt cctctgcctc     60
```

```
ctcctccacg tggctctccg ctcgctgctg caccctcctt ctgccgcctc ttcctccggg     120
cgccgcgggc agctcccgcc ggggccaccg ggcctgccga tcctcggcgc gctgccactc     180
gtgggcccag ccccgcacgc cggcctggcc gcgctggcgc gcaagtacgg tcccatcatg     240
tacctgaaga tgggcacggc cggcgtggtg gtggcgtcgt ccccgcgcgc ggcgcggacg     300
ttcctcaagg cgctggacgc gcggtacgcc aaccggccgg ccgtggcgag cgccgcggac     360
atcacgtacg ggcggcagaa catggtgttc gcggactacg ggcccaagtg gaagctgatg     420
cggaagctcg ccagcgtgca cctgctcggc gcgcgcgcgc tcgcggactg ggcgtgcgtg     480
cggcgcggcg aggccggcca cgtgctgcgc ggcgtggcgg aggcggccgc ggccggcagg     540
cccgtcgtcg tgccggagct gctcgtgtgc gccctcgcca acatcgtcgg gcagatcaca     600
gtgagcaagc gggtgttcga cgcgcagggg gacgactcga acaggtgagg atgggaggtc     660
catgaaatcc taccagctgt gagcatgcat aaaagttcat ttggaaagaa aagaacatat     720
ttttcttaca aatttatgct tactgtttct ttaagtttcg ataaagtttg taaaaaaaat     780
ttaggctagt ttgaaactcc atttaggatt tctattttcc aaagaaaaat aaacgaattt     840
ctcttgaaaa aatgaaaatt ctttagaaaa ataggttctc aaactagccc tcaataaaac     900
ttaatgcgat cgttttctct gactctcatt catctttctc tggttatcta attgggtcct     960
tgagagatga gtttacctgc ttgtccttta ttattgcaaa gacaacatat ctgatgcaca    1020
tggaacattg gtgcacatgg tgcacatatg aaatcatcac cactcatttt aaatctaacg    1080
tctatagttg tttgatatat tttattaagg acaccctcca acgtggtggt gtgtagtggt    1140
ggaaggtgtt atttgtaaat tgaataatca actagagacg ttagatctaa aatgagtggt    1200
gatgatttaa tatgtgcacc atgtgcacca gtcttctatg tgcaccagat atgtcctcta    1260
ttgcaaatgc tagacggaac accagctagc actagcagac tgtttatgtg gaaagaaaaa    1320
acttaaaaag atcagctagg aagctgctgt catctgtacg tatatatggt gaagactgaa    1380
caatctgcat gacaagcaaa acttagctta aaagcgaaaa gagcgatgga aacggccgct    1440
cgataaataa ttaatgagag tcttgggatt tttcatgcat ggaaaaaaac aaagctggca    1500
tttttcatct aatataatat ataacgctga tatcatattg cgtgcagata caaggacatg    1560
atcgtgtcgc tgctgaccgg cacgggcatg ttcaacatca gcgacttcgt gccggcgctg    1620
gcgcgtctgg acctgcaggg cgtgcaggcg aagctgtggc gcgtccaccg ccagttcgac    1680
ggcctcatca ccaagctgct ggccgagcac gccgcgacgg ccgcggaccg cgcgcgccag    1740
ggccgcccgg acttcgtcga ccggctccgc gccacgatgg acgccggcgc cgccgccgac    1800
gacgagagcg gcgagaccat caccgaggtc aacatcaagg gcctcatctt cgtaagctcc    1860
ctgctttttc ctcgccccca accatgcatc atcatatgca cttatatttt acacttgctc    1920
ggttttcctt tagtaactaa ctaatccgtc gcagctgcga tacacgtagc actagtacta    1980
cagcgatggg tcatcggtaa ctgaatctaa ggtgcaatag agtgcacggc cgcgggatca    2040
tggcgtgaca tgggagctaa gctaagccag tggccaccta acgaaggcac tgaccgaaag    2100
ctcagtggcg tgttaggtgg agatagtgga tcgagttgtt ggaaagacaa tatcaaaacc    2160
actctccaat tgatgatgtg tagggcctgc agtgttttga atccaccttg tttggtcgaa    2220
cacattacta gagtgaaata tggttccaat gttaattgat agcgcgaaag ggtctctagc    2280
gtaatggtta aaccttccga gtagcacatc caggttgggt tcgatcctct cgagggcgaa    2340
ttttcaagct ttgttaaaaa aattatctcg ttgtgccccg tccgctctca ggaatcgata    2400
```

-continued

```
ttctacacga caccctccga ctagtgacag ttgattgact cgttagtgat gagaagccat   2460

gctaaaaaag tggagacgta gatatgatag aggttccctt tcctaagcaa acgtgaatgc   2520

tatgaaaatt atgcagttta aaaaaaactt taaagataaa caggaattct ctttttgga    2580

acaaacaata cgaatgcacc tccaaatatc ttatcgagtc gacttttatg gaattattgt   2640

ttttgttatt tctaagatgg gagcccaaaa tcacatacaa attattcagt gaatgcctcg   2700

gtgttttttt attagttaag ggctctcatt tttttcaagg gatttttatt tttttccaaa   2760

agaaaataaa ctaatcctct ttagaaaaat ggaaatctat tggagaaatg aggttcctaa   2820

actagctcta acagtgagtc agttaatcag gagaagatat tagactcctg tatagtgtgc   2880

agcaaccaca tccgattctg acgttttagc ttaatgttcg ctatgtagac gtcgggcata   2940

gggaatgcat tgctaccaga acacgaatga cagctatgca agtctctaga acgttggagt   3000

agttaacaaa cgtgatagat gtaacctctg gatcatggta tgatgtcatt tcctagacta   3060

gaagaattgg tagtcaaatc gagcaaagtc ccgaaagcac actgggcttt cgacacagtg   3120

ataccaaaga tgctgaaaag aactgaggca cgataaactg ttcggtgttg gtgtaaacga   3180

ccaaagatgc tgaaaataac tgatcgtcac catccgtgaa tctaactttc gacacactgt   3240

taccaaatcc ttcgtcaaaa ttacaggaat aattaaggcg cttagacgat gataaaccat   3300

tttttgtcac taattaacca cactgttctt tgcttgaccg tgacaaaaaa aaactttttt   3360

gtgaagcagt gttgccgtaa accacaacca tcatgaactc acttgccttg tcatatgtac   3420

ttgtaccatc gaacgccgcg cgctaagaca atgcaccacc cttcaagtct tagctcactg   3480

ataccgctaa ttaagttaga taatgtcgat tactagttgt cttacttcga actatttctt   3540

ttcggcaaac tgaagtaaag acaacgtttt gttccgcagg acatgttcac ggcgggtacg   3600

gacacgtcgt cgatcatcgt ggagtgggcg atggcggaga tgctcaagaa cccgaccgtc   3660

atggcgcgcg cgcaggagga gctggaccgc gcggtgggcc ggggccggcg cctggaggag   3720

tcggacctgc ccggcctccc ctacctgcag gcggtgtgca aggaggccat gcggctgcac   3780

ccgtccacgc cgctcagcct cccgcacttc tccttggacg cctgcgacga cgtcgacggc   3840

taccgcgtcc cggccaacac ccgcctgctc gtcaacgtct gggccatcgg ccgggacccg   3900

gaggcctggg agaggcccct cgacttccgc cccgagcgct tcctgcccgg gggcggcgcg   3960

gagaaggtcg acccccctggg gaactgcttc gagctcatcc cgttcggcgc cggccggagg  4020

atctgcgcgg ggaagctggc gggcatggtg ttcgtgcagt acttcctggg cacgctgctg   4080

cacgcgttcg actggcgcct gcctgacggc gaggagaagc tggacatgag cgagacgttc   4140

ggcctcgcgc tgcccaaggc agtgccgctc cgcgccgtcg ccacgccacg gctcgtgccg   4200

gaagcctatg cctga                                                    4215
```

<210> SEQ ID NO 24
<211> LENGTH: 527
<212> TYPE: PRT
<213> ORGANISM: Artificial Sequence
<220> FEATURE:
<223> OTHER INFORMATION: amino acid sequence of F35H mutant R252W

<400> SEQUENCE: 24

```
Met Gln Leu Ala Ala Leu Cys Thr Asp Pro Val Val Leu Cys Ser Ala
1               5                   10                  15

Phe Leu Cys Leu Leu Leu His Val Ala Leu Arg Ser Leu Leu His Pro
            20                  25                  30

Pro Ser Ala Ala Ser Ser Ser Gly Arg Arg Gly Gln Leu Pro Pro Gly
```

-continued

```
        35                  40                  45

Pro Pro Gly Leu Pro Ile Leu Gly Ala Leu Pro Leu Val Gly Pro Ala
    50                  55                  60

Pro His Ala Gly Leu Ala Ala Leu Ala Arg Lys Tyr Gly Pro Ile Met
65                  70                  75                  80

Tyr Leu Lys Met Gly Thr Ala Gly Val Val Val Ala Ser Ser Pro Arg
                85                  90                  95

Ala Ala Arg Thr Phe Leu Lys Ala Leu Asp Ala Arg Tyr Ala Asn Arg
            100                 105                 110

Pro Ala Val Ala Ser Ala Ala Asp Ile Thr Tyr Gly Arg Gln Asn Met
        115                 120                 125

Val Phe Ala Asp Tyr Gly Pro Lys Trp Lys Leu Met Arg Lys Leu Ala
    130                 135                 140

Ser Val His Leu Leu Gly Ala Arg Ala Leu Ala Asp Trp Ala Cys Val
145                 150                 155                 160

Arg Arg Gly Glu Ala Gly His Val Leu Arg Gly Val Ala Glu Ala Ala
                165                 170                 175

Ala Ala Gly Arg Pro Val Val Val Pro Glu Leu Leu Val Cys Ala Leu
            180                 185                 190

Ala Asn Ile Val Gly Gln Ile Thr Val Ser Lys Arg Val Phe Asp Ala
        195                 200                 205

Gln Gly Asp Asp Ser Asn Arg Tyr Lys Asp Met Ile Val Ser Leu Leu
    210                 215                 220

Thr Gly Thr Gly Met Phe Asn Ile Ser Asp Phe Val Pro Ala Leu Ala
225                 230                 235                 240

Arg Leu Asp Leu Gln Gly Val Gln Ala Lys Leu Trp Arg Val His Arg
                245                 250                 255

Gln Phe Asp Gly Leu Ile Thr Lys Leu Leu Ala Glu His Ala Ala Thr
            260                 265                 270

Ala Ala Asp Arg Ala Arg Gln Gly Arg Pro Asp Phe Val Asp Arg Leu
        275                 280                 285

Arg Ala Thr Met Asp Ala Gly Ala Ala Ala Asp Asp Glu Ser Gly Glu
    290                 295                 300

Thr Ile Thr Glu Val Asn Ile Lys Gly Leu Ile Phe Asp Met Phe Thr
305                 310                 315                 320

Ala Gly Thr Asp Thr Ser Ser Ile Ile Val Glu Trp Ala Met Ala Glu
                325                 330                 335

Met Leu Lys Asn Pro Thr Val Met Ala Arg Ala Gln Glu Glu Leu Asp
            340                 345                 350

Arg Ala Val Gly Arg Gly Arg Arg Leu Glu Glu Ser Asp Leu Pro Gly
        355                 360                 365

Leu Pro Tyr Leu Gln Ala Val Cys Lys Glu Ala Met Arg Leu His Pro
    370                 375                 380

Ser Thr Pro Leu Ser Leu Pro His Phe Ser Leu Asp Ala Cys Asp Asp
385                 390                 395                 400

Val Asp Gly Tyr Arg Val Pro Ala Asn Thr Arg Leu Leu Val Asn Val
                405                 410                 415

Trp Ala Ile Gly Arg Asp Pro Glu Ala Trp Glu Arg Pro Leu Asp Phe
            420                 425                 430

Arg Pro Glu Arg Phe Leu Pro Gly Gly Gly Ala Glu Lys Val Asp Pro
        435                 440                 445

Leu Gly Asn Cys Phe Glu Leu Ile Pro Phe Gly Ala Gly Arg Arg Ile
    450                 455                 460
```

```
Cys Ala Gly Lys Leu Ala Gly Met Val Phe Val Gln Tyr Phe Leu Gly
465                 470                 475                 480

Thr Leu Leu His Ala Phe Asp Trp Arg Leu Pro Asp Gly Glu Glu Lys
                485                 490                 495

Leu Asp Met Ser Glu Thr Phe Gly Leu Ala Leu Pro Lys Ala Val Pro
            500                 505                 510

Leu Arg Ala Val Ala Thr Pro Arg Leu Val Pro Glu Ala Tyr Ala
        515                 520                 525


<210> SEQ ID NO 25
<211> LENGTH: 4215
<212> TYPE: DNA
<213> ORGANISM: Artificial Sequence
<220> FEATURE:
<223> OTHER INFORMATION: genomic DNA of F35H mutant R405H

<400> SEQUENCE: 25

atgcagctcg cggcgttgtg caccgacccc gtggtgctgt gcagcgcctt cctctgcctc      60

ctcctccacg tggctctccg ctcgctgctg caccctcctt ctgccgcctc ttcctccggg     120

cgccgcgggc agctcccgcc ggggccaccg ggcctgccga tcctcggcgc gctgccactc     180

gtgggcccag ccccgcacgc cggcctggcc gcgctggcgc gcaagtacgg tcccatcatg     240

tacctgaaga tgggcacggc cggcgtggtg gtggcgtcgt ccccgcgcgc ggcgcggacg     300

ttcctcaagg cgctggacgc gcggtacgcc aaccggccgg ccgtggcgag cgccgcggac     360

atcacgtacg ggcggcagaa catggtgttc gcggactacg ggcccaagtg gaagctgatg     420

cggaagctcg ccagcgtgca cctgctcggc gcgcgcgcgc tcgcggactg ggcgtgcgtg     480

cggcgcggcg aggccggcca cgtgctgcgc ggcgtggcgg aggcggccgc ggccggcagg     540

cccgtcgtcg tgccggagct gctcgtgtgc gccctcgcca acatcgtcgg gcagatcaca     600

gtgagcaagc gggtgttcga cgcgcagggg gacgactcga acaggtgagg atgggaggtc     660

catgaaatcc taccagctgt gagcatgcat aaaagttcat ttggaaagaa aagaacatat     720

ttttcttaca aatttatgct tactgtttct ttaagtttcg ataaagtttg taaaaaaaat     780

ttaggctagt ttgaaactcc atttaggatt tctattttcc aaagaaaaat aaacgaattt     840

ctcttgaaaa aatgaaaatt ctttagaaaa ataggttctc aaactagccc tcaataaaac     900

ttaatgcgat cgttttctct gactctcatt catctttctc tggttatcta attgggtcct     960

tgagagatga gtttacctgc ttgtccttta ttattgcaaa gacaacatat ctgatgcaca    1020

tggaacattg gtgcacatgg tgcacatatg aaatcatcac cactcatttt aaatctaacg    1080

tctatagttg tttgatatat tttattaagg acaccctcca acgtggtggt gtgtagtggt    1140

ggaaggtgtt atttgtaaat tgaataatca actagagacg ttagatctaa aatgagtggt    1200

gatgatttaa tatgtgcacc atgtgcacca gtcttctatg tgcaccagat atgtcctcta    1260

ttgcaaatgc tagacggaac accagctagc actagcagac tgtttatgtg gaaagaaaaa    1320

acttaaaaag atcagctagg aagctgctgt catctgtacg tatatatggt gaagactgaa    1380

caatctgcat gacaagcaaa acttagctta aaagcgaaaa gagcgatgga aacggccgct    1440

cgataaataa ttaatgagag tcttgggatt tttcatgcat ggaaaaaaac aaagctggca    1500

tttttcatct aatataatat ataacgctga tatcatattg cgtgcagata caaggacatg    1560

atcgtgtcgc tgctgaccgg cacgggcatg ttcaacatca gcgacttcgt gccggcgctg    1620

gcgcgtctgg acctgcaggg cgtgcaggcg aagctgcggc gcgtccaccg ccagttcgac    1680
```

-continued

```
ggcctcatca ccaagctgct ggccgagcac gccgcgacgg ccgcggaccg cgcgcgccag   1740
ggccgcccgg acttcgtcga ccggctccgc gccacgatgg acgccggcgc cgccgccgac   1800
gacgagagcg gcgagaccat caccgaggtc aacatcaagg gcctcatctt cgtaagctcc   1860
ctgctttttc ctcgccccca accatgcatc atcatatgca cttatatttt acacttgctc   1920
ggttttcctt tagtaactaa ctaatccgtc gcagctgcga tacacgtagc actagtacta   1980
cagcgatggg tcatcggtaa ctgaatctaa ggtgcaatag agtgcacggc cgcgggatca   2040
tggcgtgaca tgggagctaa gctaagccag tggccaccta acgaaggcac tgaccgaaag   2100
ctcagtggcg tgttaggtgg agatagtgga tcgagttgtt ggaaagacaa tatcaaaacc   2160
actctccaat tgatgatgtg tagggcctgc agtgttttga atccaccttg tttggtcgaa   2220
cacattacta gagtgaaata tggttccaat gttaattgat agcgcgaaag ggtctctagc   2280
gtaatggtta aaccttccga gtagcacatc caggttgggt tcgatcctct cgagggcgaa   2340
ttttcaagct ttgttaaaaa aattatctcg ttgtgccccg tccgctctca ggaatcgata   2400
ttctacacga caccctccga ctagtgacag ttgattgact cgttagtgat gagaagccat   2460
gctaaaaaag tggagacgta gatatgatag aggttccctt tcctaagcaa acgtgaatgc   2520
tatgaaaatt atgcagttta aaaaaaactt taaagataaa caggaattct cttttttgga   2580
acaaacaata cgaatgcacc tccaaatatc ttatcgagtc gacttttatg gaattattgt   2640
ttttgttatt tctaagatgg gagcccaaaa tcacatacaa attattcagt gaatgcctcg   2700
gtgttttttt attagttaag ggctctcatt tttttcaagg gatttttatt tttttccaaa   2760
agaaaataaa ctaatcctct ttagaaaaat ggaaatctat tggagaaatg aggttcctaa   2820
actagctcta acagtgagtc agttaatcag gagaagatat tagactcctg tatagtgtgc   2880
agcaaccaca tccgattctg acgttttagc ttaatgttcg ctatgtagac gtcgggcata   2940
gggaatgcat tgctaccaga acacgaatga cagctatgca agtctctaga acgttggagt   3000
agttaacaaa cgtgatagat gtaacctctg gatcatggta tgatgtcatt tcctagacta   3060
gaagaattgg tagtcaaatc gagcaaagtc ccgaaagcac actgggcttt cgacacagtg   3120
ataccaaaga tgctgaaaag aactgaggca cgataaactg ttcggtgttg gtgtaaacga   3180
ccaaagatgc tgaaaataac tgatcgtcac catccgtgaa tctaactttc gacacactgt   3240
taccaaatcc ttcgtcaaaa ttacaggaat aattaaggcg cttagacgat gataaaccat   3300
tttttgtcac taattaacca cactgttctt tgcttgaccg tgacaaaaaa aaactttttt   3360
gtgaagcagt gttgccgtaa accacaacca tcatgaactc acttgccttg tcatatgtac   3420
ttgtaccatc gaacgccgcg cgctaagaca atgcaccacc cttcaagtct tagctcactg   3480
ataccgctaa ttaagttaga taatgtcgat tactagttgt cttacttcga actatttctt   3540
ttcggcaaac tgaagtaaag acaacgtttt gttccgcagg acatgttcac ggcgggtacg   3600
gacacgtcgt cgatcatcgt ggagtgggcg atggcggaga tgctcaagaa cccgaccgtc   3660
atggcgcgcg cgcaggagga gctggaccgc gcggtgggcc ggggccggcg cctggaggag   3720
tcggacctgc ccggcctccc ctacctgcag gcggtgtgca aggaggccat gcggctgcac   3780
ccgtccacgc cgctcagcct cccgcacttc tccttggacg cctgcgacga cgtcgacggc   3840
taccacgtcc cggccaacac ccgcctgctc gtcaacgtct gggccatcgg ccgggacccg   3900
gaggcctggg agaggcccct cgacttccgc cccgagcgct tcctgcccgg gggcggcgcg   3960
gagaaggtcg accccctggg gaactgcttc gagctcatcc cgttcggcgc cggccggagg   4020
atctgcgcgg ggaagctggc gggcatggtg ttcgtgcagt acttcctggg cacgctgctg   4080
```

```
cacgcgttcg actggcgcct gcctgacggc gaggagaagc tggacatgag cgagacgttc   4140

ggcctcgcgc tgcccaaggc agtgccgctc cgcgccgtcg ccacgccacg gctcgtgccg   4200

gaagcctatg cctga                                                    4215


<210> SEQ ID NO 26
<211> LENGTH: 527
<212> TYPE: PRT
<213> ORGANISM: Artificial Sequence
<220> FEATURE:
<223> OTHER INFORMATION: amino acid sequence of F35H mutant R405H

<400> SEQUENCE: 26

Met Gln Leu Ala Ala Leu Cys Thr Asp Pro Val Val Leu Cys Ser Ala
1               5                   10                  15

Phe Leu Cys Leu Leu Leu His Val Ala Leu Arg Ser Leu Leu His Pro
            20                  25                  30

Pro Ser Ala Ala Ser Ser Ser Gly Arg Arg Gly Gln Leu Pro Pro Gly
        35                  40                  45

Pro Pro Gly Leu Pro Ile Leu Gly Ala Leu Pro Leu Val Gly Pro Ala
    50                  55                  60

Pro His Ala Gly Leu Ala Ala Leu Ala Arg Lys Tyr Gly Pro Ile Met
65                  70                  75                  80

Tyr Leu Lys Met Gly Thr Ala Gly Val Val Val Ala Ser Ser Pro Arg
                85                  90                  95

Ala Ala Arg Thr Phe Leu Lys Ala Leu Asp Ala Arg Tyr Ala Asn Arg
            100                 105                 110

Pro Ala Val Ala Ser Ala Ala Asp Ile Thr Tyr Gly Arg Gln Asn Met
        115                 120                 125

Val Phe Ala Asp Tyr Gly Pro Lys Trp Lys Leu Met Arg Lys Leu Ala
    130                 135                 140

Ser Val His Leu Leu Gly Ala Arg Ala Leu Ala Asp Trp Ala Cys Val
145                 150                 155                 160

Arg Arg Gly Glu Ala Gly His Val Leu Arg Gly Val Ala Glu Ala Ala
                165                 170                 175

Ala Ala Gly Arg Pro Val Val Val Pro Glu Leu Leu Val Cys Ala Leu
            180                 185                 190

Ala Asn Ile Val Gly Gln Ile Thr Val Ser Lys Arg Val Phe Asp Ala
        195                 200                 205

Gln Gly Asp Asp Ser Asn Arg Tyr Lys Asp Met Ile Val Ser Leu Leu
    210                 215                 220

Thr Gly Thr Gly Met Phe Asn Ile Ser Asp Phe Val Pro Ala Leu Ala
225                 230                 235                 240

Arg Leu Asp Leu Gln Gly Val Gln Ala Lys Leu Arg Arg Val His Arg
                245                 250                 255

Gln Phe Asp Gly Leu Ile Thr Lys Leu Leu Ala Glu His Ala Ala Thr
            260                 265                 270

Ala Ala Asp Arg Ala Arg Gln Gly Arg Pro Asp Phe Val Asp Arg Leu
        275                 280                 285

Arg Ala Thr Met Asp Ala Gly Ala Ala Ala Asp Asp Glu Ser Gly Glu
    290                 295                 300

Thr Ile Thr Glu Val Asn Ile Lys Gly Leu Ile Phe Asp Met Phe Thr
305                 310                 315                 320

Ala Gly Thr Asp Thr Ser Ser Ile Ile Val Glu Trp Ala Met Ala Glu
                325                 330                 335
```

Met Leu Lys Asn Pro Thr Val Met Ala Arg Ala Gln Glu Glu Leu Asp
340 345 350

Arg Ala Val Gly Arg Gly Arg Arg Leu Glu Glu Ser Asp Leu Pro Gly
355 360 365

Leu Pro Tyr Leu Gln Ala Val Cys Lys Glu Ala Met Arg Leu His Pro
370 375 380

Ser Thr Pro Leu Ser Leu Pro His Phe Ser Leu Asp Ala Cys Asp Asp
385 390 395 400

Val Asp Gly Tyr His Val Pro Ala Asn Thr Arg Leu Leu Val Asn Val
405 410 415

Trp Ala Ile Gly Arg Asp Pro Glu Ala Trp Glu Arg Pro Leu Asp Phe
420 425 430

Arg Pro Glu Arg Phe Leu Pro Gly Gly Gly Ala Glu Lys Val Asp Pro
435 440 445

Leu Gly Asn Cys Phe Glu Leu Ile Pro Phe Gly Ala Gly Arg Arg Ile
450 455 460

Cys Ala Gly Lys Leu Ala Gly Met Val Phe Val Gln Tyr Phe Leu Gly
465 470 475 480

Thr Leu Leu His Ala Phe Asp Trp Arg Leu Pro Asp Gly Glu Glu Lys
485 490 495

Leu Asp Met Ser Glu Thr Phe Gly Leu Ala Leu Pro Lys Ala Val Pro
500 505 510

Leu Arg Ala Val Ala Thr Pro Arg Leu Val Pro Glu Ala Tyr Ala
515 520 525

<210> SEQ ID NO 27
<211> LENGTH: 4215
<212> TYPE: DNA
<213> ORGANISM: Artificial Sequence
<220> FEATURE:
<223> OTHER INFORMATION: genomic DNA of F35H mutant P407L

<400> SEQUENCE: 27
atgcagctcg cggcgttgtg caccgacccc gtggtgctgt gcagcgcctt cctctgcctc 60
ctcctccacg tggctctccg ctcgctgctg caccctcctt ctgccgcctc ttcctccggg 120
cgccgcgggc agctcccgcc ggggccaccg ggcctgccga tcctcggcgc gctgccactc 180
gtgggcccag ccccgcacgc cggcctggcc gcgctggcgc gcaagtacgg tcccatcatg 240
tacctgaaga tgggcacggc cggcgtggtg gtggcgtcgt ccccgcgcgc ggcgcggacg 300
ttcctcaagg cgctggacgc gcggtacgcc aaccggccgg ccgtggcgag cgccgcggac 360
atcacgtacg ggcggcagaa catggtgttc gcggactacg ggcccaagtg gaagctgatg 420
cggaagctcg ccagcgtgca cctgctcggc gcgcgcgcgc tcgcggactg ggcgtgcgtg 480
cggcgcggcg aggccggcca cgtgctgcgc ggcgtggcgg aggcggccgc ggccggcagg 540
cccgtcgtcg tgccggagct gctcgtgtgc gccctcgcca acatcgtcgg gcagatcaca 600
gtgagcaagc gggtgttcga cgcgcagggg gacgactcga acaggtgagg atgggaggtc 660
catgaaatcc taccagctgt gagcatgcat aaaagttcat ttggaaagaa aagaacatat 720
ttttcttaca aatttatgct tactgtttct ttaagtttcg ataaagtttg taaaaaaaat 780
ttaggctagt ttgaaactcc atttaggatt tctattttcc aaagaaaaat aaacgaattt 840
ctcttgaaaa aatgaaaatt ctttagaaaa ataggttctc aaactagccc tcaataaaac 900
ttaatgcgat cgttttctct gactctcatt catctttctc tggttatcta attgggtcct 960

-continued

```
tgagagatga gtttacctgc ttgtccttta ttattgcaaa gacaacatat ctgatgcaca   1020
tggaacattg gtgcacatgg tgcacatatg aaatcatcac cactcatttt aaatctaacg   1080
tctatagttg tttgatatat tttattaagg acaccctcca acgtggtggt gtgtagtggt   1140
ggaaggtgtt atttgtaaat tgaataatca actagagacg ttagatctaa aatgagtggt   1200
gatgatttaa tatgtgcacc atgtgcacca gtcttctatg tgcaccagat atgtcctcta   1260
ttgcaaatgc tagacggaac accagctagc actagcagac tgtttatgtg gaaagaaaaa   1320
acttaaaaag atcagctagg aagctgctgt catctgtacg tatatatggt gaagactgaa   1380
caatctgcat gacaagcaaa acttagctta aaagcgaaaa gagcgatgga aacggccgct   1440
cgataaataa ttaatgagag tcttgggatt tttcatgcat ggaaaaaaac aaagctggca   1500
tttttcatct aatataatat ataacgctga tatcatattg cgtgcagata caaggacatg   1560
atcgtgtcgc tgctgaccgg cacgggcatg ttcaacatca gcgacttcgt gccggcgctg   1620
gcgcgtctgg acctgcaggg cgtgcaggcg aagctgcggc gcgtccaccg ccagttcgac   1680
ggcctcatca ccaagctgct ggccgagcac gccgcgacgg ccgcggaccg cgcgcgccag   1740
ggccgcccgg acttcgtcga ccggctccgc gccacgatgg acgccggcgc cgccgccgac   1800
gacgagagcg gcgagaccat caccgaggtc aacatcaagg gcctcatctt cgtaagctcc   1860
ctgctttttc ctcgccccca accatgcatc atcatatgca cttatatttt acacttgctc   1920
ggttttcctt tagtaactaa ctaatccgtc gcagctgcga tacacgtagc actagtacta   1980
cagcgatggg tcatcggtaa ctgaatctaa ggtgcaatag agtgcacggc cgcgggatca   2040
tggcgtgaca tgggagctaa gctaagccag tggccaccta acgaaggcac tgaccgaaag   2100
ctcagtggcg tgttaggtgg agatagtgga tcgagttgtt ggaaagacaa tatcaaaacc   2160
actctccaat tgatgatgtg tagggcctgc agtgttttga atccaccttg tttggtcgaa   2220
cacattacta gagtgaaata tggttccaat gttaattgat agcgcgaaag ggtctctagc   2280
gtaatggtta aaccttccga gtagcacatc caggttgggt tcgatcctct cgagggcgaa   2340
ttttcaagct ttgttaaaaa aattatctcg ttgtgccccg tccgctctca ggaatcgata   2400
ttctacacga caccctccga ctagtgacag ttgattgact cgttagtgat gagaagccat   2460
gctaaaaaag tggagacgta gatatgatag aggttccctt tcctaagcaa acgtgaatgc   2520
tatgaaaatt atgcagttta aaaaaaactt taaagataaa caggaattct ctttttttgga   2580
acaaacaata cgaatgcacc tccaaatatc ttatcgagtc gacttttatg gaattattgt   2640
ttttgttatt tctaagatgg gagcccaaaa tcacatacaa attattcagt gaatgcctcg   2700
gtgttttttt attagttaag ggctctcatt tttttcaagg gatttttatt tttttccaaa   2760
agaaaataaa ctaatcctct ttagaaaaat ggaaatctat tggagaaatg aggttcctaa   2820
actagctcta acagtgagtc agttaatcag gagaagatat tagactcctg tatagtgtgc   2880
agcaaccaca tccgattctg acgttttagc ttaatgttcg ctatgtagac gtcgggcata   2940
gggaatgcat tgctaccaga acacgaatga cagctatgca agtctctaga acgttggagt   3000
agttaacaaa cgtgatagat gtaacctctg gatcatggta tgatgtcatt tcctagacta   3060
gaagaattgg tagtcaaatc gagcaaagtc ccgaaagcac actgggcttt cgacacagtg   3120
ataccaaaga tgctgaaaag aactgaggca cgataaactg ttcggtgttg gtgtaaacga   3180
ccaaagatgc tgaaaataac tgatcgtcac catccgtgaa tctaactttc gacacactgt   3240
taccaaatcc ttcgtcaaaa ttacaggaat aattaaggcg cttagacgat gataaaccat   3300
tttttgtcac taattaacca cactgttctt tgcttgaccg tgacaaaaaa aaactttttt   3360
```

-continued

```
gtgaagcagt gttgccgtaa accacaacca tcatgaactc acttgccttg tcatatgtac   3420

ttgtaccatc gaacgccgcg cgctaagaca atgcaccacc cttcaagtct tagctcactg   3480

ataccgctaa ttaagttaga taatgtcgat tactagttgt cttacttcga actatttctt   3540

ttcggcaaac tgaagtaaag acaacgtttt gttccgcagg acatgttcac ggcgggtacg   3600

gacacgtcgt cgatcatcgt ggagtgggcg atggcggaga tgctcaagaa cccgaccgtc   3660

atggcgcgcg cgcaggagga gctggaccgc gcggtgggcc ggggccggcg cctggaggag   3720

tcggacctgc ccggcctccc ctacctgcag gcggtgtgca aggaggccat gcggctgcac   3780

ccgtccacgc cgctcagcct cccgcacttc tccttggacg cctgcgacga cgtcgacggc   3840

taccgcgtcc tggccaacac ccgcctgctc gtcaacgtct gggccatcgg ccgggacccg   3900

gaggcctggg agaggcccct cgacttccgc cccgagcgct tcctgcccgg gggcggcgcg   3960

gagaaggtcg accccctggg gaactgcttc gagctcatcc cgttcggcgc cggccggagg   4020

atctgcgcgg ggaagctggc gggcatggtg ttcgtgcagt acttcctggg cacgctgctg   4080

cacgcgttcg actggcgcct gcctgacggc gaggagaagc tggacatgag cgagacgttc   4140

ggcctcgcgc tgcccaaggc agtgccgctc cgcgccgtcg ccacgccacg gctcgtgccg   4200

gaagcctatg cctga                                                    4215


<210> SEQ ID NO 28
<211> LENGTH: 527
<212> TYPE: PRT
<213> ORGANISM: Artificial Sequence
<220> FEATURE:
<223> OTHER INFORMATION: amino acid sequence of F35H mutant P407L

<400> SEQUENCE: 28

Met Gln Leu Ala Ala Leu Cys Thr Asp Pro Val Val Leu Cys Ser Ala
1               5                   10                  15

Phe Leu Cys Leu Leu Leu His Val Ala Leu Arg Ser Leu Leu His Pro
            20                  25                  30

Pro Ser Ala Ala Ser Ser Ser Gly Arg Arg Gly Gln Leu Pro Pro Gly
        35                  40                  45

Pro Pro Gly Leu Pro Ile Leu Gly Ala Leu Pro Leu Val Gly Pro Ala
    50                  55                  60

Pro His Ala Gly Leu Ala Ala Leu Ala Arg Lys Tyr Gly Pro Ile Met
65                  70                  75                  80

Tyr Leu Lys Met Gly Thr Ala Gly Val Val Val Ala Ser Ser Pro Arg
                85                  90                  95

Ala Ala Arg Thr Phe Leu Lys Ala Leu Asp Ala Arg Tyr Ala Asn Arg
            100                 105                 110

Pro Ala Val Ala Ser Ala Ala Asp Ile Thr Tyr Gly Arg Gln Asn Met
        115                 120                 125

Val Phe Ala Asp Tyr Gly Pro Lys Trp Lys Leu Met Arg Lys Leu Ala
    130                 135                 140

Ser Val His Leu Leu Gly Ala Arg Ala Leu Ala Asp Trp Ala Cys Val
145                 150                 155                 160

Arg Arg Gly Glu Ala Gly His Val Leu Arg Gly Val Ala Glu Ala Ala
                165                 170                 175

Ala Ala Gly Arg Pro Val Val Val Pro Glu Leu Leu Val Cys Ala Leu
            180                 185                 190

Ala Asn Ile Val Gly Gln Ile Thr Val Ser Lys Arg Val Phe Asp Ala
        195                 200                 205
```

Gln Gly Asp Asp Ser Asn Arg Tyr Lys Asp Met Ile Val Ser Leu Leu
210 215 220

Thr Gly Thr Gly Met Phe Asn Ile Ser Asp Phe Val Pro Ala Leu Ala
225 230 235 240

Arg Leu Asp Leu Gln Gly Val Gln Ala Lys Leu Arg Arg Val His Arg
245 250 255

Gln Phe Asp Gly Leu Ile Thr Lys Leu Leu Ala Glu His Ala Ala Thr
260 265 270

Ala Ala Asp Arg Ala Arg Gln Gly Arg Pro Asp Phe Val Asp Arg Leu
275 280 285

Arg Ala Thr Met Asp Ala Gly Ala Ala Ala Asp Asp Glu Ser Gly Glu
290 295 300

Thr Ile Thr Glu Val Asn Ile Lys Gly Leu Ile Phe Asp Met Phe Thr
305 310 315 320

Ala Gly Thr Asp Thr Ser Ser Ile Ile Val Glu Trp Ala Met Ala Glu
325 330 335

Met Leu Lys Asn Pro Thr Val Met Ala Arg Ala Gln Glu Glu Leu Asp
340 345 350

Arg Ala Val Gly Arg Gly Arg Arg Leu Glu Glu Ser Asp Leu Pro Gly
355 360 365

Leu Pro Tyr Leu Gln Ala Val Cys Lys Glu Ala Met Arg Leu His Pro
370 375 380

Ser Thr Pro Leu Ser Leu Pro His Phe Ser Leu Asp Ala Cys Asp Asp
385 390 395 400

Val Asp Gly Tyr Arg Val Leu Ala Asn Thr Arg Leu Leu Val Asn Val
405 410 415

Trp Ala Ile Gly Arg Asp Pro Glu Ala Trp Glu Arg Pro Leu Asp Phe
420 425 430

Arg Pro Glu Arg Phe Leu Pro Gly Gly Gly Ala Glu Lys Val Asp Pro
435 440 445

Leu Gly Asn Cys Phe Glu Leu Ile Pro Phe Gly Ala Gly Arg Arg Ile
450 455 460

Cys Ala Gly Lys Leu Ala Gly Met Val Phe Val Gln Tyr Phe Leu Gly
465 470 475 480

Thr Leu Leu His Ala Phe Asp Trp Arg Leu Pro Asp Gly Glu Glu Lys
485 490 495

Leu Asp Met Ser Glu Thr Phe Gly Leu Ala Leu Pro Lys Ala Val Pro
500 505 510

Leu Arg Ala Val Ala Thr Pro Arg Leu Val Pro Glu Ala Tyr Ala
515 520 525

<210> SEQ ID NO 29
<211> LENGTH: 4215
<212> TYPE: DNA
<213> ORGANISM: Artificial Sequence
<220> FEATURE:
<223> OTHER INFORMATION: genomic DNA of F35H mutant E427K

<400> SEQUENCE: 29
atgcagctcg cggcgttgtg caccgacccc gtggtgctgt gcagcgcctt cctctgcctc 60
ctcctccacg tggctctccg ctcgctgctg caccctcctt ctgccgcctc ttcctccggg 120
cgccgcgggc agctcccgcc ggggccaccg ggcctgccga tcctcggcgc gctgccactc 180
gtgggcccag ccccgcacgc cggcctggcc gcgctggcgc gcaagtacgg tcccatcatg 240

-continued

```
tacctgaaga tgggcacggc cggcgtggtg gtggcgtcgt ccccgcgcgc ggcgcggacg    300
ttcctcaagg cgctggacgc gcggtacgcc aaccggccgg ccgtggcgag cgccgcggac    360
atcacgtacg ggcggcagaa catggtgttc gcggactacg ggcccaagtg gaagctgatg    420
cggaagctcg ccagcgtgca cctgctcggc gcgcgcgcgc tcgcggactg ggcgtgcgtg    480
cggcgcggcg aggccggcca cgtgctgcgc ggcgtggcgg aggcggccgc ggccggcagg    540
cccgtcgtcg tgccggagct gctcgtgtgc gccctcgcca acatcgtcgg gcagatcaca    600
gtgagcaagc gggtgttcga cgcgcagggg gacgactcga acaggtgagg atgggaggtc    660
catgaaatcc taccagctgt gagcatgcat aaaagttcat ttggaaagaa aagaacatat    720
ttttcttaca aatttatgct tactgtttct ttaagtttcg ataaagtttg taaaaaaaat    780
ttaggctagt ttgaaactcc atttaggatt tctattttcc aaagaaaaat aaacgaattt    840
ctcttgaaaa aatgaaaatt ctttagaaaa ataggttctc aaactagccc tcaataaaac    900
ttaatgcgat cgttttctct gactctcatt catctttctc tggttatcta attgggtcct    960
tgagagatga gtttacctgc ttgtccttta ttattgcaaa gacaacatat ctgatgcaca   1020
tggaacattg gtgcacatgg tgcacatatg aaatcatcac cactcatttt aaatctaacg   1080
tctatagttg tttgatatat tttattaagg acaccctcca acgtggtggt gtgtagtggt   1140
ggaaggtgtt atttgtaaat tgaataatca actagagacg ttagatctaa aatgagtggt   1200
gatgatttaa tatgtgcacc atgtgcacca gtcttctatg tgcaccagat atgtcctcta   1260
ttgcaaatgc tagacggaac accagctagc actagcagac tgtttatgtg gaaagaaaaa   1320
acttaaaaag atcagctagg aagctgctgt catctgtacg tatatatggt gaagactgaa   1380
caatctgcat gacaagcaaa acttagctta aaagcgaaaa gagcgatgga aacggccgct   1440
cgataaataa ttaatgagag tcttgggatt tttcatgcat ggaaaaaaac aaagctggca   1500
tttttcatct aatataaatat ataacgctga tatcatattg cgtgcagata caaggacatg   1560
atcgtgtcgc tgctgaccgg cacgggcatg ttcaacatca gcgacttcgt gccggcgctg   1620
gcgcgtctgg acctgcaggg cgtgcaggcg aagctgcggc gcgtccaccg ccagttcgac   1680
ggcctcatca ccaagctgct ggccgagcac gccgcgacgg ccgcggaccg cgcgcgccag   1740
ggccgcccgg acttcgtcga ccggctccgc gccacgatgg acgccggcgc cgccgccgac   1800
gacgagagcg gcgagaccat caccgaggtc aacatcaagg gcctcatctt cgtaagctcc   1860
ctgctttttc ctcgccccca accatgcatc atcatatgca cttatatttt acacttgctc   1920
ggttttcctt tagtaactaa ctaatccgtc gcagctgcga tacacgtagc actagtacta   1980
cagcgatggg tcatcggtaa ctgaatctaa ggtgcaatag agtgcacggc cgcgggatca   2040
tggcgtgaca tgggagctaa gctaagccag tggccaccta acgaaggcac tgaccgaaag   2100
ctcagtggcg tgttaggtgg agatagtgga tcgagttgtt ggaaagacaa tatcaaaacc   2160
actctccaat tgatgatgtg tagggcctgc agtgttttga atccaccttg tttggtcgaa   2220
cacattacta gagtgaaata tggttccaat gttaattgat agcgcgaaag ggtctctagc   2280
gtaatggtta aaccttccga gtagcacatc caggttgggt tcgatcctct cgagggcgaa   2340
ttttcaagct ttgttaaaaa aattatctcg ttgtgccccg tccgctctca ggaatcgata   2400
ttctacacga caccctccga ctagtgacag ttgattgact cgttagtgat gagaagccat   2460
gctaaaaaag tggagacgta gatatgatag aggttccctt tcctaagcaa acgtgaatgc   2520
tatgaaaatt atgcagttta aaaaaaactt taaagataaa caggaattct ctttttttgga  2580
acaaacaata cgaatgcacc tccaaatatc ttatcgagtc gacttttatg gaattattgt   2640
```

ttttgttatt tctaagatgg gagcccaaaa tcacatacaa attattcagt gaatgcctcg 2700
gtgttttttt attagttaag ggctctcatt tttttcaagg gatttttatt tttttccaaa 2760
agaaaataaa ctaatcctct ttagaaaaat ggaaatctat tggagaaatg aggttcctaa 2820
actagctcta acagtgagtc agttaatcag gagaagatat tagactcctg tatagtgtgc 2880
agcaaccaca tccgattctg acgttttagc ttaatgttcg ctatgtagac gtcgggcata 2940
gggaatgcat tgctaccaga acacgaatga cagctatgca agtctctaga acgttggagt 3000
agttaacaaa cgtgatagat gtaacctctg gatcatggta tgatgtcatt tcctagacta 3060
gaagaattgg tagtcaaatc gagcaaagtc ccgaaagcac actgggcttt cgacacagtg 3120
ataccaaaga tgctgaaaag aactgaggca cgataaactg ttcggtgttg gtgtaaacga 3180
ccaaagatgc tgaaaataac tgatcgtcac catccgtgaa tctaactttc gacacactgt 3240
taccaaatcc ttcgtcaaaa ttacaggaat aattaaggcg cttagacgat gataaaccat 3300
tttttgtcac taattaacca cactgttctt tgcttgaccg tgacaaaaaa aaactttttt 3360
gtgaagcagt gttgccgtaa accacaacca tcatgaactc acttgccttg tcatatgtac 3420
ttgtaccatc gaacgccgcg cgctaagaca atgcaccacc cttcaagtct tagctcactg 3480
ataccgctaa ttaagttaga taatgtcgat tactagttgt cttacttcga actatttctt 3540
ttcggcaaac tgaagtaaag acaacgtttt gttccgcagg acatgttcac ggcgggtacg 3600
gacacgtcgt cgatcatcgt ggagtgggcg atggcggaga tgctcaagaa cccgaccgtc 3660
atggcgcgcg cgcaggagga gctggaccgc gcggtgggcc ggggccggcg cctggaggag 3720
tcggacctgc ccggcctccc ctacctgcag gcggtgtgca aggaggccat gcggctgcac 3780
ccgtccacgc cgctcagcct cccgcacttc tccttggacg cctgcgacga cgtcgacggc 3840
taccgcgtcc cggccaacac ccgcctgctc gtcaacgtct gggccatcgg ccgggacccg 3900
gaggcctgga agaggcccct cgacttccgc cccgagcgct tcctgcccgg gggcggcgcg 3960
gagaaggtcg accccctggg gaactgcttc gagctcatcc cgttcggcgc cggccggagg 4020
atctgcgcgg ggaagctggc gggcatggtg ttcgtgcagt acttcctggg cacgctgctg 4080
cacgcgttcg actggcgcct gcctgacggc gaggagaagc tggacatgag cgagacgttc 4140
ggcctcgcgc tgcccaaggc agtgccgctc cgcgccgtcg ccacgccacg gctcgtgccg 4200
gaagcctatg cctga 4215

<210> SEQ ID NO 30
<211> LENGTH: 527
<212> TYPE: PRT
<213> ORGANISM: Artificial Sequence
<220> FEATURE:
<223> OTHER INFORMATION: amino acid sequence of F35H mutant E427K

<400> SEQUENCE: 30

Met Gln Leu Ala Ala Leu Cys Thr Asp Pro Val Val Leu Cys Ser Ala
1 5 10 15

Phe Leu Cys Leu Leu Leu His Val Ala Leu Arg Ser Leu Leu His Pro
20 25 30

Pro Ser Ala Ala Ser Ser Ser Gly Arg Arg Gly Gln Leu Pro Pro Gly
35 40 45

Pro Pro Gly Leu Pro Ile Leu Gly Ala Leu Pro Leu Val Gly Pro Ala
50 55 60

Pro His Ala Gly Leu Ala Ala Leu Ala Arg Lys Tyr Gly Pro Ile Met
65 70 75 80

-continued

```
Tyr Leu Lys Met Gly Thr Ala Gly Val Val Val Ala Ser Ser Pro Arg
                85                  90                  95

Ala Ala Arg Thr Phe Leu Lys Ala Leu Asp Ala Arg Tyr Ala Asn Arg
            100                 105                 110

Pro Ala Val Ala Ser Ala Ala Asp Ile Thr Tyr Gly Arg Gln Asn Met
        115                 120                 125

Val Phe Ala Asp Tyr Gly Pro Lys Trp Lys Leu Met Arg Lys Leu Ala
    130                 135                 140

Ser Val His Leu Leu Gly Ala Arg Ala Leu Ala Asp Trp Ala Cys Val
145                 150                 155                 160

Arg Arg Gly Glu Ala Gly His Val Leu Arg Gly Val Ala Glu Ala Ala
                165                 170                 175

Ala Ala Gly Arg Pro Val Val Val Pro Glu Leu Leu Val Cys Ala Leu
            180                 185                 190

Ala Asn Ile Val Gly Gln Ile Thr Val Ser Lys Arg Val Phe Asp Ala
        195                 200                 205

Gln Gly Asp Asp Ser Asn Arg Tyr Lys Asp Met Ile Val Ser Leu Leu
    210                 215                 220

Thr Gly Thr Gly Met Phe Asn Ile Ser Asp Phe Val Pro Ala Leu Ala
225                 230                 235                 240

Arg Leu Asp Leu Gln Gly Val Gln Ala Lys Leu Arg Arg Val His Arg
                245                 250                 255

Gln Phe Asp Gly Leu Ile Thr Lys Leu Leu Ala Glu His Ala Ala Thr
            260                 265                 270

Ala Ala Asp Arg Ala Arg Gln Gly Arg Pro Asp Phe Val Asp Arg Leu
        275                 280                 285

Arg Ala Thr Met Asp Ala Gly Ala Ala Ala Asp Asp Glu Ser Gly Glu
    290                 295                 300

Thr Ile Thr Glu Val Asn Ile Lys Gly Leu Ile Phe Asp Met Phe Thr
305                 310                 315                 320

Ala Gly Thr Asp Thr Ser Ser Ile Ile Val Glu Trp Ala Met Ala Glu
                325                 330                 335

Met Leu Lys Asn Pro Thr Val Met Ala Arg Ala Gln Glu Glu Leu Asp
            340                 345                 350

Arg Ala Val Gly Arg Gly Arg Arg Leu Glu Glu Ser Asp Leu Pro Gly
        355                 360                 365

Leu Pro Tyr Leu Gln Ala Val Cys Lys Glu Ala Met Arg Leu His Pro
    370                 375                 380

Ser Thr Pro Leu Ser Leu Pro His Phe Ser Leu Asp Ala Cys Asp Asp
385                 390                 395                 400

Val Asp Gly Tyr Arg Val Pro Ala Asn Thr Arg Leu Leu Val Asn Val
                405                 410                 415

Trp Ala Ile Gly Arg Asp Pro Glu Ala Trp Lys Arg Pro Leu Asp Phe
            420                 425                 430

Arg Pro Glu Arg Phe Leu Pro Gly Gly Gly Ala Glu Lys Val Asp Pro
        435                 440                 445

Leu Gly Asn Cys Phe Glu Leu Ile Pro Phe Gly Ala Gly Arg Arg Ile
    450                 455                 460

Cys Ala Gly Lys Leu Ala Gly Met Val Phe Val Gln Tyr Phe Leu Gly
465                 470                 475                 480

Thr Leu Leu His Ala Phe Asp Trp Arg Leu Pro Asp Gly Glu Glu Lys
                485                 490                 495
```

-continued

```
Leu Asp Met Ser Glu Thr Phe Gly Leu Ala Leu Pro Lys Ala Val Pro
            500                 505                 510

Leu Arg Ala Val Ala Thr Pro Arg Leu Val Pro Glu Ala Tyr Ala
        515                 520                 525


<210> SEQ ID NO 31
<211> LENGTH: 4215
<212> TYPE: DNA
<213> ORGANISM: Artificial Sequence
<220> FEATURE:
<223> OTHER INFORMATION: genomic DNA of F35H mutant G450R

<400> SEQUENCE: 31

atgcagctcg cggcgttgtg caccgacccc gtggtgctgt gcagcgcctt cctctgcctc     60

ctcctccacg tggctctccg ctcgctgctg caccctcctt ctgccgcctc ttcctccggg    120

cgccgcgggc agctcccgcc ggggccaccg ggcctgccga tcctcggcgc gctgccactc    180

gtgggcccag ccccgcacgc cggcctggcc gcgctggcgc gcaagtacgg tcccatcatg    240

tacctgaaga tgggcacggc cggcgtggtg gtggcgtcgt ccccgcgcgc ggcgcggacg    300

ttcctcaagg cgctggacgc gcggtacgcc aaccggccgg ccgtggcgag cgccgcggac    360

atcacgtacg ggcggcagaa catggtgttc gcggactacg ggcccaagtg gaagctgatg    420

cggaagctcg ccagcgtgca cctgctcggc gcgcgcgcgc tcgcggactg ggcgtgcgtg    480

cggcgcggcg aggccggcca cgtgctgcgc ggcgtggcgg aggcggccgc ggccggcagg    540

cccgtcgtcg tgccggagct gctcgtgtgc gccctcgcca acatcgtcgg gcagatcaca    600

gtgagcaagc gggtgttcga cgcgcagggg gacgactcga acaggtgagg atgggaggtc    660

catgaaatcc taccagctgt gagcatgcat aaaagttcat ttggaaagaa aagaacatat    720

ttttcttaca aatttatgct tactgtttct ttaagtttcg ataaagtttg taaaaaaaat    780

ttaggctagt ttgaaactcc atttaggatt tctattttcc aaagaaaaat aaacgaattt    840

ctcttgaaaa aatgaaaatt ctttagaaaa ataggttctc aaactagccc tcaataaaac    900

ttaatgcgat cgttttctct gactctcatt catctttctc tggttatcta attgggtcct    960

tgagagatga gtttacctgc ttgtccttta ttattgcaaa gacaacatat ctgatgcaca   1020

tggaacattg gtgcacatgg tgcacatatg aaatcatcac cactcatttt aaatctaacg   1080

tctatagttg tttgatatat tttattaagg acaccctcca acgtggtggt gtgtagtggt   1140

ggaaggtgtt atttgtaaat tgaataatca actagagacg ttagatctaa aatgagtggt   1200

gatgatttaa tatgtgcacc atgtgcacca gtcttctatg tgcaccagat atgtcctcta   1260

ttgcaaatgc tagacggaac accagctagc actagcagac tgtttatgtg gaaagaaaaa   1320

acttaaaaag atcagctagg aagctgctgt catctgtacg tatatatggt gaagactgaa   1380

caatctgcat gacaagcaaa acttagctta aaagcgaaaa gagcgatgga aacggccgct   1440

cgataaataa ttaatgagag tcttgggatt tttcatgcat ggaaaaaaac aaagctggca   1500

tttttcatct aatataatat ataacgctga tatcatattg cgtgcagata caaggacatg   1560

atcgtgtcgc tgctgaccgg cacgggcatg ttcaacatca gcgacttcgt gccggcgctg   1620

gcgcgtctgg acctgcaggg cgtgcaggcg aagctgcggc gcgtccaccg ccagttcgac   1680

ggcctcatca ccaagctgct ggccgagcac gccgcgacgg ccgcggaccg cgcgcgccag   1740

ggccgcccgg acttcgtcga ccggctccgc gccacgatgg acgccggcgc cgccgccgac   1800

gacgagagcg gcgagaccat caccgaggtc aacatcaagg gcctcatctt cgtaagctcc   1860

ctgctttttc ctcgccccca accatgcatc atcatatgca cttatatttt acacttgctc   1920
```

-continued

```
ggttttcctt tagtaactaa ctaatccgtc gcagctgcga tacacgtagc actagtacta   1980
cagcgatggg tcatcggtaa ctgaatctaa ggtgcaatag agtgcacggc cgcgggatca   2040
tggcgtgaca tgggagctaa gctaagccag tggccaccta acgaaggcac tgaccgaaag   2100
ctcagtggcg tgttaggtgg agatagtgga tcgagttgtt ggaaagacaa tatcaaaacc   2160
actctccaat tgatgatgtg tagggcctgc agtgttttga atccaccttg tttggtcgaa   2220
cacattacta gagtgaaata tggttccaat gttaattgat agcgcgaaag ggtctctagc   2280
gtaatggtta aaccttccga gtagcacatc caggttgggt tcgatcctct cgagggcgaa   2340
ttttcaagct ttgttaaaaa aattatctcg ttgtgccccg tccgctctca ggaatcgata   2400
ttctacacga caccctccga ctagtgacag ttgattgact cgttagtgat gagaagccat   2460
gctaaaaaag tggagacgta gatatgatag aggttccctt tcctaagcaa acgtgaatgc   2520
tatgaaaatt atgcagttta aaaaaaactt taaagataaa caggaattct ctttttttgga   2580
acaaacaata cgaatgcacc tccaaatatc ttatcgagtc gacttttatg gaattattgt   2640
ttttgttatt tctaagatgg gagcccaaaa tcacatacaa attattcagt gaatgcctcg   2700
gtgttttttt attagttaag ggctctcatt tttttcaagg gatttttatt tttttccaaa   2760
agaaaataaa ctaatcctct ttagaaaaat ggaaatctat tggagaaatg aggttcctaa   2820
actagctcta acagtgagtc agttaatcag gagaagatat tagactcctg tatagtgtgc   2880
agcaaccaca tccgattctg acgttttagc ttaatgttcg ctatgtagac gtcgggcata   2940
gggaatgcat tgctaccaga acacgaatga cagctatgca agtctctaga acgttggagt   3000
agttaacaaa cgtgatagat gtaacctctg gatcatggta tgatgtcatt tcctagacta   3060
gaagaattgg tagtcaaatc gagcaaagtc ccgaaagcac actgggcttt cgacacagtg   3120
ataccaaaga tgctgaaaag aactgaggca cgataaactg ttcggtgttg gtgtaaacga   3180
ccaaagatgc tgaaaataac tgatcgtcac catccgtgaa tctaactttc gacacactgt   3240
taccaaatcc ttcgtcaaaa ttacaggaat aattaaggcg cttagacgat gataaaccat   3300
tttttgtcac taattaacca cactgttctt tgcttgaccg tgacaaaaaa aaactttttt   3360
gtgaagcagt gttgccgtaa accacaacca tcatgaactc acttgccttg tcatatgtac   3420
ttgtaccatc gaacgccgcg cgctaagaca atgcaccacc cttcaagtct tagctcactg   3480
ataccgctaa ttaagttaga taatgtcgat tactagttgt cttacttcga actatttctt   3540
ttcggcaaac tgaagtaaag acaacgtttt gttccgcagg acatgttcac ggcgggtacg   3600
gacacgtcgt cgatcatcgt ggagtgggcg atggcggaga tgctcaagaa cccgaccgtc   3660
atggcgcgcg cgcaggagga gctggaccgc gcggtgggcc ggggccggcg cctggaggag   3720
tcggacctgc ccggcctccc ctacctgcag gcggtgtgca aggaggccat gcggctgcac   3780
ccgtccacgc cgctcagcct cccgcacttc tccttggacg cctgcgacga cgtcgacggc   3840
taccgcgtcc cggccaacac ccgcctgctc gtcaacgtct gggccatcgg ccgggacccg   3900
gaggcctggg agaggcccct cgacttccgc cccgagcgct tcctgcccgg gggcggcgcg   3960
gagaaggtcg accccctgag gaactgcttc gagctcatcc cgttcggcgc cggccggagg   4020
atctgcgcgg ggaagctggc gggcatggtg ttcgtgcagt acttcctggg cacgctgctg   4080
cacgcgttcg actggcgcct gcctgacggc gaggagaagc tggacatgag cgagacgttc   4140
ggcctcgcgc tgcccaaggc agtgccgctc cgcgccgtcg ccacgccacg gctcgtgccg   4200
gaagcctatg cctga                                                    4215
```

<210> SEQ ID NO 32
<211> LENGTH: 527
<212> TYPE: PRT
<213> ORGANISM: Artificial Sequence
<220> FEATURE:
<223> OTHER INFORMATION: amino acid sequence of F35H mutant G450R

<400> SEQUENCE: 32

```
Met Gln Leu Ala Ala Leu Cys Thr Asp Pro Val Val Leu Cys Ser Ala
1               5                   10                  15

Phe Leu Cys Leu Leu Leu His Val Ala Leu Arg Ser Leu Leu His Pro
            20                  25                  30

Pro Ser Ala Ala Ser Ser Ser Gly Arg Arg Gly Gln Leu Pro Pro Gly
        35                  40                  45

Pro Pro Gly Leu Pro Ile Leu Gly Ala Leu Pro Leu Val Gly Pro Ala
    50                  55                  60

Pro His Ala Gly Leu Ala Ala Leu Ala Arg Lys Tyr Gly Pro Ile Met
65                  70                  75                  80

Tyr Leu Lys Met Gly Thr Ala Gly Val Val Val Ala Ser Ser Pro Arg
                85                  90                  95

Ala Ala Arg Thr Phe Leu Lys Ala Leu Asp Ala Arg Tyr Ala Asn Arg
            100                 105                 110

Pro Ala Val Ala Ser Ala Ala Asp Ile Thr Tyr Gly Arg Gln Asn Met
        115                 120                 125

Val Phe Ala Asp Tyr Gly Pro Lys Trp Lys Leu Met Arg Lys Leu Ala
    130                 135                 140

Ser Val His Leu Leu Gly Ala Arg Ala Leu Ala Asp Trp Ala Cys Val
145                 150                 155                 160

Arg Arg Gly Glu Ala Gly His Val Leu Arg Gly Val Ala Glu Ala Ala
                165                 170                 175

Ala Ala Gly Arg Pro Val Val Val Pro Glu Leu Leu Val Cys Ala Leu
            180                 185                 190

Ala Asn Ile Val Gly Gln Ile Thr Val Ser Lys Arg Val Phe Asp Ala
        195                 200                 205

Gln Gly Asp Asp Ser Asn Arg Tyr Lys Asp Met Ile Val Ser Leu Leu
    210                 215                 220

Thr Gly Thr Gly Met Phe Asn Ile Ser Asp Phe Val Pro Ala Leu Ala
225                 230                 235                 240

Arg Leu Asp Leu Gln Gly Val Gln Ala Lys Leu Arg Arg Val His Arg
                245                 250                 255

Gln Phe Asp Gly Leu Ile Thr Lys Leu Leu Ala Glu His Ala Ala Thr
            260                 265                 270

Ala Ala Asp Arg Ala Arg Gln Gly Arg Pro Asp Phe Val Asp Arg Leu
        275                 280                 285

Arg Ala Thr Met Asp Ala Gly Ala Ala Ala Asp Asp Glu Ser Gly Glu
    290                 295                 300

Thr Ile Thr Glu Val Asn Ile Lys Gly Leu Ile Phe Asp Met Phe Thr
305                 310                 315                 320

Ala Gly Thr Asp Thr Ser Ser Ile Ile Val Glu Trp Ala Met Ala Glu
                325                 330                 335

Met Leu Lys Asn Pro Thr Val Met Ala Arg Ala Gln Glu Glu Leu Asp
            340                 345                 350

Arg Ala Val Gly Arg Gly Arg Arg Leu Glu Glu Ser Asp Leu Pro Gly
        355                 360                 365
```

-continued

```
Leu Pro Tyr Leu Gln Ala Val Cys Lys Glu Ala Met Arg Leu His Pro
    370                 375                 380

Ser Thr Pro Leu Ser Leu Pro His Phe Ser Leu Asp Ala Cys Asp Asp
385                 390                 395                 400

Val Asp Gly Tyr Arg Val Pro Ala Asn Thr Arg Leu Leu Val Asn Val
                405                 410                 415

Trp Ala Ile Gly Arg Asp Pro Glu Ala Trp Glu Arg Pro Leu Asp Phe
            420                 425                 430

Arg Pro Glu Arg Phe Leu Pro Gly Gly Gly Ala Glu Lys Val Asp Pro
        435                 440                 445

Leu Arg Asn Cys Phe Glu Leu Ile Pro Phe Gly Ala Gly Arg Arg Ile
    450                 455                 460

Cys Ala Gly Lys Leu Ala Gly Met Val Phe Val Gln Tyr Phe Leu Gly
465                 470                 475                 480

Thr Leu Leu His Ala Phe Asp Trp Arg Leu Pro Asp Gly Glu Glu Lys
                485                 490                 495

Leu Asp Met Ser Glu Thr Phe Gly Leu Ala Leu Pro Lys Ala Val Pro
            500                 505                 510

Leu Arg Ala Val Ala Thr Pro Arg Leu Val Pro Glu Ala Tyr Ala
        515                 520                 525


<210> SEQ ID NO 33
<211> LENGTH: 4215
<212> TYPE: DNA
<213> ORGANISM: Artificial Sequence
<220> FEATURE:
<223> OTHER INFORMATION: genomic DNA of F35H mutant P429S

<400> SEQUENCE: 33

atgcagctcg cggcgttgtg caccgacccc gtggtgctgt gcagcgcctt cctctgcctc     60

ctcctccacg tggctctccg ctcgctgctg caccctcctt ctgccgcctc ttcctccggg    120

cgccgcgggc agctcccgcc ggggccaccg ggcctgccga tcctcggcgc gctgccactc    180

gtgggcccag ccccgcacgc cggcctggcc gcgctggcgc gcaagtacgg tcccatcatg    240

tacctgaaga tgggcacggc cggcgtggtg gtggcgtcgt ccccgcgcgc ggcgcggacg    300

ttcctcaagg cgctggacgc gcggtacgcc aaccggccgg ccgtggcgag cgccgcggac    360

atcacgtacg ggcggcagaa catggtgttc gcggactacg ggcccaagtg gaagctgatg    420

cggaagctcg ccagcgtgca cctgctcggc gcgcgcgcgc tcgcggactg ggcgtgcgtg    480

cggcgcggcg aggccggcca cgtgctgcgc ggcgtggcgg aggcggccgc ggccggcagg    540

cccgtcgtcg tgccggagct gctcgtgtgc gccctcgcca acatcgtcgg gcagatcaca    600

gtgagcaagc gggtgttcga cgcgcagggg gacgactcga acaggtgagg atgggaggtc    660

catgaaatcc taccagctgt gagcatgcat aaaagttcat ttggaaagaa aagaacatat    720

ttttcttaca aatttatgct tactgtttct ttaagtttcg ataaagtttg taaaaaaaat    780

ttaggctagt ttgaaactcc atttaggatt tctattttcc aaagaaaaat aaacgaattt    840

ctcttgaaaa aatgaaaatt ctttagaaaa ataggttctc aaactagccc tcaataaaac    900

ttaatgcgat cgttttctct gactctcatt catctttctc tggttatcta attgggtcct    960

tgagagatga gtttacctgc ttgtccttta ttattgcaaa gacaacatat ctgatgcaca   1020

tggaacattg gtgcacatgg tgcacatatg aaatcatcac cactcatttt aaatctaacg   1080

tctatagttg tttgatatat tttattaagg acaccctcca acgtggtggt gtgtagtggt   1140

ggaaggtgtt atttgtaaat tgaataatca actagagacg ttagatctaa aatgagtggt   1200
```

```
gatgatttaa tatgtgcacc atgtgcacca gtcttctatg tgcaccagat atgtcctcta   1260
ttgcaaatgc tagacggaac accagctagc actagcagac tgtttatgtg gaaagaaaaa   1320
acttaaaaag atcagctagg aagctgctgt catctgtacg tatatatggt gaagactgaa   1380
caatctgcat gacaagcaaa acttagctta aaagcgaaaa gagcgatgga aacggccgct   1440
cgataaataa ttaatgagag tcttgggatt tttcatgcat ggaaaaaaac aaagctggca   1500
tttttcatct aatataatat ataacgctga tatcatattg cgtgcagata caaggacatg   1560
atcgtgtcgc tgctgaccgg cacgggcatg ttcaacatca gcgacttcgt gccggcgctg   1620
gcgcgtctgg acctgcaggg cgtgcaggcg aagctgcggc gcgtccaccg ccagttcgac   1680
ggcctcatca ccaagctgct ggccgagcac gccgcgacgg ccgcggaccg cgcgcgccag   1740
ggccgcccgg acttcgtcga ccggctccgc gccacgatgg acgccggcgc cgccgccgac   1800
gacgagagcg gcgagaccat caccgaggtc aacatcaagg gcctcatctt cgtaagctcc   1860
ctgctttttc ctcgccccca accatgcatc atcatatgca cttatatttt acacttgctc   1920
ggttttcctt tagtaactaa ctaatccgtc gcagctgcga tacacgtagc actagtacta   1980
cagcgatggg tcatcggtaa ctgaatctaa ggtgcaatag agtgcacggc cgcgggatca   2040
tggcgtgaca tgggagctaa gctaagccag tggccaccta acgaaggcac tgaccgaaag   2100
ctcagtggcg tgttaggtgg agatagtgga tcgagttgtt ggaaagacaa tatcaaaacc   2160
actctccaat tgatgatgtg tagggcctgc agtgttttga atccaccttg tttggtcgaa   2220
cacattacta gagtgaaata tggttccaat gttaattgat agcgcgaaag ggtctctagc   2280
gtaatggtta aaccttccga gtagcacatc caggttgggt tcgatcctct cgagggcgaa   2340
ttttcaagct ttgttaaaaa aattatctcg ttgtgccccg tccgctctca ggaatcgata   2400
ttctacacga caccctccga ctagtgacag ttgattgact cgttagtgat gagaagccat   2460
gctaaaaaag tggagacgta gatatgatag aggttccctt tcctaagcaa acgtgaatgc   2520
tatgaaaatt atgcagttta aaaaaaactt taaagataaa caggaattct cttttttgga   2580
acaaacaata cgaatgcacc tccaaatatc ttatcgagtc gacttttatg gaattattgt   2640
ttttgttatt tctaagatgg gagcccaaaa tcacatacaa attattcagt gaatgcctcg   2700
gtgttttttt attagttaag ggctctcatt tttttcaagg gatttttatt tttttccaaa   2760
agaaaataaa ctaatcctct ttagaaaaat ggaaatctat tggagaaatg aggttcctaa   2820
actagctcta acagtgagtc agttaatcag gagaagatat tagactcctg tatagtgtgc   2880
agcaaccaca tccgattctg acgttttagc ttaatgttcg ctatgtagac gtcgggcata   2940
gggaatgcat tgctaccaga acacgaatga cagctatgca agtctctaga acgttggagt   3000
agttaacaaa cgtgatagat gtaacctctg gatcatggta tgatgtcatt tcctagacta   3060
gaagaattgg tagtcaaatc gagcaaagtc ccgaaagcac actgggcttt cgacacagtg   3120
ataccaaaga tgctgaaaag aactgaggca cgataaactg ttcggtgttg gtgtaaacga   3180
ccaaagatgc tgaaaataac tgatcgtcac catccgtgaa tctaactttc gacacactgt   3240
taccaaatcc ttcgtcaaaa ttacaggaat aattaaggcg cttagacgat gataaaccat   3300
tttttgtcac taattaacca cactgttctt tgcttgaccg tgacaaaaaa aaactttttt   3360
gtgaagcagt gttgccgtaa accacaacca tcatgaactc acttgccttg tcatatgtac   3420
ttgtaccatc gaacgccgcg cgctaagaca atgcaccacc cttcaagtct tagctcactg   3480
ataccgctaa ttaagttaga taatgtcgat tactagttgt cttacttcga actatttctt   3540
```

-continued

```
ttcggcaaac tgaagtaaag acaacgtttt gttccgcagg acatgttcac ggcgggtacg   3600

gacacgtcgt cgatcatcgt ggagtgggcg atggcggaga tgctcaagaa cccgaccgtc   3660

atggcgcgcg cgcaggagga gctggaccgc gcggtgggcc ggggccggcg cctggaggag   3720

tcggacctgc ccggcctccc ctacctgcag gcggtgtgca aggaggccat gcggctgcac   3780

ccgtccacgc cgctcagcct cccgcacttc tccttggacg cctgcgacga cgtcgacggc   3840

taccgcgtcc cggccaacac ccgcctgctc gtcaacgtct gggccatcgg ccgggacccg   3900

gaggcctggg agaggtccct cgacttccgc cccgagcgct tcctgcccgg gggcggcgcg   3960

gagaaggtcg accccctggg gaactgcttc gagctcatcc cgttcggcgc cggccggagg   4020

atctgcgcgg ggaagctggc gggcatggtg ttcgtgcagt acttcctggg cacgctgctg   4080

cacgcgttcg actggcgcct gcctgacggc gaggagaagc tggacatgag cgagacgttc   4140

ggcctcgcgc tgcccaaggc agtgccgctc cgcgccgtcg ccacgccacg gctcgtgccg   4200

gaagcctatg cctga                                                    4215


<210> SEQ ID NO 34
<211> LENGTH: 527
<212> TYPE: PRT
<213> ORGANISM: Artificial Sequence
<220> FEATURE:
<223> OTHER INFORMATION: amino acid sequence of F35H mutant P429S

<400> SEQUENCE: 34

Met Gln Leu Ala Ala Leu Cys Thr Asp Pro Val Val Leu Cys Ser Ala
1               5                   10                  15

Phe Leu Cys Leu Leu Leu His Val Ala Leu Arg Ser Leu Leu His Pro
            20                  25                  30

Pro Ser Ala Ala Ser Ser Ser Gly Arg Arg Gly Gln Leu Pro Pro Gly
        35                  40                  45

Pro Pro Gly Leu Pro Ile Leu Gly Ala Leu Pro Leu Val Gly Pro Ala
    50                  55                  60

Pro His Ala Gly Leu Ala Ala Leu Ala Arg Lys Tyr Gly Pro Ile Met
65                  70                  75                  80

Tyr Leu Lys Met Gly Thr Ala Gly Val Val Val Ala Ser Ser Pro Arg
                85                  90                  95

Ala Ala Arg Thr Phe Leu Lys Ala Leu Asp Ala Arg Tyr Ala Asn Arg
            100                 105                 110

Pro Ala Val Ala Ser Ala Ala Asp Ile Thr Tyr Gly Arg Gln Asn Met
        115                 120                 125

Val Phe Ala Asp Tyr Gly Pro Lys Trp Lys Leu Met Arg Lys Leu Ala
    130                 135                 140

Ser Val His Leu Leu Gly Ala Arg Ala Leu Ala Asp Trp Ala Cys Val
145                 150                 155                 160

Arg Arg Gly Glu Ala Gly His Val Leu Arg Gly Val Ala Glu Ala Ala
                165                 170                 175

Ala Ala Gly Arg Pro Val Val Val Pro Glu Leu Leu Val Cys Ala Leu
            180                 185                 190

Ala Asn Ile Val Gly Gln Ile Thr Val Ser Lys Arg Val Phe Asp Ala
        195                 200                 205

Gln Gly Asp Asp Ser Asn Arg Tyr Lys Asp Met Ile Val Ser Leu Leu
    210                 215                 220

Thr Gly Thr Gly Met Phe Asn Ile Ser Asp Phe Val Pro Ala Leu Ala
225                 230                 235                 240
```

```
Arg Leu Asp Leu Gln Gly Val Gln Ala Lys Leu Arg Arg Val His Arg
                245                 250                 255

Gln Phe Asp Gly Leu Ile Thr Lys Leu Leu Ala Glu His Ala Ala Thr
            260                 265                 270

Ala Ala Asp Arg Ala Arg Gln Gly Arg Pro Asp Phe Val Asp Arg Leu
        275                 280                 285

Arg Ala Thr Met Asp Ala Gly Ala Ala Ala Asp Asp Glu Ser Gly Glu
    290                 295                 300

Thr Ile Thr Glu Val Asn Ile Lys Gly Leu Ile Phe Asp Met Phe Thr
305                 310                 315                 320

Ala Gly Thr Asp Thr Ser Ser Ile Ile Val Glu Trp Ala Met Ala Glu
                325                 330                 335

Met Leu Lys Asn Pro Thr Val Met Ala Arg Ala Gln Glu Glu Leu Asp
            340                 345                 350

Arg Ala Val Gly Arg Gly Arg Arg Leu Glu Glu Ser Asp Leu Pro Gly
        355                 360                 365

Leu Pro Tyr Leu Gln Ala Val Cys Lys Glu Ala Met Arg Leu His Pro
    370                 375                 380

Ser Thr Pro Leu Ser Leu Pro His Phe Ser Leu Asp Ala Cys Asp Asp
385                 390                 395                 400

Val Asp Gly Tyr Arg Val Pro Ala Asn Thr Arg Leu Leu Val Asn Val
                405                 410                 415

Trp Ala Ile Gly Arg Asp Pro Glu Ala Trp Glu Arg Ser Leu Asp Phe
            420                 425                 430

Arg Pro Glu Arg Phe Leu Pro Gly Gly Gly Ala Glu Lys Val Asp Pro
        435                 440                 445

Leu Gly Asn Cys Phe Glu Leu Ile Pro Phe Gly Ala Gly Arg Arg Ile
    450                 455                 460

Cys Ala Gly Lys Leu Ala Gly Met Val Phe Val Gln Tyr Phe Leu Gly
465                 470                 475                 480

Thr Leu Leu His Ala Phe Asp Trp Arg Leu Pro Asp Gly Glu Glu Lys
                485                 490                 495

Leu Asp Met Ser Glu Thr Phe Gly Leu Ala Leu Pro Lys Ala Val Pro
            500                 505                 510

Leu Arg Ala Val Ala Thr Pro Arg Leu Val Pro Glu Ala Tyr Ala
        515                 520                 525
```

<210> SEQ ID NO 35
<211> LENGTH: 4215
<212> TYPE: DNA
<213> ORGANISM: Artificial Sequence
<220> FEATURE:
<223> OTHER INFORMATION: genomic DNA of F35H mutant P429L

<400> SEQUENCE: 35

```
atgcagctcg cggcgttgtg caccgacccc gtggtgctgt gcagcgcctt cctctgcctc      60

ctcctccacg tggctctccg ctcgctgctg caccctcctt ctgccgcctc ttcctccggg     120

cgccgcgggc agctcccgcc ggggccaccg ggcctgccga tcctcggcgc gctgccactc     180

gtgggcccag ccccgcacgc cggcctggcc gcgctggcgc gcaagtacgg tcccatcatg     240

tacctgaaga tgggcacggc cggcgtggtg gtggcgtcgt ccccgcgcgc ggcgcggacg     300

ttcctcaagg cgctggacgc gcggtacgcc aaccggccgg ccgtggcgag cgccgcggac     360

atcacgtacg ggcggcagaa catggtgttc gcggactacg ggcccaagtg gaagctgatg     420

cggaagctcg ccagcgtgca cctgctcggc gcgcgcgcgc tcgcggactg ggcgtgcgtg     480
```

-continued

```
cggcgcggcg aggccggcca cgtgctgcgc ggcgtggcgg aggcggccgc ggccggcagg    540
cccgtcgtcg tgccggagct gctcgtgtgc gccctcgcca acatcgtcgg gcagatcaca    600
gtgagcaagc gggtgttcga cgcgcagggg gacgactcga acaggtgagg atgggaggtc    660
catgaaatcc taccagctgt gagcatgcat aaaagttcat ttggaaagaa aagaacatat    720
ttttcttaca aatttatgct tactgtttct ttaagtttcg ataaagtttg taaaaaaaat    780
ttaggctagt ttgaaactcc atttaggatt tctattttcc aaagaaaaat aaacgaattt    840
ctcttgaaaa aatgaaaatt ctttagaaaa ataggttctc aaactagccc tcaataaaac    900
ttaatgcgat cgttttctct gactctcatt catctttctc tggttatcta attgggtcct    960
tgagagatga gtttacctgc ttgtccttta ttattgcaaa gacaacatat ctgatgcaca   1020
tggaacattg gtgcacatgg tgcacatatg aaatcatcac cactcatttt aaatctaacg   1080
tctatagttg tttgatatat tttattaagg acaccctcca acgtggtggt gtgtagtggt   1140
ggaaggtgtt atttgtaaat tgaataatca actagagacg ttagatctaa aatgagtggt   1200
gatgatttaa tatgtgcacc atgtgcacca gtcttctatg tgcaccagat atgtcctcta   1260
ttgcaaatgc tagacggaac accagctagc actagcagac tgtttatgtg gaaagaaaaa   1320
acttaaaaag atcagctagg aagctgctgt catctgtacg tatatatggt gaagactgaa   1380
caatctgcat gacaagcaaa acttagctta aaagcgaaaa gagcgatgga aacggccgct   1440
cgataaataa ttaatgagag tcttgggatt tttcatgcat ggaaaaaaac aaagctggca   1500
tttttcatct aatataatat ataacgctga tatcatattg cgtgcagata caaggacatg   1560
atcgtgtcgc tgctgaccgg cacgggcatg ttcaacatca gcgacttcgt gccggcgctg   1620
gcgcgtctgg acctgcaggg cgtgcaggcg aagctgcggc gcgtccaccg ccagttcgac   1680
ggcctcatca ccaagctgct ggccgagcac gccgcgacgg ccgcggaccg cgcgcgccag   1740
ggccgcccgg acttcgtcga ccggctccgc gccacgatgg acgccggcgc cgccgccgac   1800
gacgagagcg gcgagaccat caccgaggtc aacatcaagg gcctcatctt cgtaagctcc   1860
ctgctttttc ctcgccccca accatgcatc atcatatgca cttatatttt acacttgctc   1920
ggttttcctt tagtaactaa ctaatccgtc gcagctgcga tacacgtagc actagtacta   1980
cagcgatggg tcatcggtaa ctgaatctaa ggtgcaatag agtgcacggc cgcgggatca   2040
tggcgtgaca tgggagctaa gctaagccag tggccaccta acgaaggcac tgaccgaaag   2100
ctcagtggcg tgttaggtgg agatagtgga tcgagttgtt ggaaagacaa tatcaaaacc   2160
actctccaat tgatgatgtg tagggcctgc agtgttttga atccaccttg tttggtcgaa   2220
cacattacta gagtgaaata tggttccaat gttaattgat agcgcgaaag ggtctctagc   2280
gtaatggtta aaccttccga gtagcacatc caggttgggt tcgatcctct cgagggcgaa   2340
ttttcaagct ttgttaaaaa aattatctcg ttgtgccccg tccgctctca ggaatcgata   2400
ttctacacga caccctccga ctagtgacag ttgattgact cgttagtgat gagaagccat   2460
gctaaaaaag tggagacgta gatatgatag aggttccctt tcctaagcaa acgtgaatgc   2520
tatgaaaatt atgcagttta aaaaaaactt taaagataaa caggaattct ctttttttgga   2580
acaaacaata cgaatgcacc tccaaatatc ttatcgagtc gacttttatg gaattattgt   2640
ttttgttatt tctaagatgg gagcccaaaa tcacatacaa attattcagt gaatgcctcg   2700
gtgttttttt attagttaag ggctctcatt tttttcaagg gatttttatt tttttccaaa   2760
agaaaataaa ctaatcctct ttagaaaaat ggaaatctat tggagaaatg aggttcctaa   2820
```

-continued actagctcta acagtgagtc agttaatcag gagaagatat tagactcctg tatagtgtgc 2880
agcaaccaca tccgattctg acgttttagc ttaatgttcg ctatgtagac gtcgggcata 2940
gggaatgcat tgctaccaga acacgaatga cagctatgca agtctctaga acgttggagt 3000
agttaacaaa cgtgatagat gtaacctctg gatcatggta tgatgtcatt tcctagacta 3060
gaagaattgg tagtcaaatc gagcaaagtc ccgaaagcac actgggcttt cgacacagtg 3120
ataccaaaga tgctgaaaag aactgaggca cgataaactg ttcggtgttg gtgtaaacga 3180
ccaaagatgc tgaaaataac tgatcgtcac catccgtgaa tctaactttc gacacactgt 3240
taccaaatcc ttcgtcaaaa ttacaggaat aattaaggcg cttagacgat gataaaccat 3300
tttttgtcac taattaacca cactgttctt tgcttgaccg tgacaaaaaa aaactttttt 3360
gtgaagcagt gttgccgtaa accacaacca tcatgaactc acttgccttg tcatatgtac 3420
ttgtaccatc gaacgccgcg cgctaagaca atgcaccacc cttcaagtct tagctcactg 3480
ataccgctaa ttaagttaga taatgtcgat tactagttgt cttacttcga actatttctt 3540
ttcggcaaac tgaagtaaag acaacgtttt gttccgcagg acatgttcac ggcgggtacg 3600
gacacgtcgt cgatcatcgt ggagtgggcg atggcggaga tgctcaagaa cccgaccgtc 3660
atggcgcgcg cgcaggagga gctggaccgc gcggtgggcc ggggccggcg cctggaggag 3720
tcggacctgc ccggcctccc ctacctgcag gcggtgtgca aggaggccat gcggctgcac 3780
ccgtccacgc cgctcagcct cccgcacttc tccttggacg cctgcgacga cgtcgacggc 3840
taccgcgtcc cggccaacac ccgcctgctc gtcaacgtct gggccatcgg ccgggacccg 3900
gaggcctggg agaggctcct cgacttccgc cccgagcgct tcctgcccgg gggcggcgcg 3960
gagaaggtcg acccccctggg gaactgcttc gagctcatcc cgttcggcgc cggccggagg 4020
atctgcgcgg ggaagctggc gggcatggtg ttcgtgcagt acttcctggg cacgctgctg 4080
cacgcgttcg actggcgcct gcctgacggc gaggagaagc tggacatgag cgagacgttc 4140
ggcctcgcgc tgcccaaggc agtgccgctc cgcgccgtcg ccacgccacg gctcgtgccg 4200
gaagcctatg cctga 4215

<210> SEQ ID NO 36
<211> LENGTH: 527
<212> TYPE: PRT
<213> ORGANISM: Artificial Sequence
<220> FEATURE:
<223> OTHER INFORMATION: amino acid sequence of F35H mutant P429L

<400> SEQUENCE: 36

Met Gln Leu Ala Ala Leu Cys Thr Asp Pro Val Val Leu Cys Ser Ala
1 5 10 15

Phe Leu Cys Leu Leu Leu His Val Ala Leu Arg Ser Leu Leu His Pro
20 25 30

Pro Ser Ala Ala Ser Ser Ser Gly Arg Arg Gly Gln Leu Pro Pro Gly
35 40 45

Pro Pro Gly Leu Pro Ile Leu Gly Ala Leu Pro Leu Val Gly Pro Ala
50 55 60

Pro His Ala Gly Leu Ala Ala Leu Ala Arg Lys Tyr Gly Pro Ile Met
65 70 75 80

Tyr Leu Lys Met Gly Thr Ala Gly Val Val Val Ala Ser Ser Pro Arg
85 90 95

Ala Ala Arg Thr Phe Leu Lys Ala Leu Asp Ala Arg Tyr Ala Asn Arg
100 105 110

-continued

```
Pro Ala Val Ala Ser Ala Ala Asp Ile Thr Tyr Gly Arg Gln Asn Met
        115                 120                 125

Val Phe Ala Asp Tyr Gly Pro Lys Trp Lys Leu Met Arg Lys Leu Ala
    130                 135                 140

Ser Val His Leu Leu Gly Ala Arg Ala Leu Ala Asp Trp Ala Cys Val
145                 150                 155                 160

Arg Arg Gly Glu Ala Gly His Val Leu Arg Gly Val Ala Glu Ala Ala
                165                 170                 175

Ala Ala Gly Arg Pro Val Val Val Pro Glu Leu Leu Val Cys Ala Leu
            180                 185                 190

Ala Asn Ile Val Gly Gln Ile Thr Val Ser Lys Arg Val Phe Asp Ala
        195                 200                 205

Gln Gly Asp Asp Ser Asn Arg Tyr Lys Asp Met Ile Val Ser Leu Leu
    210                 215                 220

Thr Gly Thr Gly Met Phe Asn Ile Ser Asp Phe Val Pro Ala Leu Ala
225                 230                 235                 240

Arg Leu Asp Leu Gln Gly Val Gln Ala Lys Leu Arg Arg Val His Arg
                245                 250                 255

Gln Phe Asp Gly Leu Ile Thr Lys Leu Leu Ala Glu His Ala Ala Thr
            260                 265                 270

Ala Ala Asp Arg Ala Arg Gln Gly Arg Pro Asp Phe Val Asp Arg Leu
        275                 280                 285

Arg Ala Thr Met Asp Ala Gly Ala Ala Ala Asp Asp Glu Ser Gly Glu
    290                 295                 300

Thr Ile Thr Glu Val Asn Ile Lys Gly Leu Ile Phe Asp Met Phe Thr
305                 310                 315                 320

Ala Gly Thr Asp Thr Ser Ser Ile Ile Val Glu Trp Ala Met Ala Glu
                325                 330                 335

Met Leu Lys Asn Pro Thr Val Met Ala Arg Ala Gln Glu Glu Leu Asp
            340                 345                 350

Arg Ala Val Gly Arg Gly Arg Arg Leu Glu Glu Ser Asp Leu Pro Gly
        355                 360                 365

Leu Pro Tyr Leu Gln Ala Val Cys Lys Glu Ala Met Arg Leu His Pro
    370                 375                 380

Ser Thr Pro Leu Ser Leu Pro His Phe Ser Leu Asp Ala Cys Asp Asp
385                 390                 395                 400

Val Asp Gly Tyr Arg Val Pro Ala Asn Thr Arg Leu Leu Val Asn Val
                405                 410                 415

Trp Ala Ile Gly Arg Asp Pro Glu Ala Trp Glu Arg Leu Leu Asp Phe
            420                 425                 430

Arg Pro Glu Arg Phe Leu Pro Gly Gly Gly Ala Glu Lys Val Asp Pro
        435                 440                 445

Leu Gly Asn Cys Phe Glu Leu Ile Pro Phe Gly Ala Gly Arg Arg Ile
    450                 455                 460

Cys Ala Gly Lys Leu Ala Gly Met Val Phe Val Gln Tyr Phe Leu Gly
465                 470                 475                 480

Thr Leu Leu His Ala Phe Asp Trp Arg Leu Pro Asp Gly Glu Glu Lys
                485                 490                 495

Leu Asp Met Ser Glu Thr Phe Gly Leu Ala Leu Pro Lys Ala Val Pro
            500                 505                 510

Leu Arg Ala Val Ala Thr Pro Arg Leu Val Pro Glu Ala Tyr Ala
        515                 520                 525
```

<210> SEQ ID NO 37
<211> LENGTH: 4215
<212> TYPE: DNA
<213> ORGANISM: Artificial Sequence
<220> FEATURE:
<223> OTHER INFORMATION: genomic DNA of F35H mutant R436C

<400> SEQUENCE: 37

```
atgcagctcg cggcgttgtg caccgacccc gtggtgctgt gcagcgcctt cctctgcctc     60
ctcctccacg tggctctccg ctcgctgctg caccctcctt ctgccgcctc ttcctccggg    120
cgccgcgggc agctcccgcc ggggccaccg ggcctgccga tcctcggcgc gctgccactc    180
gtgggcccag ccccgcacgc cggcctggcc gcgctggcgc gcaagtacgg tcccatcatg    240
tacctgaaga tgggcacggc cggcgtggtg gtggcgtcgt ccccgcgcgc ggcgcggacg    300
ttcctcaagg cgctggacgc gcggtacgcc aaccggccgg ccgtggcgag cgccgcggac    360
atcacgtacg ggcggcagaa catggtgttc gcggactacg ggcccaagtg gaagctgatg    420
cggaagctcg ccagcgtgca cctgctcggc gcgcgcgcgc tcgcggactg ggcgtgcgtg    480
cggcgcggcg aggccggcca cgtgctgcgc ggcgtggcgg aggcggccgc ggccggcagg    540
cccgtcgtcg tgccggagct gctcgtgtgc gccctcgcca acatcgtcgg gcagatcaca    600
gtgagcaagc gggtgttcga cgcgcagggg gacgactcga acaggtgagg atgggaggtc    660
catgaaatcc taccagctgt gagcatgcat aaaagttcat ttggaaagaa aagaacatat    720
ttttcttaca aatttatgct tactgtttct ttaagtttcg ataaagtttg taaaaaaaat    780
ttaggctagt ttgaaactcc atttaggatt tctattttcc aaagaaaaat aaacgaattt    840
ctcttgaaaa aatgaaaatt ctttagaaaa ataggttctc aaactagccc tcaataaaac    900
ttaatgcgat cgttttctct gactctcatt catctttctc tggttatcta attgggtcct    960
tgagagatga gtttacctgc ttgtccttta ttattgcaaa gacaacatat ctgatgcaca   1020
tggaacattg gtgcacatgg tgcacatatg aaatcatcac cactcatttt aaatctaacg   1080
tctatagttg tttgatatat tttattaagg acaccctcca acgtggtggt gtgtagtggt   1140
ggaaggtgtt atttgtaaat tgaataatca actagagacg ttagatctaa aatgagtggt   1200
gatgatttaa tatgtgcacc atgtgcacca gtcttctatg tgcaccagat atgtcctcta   1260
ttgcaaatgc tagacggaac accagctagc actagcagac tgtttatgtg gaaagaaaaa   1320
acttaaaaag atcagctagg aagctgctgt catctgtacg tatatatggt gaagactgaa   1380
caatctgcat gacaagcaaa acttagctta aaagcgaaaa gagcgatgga aacggccgct   1440
cgataaataa ttaatgagag tcttgggatt tttcatgcat ggaaaaaaac aaagctggca   1500
tttttcatct aatataatat ataacgctga tatcatattg cgtgcagata caaggacatg   1560
atcgtgtcgc tgctgaccgg cacgggcatg ttcaacatca gcgacttcgt gccggcgctg   1620
gcgcgtctgg acctgcaggg cgtgcaggcg aagctgcggc gcgtccaccg ccagttcgac   1680
ggcctcatca ccaagctgct ggccgagcac gccgcgacgg ccgcggaccg cgcgcgccag   1740
ggccgcccgg acttcgtcga ccggctccgc gccacgatgg acgccggcgc cgccgccgac   1800
gacgagagcg gcgagaccat caccgaggtc aacatcaagg gcctcatctt cgtaagctcc   1860
ctgctttttc ctcgccccca accatgcatc atcatatgca cttatatttt acacttgctc   1920
ggttttcctt tagtaactaa ctaatccgtc gcagctgcga tacacgtagc actagtacta   1980
cagcgatggg tcatcggtaa ctgaatctaa ggtgcaatag agtgcacggc cgcgggatca   2040
tggcgtgaca tgggagctaa gctaagccag tggccaccta acgaaggcac tgaccgaaag   2100
```

-continued

```
ctcagtggcg tgttaggtgg agatagtgga tcgagttgtt ggaaagacaa tatcaaaacc   2160
actctccaat tgatgatgtg tagggcctgc agtgttttga atccaccttg tttggtcgaa   2220
cacattacta gagtgaaata tggttccaat gttaattgat agcgcgaaag ggtctctagc   2280
gtaatggtta aaccttccga gtagcacatc caggttgggt tcgatcctct cgagggcgaa   2340
ttttcaagct ttgttaaaaa aattatctcg ttgtgccccg tccgctctca ggaatcgata   2400
ttctacacga caccctccga ctagtgacag ttgattgact cgttagtgat gagaagccat   2460
gctaaaaaag tggagacgta gatatgatag aggttccctt tcctaagcaa acgtgaatgc   2520
tatgaaaatt atgcagttta aaaaaaactt taaagataaa caggaattct ctttttgga    2580
acaaacaata cgaatgcacc tccaaatatc ttatcgagtc gacttttatg gaattattgt   2640
ttttgttatt tctaagatgg gagcccaaaa tcacatacaa attattcagt gaatgcctcg   2700
gtgttttttt attagttaag ggctctcatt tttttcaagg gatttttatt tttttccaaa   2760
agaaaataaa ctaatcctct ttagaaaaat ggaaatctat tggagaaatg aggttcctaa   2820
actagctcta acagtgagtc agttaatcag gagaagatat tagactcctg tatagtgtgc   2880
agcaaccaca tccgattctg acgttttagc ttaatgttcg ctatgtagac gtcgggcata   2940
gggaatgcat tgctaccaga acacgaatga cagctatgca agtctctaga acgttggagt   3000
agttaacaaa cgtgatagat gtaacctctg gatcatggta tgatgtcatt tcctagacta   3060
gaagaattgg tagtcaaatc gagcaaagtc ccgaaagcac actgggcttt cgacacagtg   3120
ataccaaaga tgctgaaaag aactgaggca cgataaactg ttcggtgttg gtgtaaacga   3180
ccaaagatgc tgaaaataac tgatcgtcac catccgtgaa tctaactttc gacacactgt   3240
taccaaatcc ttcgtcaaaa ttacaggaat aattaaggcg cttagacgat gataaaccat   3300
tttttgtcac taattaacca cactgttctt tgcttgaccg tgacaaaaaa aaactttttt   3360
gtgaagcagt gttgccgtaa accacaacca tcatgaactc acttgccttg tcatatgtac   3420
ttgtaccatc gaacgccgcg cgctaagaca atgcaccacc cttcaagtct tagctcactg   3480
ataccgctaa ttaagttaga taatgtcgat tactagttgt cttacttcga actatttctt   3540
ttcggcaaac tgaagtaaag acaacgtttt gttccgcagg acatgttcac ggcgggtacg   3600
gacacgtcgt cgatcatcgt ggagtgggcg atggcggaga tgctcaagaa cccgaccgtc   3660
atggcgcgcg cgcaggagga gctggaccgc gcggtgggcc ggggccggcg cctggaggag   3720
tcggacctgc ccggcctccc ctacctgcag gcggtgtgca aggaggccat gcggctgcac   3780
ccgtccacgc cgctcagcct cccgcacttc tccttggacg cctgcgacga cgtcgacggc   3840
taccgcgtcc cggccaacac ccgcctgctc gtcaacgtct gggccatcgg ccgggacccg   3900
gaggcctggg agaggcccct cgacttccgc cccgagtgct tcctgcccgg gggcggcgcg   3960
gagaaggtcg accccctggg gaactgcttc gagctcatcc cgttcggcgc cggccggagg   4020
atctgcgcgg ggaagctggc gggcatggtg ttcgtgcagt acttcctggg cacgctgctg   4080
cacgcgttcg actggcgcct gcctgacggc gaggagaagc tggacatgag cgagacgttc   4140
ggcctcgcgc tgcccaaggc agtgccgctc cgcgccgtcg ccacgccacg gctcgtgccg   4200
gaagcctatg cctga                                                    4215
```

<210> SEQ ID NO 38
<211> LENGTH: 527
<212> TYPE: PRT
<213> ORGANISM: Artificial Sequence
<220> FEATURE:
<223> OTHER INFORMATION: amino acid sequence of F35H mutant R436C

<400> SEQUENCE: 38

```
Met Gln Leu Ala Ala Leu Cys Thr Asp Pro Val Val Leu Cys Ser Ala
1               5                   10                  15

Phe Leu Cys Leu Leu Leu His Val Ala Leu Arg Ser Leu Leu His Pro
            20                  25                  30

Pro Ser Ala Ala Ser Ser Ser Gly Arg Arg Gly Gln Leu Pro Pro Gly
        35                  40                  45

Pro Pro Gly Leu Pro Ile Leu Gly Ala Leu Pro Leu Val Gly Pro Ala
    50                  55                  60

Pro His Ala Gly Leu Ala Ala Leu Ala Arg Lys Tyr Gly Pro Ile Met
65                  70                  75                  80

Tyr Leu Lys Met Gly Thr Ala Gly Val Val Val Ala Ser Ser Pro Arg
                85                  90                  95

Ala Ala Arg Thr Phe Leu Lys Ala Leu Asp Ala Arg Tyr Ala Asn Arg
            100                 105                 110

Pro Ala Val Ala Ser Ala Ala Asp Ile Thr Tyr Gly Arg Gln Asn Met
        115                 120                 125

Val Phe Ala Asp Tyr Gly Pro Lys Trp Lys Leu Met Arg Lys Leu Ala
    130                 135                 140

Ser Val His Leu Leu Gly Ala Arg Ala Leu Ala Asp Trp Ala Cys Val
145                 150                 155                 160

Arg Arg Gly Glu Ala Gly His Val Leu Arg Gly Val Ala Glu Ala Ala
                165                 170                 175

Ala Ala Gly Arg Pro Val Val Val Pro Glu Leu Leu Val Cys Ala Leu
            180                 185                 190

Ala Asn Ile Val Gly Gln Ile Thr Val Ser Lys Arg Val Phe Asp Ala
        195                 200                 205

Gln Gly Asp Asp Ser Asn Arg Tyr Lys Asp Met Ile Val Ser Leu Leu
    210                 215                 220

Thr Gly Thr Gly Met Phe Asn Ile Ser Asp Phe Val Pro Ala Leu Ala
225                 230                 235                 240

Arg Leu Asp Leu Gln Gly Val Gln Ala Lys Leu Arg Arg Val His Arg
                245                 250                 255

Gln Phe Asp Gly Leu Ile Thr Lys Leu Leu Ala Glu His Ala Ala Thr
            260                 265                 270

Ala Ala Asp Arg Ala Arg Gln Gly Arg Pro Asp Phe Val Asp Arg Leu
        275                 280                 285

Arg Ala Thr Met Asp Ala Gly Ala Ala Ala Asp Asp Glu Ser Gly Glu
    290                 295                 300

Thr Ile Thr Glu Val Asn Ile Lys Gly Leu Ile Phe Asp Met Phe Thr
305                 310                 315                 320

Ala Gly Thr Asp Thr Ser Ser Ile Ile Val Glu Trp Ala Met Ala Glu
                325                 330                 335

Met Leu Lys Asn Pro Thr Val Met Ala Arg Ala Gln Glu Glu Leu Asp
            340                 345                 350

Arg Ala Val Gly Arg Gly Arg Arg Leu Glu Glu Ser Asp Leu Pro Gly
        355                 360                 365

Leu Pro Tyr Leu Gln Ala Val Cys Lys Glu Ala Met Arg Leu His Pro
    370                 375                 380

Ser Thr Pro Leu Ser Leu Pro His Phe Ser Leu Asp Ala Cys Asp Asp
385                 390                 395                 400

Val Asp Gly Tyr Arg Val Pro Ala Asn Thr Arg Leu Leu Val Asn Val
```

405 410 415

Trp Ala Ile Gly Arg Asp Pro Glu Ala Trp Glu Arg Pro Leu Asp Phe
420 425 430

Arg Pro Glu Cys Phe Leu Pro Gly Gly Gly Ala Glu Lys Val Asp Pro
435 440 445

Leu Gly Asn Cys Phe Glu Leu Ile Pro Phe Gly Ala Gly Arg Arg Ile
450 455 460

Cys Ala Gly Lys Leu Ala Gly Met Val Phe Val Gln Tyr Phe Leu Gly
465 470 475 480

Thr Leu Leu His Ala Phe Asp Trp Arg Leu Pro Asp Gly Glu Glu Lys
485 490 495

Leu Asp Met Ser Glu Thr Phe Gly Leu Ala Leu Pro Lys Ala Val Pro
500 505 510

Leu Arg Ala Val Ala Thr Pro Arg Leu Val Pro Glu Ala Tyr Ala
515 520 525

<210> SEQ ID NO 39
<211> LENGTH: 4215
<212> TYPE: DNA
<213> ORGANISM: Artificial Sequence
<220> FEATURE:
<223> OTHER INFORMATION: genomic DNA of F35H mutant Q44stop

<400> SEQUENCE: 39
atgcagctcg cggcgttgtg caccgacccc gtggtgctgt gcagcgcctt cctctgcctc 60
ctcctccacg tggctctccg ctcgctgctg caccctcctt ctgccgcctc ttcctccggg 120
cgccgcgggt agctcccgcc ggggccaccg ggcctgccga tcctcggcgc gctgccactc 180
gtgggcccag ccccgcacgc cggcctggcc gcgctggcgc gcaagtacgg tcccatcatg 240
tacctgaaga tgggcacggc cggcgtggtg gtggcgtcgt ccccgcgcgc ggcgcggacg 300
ttcctcaagg cgctggacgc gcggtacgcc aaccggccgg ccgtggcgag cgccgcggac 360
atcacgtacg ggcggcagaa catggtgttc gcggactacg ggcccaagtg gaagctgatg 420
cggaagctcg ccagcgtgca cctgctcggc gcgcgcgcgc tcgcggactg ggcgtgcgtg 480
cggcgcggcg aggccggcca cgtgctgcgc ggcgtggcgg aggcggccgc ggccggcagg 540
cccgtcgtcg tgccggagct gctcgtgtgc gccctcgcca acatcgtcgg gcagatcaca 600
gtgagcaagc gggtgttcga cgcgcagggg gacgactcga acaggtgagg atgggaggtc 660
catgaaatcc taccagctgt gagcatgcat aaaagttcat ttggaaagaa aagaacatat 720
ttttcttaca aatttatgct tactgtttct ttaagtttcg ataaagtttg taaaaaaaat 780
ttaggctagt ttgaaactcc atttaggatt tctattttcc aaagaaaaat aaacgaattt 840
ctcttgaaaa aatgaaaatt ctttagaaaa ataggttctc aaactagccc tcaataaaac 900
ttaatgcgat cgttttctct gactctcatt catctttctc tggttatcta attgggtcct 960
tgagagatga gtttacctgc ttgtccttta ttattgcaaa gacaacatat ctgatgcaca 1020
tggaacattg gtgcacatgg tgcacatatg aaatcatcac cactcatttt aaatctaacg 1080
tctatagttg tttgatatat tttattaagg acaccctcca acgtggtggt gtgtagtggt 1140
ggaaggtgtt atttgtaaat tgaataatca actagagacg ttagatctaa aatgagtggt 1200
gatgatttaa tatgtgcacc atgtgcacca gtcttctatg tgcaccagat atgtcctcta 1260
ttgcaaatgc tagacggaac accagctagc actagcagac tgtttatgtg gaaagaaaaa 1320
acttaaaaag atcagctagg aagctgctgt catctgtacg tatatatggt gaagactgaa 1380

-continued

```
caatctgcat gacaagcaaa acttagctta aaagcgaaaa gagcgatgga aacggccgct   1440
cgataaataa ttaatgagag tcttgggatt tttcatgcat ggaaaaaaac aaagctggca   1500
tttttcatct aatataatat ataacgctga tatcatattg cgtgcagata caaggacatg   1560
atcgtgtcgc tgctgaccgg cacgggcatg ttcaacatca gcgacttcgt gccggcgctg   1620
gcgcgtctgg acctgcaggg cgtgcaggcg aagctgcggc gcgtccaccg ccagttcgac   1680
ggcctcatca ccaagctgct ggccgagcac gccgcgacgg ccgcggaccg cgcgcgccag   1740
ggccgcccgg acttcgtcga ccggctccgc gccacgatgg acgccggcgc cgccgccgac   1800
gacgagagcg gcgagaccat caccgaggtc aacatcaagg gcctcatctt cgtaagctcc   1860
ctgctttttc ctcgccccca accatgcatc atcatatgca cttatatttt acacttgctc   1920
ggttttcctt tagtaactaa ctaatccgtc gcagctgcga tacacgtagc actagtacta   1980
cagcgatggg tcatcggtaa ctgaatctaa ggtgcaatag agtgcacggc cgcgggatca   2040
tggcgtgaca tgggagctaa gctaagccag tggccaccta acgaaggcac tgaccgaaag   2100
ctcagtggcg tgttaggtgg agatagtgga tcgagttgtt ggaaagacaa tatcaaaacc   2160
actctccaat tgatgatgtg tagggcctgc agtgttttga atccaccttg tttggtcgaa   2220
cacattacta gagtgaaata tggttccaat gttaattgat agcgcgaaag ggtctctagc   2280
gtaatggtta aaccttccga gtagcacatc caggttgggt tcgatcctct cgagggcgaa   2340
ttttcaagct ttgttaaaaa aattatctcg ttgtgccccg tccgctctca ggaatcgata   2400
ttctacacga caccctccga ctagtgacag ttgattgact cgttagtgat gagaagccat   2460
gctaaaaaag tggagacgta gatatgatag aggttccctt tcctaagcaa acgtgaatgc   2520
tatgaaaatt atgcagttta aaaaaaactt taaagataaa caggaattct ctttttttgga   2580
acaaacaata cgaatgcacc tccaaatatc ttatcgagtc gacttttatg gaattattgt   2640
ttttgttatt tctaagatgg gagcccaaaa tcacatacaa attattcagt gaatgcctcg   2700
gtgttttttt attagttaag ggctctcatt tttttcaagg gatttttatt tttttccaaa   2760
agaaaataaa ctaatcctct ttagaaaaat ggaaatctat tggagaaatg aggttcctaa   2820
actagctcta acagtgagtc agttaatcag gagaagatat tagactcctg tatagtgtgc   2880
agcaaccaca tccgattctg acgttttagc ttaatgttcg ctatgtagac gtcgggcata   2940
gggaatgcat tgctaccaga acacgaatga cagctatgca agtctctaga acgttggagt   3000
agttaacaaa cgtgatagat gtaacctctg gatcatggta tgatgtcatt tcctagacta   3060
gaagaattgg tagtcaaatc gagcaaagtc ccgaaagcac actgggcttt cgacacagtg   3120
ataccaaaga tgctgaaaag aactgaggca cgataaactg ttcggtgttg gtgtaaacga   3180
ccaaagatgc tgaaaataac tgatcgtcac catccgtgaa tctaactttc gacacactgt   3240
taccaaatcc ttcgtcaaaa ttacaggaat aattaaggcg cttagacgat gataaaccat   3300
tttttgtcac taattaacca cactgttctt tgcttgaccg tgacaaaaaa aaactttttt   3360
gtgaagcagt gttgccgtaa accacaacca tcatgaactc acttgccttg tcatatgtac   3420
ttgtaccatc gaacgccgcg cgctaagaca atgcaccacc cttcaagtct tagctcactg   3480
ataccgctaa ttaagttaga taatgtcgat tactagttgt cttacttcga actatttctt   3540
ttcggcaaac tgaagtaaag acaacgtttt gttccgcagg acatgttcac ggcgggtacg   3600
gacacgtcgt cgatcatcgt ggagtgggcg atggcggaga tgctcaagaa cccgaccgtc   3660
atggcgcgcg cgcaggagga gctggaccgc gcggtgggcc ggggccggcg cctggaggag   3720
tcggacctgc ccggcctccc ctacctgcag gcggtgtgca aggaggccat gcggctgcac   3780
```

-continued

```
ccgtccacgc cgctcagcct cccgcacttc tccttggacg cctgcgacga cgtcgacggc   3840

taccgcgtcc cggccaacac ccgcctgctc gtcaacgtct gggccatcgg ccgggacccg   3900

gaggcctggg agaggcccct cgacttccgc cccgagcgct tcctgcccgg gggcggcgcg   3960

gagaaggtcg accccctggg gaactgcttc gagctcatcc cgttcggcgc cggccggagg   4020

atctgcgcgg ggaagctggc gggcatggtg ttcgtgcagt acttcctggg cacgctgctg   4080

cacgcgttcg actggcgcct gcctgacggc gaggagaagc tggacatgag cgagacgttc   4140

ggcctcgcgc tgcccaaggc agtgccgctc cgcgccgtcg ccacgccacg gctcgtgccg   4200

gaagcctatg cctga                                                    4215


<210> SEQ ID NO 40
<211> LENGTH: 43
<212> TYPE: PRT
<213> ORGANISM: Artificial Sequence
<220> FEATURE:
<223> OTHER INFORMATION: amino acid sequence of F35H mutant Q44stop

<400> SEQUENCE: 40

Met Gln Leu Ala Ala Leu Cys Thr Asp Pro Val Val Leu Cys Ser Ala
1               5                   10                  15

Phe Leu Cys Leu Leu Leu His Val Ala Leu Arg Ser Leu Leu His Pro
            20                  25                  30

Pro Ser Ala Ala Ser Ser Ser Gly Arg Arg Gly
        35                  40
```